United States Patent
Gauthier et al.

(10) Patent No.: US 10,246,510 B2
(45) Date of Patent: Apr. 2, 2019

(54) KIR3DL2 BINDING AGENTS

(71) Applicant: INNATE PHARMA, Marseilles (FR)

(72) Inventors: Laurent Gauthier, Marseilles (FR); Benjamin Rossi, Marseilles (FR); Hélène Sicard, Marseilles (FR); Carine Paturel, Marcy l'Étoile (FR)

(73) Assignee: INNATE PHARMA, Marseilles (FR)

( * ) Notice: Subject to any disclaimer, the term of this patent is extended or adjusted under 35 U.S.C. 154(b) by 604 days.

(21) Appl. No.: 14/429,416

(22) PCT Filed: Sep. 17, 2013

(86) PCT No.: PCT/EP2013/069293
§ 371 (c)(1),
(2) Date: Mar. 19, 2015

(87) PCT Pub. No.: WO2014/044681
PCT Pub. Date: Mar. 27, 2014

(65) Prior Publication Data
US 2015/0291692 A1    Oct. 15, 2015

Related U.S. Application Data

(60) Provisional application No. 61/702,823, filed on Sep. 19, 2012.

(51) Int. Cl.
| | | |
|---|---|---|
| C07K 16/28 | (2006.01) | |
| G01N 33/569 | (2006.01) | |
| A61K 47/68 | (2017.01) | |
| A61K 39/00 | (2006.01) | |

(52) U.S. Cl.
CPC ...... *C07K 16/2803* (2013.01); *A61K 47/6803* (2017.08); *A61K 47/6849* (2017.08); *G01N 33/56972* (2013.01); *A61K 2039/505* (2013.01); *C07K 2317/24* (2013.01); *C07K 2317/33* (2013.01); *C07K 2317/34* (2013.01); *C07K 2317/51* (2013.01); *C07K 2317/565* (2013.01); *C07K 2317/732* (2013.01); *C07K 2317/734* (2013.01); *C07K 2317/77* (2013.01); *C07K 2317/92* (2013.01); *G01N 2333/70503* (2013.01); *G01N 2800/24* (2013.01); *G01N 2800/52* (2013.01); *G01N 2800/7028* (2013.01); *G01N 2800/7095* (2013.01)

(58) Field of Classification Search
None
See application file for complete search history.

(56) References Cited

U.S. PATENT DOCUMENTS

| 7,399,595 B2 | 7/2008 | Bensussan et al. |
| 7,919,085 B2 | 4/2011 | Bensussan et al. |
| 8,268,308 B2 | 9/2012 | Bensussan et al. |
| 8,518,655 B2 | 8/2013 | Bensussan et al. |
| 2012/0064081 A1 | 3/2012 | Anfossi et al. |
| 2016/0130346 A1 * | 5/2016 | Gaulard ............ C07K 16/2803 424/144.1 |

FOREIGN PATENT DOCUMENTS

| WO | WO 02/50122 | 6/2002 | |
| WO | WO 2010/081890 | 7/2010 | |
| WO | WO-2010081890 A1 * | 7/2010 | ......... C07K 16/2803 |

OTHER PUBLICATIONS

Sivori et al. (Blood. 2010;116(10):1637-1647). (Year: 2010).*
Harlow et al. (Antibodies, A Laboratory Manual, Cold Spring Harbor laboratory, 1988, pp. 37-47, cited herewith) (Year: 1988).*
Edwards et al. (J. Mol. Biol. (2003) 334, 103-118). (Year: 2003).*
Meyer et al. (British Journal of Haematology, 2018, 180, 808-820). (Year: 2018).*
Lloyd et al., Protein Engineering, Design & Selection vol. 22 No. 3 pp. 159-168, 2009. (Year: 2009).*
Robert W. Bahr, Deputy Commissioner for Patent Examination Policy, Memorandum of Feb. 22, 2018, 2 pages. (Year: 2018).*
Pende, D. et al. "The Natural Killer Cell Receptor Specific for HLA-A Allotypes: A Novel Member of the p58/p70 Family of Inhibitory Receptors That Is Characterized by Three Immunoglobulin-like Domains and Is Expressed as a 140-kD Disulphide-linked Dimer" *Journal of Experimental Medicine*, Aug. 1, 1996, pp. 505-518, vol. 184, No. 2.
Brando, C. et al. "Receptors and lytic mediators regulating anti-tumor activity by the leukemic killer T cell line TALL-104" *Journal of Leukocyte Biology*, Aug. 2005, pp. 359-371, vol. 78, No. 2.
Bagot, M. et al. "Les lymphomes T epidermotropes comme modeles de progression tumorale" *Medicine/Sciences*, Feb. 2006, pp. 192-196, vol. 22, No. 2.
Database EMBL [Online] Accession No. AZX09943, "Anti-BKB2R humanized antibody heavy chain variable region (H37), SEQ 5" Aug. 2, 2012, p. 1, XP-002718577.
Database EMBL [Online] Accession No. AZT60725, "Anti-myostatin monoclonal antibody 12A5-1 clone VL region, SEQ ID 1" Mar. 29, 2012, p. 1, XP-002718578.

(Continued)

*Primary Examiner* — Zachary S Skelding
(74) *Attorney, Agent, or Firm* — Saliwanchik, Lloyd & Eisenschenk

(57) ABSTRACT

The present invention relates to methods for the treatment of cancer and inflammatory disease using antibodies (e.g. monoclonal antibodies), antibody fragments, and derivatives thereof that specifically bind KIR3DL2. The invention also relates to antibodies, cells producing such antibodies; methods of making such antibodies; fragments, variants, and derivatives of the antibodies; pharmaceutical compositions comprising the same.

20 Claims, 14 Drawing Sheets
Specification includes a Sequence Listing.

(56) References Cited

OTHER PUBLICATIONS

Marie-Cardine, A. et al. "Novel therapeutic and diagnostic antibodies against KIR3DL2, a unique tumor antigen overexpressed on subtypes of T cell lymphomas" *Journal of ImmunoTherapy of Cancer*, Nov. 7, 2013, p. P45, vol. 1, Suppl. 1.
Written Opinion in International Application No. PCT/EP2013/069293, dated Jan. 30, 2014, pp. 1-11.

\* cited by examiner

SEQUENCE LISTING

```
<160> NUMBER OF SEQ ID NOS: 182

<210> SEQ ID NO 1
<211> LENGTH: 434
<212> TYPE: PRT
<213> ORGANISM: homo sapiens

<400> SEQUENCE: 1

Leu Met Gly Gly Gln Asp Lys Pro Phe Leu Ser Ala Arg Pro Ser Thr
1               5                   10                  15

Val Val Pro Arg Gly Gly His Val Ala Leu Gln Cys His Tyr Arg Arg
                20                  25                  30

Gly Phe Asn Asn Phe Met Leu Tyr Lys Glu Asp Arg Ser His Val Pro
            35                  40                  45

Ile Phe His Gly Arg Ile Phe Gln Glu Ser Phe Ile Met Gly Pro Val
        50                  55                  60

Thr Pro Ala His Ala Gly Thr Tyr Arg Cys Arg Gly Ser Arg Pro His
65                  70                  75                  80

Ser Leu Thr Gly Trp Ser Ala Pro Ser Asn Pro Leu Val Ile Met Val
                85                  90                  95

Thr Gly Asn His Arg Lys Pro Ser Leu Leu Ala His Pro Gly Pro Leu
            100                 105                 110

Leu Lys Ser Gly Glu Thr Val Ile Leu Gln Cys Trp Ser Asp Val Met
        115                 120                 125

Phe Glu His Phe Phe Leu His Arg Glu Gly Ile Ser Glu Asp Pro Ser
    130                 135                 140

Arg Leu Val Gly Gln Ile His Asp Gly Val Ser Lys Ala Asn Phe Ser
145                 150                 155                 160

Ile Gly Pro Leu Met Pro Val Leu Ala Gly Thr Tyr Arg Cys Tyr Gly
                165                 170                 175

Ser Val Pro His Ser Pro Tyr Gln Leu Ser Ala Pro Ser Asp Pro Leu
            180                 185                 190
```

-continued

Asp Ile Val Ile Thr Gly Leu Tyr Glu Lys Pro Ser Leu Ser Ala Gln
            195                 200                 205

Pro Gly Pro Thr Val Gln Ala Gly Glu Asn Val Thr Leu Ser Cys Ser
    210                 215                 220

Ser Trp Ser Ser Tyr Asp Ile Tyr His Leu Ser Arg Glu Gly Glu Ala
225                 230                 235                 240

His Glu Arg Arg Leu Arg Ala Val Pro Lys Val Asn Arg Thr Phe Gln
                245                 250                 255

Ala Asp Phe Pro Leu Gly Pro Ala Thr His Gly Gly Thr Tyr Arg Cys
            260                 265                 270

Phe Gly Ser Phe Arg Ala Leu Pro Cys Val Trp Ser Asn Ser Ser Asp
            275                 280                 285

Pro Leu Leu Val Ser Val Thr Gly Asn Pro Ser Ser Ser Trp Pro Ser
    290                 295                 300

Pro Thr Glu Pro Ser Ser Lys Ser Gly Ile Cys Arg His Leu His Val
305                 310                 315                 320

Leu Ile Gly Thr Ser Val Val Ile Phe Leu Phe Ile Leu Leu Leu Phe
                325                 330                 335

Phe Leu Leu Tyr Arg Trp Cys Ser Asn Lys Lys Asn Ala Ala Val Met
            340                 345                 350

Asp Gln Glu Pro Ala Gly Asp Arg Thr Val Asn Arg Gln Asp Ser Asp
            355                 360                 365

Glu Gln Asp Pro Gln Glu Val Thr Tyr Ala Gln Leu Asp His Cys Val
    370                 375                 380

Phe Ile Gln Arg Lys Ile Ser Arg Pro Ser Gln Arg Pro Lys Thr Pro
385                 390                 395                 400

Leu Thr Asp Thr Ser Val Tyr Thr Glu Leu Pro Asn Ala Glu Pro Arg
                405                 410                 415

Ser Lys Val Val Ser Cys Pro Arg Ala Pro Gln Ser Gly Leu Glu Gly
            420                 425                 430

Val Phe

<210> SEQ ID NO 2
<211> LENGTH: 117
<212> TYPE: PRT
<213> ORGANISM: Mus musculus

<400> SEQUENCE: 2

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Arg Met Asn Ser Leu Arg Ala Glu Asp Thr Gly Ile Tyr
                85                  90                  95

Tyr Cys Thr Gly Gly Tyr Tyr Pro Val Tyr Trp Gly Gln Gly Thr Leu
            100                 105                 110

Val Thr Val Ser Ala
            115

<210> SEQ ID NO 3
<211> LENGTH: 106
<212> TYPE: PRT
<213> ORGANISM: Mus musculus

<400> SEQUENCE: 3

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Asn
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Phe Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Leu Ala Thr Tyr Tyr Cys Leu Gln Tyr Asp Asn Leu Leu Thr
                85                  90                  95

Phe Gly Gly Gly Thr Lys Leu Glu Ile Lys
            100                 105

<210> SEQ ID NO 4
<211> LENGTH: 5
<212> TYPE: PRT
<213> ORGANISM: mus musculus

<400> SEQUENCE: 4

Asp Ala Trp Met Asp
1               5

<210> SEQ ID NO 5
<211> LENGTH: 6
<212> TYPE: PRT
<213> ORGANISM: mus musculus

<400> SEQUENCE: 5

Gly Phe Thr Phe Ser Asp
1               5

<210> SEQ ID NO 6
<211> LENGTH: 10
<212> TYPE: PRT
<213> ORGANISM: Mus musculus

<400> SEQUENCE: 6

Gly Phe Thr Phe Ser Asp Ala Trp Met Asp
1               5                   10

<210> SEQ ID NO 7
<211> LENGTH: 16
<212> TYPE: PRT
<213> ORGANISM: Mus musculus

<400> SEQUENCE: 7

Ile Arg Ser Lys Ala Asn Asn His Ala Thr Tyr Tyr Ala Glu Ser Val
1               5                   10                  15

<210> SEQ ID NO 8
<211> LENGTH: 9
<212> TYPE: PRT
<213> ORGANISM: mus musculus

<400> SEQUENCE: 8

Ile Arg Ser Lys Ala Asn Asn His Ala
1               5

<210> SEQ ID NO 9
<211> LENGTH: 6
<212> TYPE: PRT
<213> ORGANISM: Mus musculus

<400> SEQUENCE: 9

Gly Tyr Tyr Pro Val Tyr
1               5

<210> SEQ ID NO 10
<211> LENGTH: 11
<212> TYPE: PRT
<213> ORGANISM: Mus musculus

<400> SEQUENCE: 10

Lys Ala Ser Gln Asp Ile Asn Lys Asn Ile Ala
1               5                   10

<210> SEQ ID NO 11
<211> LENGTH: 7
<212> TYPE: PRT
<213> ORGANISM: Mus musculus

<400> SEQUENCE: 11

Tyr Thr Ser Thr Leu Gln Pro
1               5

<210> SEQ ID NO 12
<211> LENGTH: 8
<212> TYPE: PRT
<213> ORGANISM: Mus musculus

<400> SEQUENCE: 12

Leu Gln Tyr Asp Asn Leu Leu Thr
1               5

<210> SEQ ID NO 13
<211> LENGTH: 119
<212> TYPE: PRT
<213> ORGANISM: Mus musculus

<400> SEQUENCE: 13

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Asn Gly Asn Phe Gly Tyr Tyr Phe Asp Tyr Trp Gly Gln Gly
            100                 105                 110

```
Thr Thr Leu Thr Val Ser Ser
            115

<210> SEQ ID NO 14
<211> LENGTH: 112
<212> TYPE: PRT
<213> ORGANISM: Mus musculus

<400> SEQUENCE: 14

Asp Val Leu Met Thr Gln Thr Pro Leu Ser Leu Pro Val Ser Leu Gly
1               5                   10                  15

Asp Gln Ala Ser Phe Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Ser Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 15
<211> LENGTH: 5
<212> TYPE: PRT
<213> ORGANISM: Mus musculus

<400> SEQUENCE: 15

Asn Phe Gly Met Asn
1               5

<210> SEQ ID NO 16
<211> LENGTH: 6
<212> TYPE: PRT
<213> ORGANISM: mus musculus

<400> SEQUENCE: 16

Gly Tyr Thr Phe Thr Asn
1               5

<210> SEQ ID NO 17
<211> LENGTH: 10
<212> TYPE: PRT
<213> ORGANISM: Mus musculus

<400> SEQUENCE: 17

Gly Tyr Thr Phe Thr Asn Phe Gly Met Asn
1               5                   10

<210> SEQ ID NO 18
<211> LENGTH: 15
<212> TYPE: PRT
<213> ORGANISM: Mus musculus

<400> SEQUENCE: 18

Trp Ile Asn Thr Tyr Thr Gly Glu Pro Thr Tyr Ala Asp Asp Phe
1               5                   10                  15

<210> SEQ ID NO 19
<211> LENGTH: 8
```

```
<212> TYPE: PRT
<213> ORGANISM: mus musculus

<400> SEQUENCE: 19

Trp Ile Asn Thr Tyr Thr Gly Glu
1               5

<210> SEQ ID NO 20
<211> LENGTH: 10
<212> TYPE: PRT
<213> ORGANISM: Mus musculus

<400> SEQUENCE: 20

Asn Gly Asn Phe Gly Tyr Tyr Phe Asp Tyr
1               5                   10

<210> SEQ ID NO 21
<211> LENGTH: 16
<212> TYPE: PRT
<213> ORGANISM: Mus musculus

<400> SEQUENCE: 21

Arg Ser Ser Gln Asn Ile Val His Ser Asn Gly Asn Thr Tyr Leu Glu
1               5                   10                  15

<210> SEQ ID NO 22
<211> LENGTH: 7
<212> TYPE: PRT
<213> ORGANISM: Mus musculus

<400> SEQUENCE: 22

Lys Val Ser Asn Arg Phe Ser
1               5

<210> SEQ ID NO 23
<211> LENGTH: 9
<212> TYPE: PRT
<213> ORGANISM: Mus musculus

<400> SEQUENCE: 23

Phe Gln Gly Ser His Val Pro Phe Thr
1               5

<210> SEQ ID NO 24
<211> LENGTH: 118
<212> TYPE: PRT
<213> ORGANISM: Mus musculus

<400> SEQUENCE: 24

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Tyr Ala Asp Asp Phe
    50                  55                  60

Lys Gly Arg Phe Ala Phe Ser Leu Glu Thr Ser Ala Thr Thr Ala Tyr
65                  70                  75                  80

Leu Gln Ile Asn Asn Leu Lys Asn Glu Asp Met Ala Thr Tyr Phe Cys
                85                  90                  95

Ser Arg Ser Phe Gly Ser Thr Tyr Gly Asp Tyr Trp Gly Gln Gly Thr
```

```
                  100                 105                 110

Thr Leu Thr Val Ser Ser
        115

<210> SEQ ID NO 25
<211> LENGTH: 112
<212> TYPE: PRT
<213> ORGANISM: Mus musculus

<400> SEQUENCE: 25

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 26
<211> LENGTH: 5
<212> TYPE: PRT
<213> ORGANISM: mus musculus

<400> SEQUENCE: 26

Asn Tyr Gly Met Asn
1               5

<210> SEQ ID NO 27
<211> LENGTH: 10
<212> TYPE: PRT
<213> ORGANISM: Mus musculus

<400> SEQUENCE: 27

Gly Tyr Thr Phe Thr Asn Tyr Gly Met Asn
1               5                   10

<210> SEQ ID NO 28
<211> LENGTH: 9
<212> TYPE: PRT
<213> ORGANISM: Mus musculus

<400> SEQUENCE: 28

Ser Phe Gly Ser Thr Tyr Gly Asp Tyr
1               5

<210> SEQ ID NO 29
<211> LENGTH: 16
<212> TYPE: PRT
<213> ORGANISM: Mus musculus

<400> SEQUENCE: 29

Arg Ser Ser Gln Thr Ile Val His Ser Asn Gly Asn Thr Tyr Leu Glu
1               5                   10                  15
```

<210> SEQ ID NO 30
<211> LENGTH: 7
<212> TYPE: PRT
<213> ORGANISM: Mus musculus

<400> SEQUENCE: 30

Lys Val Ser Asn Arg Phe Ser
1               5

<210> SEQ ID NO 31
<211> LENGTH: 9
<212> TYPE: PRT
<213> ORGANISM: Mus musculus

<400> SEQUENCE: 31

Phe Gln Gly Ser His Val Pro Trp Thr
1               5

<210> SEQ ID NO 32
<211> LENGTH: 157
<212> TYPE: PRT
<213> ORGANISM: mus musculus

<400> SEQUENCE: 32

Gln Ile Gln Leu Val Gln Ser Gly Pro Glu Leu Lys Asn Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala His Gly Pro Trp Leu Ala Tyr Trp Gly Gln Gly Thr Leu Val Thr
            100                 105                 110

Val Ser Thr Ala Lys Thr Thr Ala Pro Ser Val Tyr Pro Leu Ala Pro
        115                 120                 125

Val Cys Gly Asp Thr Thr Gly Ser Ser Val Thr Leu Gly Cys Leu Val
    130                 135                 140

Lys Asn Arg Ile Pro Ala Ala Ala Met Ala Ala Gly Ala
145                 150                 155

<210> SEQ ID NO 33
<211> LENGTH: 107
<212> TYPE: PRT
<213> ORGANISM: mus musculus

<400> SEQUENCE: 33

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Leu Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

-continued

Ser Gly Ser Gly Gln Asp Phe Ser Leu Thr Ile Ser Ser Leu Glu Cys
65                  70                  75                  80

Glu Asp Met Gly Ile Tyr Tyr Cys Leu Gln Tyr Asp Glu Leu Pro Tyr
                85                  90                  95

Thr Phe Gly Gly Gly Thr Thr Leu Glu Ile Lys
            100                 105

<210> SEQ ID NO 34
<211> LENGTH: 6
<212> TYPE: PRT
<213> ORGANISM: mus musculus

<400> SEQUENCE: 34

Gly Tyr Ile Phe Thr Asn
1               5

<210> SEQ ID NO 35
<211> LENGTH: 10
<212> TYPE: PRT
<213> ORGANISM: mus musculus

<400> SEQUENCE: 35

Gly Tyr Ile Phe Thr Asn Tyr Gly Met Asn
1               5                   10

<210> SEQ ID NO 36
<211> LENGTH: 17
<212> TYPE: PRT
<213> ORGANISM: mus musculus

<400> SEQUENCE: 36

Trp Ile Asn Thr Tyr Thr Gly Glu Pro Thr Tyr Ala Asp Asp Phe Lys
1               5                   10                  15

Gly

<210> SEQ ID NO 37
<211> LENGTH: 10
<212> TYPE: PRT
<213> ORGANISM: mus musculus

<400> SEQUENCE: 37

Trp Ile Asn Thr Tyr Thr Gly Glu Pro Thr
1               5                   10

<210> SEQ ID NO 38
<211> LENGTH: 6
<212> TYPE: PRT
<213> ORGANISM: mus musculus

<400> SEQUENCE: 38

Gly Pro Trp Leu Ala Tyr
1               5

<210> SEQ ID NO 39
<211> LENGTH: 11
<212> TYPE: PRT
<213> ORGANISM: mus musculus

<400> SEQUENCE: 39

Lys Ala Ser Gln Asp Ile Asn Ser Tyr Leu Ser
1               5                   10

<210> SEQ ID NO 40

<211> LENGTH: 7
<212> TYPE: PRT
<213> ORGANISM: mus musculus

<400> SEQUENCE: 40

Arg Ala Asn Arg Leu Val Asp
1               5

<210> SEQ ID NO 41
<211> LENGTH: 9
<212> TYPE: PRT
<213> ORGANISM: mus musculus

<400> SEQUENCE: 41

Leu Gln Tyr Asp Glu Leu Pro Tyr Thr
1               5

<210> SEQ ID NO 42
<211> LENGTH: 112
<212> TYPE: PRT
<213> ORGANISM: mus musculus

<400> SEQUENCE: 42

Gln Leu Val Gln Ser Gly Pro Glu Leu Lys Asn Pro Gly Glu Thr Val
1               5                   10                  15

Lys Ile Ser Cys Lys Ala Ser Gly Tyr Thr Phe Thr Asn Tyr Gly Met
            20                  25                  30

Asn Trp Val Lys Gln Ala Pro Gly Lys Gly Leu Lys Trp Met Gly Trp
        35                  40                  45

Ile Asn Thr Tyr Thr Gly Glu Pro Thr Tyr Ala Asp Asp Phe Lys Gly
    50                  55                  60

Arg Phe Ala Phe Ser Leu Glu Thr Ser Ala Ser Thr Ala Tyr Leu Gln
65                  70                  75                  80

Ile Asn Asn Leu Lys Asn Glu Asp Thr Ala Thr Tyr Phe Cys Ala His
                85                  90                  95

Gly Pro Trp Leu Ala Tyr Trp Gly Gln Gly Thr Leu Val Thr Val Ser
            100                 105                 110

<210> SEQ ID NO 43
<211> LENGTH: 107
<212> TYPE: PRT
<213> ORGANISM: mus musculus

<400> SEQUENCE: 43

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Val Tyr
            20                  25                  30

Leu Ser Trp Phe Gln Gln Lys Pro Gly Lys Ser Pro Lys Thr Leu Ile
        35                  40                  45

Tyr Arg Ala Ile Arg Leu Val Asp Gly Val Pro Ser Arg Phe Ser Gly
    50                  55                  60

Ser Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Glu Leu Pro Tyr
                85                  90                  95

Thr Phe Gly Gly Gly Thr Lys Leu Glu Ile Glu
            100                 105

```
<210> SEQ ID NO 44
<211> LENGTH: 11
<212> TYPE: PRT
<213> ORGANISM: mus musculus

<400> SEQUENCE: 44

Lys Ala Ser Gln Asp Ile Asn Val Tyr Leu Ser
1               5                   10

<210> SEQ ID NO 45
<211> LENGTH: 7
<212> TYPE: PRT
<213> ORGANISM: mus musculus

<400> SEQUENCE: 45

Arg Ala Ile Arg Leu Val Asp
1               5

<210> SEQ ID NO 46
<211> LENGTH: 119
<212> TYPE: PRT
<213> ORGANISM: Mus musculus

<400> SEQUENCE: 46

Glu Val Gln Leu Gln Gln Ser Gly Pro Glu Leu Val Lys Pro Gly Ala
1               5                   10                  15

Ser Met Lys Ile Ser Cys Lys Ala Ser His Tyr Ser Phe Ile Gly Tyr
            20                  25                  30

Thr Met Asn Trp Val Lys Gln Arg His Gly Lys Asn Leu Glu Trp Ile
        35                  40                  45

Gly Leu Ile Asn Pro Tyr Asn Gly Asp Thr Thr Tyr Asn Gln Lys Phe
    50                  55                  60

Lys Gly Lys Ala Ser Leu Thr Val Asp Lys Ser Ser Thr Ala Tyr
65                  70                  75                  80

Met Glu Ile Leu Ser Leu Thr Ser Glu Asp Ser Ala Val Tyr Tyr Cys
                85                  90                  95

Ala Arg Glu Asn Trp Gly Tyr Pro Tyr Ala Met Asp Tyr Trp Gly Gln
            100                 105                 110

Gly Thr Ser Val Thr Val Ser
        115

<210> SEQ ID NO 47
<211> LENGTH: 111
<212> TYPE: PRT
<213> ORGANISM: mus musculus

<400> SEQUENCE: 47

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Phe
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Arg Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95
```

-continued

```
Glu Val Pro Tyr Thr Phe Gly Gly Gly Thr Lys Leu Glu Ile Lys
            100                 105                 110

<210> SEQ ID NO 48
<211> LENGTH: 5
<212> TYPE: PRT
<213> ORGANISM: Mus musculus

<400> SEQUENCE: 48

Gly Tyr Thr Met Asn
1               5

<210> SEQ ID NO 49
<211> LENGTH: 6
<212> TYPE: PRT
<213> ORGANISM: mus musculus

<400> SEQUENCE: 49

His Tyr Ser Phe Ile Gly
1               5

<210> SEQ ID NO 50
<211> LENGTH: 10
<212> TYPE: PRT
<213> ORGANISM: mus musculus

<400> SEQUENCE: 50

His Tyr Ser Phe Ile Gly Tyr Thr Met Asn
1               5                   10

<210> SEQ ID NO 51
<211> LENGTH: 17
<212> TYPE: PRT
<213> ORGANISM: mus musculus

<400> SEQUENCE: 51

Leu Ile Asn Pro Tyr Asn Gly Asp Thr Thr Tyr Asn Gln Lys Phe Lys
1               5                   10                  15
Gly

<210> SEQ ID NO 52
<211> LENGTH: 10
<212> TYPE: PRT
<213> ORGANISM: mus musculus

<400> SEQUENCE: 52

Leu Ile Asn Pro Tyr Asn Gly Asp Thr Thr
1               5                   10

<210> SEQ ID NO 53
<211> LENGTH: 11
<212> TYPE: PRT
<213> ORGANISM: mus musculus

<400> SEQUENCE: 53

Glu Asn Trp Gly Tyr Pro Tyr Ala Met Asp Tyr
1               5                   10

<210> SEQ ID NO 54
<211> LENGTH: 15
<212> TYPE: PRT
<213> ORGANISM: mus musculus

<400> SEQUENCE: 54
```

```
Arg Ala Ser Glu Ser Val Asp Asn Phe Gly Ile Ser Phe Met Asn
1               5                   10                  15

<210> SEQ ID NO 55
<211> LENGTH: 7
<212> TYPE: PRT
<213> ORGANISM: mus musculus

<400> SEQUENCE: 55

Ala Ala Ser Asn Gln Gly Ser
1               5

<210> SEQ ID NO 56
<211> LENGTH: 9
<212> TYPE: PRT
<213> ORGANISM: mus musculus

<400> SEQUENCE: 56

Gln Gln Ser Lys Glu Val Pro Tyr Thr
1               5

<210> SEQ ID NO 57
<211> LENGTH: 117
<212> TYPE: PRT
<213> ORGANISM: homo sapiens

<400> SEQUENCE: 57

Pro Leu Met Gly Gly Gln Asp Lys Pro Phe Leu Ser Ala Arg Pro Ser
1               5                   10                  15

Thr Val Val Pro Arg Gly Gly His Val Ala Leu Gln Cys His Tyr Arg
                20                  25                  30

Arg Gly Phe Asn Asn Phe Met Leu Tyr Lys Glu Asp Arg Ser His Val
            35                  40                  45

Pro Ile Phe His Gly Arg Ile Phe Gln Glu Ser Phe Ile Met Gly Pro
        50                  55                  60

Val Thr Pro Ala His Ala Gly Thr Tyr Arg Cys Arg Gly Ser Arg Pro
65                  70                  75                  80

His Ser Leu Thr Gly Trp Ser Ala Pro Ser Asn Pro Leu Val Ile Met
                85                  90                  95

Val Thr Gly Asn His Arg Lys Pro Ser Leu Leu Ala His Pro Gly Pro
                100                 105                 110

Leu Leu Lys Ser Gly
            115

<210> SEQ ID NO 58
<211> LENGTH: 100
<212> TYPE: PRT
<213> ORGANISM: homo sapiens

<400> SEQUENCE: 58

Thr Val Ile Leu Gln Cys Trp Ser Asp Val Met Phe Glu His Phe Phe
1               5                   10                  15

Leu His Arg Glu Gly Ile Ser Glu Asp Pro Ser Arg Leu Val Gly Gln
                20                  25                  30

Ile His Asp Gly Val Ser Lys Ala Asn Phe Ser Ile Gly Pro Leu Met
            35                  40                  45

Pro Val Leu Ala Gly Thr Tyr Arg Cys Tyr Gly Ser Val Pro His Ser
        50                  55                  60

Pro Tyr Gln Leu Ser Ala Pro Ser Asp Pro Leu Asp Ile Val Ile Thr
65                  70                  75                  80
```

```
Gly Leu Tyr Glu Lys Pro Ser Leu Ser Ala Gln Pro Gly Pro Thr Val
            85                  90                  95

Gln Ala Gly Glu
        100

<210> SEQ ID NO 59
<211> LENGTH: 102
<212> TYPE: PRT
<213> ORGANISM: Homo sapiens

<400> SEQUENCE: 59

Asn Val Thr Leu Ser Cys Ser Ser Trp Ser Tyr Asp Ile Tyr His
1               5                   10                  15

Leu Ser Arg Glu Gly Glu Ala His Glu Arg Arg Leu Arg Ala Val Pro
            20                  25                  30

Lys Val Asn Arg Thr Phe Gln Ala Asp Phe Pro Leu Gly Pro Ala Thr
        35                  40                  45

His Gly Gly Thr Tyr Arg Cys Phe Gly Ser Phe Arg Ala Leu Pro Cys
    50                  55                  60

Val Trp Ser Asn Ser Ser Asp Pro Leu Leu Val Ser Val Thr Gly Asn
65                  70                  75                  80

Pro Ser Ser Ser Trp Pro Ser Pro Thr Glu Pro Ser Ser Lys Ser Gly
            85                  90                  95

Ile Cys Arg His Leu His
        100

<210> SEQ ID NO 60
<211> LENGTH: 72
<212> TYPE: DNA
<213> ORGANISM: Homo sapiens

<400> SEQUENCE: 60
aagctagcgg taagcctatc cctaaccctc tcctcggtct cgattctacg ctcatgggtg      60
gtcaggacaa ac                                                         72

<210> SEQ ID NO 61
<211> LENGTH: 29
<212> TYPE: DNA
<213> ORGANISM: Homo sapiens

<400> SEQUENCE: 61
tgggacgact ttagtcctcc tcctaggaa                                       29

<210> SEQ ID NO 62
<211> LENGTH: 71
<212> TYPE: DNA
<213> ORGANISM: Homo sapiens

<400> SEQUENCE: 62
aagctagcgg taagcctatc cctaaccctc tcctcggtct cgattctacg acagtcatcc      60
tgcaatgttg g                                                          71

<210> SEQ ID NO 63
<211> LENGTH: 29
<212> TYPE: DNA
<213> ORGANISM: Homo sapiens

<400> SEQUENCE: 63
gggtgccaag tccgtcctct ccctaggaa                                       29
```

<210> SEQ ID NO 64
<211> LENGTH: 71
<212> TYPE: DNA
<213> ORGANISM: Homo sapiens

<400> SEQUENCE: 64
aagctagcgg taagcctatc cctaaccctc tcctcggtct cgattctacg aacgtgacct    60
tgtcctgtag c                                                        71

<210> SEQ ID NO 65
<211> LENGTH: 29
<212> TYPE: DNA
<213> ORGANISM: Homo sapiens

<400> SEQUENCE: 65
ccatagacgt ctgtggacgt acctaggaa                                     29

<210> SEQ ID NO 66
<211> LENGTH: 90
<212> TYPE: DNA
<213> ORGANISM: Homo sapiens

<400> SEQUENCE: 66
actaatgcca ccaccaaggc ggctggtggt gccctgcagt caacagccag tctcttcgtg    60
gtctcactct ctcttctgca tctctactct                                    90

<210> SEQ ID NO 67
<211> LENGTH: 30
<212> TYPE: PRT
<213> ORGANISM: Homo sapiens

<400> SEQUENCE: 67

Thr Asn Ala Thr Thr Lys Ala Ala Gly Gly Ala Leu Gln Ser Thr Ala
1               5                   10                  15

Ser Leu Phe Val Val Ser Leu Ser Leu Leu His Leu Tyr Ser
            20                  25                  30

<210> SEQ ID NO 68
<211> LENGTH: 40
<212> TYPE: DNA
<213> ORGANISM: Homo sapiens

<400> SEQUENCE: 68
acccaagctg gctagcatgt cgctcacggt cgtcagcatg                         40

<210> SEQ ID NO 69
<211> LENGTH: 38
<212> TYPE: DNA
<213> ORGANISM: Homo sapiens

<400> SEQUENCE: 69
agcacagtgg cggccgccta gaaaaccccc tcaagacc                           38

<210> SEQ ID NO 70
<211> LENGTH: 36
<212> TYPE: DNA
<213> ORGANISM: Homo sapiens

<400> SEQUENCE: 70
gccacaggtg catatgagaa accttctctc tcagcc                             36

```
<210> SEQ ID NO 71
<211> LENGTH: 35
<212> TYPE: DNA
<213> ORGANISM: Homo sapiens

<400> SEQUENCE: 71
tgggtcactt gcggctgacc acacgcaggg caggg                          35

<210> SEQ ID NO 72
<211> LENGTH: 36
<212> TYPE: DNA
<213> ORGANISM: Homo sapiens

<400> SEQUENCE: 72
cgtgccctgc cctacgtgtg gtcaaactca agtgac                         36

<210> SEQ ID NO 73
<211> LENGTH: 39
<212> TYPE: DNA
<213> ORGANISM: Homo sapiens

<400> SEQUENCE: 73
atgcaggtgt ctggggatac cagatttgga gcttggttc                      39

<210> SEQ ID NO 74
<211> LENGTH: 51
<212> TYPE: DNA
<213> ORGANISM: Homo sapiens

<400> SEQUENCE: 74
ccgaagagtc acgtgtcctc ctcgaggcac cacagtgctg ggccaggcag a        51

<210> SEQ ID NO 75
<211> LENGTH: 33
<212> TYPE: DNA
<213> ORGANISM: Homo sapiens

<400> SEQUENCE: 75
cacgtgactc ttcggtgtca ctatcgtcgt ggg                            33

<210> SEQ ID NO 76
<211> LENGTH: 35
<212> TYPE: DNA
<213> ORGANISM: Homo sapiens

<400> SEQUENCE: 76
cacagggctc atgttgaagc tctcctggaa tattc                          35

<210> SEQ ID NO 77
<211> LENGTH: 28
<212> TYPE: DNA
<213> ORGANISM: Homo sapiens

<400> SEQUENCE: 77
aacatgagcc ctgtgacccc agcacatg                                  28

<210> SEQ ID NO 78
<211> LENGTH: 35
<212> TYPE: DNA
<213> ORGANISM: Homo sapiens

<400> SEQUENCE: 78
attgttaaac ctatgacgat agtgacactg aagag                          35
```

<210> SEQ ID NO 79
<211> LENGTH: 27
<212> TYPE: DNA
<213> ORGANISM: Homo sapiens

<400> SEQUENCE: 79
cataggttta acaatttcat gctgtac                                27

<210> SEQ ID NO 80
<211> LENGTH: 37
<212> TYPE: DNA
<213> ORGANISM: Homo sapiens

<400> SEQUENCE: 80
gatgggaatg tggattctgt cttctttgta cagcatg                     37

<210> SEQ ID NO 81
<211> LENGTH: 33
<212> TYPE: DNA
<213> ORGANISM: Homo sapiens

<400> SEQUENCE: 81
atccacattc ccatcttcca cggcagaata ttc                         33

<210> SEQ ID NO 82
<211> LENGTH: 31
<212> TYPE: DNA
<213> ORGANISM: Homo sapiens

<400> SEQUENCE: 82
atgtgctgtg gtcacagggc ccatgatgaa g                           31

<210> SEQ ID NO 83
<211> LENGTH: 29
<212> TYPE: DNA
<213> ORGANISM: Homo sapiens

<400> SEQUENCE: 83
gtgaccacag cacatgcagg gacctacag                              29

<210> SEQ ID NO 84
<211> LENGTH: 34
<212> TYPE: DNA
<213> ORGANISM: Homo sapiens

<400> SEQUENCE: 84
gggggagtgt gggtgtgaac cccgacatct gtag                        34

<210> SEQ ID NO 85
<211> LENGTH: 31
<212> TYPE: DNA
<213> ORGANISM: Homo sapiens

<400> SEQUENCE: 85
cacccacact cccccactgg gtggtcggca c                           31

<210> SEQ ID NO 86
<211> LENGTH: 36
<212> TYPE: DNA
<213> ORGANISM: Homo sapiens

<400> SEQUENCE: 86

```
ttgcaggatg actctctctc ctgatttcac cagggg                                 36

<210> SEQ ID NO 87
<211> LENGTH: 30
<212> TYPE: DNA
<213> ORGANISM: Homo sapiens

<400> SEQUENCE: 87
agagtcatcc tgcaatgttg gtcagatgtc                                        30

<210> SEQ ID NO 88
<211> LENGTH: 36
<212> TYPE: DNA
<213> ORGANISM: Homo sapiens

<400> SEQUENCE: 88
ctcaaacatg atatctgacc aacattgcag gatgac                                 36

<210> SEQ ID NO 89
<211> LENGTH: 30
<212> TYPE: DNA
<213> ORGANISM: Homo sapiens

<400> SEQUENCE: 89
gatatcatgt ttgagcactt ctttctgcac                                        30

<210> SEQ ID NO 90
<211> LENGTH: 40
<212> TYPE: DNA
<213> ORGANISM: Homo sapiens

<400> SEQUENCE: 90
aagggcaagc atcatgggac cgatggagaa gttggccttg                             40

<210> SEQ ID NO 91
<211> LENGTH: 38
<212> TYPE: DNA
<213> ORGANISM: Homo sapiens

<400> SEQUENCE: 91
atgatgcttg cccttgcagg aacctacaga tgttatgg                               38

<210> SEQ ID NO 92
<211> LENGTH: 40
<212> TYPE: DNA
<213> ORGANISM: Homo sapiens

<400> SEQUENCE: 92
tagagatccc atctttgtgc agaaagaagt gctcaaacat                             40

<210> SEQ ID NO 93
<211> LENGTH: 37
<212> TYPE: DNA
<213> ORGANISM: Homo sapiens

<400> SEQUENCE: 93
aagatgggat ctctaaggac ccctcacgcc tcgttgg                                37

<210> SEQ ID NO 94
<211> LENGTH: 35
<212> TYPE: DNA
<213> ORGANISM: Homo sapiens

<400> SEQUENCE: 94
``` ggggtgtga gtaacagaac cataacatct gtagg                           35

<210> SEQ ID NO 95
<211> LENGTH: 31
<212> TYPE: DNA
<213> ORGANISM: Homo sapiens

<400> SEQUENCE: 95
gttactcaca ccccctatca gttgtcagct c                              31

<210> SEQ ID NO 96
<211> LENGTH: 38
<212> TYPE: DNA
<213> ORGANISM: Homo sapiens

<400> SEQUENCE: 96
atatgcacct gtggccacga tgtccagggg gtcactgg                       38

<210> SEQ ID NO 97
<211> LENGTH: 30
<212> TYPE: DNA
<213> ORGANISM: Homo sapiens

<400> SEQUENCE: 97
gccgcaagtg acccactgct tgtttctgtc                                30

<210> SEQ ID NO 98
<211> LENGTH: 40
<212> TYPE: DNA
<213> ORGANISM: Homo sapiens

<400> SEQUENCE: 98
ggcctctcct gcctgaaccg cggggcccgg ctgggctgag                     40

<210> SEQ ID NO 99
<211> LENGTH: 36
<212> TYPE: DNA
<213> ORGANISM: Homo sapiens

<400> SEQUENCE: 99
caggcaggag aggccgtgac cttgtcctgt agctcc                         36

<210> SEQ ID NO 100
<211> LENGTH: 33
<212> TYPE: DNA
<213> ORGANISM: Homo sapiens

<400> SEQUENCE: 100
ataggagctc gcggagctac aggacaaggt cac                            33

<210> SEQ ID NO 101
<211> LENGTH: 33
<212> TYPE: DNA
<213> ORGANISM: Homo sapiens

<400> SEQUENCE: 101
tccgcgagct cctatgacat ctaccatctg tcc                            33

<210> SEQ ID NO 102
<211> LENGTH: 42
<212> TYPE: DNA
<213> ORGANISM: Homo sapiens

```
<400> SEQUENCE: 102
atgggcctcc ccttccctgg acagatggta catgtcatag ga                    42

<210> SEQ ID NO 103
<211> LENGTH: 36
<212> TYPE: DNA
<213> ORGANISM: Homo sapiens

<400> SEQUENCE: 103 gaagggagg cccatgaacg taggctccct gcagtg                            36

<210> SEQ ID NO 104
<211> LENGTH: 36
<212> TYPE: DNA
<213> ORGANISM: Homo sapiens

<400> SEQUENCE: 104
atgtgctcca ccttccctgg acagatggta gatgtc                           36

<210> SEQ ID NO 105
<211> LENGTH: 36
<212> TYPE: DNA
<213> ORGANISM: Homo sapiens

<400> SEQUENCE: 105
gaaggtggag cacatgaacg taggctccgt gcagtg                           36

<210> SEQ ID NO 106
<211> LENGTH: 36
<212> TYPE: DNA
<213> ORGANISM: Homo sapiens

<400> SEQUENCE: 106
tctgttgacc ttggccactg cacggagcct acgttc                           36

<210> SEQ ID NO 107
<211> LENGTH: 30
<212> TYPE: DNA
<213> ORGANISM: Homo sapiens

<400> SEQUENCE: 107
gccaaggtca acagaacatt ccaggcagac                                  30

<210> SEQ ID NO 108
<211> LENGTH: 37
<212> TYPE: DNA
<213> ORGANISM: Homo sapiens

<400> SEQUENCE: 108
cgcggcgggc gcgtgacgga aagagccgaa gcatctg                          37

<210> SEQ ID NO 109
<211> LENGTH: 35
<212> TYPE: DNA
<213> ORGANISM: Homo sapiens

<400> SEQUENCE: 109
cacgcgcccg ccgcgtggtc aaactcaagt gaccc                            35

<210> SEQ ID NO 110
<211> LENGTH: 40
<212> TYPE: DNA
<213> ORGANISM: Homo sapiens
```

<400> SEQUENCE: 110
ctcgcagggc gagtgacgga aagagccgaa gcatctgtag                                40

<210> SEQ ID NO 111
<211> LENGTH: 35
<212> TYPE: DNA
<213> ORGANISM: Homo sapiens

<400> SEQUENCE: 111
cactcgccct gcgagtggtc aaactcaagt gaccc                                    35

<210> SEQ ID NO 112
<211> LENGTH: 30
<212> TYPE: DNA
<213> ORGANISM: Homo sapiens

<400> SEQUENCE: 112
gtagggcagg gcacggaaag agccgaagca                                          30

<210> SEQ ID NO 113
<211> LENGTH: 25
<212> TYPE: DNA
<213> ORGANISM: Homo sapiens

<400> SEQUENCE: 113
cccagacacc tgcatgttct gattg                                               25

<210> SEQ ID NO 114
<211> LENGTH: 117
<212> TYPE: PRT
<213> ORGANISM: Artificial
<220> FEATURE:
<223> OTHER INFORMATION: Chimeric human-mouse

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Gly Arg Ile Arg Ser Lys Ala Asn Asn His Ala Thr Ala Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Gly Gly Tyr Tyr Pro Val Tyr Trp Gly Gln Gly Thr Leu
            100                 105                 110

Val Thr Val Ser Ser
        115

<210> SEQ ID NO 115
<211> LENGTH: 351
<212> TYPE: DNA
<213> ORGANISM: Artificial
<220> FEATURE:
<223> OTHER INFORMATION: Chimeric human-mouse

<400> SEQUENCE: 115

```
gaggtgcagc tggtggagtc tggggaggc ttggtccagc ctggagggtc cctgagactc      60
tcctgtgcag cctctggatt caccttcagt gacgcctgga tggactgggt ccgccaggct    120
ccagggaagg ggctggagtg ggttggccgt attagaagca aagctaacaa tcacgccaca    180
gcatacgccg cgtctgtgaa aggcagattc accatctcaa gagatgattc aaagaactca    240
ctgtatctgc aaatgaacag cctgaaaacc gaggacacgg ccgtgtatta ctgtaccggt    300
ggttactacc ctgtttactg gggccaaggg actctggtca ctgtctcttc a             351
```

```
<210> SEQ ID NO 116
<211> LENGTH: 117
<212> TYPE: PRT
<213> ORGANISM: Artificial
<220> FEATURE:
<223> OTHER INFORMATION: Chimeric human-mouse

<400> SEQUENCE: 116
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Gly Glu Ile Arg Ser Lys Ala Asn Asn His Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Gly Gly Tyr Tyr Pro Val Tyr Trp Gly Gln Gly Thr Leu
            100                 105                 110

Val Thr Val Ser Ser
        115
```

```
<210> SEQ ID NO 117
<211> LENGTH: 351
<212> TYPE: DNA
<213> ORGANISM: Artificial
<220> FEATURE:
<223> OTHER INFORMATION: Chimeric human-mouse

<400> SEQUENCE: 117
```

```
gaggtgcagc tggtggagtc tggggaggc ttggtccagc ctggagggtc cctgagactc      60
tcctgtgcag cctctggatt caccttcagt gacgcctgga tggactgggt ccgccaggct    120
ccagggaagg ggctggagtg ggttggcgag attagaagca aagctaacaa tcacgccaca    180
tactacgccg cgtctgtgaa aggcagattc accatctcaa gagatgattc aaagaactca    240
ctgtatctgc aaatgaacag cctgaaaacc gaggacacgg ccgtgtatta ctgtaccggt    300
ggttactacc ctgtttactg gggccaaggg actctggtca ctgtctcttc a             351
```

```
<210> SEQ ID NO 118
<211> LENGTH: 117
<212> TYPE: PRT
<213> ORGANISM: Artificial
<220> FEATURE:
<223> OTHER INFORMATION: Chimeric human-mouse

<400> SEQUENCE: 118
```

```
Glu Val Gln Leu Val Glu Ser Gly Gly Gly Leu Val Gln Pro Gly Gly
```

```
              1               5              10              15
            Ser Leu Arg Leu Ser Cys Ala Ala Ser Gly Phe Thr Phe Ser Asp Ala
                            20                  25                  30

Trp Met Asp Trp Val Arg Gln Ala Pro Gly Lys Gly Leu Glu Trp Val
                            35                  40                  45

Ala Glu Ile Arg Ser Lys Ala Asn Asn His Ala Thr Tyr Tyr Ala Ala
                            50                  55                  60

Ser Val Lys Gly Arg Phe Thr Ile Ser Arg Asp Asp Ser Lys Asn Ser
             65                  70                  75                  80

Val Tyr Leu Gln Met Asn Ser Leu Lys Thr Glu Asp Thr Ala Val Tyr
                            85                  90                  95

Tyr Cys Thr Gly Gly Tyr Tyr Pro Val Tyr Trp Gly Gln Gly Thr Leu
                           100                 105                 110

Val Thr Val Ser Ser
                           115

<210> SEQ ID NO 119
<211> LENGTH: 351
<212> TYPE: DNA
<213> ORGANISM: Artificial
<220> FEATURE:
<223> OTHER INFORMATION: Chimeric human-mouse

<400> SEQUENCE: 119
gaggtgcagc tggtggagtc tgggggaggc ttggtccagc ctggagggtc cctgagactc      60
tcctgtgcag cctctggatt caccttcagt gacgcctgga tggactgggt ccgccaggct     120
ccagggaagg ggctggagtg ggttgccgag attagaagca agctaacaa tcacgccaca      180 tactacgccg cgtctgtgaa aggcagattc accatctcaa gagatgattc aaagaactca     240
gtgtatctgc aaatgaacag cctgaaaacc gaggacacgg ccgtgtatta ctgtaccggt     300
ggttactacc ctgtttactg gggccaaggg actctggtca ctgtctcttc a              351

<210> SEQ ID NO 120
<211> LENGTH: 106
<212> TYPE: PRT
<213> ORGANISM: Artificial
<220> FEATURE:
<223> OTHER INFORMATION: Chimeric human-mouse

<400> SEQUENCE: 120

Asp Ile Gln Met Thr Gln Ser Pro Ser Ser Leu Ser Ala Ser Val Gly
             1               5                  10                  15

Asp Arg Val Thr Ile Thr Cys Lys Ala Ser Gln Asp Ile Asn Lys Asn
                            20                  25                  30

Ile Ala Trp Tyr Gln Gln Lys Pro Gly Lys Ala Pro Lys Leu Leu Ile
                            35                  40                  45

Tyr Tyr Thr Ser Thr Leu Gln Pro Gly Val Pro Ser Arg Phe Ser Gly
                            50                  55                  60

Ser Gly Ser Gly Thr Asp Phe Thr Phe Thr Ile Ser Ser Leu Gln Pro
             65                  70                  75                  80

Glu Asp Ile Ala Thr Tyr Tyr Cys Leu Gln Tyr Asp Asn Leu Leu Thr
                            85                  90                  95

Phe Gly Gly Gly Thr Lys Val Glu Ile Lys
                           100                 105

<210> SEQ ID NO 121
<211> LENGTH: 318
```

```
<212> TYPE: DNA
<213> ORGANISM: Artificial
<220> FEATURE:
<223> OTHER INFORMATION: Chimeric human-mouse

<400> SEQUENCE: 121
gacatccaga tgacccagtc tccatcctcc ctgtctgcat ctgtaggaga cagagtcacc    60
atcacttgca aggcgagtca ggacattaac aagaatatag cttggtatca gcagaaacca   120
gggaaagccc ctaagctcct gatctactat acatccactt tgcaaccagg ggtcccatca   180
aggttcagtg aagtggatc tgggacagat tttactttca ccatcagcag cctgcagcct    240
gaagatattg caacatatta ctgtctacag tatgataatc tccttacgtt cggagggggg    300
accaaggtgg aaataaaa                                                318

<210> SEQ ID NO 122
<211> LENGTH: 106
<212> TYPE: PRT
<213> ORGANISM: Artificial
<220> FEATURE:
<223> OTHER INFORMATION: Chimeric human-mouse

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Asn
            20                  25                  30

Ile Ala Trp Tyr Gln His Lys Pro Gly Lys Ala Pro Lys Leu Leu Ile
        35                  40                  45

His Tyr Thr Ser Thr Leu Gln Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Leu Thr
                85                  90                  95

Phe Gly Gly Gly Thr Lys Val Glu Ile Lys
            100                 105

<210> SEQ ID NO 123
<211> LENGTH: 318
<212> TYPE: DNA
<213> ORGANISM: Artificial
<220> FEATURE:
<223> OTHER INFORMATION: Chimeric human-mouse

<400> SEQUENCE: 123
gacatccaga tgacccagtc tccatcctcc ctgtctgcat ctgtaggaga cagagtcacc    60
atcacttgca aggcgagtca ggacattaac aagaatatag cttggtatca gcataaacca   120
gggaaagccc ctaagctcct gatccactat acatccactt tgcaaccagg ggtcccatca   180
aggttcagtg aagtggatc tgggacagat tttactttca ccatcagcag cctgcagcct    240
gaagatattg caacatatta ctgtctacag tatgataatc tccttacgtt cggagggggg    300
accaaggtgg aaataaaa                                                318

<210> SEQ ID NO 124
<211> LENGTH: 106
<212> TYPE: PRT
<213> ORGANISM: Artificial
<220> FEATURE:
<223> OTHER INFORMATION: Chimeric human-mouse
```

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Asn
            20                  25                  30

Ile Ala Trp Tyr Gln His Lys Pro Gly Lys Ala Pro Lys Leu Leu Ile
        35                  40                  45

His Tyr Thr Ser Thr Leu Gln Pro Gly Val Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Leu Thr
                85                  90                  95

Phe Gly Gly Gly Thr Lys Val Glu Ile Lys
            100                 105

<210> SEQ ID NO 125
<211> LENGTH: 318
<212> TYPE: DNA
<213> ORGANISM: Artificial
<220> FEATURE:
<223> OTHER INFORMATION: Chimeric human-mouse

<400> SEQUENCE: 125
gacatccaga tgacccagtc tccatcctcc ctgtctgcat ctgtaggaga cagagtcacc     60
atcacttgca aggcgagtca ggacattaac aagaatatag cttggtatca gcataaacca    120
gggaaagccc ctaagctcct gatccactat acatccactt tgcaaccagg ggtcccatca    180
aggttcagtg gaagtggatc tgggagagat tatactttca ccatcagcag cctgcagcct    240
gaagatattg caacatatta ctgtctacag tatgataatc tccttacgtt cggaggggg     300 accaaggtgg aaataaaa                                                  318

<210> SEQ ID NO 126
<211> LENGTH: 16
<212> TYPE: PRT
<213> ORGANISM: Mus musculus
<220> FEATURE:
<221> NAME/KEY: MISC_FEATURE
<222> LOCATION: (5)..(5)
<223> OTHER INFORMATION: Any naturally occurring amino acid

<400> SEQUENCE: 126

Arg Ser Ser Gln Xaa Ile Val His Ser Asn Gly Asn Thr Tyr Leu Glu
1               5                   10                  15

<210> SEQ ID NO 127
<211> LENGTH: 16
<212> TYPE: PRT
<213> ORGANISM: Mus musculus
<220> FEATURE:
<221> NAME/KEY: MISC_FEATURE
<222> LOCATION: (1)..(2)
<223> OTHER INFORMATION: Any naturally occurring amino acid
<220> FEATURE:
<221> NAME/KEY: MISC_FEATURE
<222> LOCATION: (5)..(5)
<223> OTHER INFORMATION: Any naturally occurring amino acid
<220> FEATURE:
<221> NAME/KEY: MISC_FEATURE
<222> LOCATION: (7)..(9)
<223> OTHER INFORMATION: Any naturally occurring amino acid
<220> FEATURE:

```
<221> NAME/KEY: MISC_FEATURE
<222> LOCATION: (11)..(11)
<223> OTHER INFORMATION: Any naturally occurring amino acid
<220> FEATURE:
<221> NAME/KEY: MISC_FEATURE
<222> LOCATION: (13)..(16)
<223> OTHER INFORMATION: Any naturally occurring amino acid

<400> SEQUENCE: 127

Xaa Xaa Ser Gln Xaa Ile Xaa Xaa Xaa Asn Xaa Asn Xaa Xaa Xaa Xaa
1               5                   10                  15

<210> SEQ ID NO 128
<211> LENGTH: 8
<212> TYPE: PRT
<213> ORGANISM: Mus musculus
<220> FEATURE:
<221> NAME/KEY: MISC_FEATURE
<222> LOCATION: (1)..(2)
<223> OTHER INFORMATION: Any naturally occurring amino acid
<220> FEATURE:
<221> NAME/KEY: MISC_FEATURE
<222> LOCATION: (8)..(8)
<223> OTHER INFORMATION: Any naturally occurring amino acid

<400> SEQUENCE: 128

Xaa Xaa Thr Ser Thr Leu Gln Xaa
1               5

<210> SEQ ID NO 129
<211> LENGTH: 9
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: Any naturally occurring amino acid
<220> FEATURE:
<221> NAME/KEY: MISC_FEATURE
<222> LOCATION: (3)..(8)
<223> OTHER INFORMATION: Any naturally occurring amino acid

<400> SEQUENCE: 129

Xaa Gln Xaa Xaa Xaa Xaa Xaa Xaa Thr
1               5

<210> SEQ ID NO 130
<211> LENGTH: 9
<212> TYPE: PRT
<213> ORGANISM: Mus musculus
<220> FEATURE:
<221> NAME/KEY: MISC_FEATURE
<222> LOCATION: (8)..(8)
<223> OTHER INFORMATION: Any naturally occurring amino acid

<400> SEQUENCE: 130

Phe Gln Gly Ser His Val Pro Xaa Thr
1               5

<210> SEQ ID NO 131
<211> LENGTH: 10
<212> TYPE: PRT
<213> ORGANISM: Mus musculus
<220> FEATURE:
<221> NAME/KEY: MISC_FEATURE
<222> LOCATION: (7)..(7)
<223> OTHER INFORMATION: Any naturally occurring amino acid

<400> SEQUENCE: 131

Gly Tyr Thr Phe Thr Asn Xaa Gly Met Asn
```

-continued

```
<210> SEQ ID NO 132
<211> LENGTH: 10
<212> TYPE: PRT
<213> ORGANISM: Mus musculus
<220> FEATURE:
<221> NAME/KEY: MISC_FEATURE
<222> LOCATION: (2)..(2)
<223> OTHER INFORMATION: Any naturally occurring amino acid
<220> FEATURE:
<221> NAME/KEY: MISC_FEATURE
<222> LOCATION: (5)..(8)
<223> OTHER INFORMATION: Any naturally occurring amino acid
<220> FEATURE:
<221> NAME/KEY: MISC_FEATURE
<222> LOCATION: (10)..(10)
<223> OTHER INFORMATION: Any naturally occurring amino acid

<400> SEQUENCE: 132

Gly Xaa Thr Phe Xaa Xaa Xaa Xaa Met Xaa
1               5                   10

<210> SEQ ID NO 133
<211> LENGTH: 15
<212> TYPE: PRT
<213> ORGANISM: Mus musculus
<220> FEATURE:
<221> NAME/KEY: MISC_FEATURE
<222> LOCATION: (2)..(3)
<223> OTHER INFORMATION: Any naturally occurring amino acid
<220> FEATURE:
<221> NAME/KEY: MISC_FEATURE
<222> LOCATION: (6)..(10)
<223> OTHER INFORMATION: Any naturally occurring amino acid
<220> FEATURE:
<221> NAME/KEY: MISC_FEATURE
<222> LOCATION: (13)..(15)
<223> OTHER INFORMATION: Any naturally occurring amino acid

<400> SEQUENCE: 133

Asn Xaa Xaa Thr Tyr Xaa Xaa Xaa Xaa Xaa Tyr Ala Xaa Xaa Xaa
1               5                   10                  15

<210> SEQ ID NO 134
<211> LENGTH: 21
<212> TYPE: PRT
<213> ORGANISM: Mus musculus
<220> FEATURE:
<221> NAME/KEY: MISC_FEATURE
<222> LOCATION: (1)..(6)
<223> OTHER INFORMATION: Any naturally occurring amino acid
<220> FEATURE:
<221> NAME/KEY: MISC_FEATURE
<222> LOCATION: (8)..(9)
<223> OTHER INFORMATION: Any naturally occurring amino acid
<220> FEATURE:
<221> NAME/KEY: MISC_FEATURE
<222> LOCATION: (12)..(16)
<223> OTHER INFORMATION: Any naturally occurring amino acid
<220> FEATURE:
<221> NAME/KEY: MISC_FEATURE
<222> LOCATION: (19)..(21)
<223> OTHER INFORMATION: Any naturally occurring amino acid

<400> SEQUENCE: 134

Xaa Xaa Xaa Xaa Xaa Xaa Asn Xaa Xaa Thr Tyr Xaa Xaa Xaa Xaa Xaa
1               5                   10                  15

Tyr Ala Xaa Xaa Xaa
            20
```

```
<210> SEQ ID NO 135
<211> LENGTH: 11
<212> TYPE: PRT
<213> ORGANISM: Mus musculus
<220> FEATURE:
<221> NAME/KEY: MISC_FEATURE
<222> LOCATION: (1)..(4)
<223> OTHER INFORMATION: Any naturally occurring amino acid
<220> FEATURE:
<221> NAME/KEY: MISC_FEATURE
<222> LOCATION: (6)..(7)
<223> OTHER INFORMATION: Any naturally occurring amino acid
<220> FEATURE:
<221> NAME/KEY: MISC_FEATURE
<222> LOCATION: (9)..(9)
<223> OTHER INFORMATION: Any naturally occurring amino acid

<400> SEQUENCE: 135

Xaa Xaa Xaa Xaa Gly Xaa Xaa Tyr Xaa Asp Tyr
1               5                   10

<210> SEQ ID NO 136
<211> LENGTH: 41
<212> TYPE: DNA
<213> ORGANISM: HOMO SAPIENS

<400> SEQUENCE: 136
tgtggtcaca gggcccatga tgaagctctc ctggaatatt c                           41

<210> SEQ ID NO 137
<211> LENGTH: 36
<212> TYPE: DNA
<213> ORGANISM: HOMO SAPIENS

<400> SEQUENCE: 137
ggccctgtga ccacagcaca tgcagggacc tacaga                                 36

<210> SEQ ID NO 138
<211> LENGTH: 39
<212> TYPE: DNA
<213> ORGANISM: HOMO SAPIENS

<400> SEQUENCE: 138
gtcactggga gctgacaact datagggggt gtgagtaac                              39

<210> SEQ ID NO 139
<211> LENGTH: 38
<212> TYPE: DNA
<213> ORGANISM: HOMO SAPIENS

<400> SEQUENCE: 139
tcagctccca gtgacccccct ggacatcgtg atcacagg                              38

<210> SEQ ID NO 140
<211> LENGTH: 36
<212> TYPE: DNA
<213> ORGANISM: HOMO SAPIENS

<400> SEQUENCE: 140
gatatctgac caacattgca ggatgactgt ctctcc                                 36

<210> SEQ ID NO 141
<211> LENGTH: 36
<212> TYPE: DNA
<213> ORGANISM: HOMO SAPIENS

<400> SEQUENCE: 141
```

```
tgttggtcag atatcatgtt tgagcacttc tttctg                              36

<210> SEQ ID NO 142
<211> LENGTH: 36
<212> TYPE: DNA
<213> ORGANISM: HOMO SAPIENS

<400> SEQUENCE: 142
ggaggaagga gcagaaccat aacatctgta ggttcc                              36

<210> SEQ ID NO 143
<211> LENGTH: 36
<212> TYPE: DNA
<213> ORGANISM: HOMO SAPIENS

<400> SEQUENCE: 143
tctgctcctt cctcccccta tcagttgtca gctccc                              36

<210> SEQ ID NO 144
<211> LENGTH: 33
<212> TYPE: DNA
<213> ORGANISM: HOMO SAPIENS

<400> SEQUENCE: 144
gatcaccagg gggttgctgg gagccgacca ccc                                 33

<210> SEQ ID NO 145
<211> LENGTH: 45
<212> TYPE: DNA
<213> ORGANISM: HOMO SAPIENS

<400> SEQUENCE: 145
aaccccctgg tgatcatggt cacaggaagc tccagaaaac cttcc                    45

<210> SEQ ID NO 146
<211> LENGTH: 45
<212> TYPE: DNA
<213> ORGANISM: HOMO SAPIENS

<400> SEQUENCE: 146
gtccaggggg tcactcccag ctgacaacgc ataggggag tgagg                     45

<210> SEQ ID NO 147
<211> LENGTH: 31
<212> TYPE: DNA
<213> ORGANISM: HOMO SAPIENS

<400> SEQUENCE: 147
agtgaccccc tggacatcgt gatcacaggt c                                   31

<210> SEQ ID NO 148
<211> LENGTH: 37
<212> TYPE: DNA
<213> ORGANISM: HOMO SAPIENS

<400> SEQUENCE: 148
agagatccca tctctgtgca gaaagaagga cgaaaac                             37

<210> SEQ ID NO 149
<211> LENGTH: 33
<212> TYPE: DNA
<213> ORGANISM: HOMP SAPIENS
```

<400> SEQUENCE: 149
agagatggga tctctgagga cccctcaagc ctc          33

<210> SEQ ID NO 150
<211> LENGTH: 33
<212> TYPE: DNA
<213> ORGANISM: HOMO SAPIENS

<400> SEQUENCE: 150
atggatcgat ccagcgaggc gtgagggtc ctc           33

<210> SEQ ID NO 151
<211> LENGTH: 33
<212> TYPE: DNA
<213> ORGANISM: HOMO SAPIENS

<400> SEQUENCE: 151
gctggatcga tccatgatgg ggtctccaag gcc          33

<210> SEQ ID NO 152
<211> LENGTH: 45
<212> TYPE: DNA
<213> ORGANISM: HOMO SAPIENS

<400> SEQUENCE: 152
ctcagagatc ccatctctgt gcagaaagaa gtgctcaaac gcgac    45

<210> SEQ ID NO 153
<211> LENGTH: 46
<212> TYPE: DNA
<213> ORGANISM: HOMO SAPIENS

<400> SEQUENCE: 153
gatgggatct ctgaggaccc ctcacgcctc gttggacagg cccatg   46

<210> SEQ ID NO 154
<211> LENGTH: 35
<212> TYPE: DNA
<213> ORGANISM: HOMO SAPIENS

<400> SEQUENCE: 154
tcctcctcga ggcaccacag tgctgggcca ggcag        35

<210> SEQ ID NO 155
<211> LENGTH: 41
<212> TYPE: DNA
<213> ORGANISM: HOMO SAPIENS

<400> SEQUENCE: 155
gtgcctcgag gaggacacgt gactcttcgg tgtcactatc g    41

<210> SEQ ID NO 156
<211> LENGTH: 34
<212> TYPE: DNA
<213> ORGANISM: HOMO SAPIENS

<400> SEQUENCE: 156
tggggtcaca gggctcatgt tgaagctctc ctgg         34

<210> SEQ ID NO 157
<211> LENGTH: 41
<212> TYPE: DNA
<213> ORGANISM: HOMO SAPIENS

```
<400> SEQUENCE: 157
agccctgtga ccccagcaca tgcagggacc tacagatgtc g                                41

<210> SEQ ID NO 158
<211> LENGTH: 33
<212> TYPE: DNA
<213> ORGANISM: HOMO SAPIENS

<400> SEQUENCE: 158
ggcagccagg gagggtttgt cctgaccacc cat                                         33

<210> SEQ ID NO 159
<211> LENGTH: 35
<212> TYPE: DNA
<213> ORGANISM: HOMO SAPIENS

<400> SEQUENCE: 159
ccctccctgg ctgcccggcc cagcactgtg gtgcc                                       35

<210> SEQ ID NO 160
<211> LENGTH: 36
<212> TYPE: DNA
<213> ORGANISM: HOMO SAPIENS

<400> SEQUENCE: 160
cccacgacga taggaacact gaagagccac gtgtcc                                      36

<210> SEQ ID NO 161
<211> LENGTH: 36
<212> TYPE: DNA
<213> ORGANISM: HOMO SAPIENS

<400> SEQUENCE: 161
tcctatcgtc gtggggctaa caatttcatg ctgtac                                      36

<210> SEQ ID NO 162
<211> LENGTH: 34
<212> TYPE: DNA
<213> ORGANISM: HOMO SAPIENS

<400> SEQUENCE: 162
tatgctgccg tgggcgatgg gaacgtggct tctg                                        34

<210> SEQ ID NO 163
<211> LENGTH: 33
<212> TYPE: DNA
<213> ORGANISM: HOMO SAPIENS

<400> SEQUENCE: 163
gcccacggca gcatattcca ggagagcttc atc                                         33

<210> SEQ ID NO 164
<211> LENGTH: 35
<212> TYPE: DNA
<213> ORGANISM: HOMO SAPIENS

<400> SEQUENCE: 164
gaagctcgcc gagaatattc tgccgtggaa gatgg                                       35

<210> SEQ ID NO 165
<211> LENGTH: 33
<212> TYPE: DNA
```

<213> ORGANISM: HOMO SAPIENS

<400> SEQUENCE: 165
ttctcggcga gcttcatcat gggccctgtg acc          33

<210> SEQ ID NO 166
<211> LENGTH: 36
<212> TYPE: DNA
<213> ORGANISM: HOMO SAPIENS

<400> SEQUENCE: 166
tcctcgaggc accacagtgg cggaccgggc agacag       36

<210> SEQ ID NO 167
<211> LENGTH: 37
<212> TYPE: DNA
<213> ORGANISM: HOMO SAPIENS

<400> SEQUENCE: 167
gtggtgcctc gaggaggatc cgtggctctt cagtgtc      37

<210> SEQ ID NO 168
<211> LENGTH: 31
<212> TYPE: DNA
<213> ORGANISM: HOMO SAPIENS

<400> SEQUENCE: 168
gtcctcttgg atcccatctc tgtgcagaaa g            31

<210> SEQ ID NO 169
<211> LENGTH: 32
<212> TYPE: DNA
<213> ORGANISM: HOMO SAPIENS

<400> SEQUENCE: 169
gggatccaag aggacccctc acgcctcgtt gg           32

<210> SEQ ID NO 170
<211> LENGTH: 455
<212> TYPE: PRT
<213> ORGANISM: Homo sapiens

<400> SEQUENCE: 170

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Leu Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys

```
                130                 135                 140
Trp Ser Asp Val Met Phe Glu His Phe Phe Leu His Arg Asp Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
                180                 185                 190

Tyr Arg Cys Tyr Gly Ser Val Pro His Ser Pro Tyr Gln Leu Ser Ala
                195                 200                 205

Pro Ser Asp Pro Leu Asp Ile Val Ile Thr Gly Leu Tyr Glu Lys Pro
210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
                260                 265                 270

Asn Arg Thr Phe Gln Ala Asp Phe Pro Leu Gly Pro Ala Thr His Gly
                275                 280                 285

Gly Thr Tyr Arg Cys Phe Gly Ser Phe Arg Ala Leu Pro Cys Val Trp
                290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

Arg His Leu His Val Leu Ile Gly Thr Ser Val Val Ile Phe Leu Phe
                340                 345                 350

Ile Leu Leu Leu Phe Phe Leu Leu Tyr Arg Trp Cys Ser Asn Lys Lys
                355                 360                 365

Asn Ala Ala Val Met Asp Gln Glu Pro Ala Gly Asp Arg Thr Val Asn
370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Leu Thr Asp Thr Ser Val Tyr Thr Glu Leu Pro
                420                 425                 430

Asn Ala Glu Pro Arg Ser Lys Val Val Ser Cys Pro Arg Ala Pro Gln
                435                 440                 445

Ser Gly Leu Glu Gly Val Phe
    450                 455

<210> SEQ ID NO 171
<211> LENGTH: 455
<212> TYPE: PRT
<213> ORGANISM: HOMO SAPIENS

<400> SEQUENCE: 171

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
                20                  25                  30

Ala Arg Pro Ser Thr Val Val Pro Arg Gly Gly His Val Ala Leu Gln
                35                  40                  45
```

-continued

```
Cys His Tyr Arg Arg Gly Phe Asn Asn Phe Met Leu Tyr Lys Glu Asp
     50                  55                  60

Arg Ser His Val Pro Ile Phe His Gly Arg Ile Phe Gln Glu Ser Phe
 65                  70                  75                  80

Ile Met Gly Pro Val Thr Pro Ala His Ala Gly Thr Tyr Arg Cys Arg
                 85                  90                  95

Gly Ser Arg Pro His Ser Leu Thr Gly Trp Ser Ala Pro Ser Asn Pro
                100                 105                 110

Leu Val Ile Met Val Thr Gly Asn His Arg Lys Pro Ser Leu Leu Ala
            115                 120                 125

His Pro Gly Pro Leu Leu Lys Ser Gly Glu Thr Val Ile Leu Gln Cys
130                 135                 140

Trp Ser Asp Val Met Phe Glu His Phe Phe Leu His Arg Glu Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
                180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
                260                 265                 270

Asn Arg Thr Phe Gln Ala Asp Phe Pro Leu Gly Pro Ala Thr His Gly
                275                 280                 285

Gly Thr Tyr Arg Cys Phe Gly Ser Phe Arg Ala Leu Pro Cys Val Trp
        290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

Arg His Leu His Val Leu Ile Gly Thr Ser Val Val Ile Phe Leu Phe
                340                 345                 350

Ile Leu Leu Leu Phe Phe Leu Leu Tyr Arg Trp Cys Ser Asn Lys Lys
            355                 360                 365

Asn Ala Ala Val Met Asp Gln Glu Pro Ala Gly Asp Arg Thr Val Asn
370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Leu Thr Asp Thr Ser Val Tyr Thr Glu Leu Pro
                420                 425                 430

Asn Ala Glu Pro Arg Ser Lys Val Val Ser Cys Pro Arg Ala Pro Gln
                435                 440                 445

Ser Gly Leu Glu Gly Val Phe
450                 455
```

-continued

```
<210> SEQ ID NO 172
<211> LENGTH: 455
<212> TYPE: PRT
<213> ORGANISM: Homo sapiens

<400> SEQUENCE: 172

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Val Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys
    130                 135                 140

Trp Ser Asp Val Met Phe Glu His Phe Phe Leu His Arg Glu Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
    210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg Ala Leu Pro Cys Val Trp
    290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

Arg His Leu His Val Leu Ile Gly Thr Ser Val Val Ile Phe Leu Phe
            340                 345                 350

Ile Leu Leu Leu Phe Phe Leu Leu Tyr Arg Trp Cys Ser Asn Lys Lys
        355                 360                 365

Asn Ala Ala Val Met Asp Gln Glu Pro Ala Gly Asp Arg Thr Val Asn
    370                 375                 380
```

-continued

```
Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
            405                 410                 415

Arg Pro Lys Thr Pro Leu Thr Asp Thr Ser Val Tyr Thr Glu Leu Pro
        420                 425                 430

Asn Ala Glu Pro Arg Ser Lys Val Val Ser Cys Pro Arg Ala Pro Gln
    435                 440                 445

Ser Gly Leu Glu Gly Val Phe
    450                 455

<210> SEQ ID NO 173
<211> LENGTH: 455
<212> TYPE: PRT
<213> ORGANISM: HOMO SAPIENS

<400> SEQUENCE: 173

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Ala Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Val Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys
    130                 135                 140

Trp Ser Asp Val Met Phe Glu His Phe Phe Leu His Arg Glu Gly Ile
145                 150                 155                 160

Ser Glu Asp Pro Ser His Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
    210                 215                 220

Ser Leu Ser Pro Gln Pro Gly Pro Thr Val Gln Ala Gly Glu Asn Val
225                 230                 235                 240

Thr Leu Ser Cys Ser Ser Trp Ser Ser Tyr Asp Thr Tyr His Leu Ser
                245                 250                 255

Arg Glu Gly Glu Ala His Glu Arg Arg Leu Arg Ala Val Pro Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg Ala Leu Pro Cys Val Trp
    290                 295                 300
```

```
Ser Asn Ser Ser Asp Pro Leu Leu Val Ser Val Thr Gly Asn Pro Ser
305                 310                 315                 320

Ser Ser Trp Pro Ser Pro Thr Glu Pro Ser Lys Ser Gly Ile Cys
            325                 330                 335

Arg His Leu His Val Leu Ile Gly Thr Ser Val Ile Phe Leu Phe
                340                 345                 350

Ile Leu Leu Leu Phe Phe Leu Leu Tyr Arg Trp Cys Ser Asn Lys Lys
            355                 360                 365

Asn Ala Ala Val Met Asp Gln Glu Pro Ala Gly Asp Arg Thr Val Asn
370                 375                 380

Arg Gln Asp Ser Asp Glu Gln Asp Pro Gln Val Thr Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Leu Thr Asp Thr Ser Val Tyr Thr Glu Leu Pro
            420                 425                 430

Asn Ala Glu Pro Arg Ser Lys Val Val Ser Cys Pro Arg Ala Pro Gln
            435                 440                 445

Ser Gly Leu Glu Gly Val Phe
    450                 455

<210> SEQ ID NO 174
<211> LENGTH: 455
<212> TYPE: PRT
<213> ORGANISM: HOMO SAPIENS

<400> SEQUENCE: 174

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Val Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys
130                 135                 140

Trp Ser Asp Val Met Phe Glu His Phe Leu His Arg Glu Gly Ile
145                 150                 155                 160

Ser Glu Asp Pro Ser His Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
```

-continued

```
             210                 215                 220
Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Leu Arg Ala Val Pro Lys Val
                    260                 265                 270

Asn Arg Thr Phe Gln Ala Asp Phe Pro Leu Gly Pro Ala Thr His Gly
                275                 280                 285

Gly Thr Tyr Arg Cys Phe Gly Ser Phe Arg Ala Leu Pro Cys Val Trp
            290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

Arg His Leu His Val Leu Ile Gly Thr Ser Val Val Ile Phe Leu Phe
                340                 345                 350

Ile Leu Leu Leu Phe Phe Leu Leu Tyr Arg Trp Cys Ser Asn Lys Lys
                355                 360                 365

Asn Ala Ala Val Met Asp Gln Glu Pro Ala Gly Asp Arg Thr Val Asn
                370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Leu Thr Asp Thr Ser Val Tyr Thr Glu Leu Pro
                420                 425                 430

Asn Ala Glu Pro Arg Ser Lys Val Val Ser Cys Pro Arg Ala Pro Gln
                435                 440                 445

Ser Gly Leu Glu Gly Val Phe
    450                 455

<210> SEQ ID NO 175
<211> LENGTH: 428
<212> TYPE: PRT
<213> ORGANISM: Homo sapiens

<400> SEQUENCE: 175

Lys Pro Phe Leu Ser Ala Arg Pro Ser Thr Val Val Pro Arg Gly Gly
1               5                   10                  15

His Val Ala Leu Gln Cys His Tyr Arg Arg Gly Phe Asn Asn Phe Met
                20                  25                  30

Leu Tyr Lys Glu Asp Arg Ser His Val Pro Ile Phe His Gly Arg Ile
            35                  40                  45

Phe Gln Glu Ser Phe Ile Met Gly Pro Val Thr Pro Ala His Ala Gly
        50                  55                  60

Thr Tyr Arg Cys Arg Gly Ser Arg Pro His Ser Leu Thr Gly Trp Ser
65                  70                  75                  80

Thr Pro Ser Asn Pro Leu Val Ile Met Val Thr Gly Asn His Arg Lys
                85                  90                  95

Pro Ser Leu Leu Ala His Pro Gly Pro Leu Leu Lys Ser Gly Glu Thr
                100                 105                 110

Val Ile Leu Gln Cys Trp Ser Asp Val Met Phe Glu His Phe Leu
            115                 120                 125
```

His Arg Glu Gly Ile Ser Glu Asp Pro Ser Arg Leu Val Gly Gln Ile
130                 135                 140

His Asp Gly Val Ser Lys Ala Asn Phe Ser Ile Gly Pro Leu Met Pro
145                 150                 155                 160

Val Leu Ala Gly Thr Tyr Arg Cys Tyr Gly Ser Val Pro His Ser Pro
                165                 170                 175

Tyr Gln Leu Ser Ala Pro Ser Asp Pro Leu Asp Ile Val Ile Thr Gly
            180                 185                 190

Leu Tyr Glu Lys Pro Ser Leu Ser Ala Gln Pro Gly Pro Thr Val Gln
        195                 200                 205

Ala Gly Glu Asn Val Thr Leu Ser Cys Ser Ser Trp Ser Ser Tyr Asp
210                 215                 220

Ile Tyr His Leu Ser Arg Glu Gly Glu Ala His Glu Arg Arg Leu Arg
225                 230                 235                 240

Ala Val Pro Lys Val Asn Arg Thr Phe Gln Ala Asp Phe Pro Leu Gly
                245                 250                 255

Pro Ala Thr His Gly Gly Thr Tyr Arg Cys Phe Gly Ser Phe Arg Ala
            260                 265                 270

Leu Pro Cys Val Trp Ser Asn Ser Ser Asp Pro Leu Leu Val Ser Val
        275                 280                 285

Thr Gly Asn Pro Ser Ser Ser Trp Pro Ser Pro Thr Glu Pro Ser Ser
290                 295                 300

Lys Ser Gly Ile Cys Arg His Leu His Val Leu Ile Gly Thr Ser Val
305                 310                 315                 320

Val Ile Phe Leu Phe Ile Leu Leu Leu Phe Phe Leu Leu Tyr Arg Trp
                325                 330                 335

Cys Ser Asn Lys Lys Asn Ala Ala Val Met Asp Gln Glu Pro Ala Gly
            340                 345                 350

Asp Arg Thr Val Asn Arg Gln Asp Ser Asp Glu Gln Asp Pro Gln Glu
        355                 360                 365

Val Thr Tyr Ala Gln Leu Asp His Cys Val Phe Ile Gln Arg Lys Ile
370                 375                 380

Ser Arg Pro Ser Gln Arg Pro Lys Thr Pro Leu Thr Asp Thr Ser Val
385                 390                 395                 400

Tyr Thr Glu Leu Pro Asn Ala Glu Pro Arg Ser Lys Val Val Ser Cys
                405                 410                 415

Pro Arg Ala Pro Gln Ser Gly Leu Glu Gly Val Phe
            420                 425

<210> SEQ ID NO 176
<211> LENGTH: 428
<212> TYPE: PRT
<213> ORGANISM: Homo sapiens

<400> SEQUENCE: 176

Lys Pro Phe Leu Ser Ala Arg Pro Ser Thr Val Val Pro Arg Gly Gly
1               5                   10                  15

His Val Ala Leu Gln Cys His Tyr Arg Arg Gly Phe Asn Asn Phe Met
                20                  25                  30

Leu Tyr Lys Glu Asp Arg Ser His Val Pro Ile Phe His Gly Arg Ile
            35                  40                  45

Phe Gln Glu Ser Phe Ile Met Gly Pro Val Thr Pro Ala His Ala Gly
        50                  55                  60

Thr Tyr Arg Cys Arg Gly Ser Arg Pro His Ser Leu Thr Gly Trp Ser
65                  70                  75                  80

```
Thr Pro Ser Asn Pro Leu Val Ile Met Val Thr Gly Asn His Arg Lys
                85                  90                  95

Pro Ser Leu Leu Ala His Pro Gly Pro Leu Leu Lys Ser Gly Glu Thr
            100                 105                 110

Val Ile Leu Gln Cys Trp Ser Asp Val Met Phe Glu His Phe Phe Leu
        115                 120                 125

His Arg Glu Gly Ile Ser Glu Asp Pro Ser Arg Leu Val Gly Gln Ile
    130                 135                 140

His Asp Gly Val Ser Lys Ala Asn Phe Ser Ile Gly Pro Leu Met Pro
145                 150                 155                 160

Val Leu Ala Gly Thr Tyr Arg Cys Tyr Gly Ser Val Pro His Ser Pro
                165                 170                 175

Tyr Gln Leu Ser Ala Pro Ser Asp Pro Leu Asp Ile Val Ile Thr Gly
            180                 185                 190

Leu Tyr Glu Lys Pro Ser Leu Ser Ala Gln Pro Gly Pro Thr Val Gln
        195                 200                 205

Ala Gly Glu Asn Val Thr Leu Ser Cys Ser Ser Trp Ser Ser Tyr Asp
    210                 215                 220

Ile Tyr His Leu Ser Arg Glu Gly Glu Ala His Glu Arg Arg Leu Arg
225                 230                 235                 240

Ala Val Pro Lys Val Asn Arg Thr Phe Gln Ala Asp Phe Pro Leu Gly
                245                 250                 255

Pro Ala Thr His Gly Gly Thr Tyr Arg Cys Phe Gly Ser Phe Arg Ala
            260                 265                 270

Leu Pro Cys Val Trp Ser Asn Ser Asp Pro Leu Leu Val Ser Val
        275                 280                 285

Thr Gly Asn Pro Ser Ser Ser Trp Pro Ser Pro Thr Glu Pro Ser Ser
    290                 295                 300

Lys Ser Gly Ile Cys Arg His Leu His Val Leu Ile Gly Thr Ser Val
305                 310                 315                 320

Val Ile Phe Leu Phe Ile Leu Leu Phe Phe Leu Leu Tyr Arg Trp
                325                 330                 335

Cys Ser Asn Lys Lys Asn Ala Ala Val Met Asp Gln Glu Pro Ala Gly
            340                 345                 350

Asp Arg Thr Val Asn Arg Gln Asp Ser Asp Glu Gln Asp Pro Gln Glu
        355                 360                 365

Val Met Tyr Ala Gln Leu Asp His Cys Val Phe Ile Gln Arg Lys Ile
    370                 375                 380

Ser Arg Pro Ser Gln Arg Pro Lys Thr Pro Leu Thr Asp Thr Ser Val
385                 390                 395                 400

Tyr Thr Glu Leu Pro Asn Ala Glu Pro Arg Ser Lys Val Val Ser Cys
                405                 410                 415

Pro Arg Ala Pro Gln Ser Gly Leu Glu Gly Val Phe
            420                 425

<210> SEQ ID NO 177
<211> LENGTH: 455
<212> TYPE: PRT
<213> ORGANISM: homo sapiens

<400> SEQUENCE: 177

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
```

-continued

```
            20                  25                  30
Ala Arg Pro Ser Thr Val Val Pro Gln Gly Gly His Val Ala Leu Gln
        35                  40                  45
Cys His Tyr Arg Arg Gly Phe Asn Asn Phe Met Leu Tyr Lys Glu Asp
        50                  55                  60
Arg Ser His Val Pro Ile Phe His Gly Arg Ile Phe Gln Glu Ser Phe
65                  70                  75                  80
Ile Met Gly Pro Val Thr Pro Ala His Ala Gly Thr Tyr Arg Cys Arg
                    85                  90                  95
Gly Ser Arg Pro His Ser Leu Thr Gly Trp Ser Ala Pro Ser Asn Pro
                100                 105                 110
Leu Val Ile Met Val Thr Gly Asn His Arg Lys Pro Ser Leu Leu Ala
                115                 120                 125
His Pro Gly Thr Leu Leu Lys Ser Gly Glu Thr Val Ile Leu Gln Cys
        130                 135                 140
Trp Ser Asp Val Met Phe Glu His Phe Phe Leu His Arg Glu Gly Ile
145                 150                 155                 160
Ser Glu Asp Pro Ser Arg Leu Val Gly Gln Ile His Asp Gly Val Ser
                    165                 170                 175
Lys Ala Asn Phe Ser Ile Gly Pro Leu Met Pro Val Leu Ala Gly Thr
                180                 185                 190
Tyr Arg Cys Tyr Gly Ser Val Pro His Ser Pro Tyr Gln Leu Ser Ala
                195                 200                 205
Pro Ser Asp Pro Leu Asp Ile Val Ile Thr Gly Leu Tyr Glu Lys Pro
        210                 215                 220
Ser Leu Ser Ala Gln Pro Gly Pro Thr Val Gln Ala Gly Glu Asn Val
225                 230                 235                 240
Thr Leu Ser Cys Ser Ser Trp Ser Ser Tyr Asp Ile Tyr His Leu Ser
                    245                 250                 255
Arg Glu Gly Glu Ala His Glu Arg Arg Leu Arg Ala Val Pro Lys Val
                260                 265                 270
Asn Arg Thr Phe Gln Ala Asp Phe Pro Leu Gly Pro Ala Thr His Gly
                275                 280                 285
Gly Thr Tyr Arg Cys Phe Gly Ser Phe Arg Ala Leu Pro Cys Val Trp
        290                 295                 300
Ser Asn Ser Ser Asp Pro Leu Leu Val Ser Val Thr Gly Asn Pro Ser
305                 310                 315                 320
Ser Ser Trp Pro Ser Pro Thr Glu Pro Ser Ser Lys Ser Gly Ile Cys
                    325                 330                 335
Arg His Leu His Val Leu Ile Gly Thr Ser Val Val Ile Phe Leu Phe
                340                 345                 350
Ile Leu Leu Leu Phe Phe Leu Leu Tyr Arg Trp Cys Ser Asn Lys Lys
        355                 360                 365
Asn Ala Ala Val Met Asp Gln Glu Pro Ala Gly Asp Arg Thr Val Asn
        370                 375                 380
Arg Gln Asp Ser Asp Glu Gln Asp Pro Gln Glu Val Thr Tyr Ala Gln
385                 390                 395                 400
Leu Asp His Cys Val Phe Ile Gln Arg Lys Ile Ser Arg Pro Ser Gln
                    405                 410                 415
Arg Pro Lys Thr Pro Pro Thr Asp Thr Ser Val Tyr Thr Glu Leu Pro
                420                 425                 430
Asn Ala Glu Pro Arg Ser Lys Val Val Ser Cys Pro Arg Ala Pro Gln
                435                 440                 445
```

```
Ser Gly Leu Glu Gly Val Phe
    450             455

<210> SEQ ID NO 178
<211> LENGTH: 455
<212> TYPE: PRT
<213> ORGANISM: HOMO SAPIENS

<400> SEQUENCE: 178

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Leu Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys
    130                 135                 140

Trp Ser Asp Val Met Phe Glu His Phe Phe Leu His Arg Glu Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
    210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe His Ala Leu Pro Cys Val Trp
    290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

Arg His Leu His Val Leu Ile Gly Thr Ser Val Val Ile Phe Leu Phe
            340                 345                 350

Ile Leu Leu Leu Phe Phe Leu Leu Tyr Arg Trp Cys Ser Asn Lys Lys
```

```
              355                 360                 365
Asn Ala Ala Val Met Asp Gln Glu Pro Ala Gly Asp Arg Thr Val Asn
    370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Leu Thr Asp Thr Ser Val Tyr Thr Glu Leu Pro
            420                 425                 430

Asn Ala Glu Pro Arg Ser Lys Val Val Ser Cys Pro Arg Ala Pro Gln
        435                 440                 445

Ser Gly Leu Glu Gly Val Phe
    450                 455

<210> SEQ ID NO 179
<211> LENGTH: 455
<212> TYPE: PRT
<213> ORGANISM: HOMO SAPIENS

<400> SEQUENCE: 179

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Val Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys
    130                 135                 140

Trp Ser Asp Val Met Phe Glu His Phe Phe Leu His Arg Glu Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
    210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
            260                 265                 270
```

```
Asn Arg Thr Phe Gln Ala Asp Phe Pro Leu Gly Pro Ala Thr His Gly
            275                 280                 285

Gly Thr Tyr Arg Cys Phe Gly Ser Phe Arg Ala Leu Pro Cys Val Trp
        290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

Arg His Leu His Val Leu Ile Gly Thr Ser Val Val Ile Phe Leu Phe
                340                 345                 350

Ile Leu Leu Leu Phe Phe Leu Leu Tyr Arg Trp Cys Ser Asn Lys Lys
            355                 360                 365

Asn Ala Ala Val Met Asp Gln Glu Pro Ala Gly Asp Arg Thr Val Asn
            370                 375                 380

Arg Gln Asp Ser Asp Glu Gln Asp Pro Gln Glu Val Met Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Leu Thr Asp Thr Ser Val Tyr Thr Glu Leu Pro
            420                 425                 430

Asn Ala Glu Pro Arg Ser Lys Val Val Ser Cys Pro Arg Ala Pro Gln
            435                 440                 445

Ser Gly Leu Glu Gly Val Phe
            450                 455

<210> SEQ ID NO 180
<211> LENGTH: 444
<212> TYPE: PRT
<213> ORGANISM: homo sapiens

<400> SEQUENCE: 180

Met Ser Leu Met Val Val Ser Met Ala Cys Val Gly Leu Phe Leu Val
1               5                   10                  15

Gln Arg Ala Gly Pro His Met Gly Gly Gln Asp Lys Pro Phe Leu Ser
            20                  25                  30

Ala Trp Pro Ser Ala Val Val Pro Arg Gly Gly His Val Thr Leu Arg
        35                  40                  45

Cys His Tyr Arg His Arg Phe Asn Asn Phe Met Leu Tyr Lys Glu Asp
    50                  55                  60

Arg Ile His Ile Pro Ile Phe His Gly Arg Ile Phe Gln Glu Ser Phe
65                  70                  75                  80

Asn Met Ser Pro Val Thr Thr Ala His Ala Gly Asn Tyr Thr Cys Arg
                85                  90                  95

Gly Ser His Pro His Ser Pro Thr Gly Trp Ser Ala Pro Ser Asn Pro
            100                 105                 110

Val Val Ile Met Val Thr Gly Asn His Arg Lys Pro Ser Leu Leu Ala
        115                 120                 125

His Pro Gly Pro Leu Val Lys Ser Gly Glu Arg Val Ile Leu Gln Cys
    130                 135                 140

Trp Ser Asp Ile Met Phe Glu His Phe Leu His Lys Glu Gly Ile
145                 150                 155                 160

Ser Lys Asp Pro Ser Arg Leu Val Gly Gln Ile His Asp Gly Val Ser
                165                 170                 175

Lys Ala Asn Phe Ser Ile Gly Pro Met Met Leu Ala Leu Ala Gly Thr
            180                 185                 190
```

-continued

```
Tyr Arg Cys Tyr Gly Ser Val Thr His Thr Pro Tyr Gln Leu Ser Ala
            195                 200                 205

Pro Ser Asp Pro Leu Asp Ile Val Val Thr Gly Pro Tyr Glu Lys Pro
    210                 215                 220

Ser Leu Ser Ala Gln Pro Gly Pro Lys Val Gln Ala Gly Glu Ser Val
225                 230                 235                 240

Thr Leu Ser Cys Ser Ser Arg Ser Ser Tyr Asp Met Tyr His Leu Ser
            245                 250                 255

Arg Glu Gly Gly Ala His Glu Arg Arg Leu Pro Ala Val Arg Lys Val
            260                 265                 270

Asn Arg Thr Phe Gln Ala Asp Phe Pro Leu Gly Pro Ala Thr His Gly
            275                 280                 285

Gly Thr Tyr Arg Cys Phe Gly Ser Phe Arg His Ser Pro Tyr Glu Trp
    290                 295                 300

Ser Asp Pro Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Asn Pro
            325                 330                 335

Arg His Leu His Ile Leu Ile Gly Thr Ser Val Val Ile Ile Leu Phe
            340                 345                 350

Ile Leu Leu Leu Phe Phe Leu Leu His Leu Trp Cys Ser Asn Lys Lys
            355                 360                 365

Asn Ala Ala Val Met Asp Gln Glu Pro Ala Gly Asn Arg Thr Ala Asn
            370                 375                 380

Ser Glu Asp Ser Asp Glu Gln Asp Pro Glu Glu Val Thr Tyr Ala Gln
385                 390                 395                 400

Leu Asp His Cys Val Phe Thr Gln Arg Lys Ile Thr Arg Pro Ser Gln
            405                 410                 415

Arg Pro Lys Thr Pro Pro Thr Asp Thr Ile Leu Tyr Thr Glu Leu Pro
            420                 425                 430

Asn Ala Lys Pro Arg Ser Lys Val Val Ser Cys Pro
            435                 440

<210> SEQ ID NO 181
<211> LENGTH: 9
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: Any naturally occurring amino acid
<220> FEATURE:
<221> NAME/KEY: MISC_FEATURE
<222> LOCATION: (4)..(5)
<223> OTHER INFORMATION: Any naturally occurring amino acid
<220> FEATURE:
<221> NAME/KEY: MISC_FEATURE
<222> LOCATION: (7)..(7)
<223> OTHER INFORMATION: Any naturally occurring amino acid

<400> SEQUENCE: 181

Xaa Phe Gly Xaa Xaa Tyr Xaa Asp Tyr
1               5

<210> SEQ ID NO 182
<211> LENGTH: 5
<212> TYPE: PRT
<213> ORGANISM: Artificial Sequence
<220> FEATURE:
<223> OTHER INFORMATION: sequence used to identify CDR-H1
```

<400> SEQUENCE: 182

Leu Glu Trp Ile Gly

KIR3DL2 BINDING AGENTS

CROSS-REFERENCE TO RELATED APPLICATIONS

This application is the U.S. national stage application of International Patent Application No. PCT/EP2013/069293, filed Sep. 17, 2013, which claims the benefit of U.S. Provisional Application No. 61/702,823, filed Sep. 19, 2012; the disclosures of which are incorporated herein by reference in their entirety; including any drawings.

REFERENCE TO SEQUENCE LISTING

The present application is being filed along with a Sequence Listing in electronic format. The Sequence Listing is provided as a file entitled "Seq-List-replace.txt", created Dec. 26, 2017, which is 95 KB in size. The information in the electronic format of the Sequence Listing is incorporated herein by reference in its entirety.

FIELD OF THE INVENTION

The present invention provides antigen-binding proteins capable of binding to KIR3DL2 polypeptides. The antibodies have increased activity in the treatment of disorders characterized by KIR3DL2-expressing cells, particularly CD4+ T cells, including malignancies such as Mycosis Fungoides and Sézary Syndrome, and other KIR3DL2-expressing autoimmune disorders.

BACKGROUND

Killer immunoglobulin-like receptors (KIR) are a family of receptors that, along with C-type lectin receptors (CD94-NKG2), are used by human NK cells and T-lymphocyte subsets to specifically recognize MHC class I molecules. Certain inhibitory and activating KIR have highly similar extracellular domains and are recognized by the same monoclonal antibody, e.g. KIR2DL1 and KIR2DS1 are both recognized by EB6, and 2DL2 and 2DS2 by GL183. Three criteria (number of extracellular Ig-like domains (domains D0, D1, D2), cytoplasmic tail length, and sequence analogy) have been used to categories the KIR proteins into 13 groups, namely KIR3DL1-2, KIR3DS1, KIR2DL1-5, and KIR2DS1-5. The nomenclature 2D for 2 domains or 3D for 3 domains give the number of Ig-like domains; receptors with either long or short cytoplasmic domains are further classified as L or S. (Pascal V. et al., 2007 J. Immunol. 179:1625-1633) The inhibitory receptors possess long (L) cytoplasmic tails (i.e., KIR2DL or KIR3DL) containing a canonical ITIM that becomes tyrosine phosphorylated upon KIR engagement of their HLA class I ligands. The phosphorylated ITIM recruits the Src homology 2 domain containing protein tyrosine phosphatases Src homology 2 domain-containing phosphatase 1 and/or Src homology 2 domain-containing phosphatase 2, which dephosphorylate cellular substrates, thus aborting the NK activation signal, i.e., sparing target cells with appropriate self-MHC class I expression. Receptors with short (S) cytoplasmic tails lack ITIMs (i.e., KIR2DS or KIR3DS). These activating KIR contain a charged residue within their transmembrane domain facilitating interaction with the signaling chain KARAP/DAP12. Engagement of the KIR3DS family of receptors has been shown to lead to a cascade of KARAP/DAP12-mediated signaling events culminating in increased NK cell cytolytic activity and the production of proinflammatory cytokines such as IFN-γ (Pascal et al. 2007) J. Immunol. 179: 1625-1633). Mature NK cells are predicted to acquire at least one inhibitory receptor specific for a self-MHC class I molecule, which generally functionally prevails over potentially auto-reactive activating molecules. It is proposed that the response of NK cells represents the integrated outcome of both activating and inhibitory signalling by KIR and other receptors.

KIR3DL2 and KIR3DL1 share relatively high amino acid identity. Amino acid identity between KIR3DL2 and KIR3DL1 in the D1 and D2 domains is highest, while amino acid identity in domain D0 is lower.

It has been reported that several malignancies, autoimmune or inflammatory disorders involve CD4+ T cells that express KIR3DL2 receptors, including malignancies (see, e.g. PCT publications WO2010/081890 and WO02/50122) and arthritic disorders driven by Th17 cells (see Bowness et al (2011) J. Immunol. 186: 2672-2680). Various publications cite the existence of antibodies reactive against various KIR3D polypeptides. The existence of two anti-KIR3DL2 antibodies have been reported: Q241 and Q66 (Pende, et al. (1996) J Exp Med 184:505-518). However, these two antibodies are of the IgM isotype (pentamers) and are not readily suited to pharmaceutical use; furthermore, if their variable regions were placed in the context of a bivalent IgG type antibody, their affinity would be expected to be low. Cells referred to as "AZ158" producing a further antibody was reported (Parolini, S., et al. (2002) In Leucocyte typing VII. D. Mason, editor. Oxford University Press, Oxford. 415-417; PCT publication WO2010/081890). A further antibody 5.133 is commercialized by Miltenyi Biotec (Auburn, Calif.). Antibodies AZ158 and 5.133 bind KIR3DL2 as well as KIR3DL1 (and further the highly homologous KIR3DS1). KIR3DL2 and KIR3DL1 share relatively high amino acid identity and various HLA ligands that bind KIR3DL2 are also recognized by KIR3DL1. Despite immunizations that gave rise to AZ158, Q241 and Q66, there is a need for improved antibodies in therapeutic and other applications.

SUMMARY OF THE INVENTION

In one aspect, the present invention results, inter alia, from the discovery of antibodies with high binding affinity that bind KIR3DL2 without binding closely related KIR3DL1 or KIR3DS1 receptors. In one embodiment, the present invention results, inter alia, from the discovery of antibodies that bind the D0 or D1 domain of KIR3DL2 polypeptides with high affinity and that are specific for KIR3DL2 over KIR3DL1.

In one aspect, the present invention also results from the discovery that the KIR3DL2 protein can undergo intracellular internalization upon binding an antibody. It is shown herein that receptor-mediated internalization of the KIR3DL2 protein is rapid and extensive. KIR3DL2 proteins have several natural ligands of the HLA-A and HLA-B family, including HLA-A3, -A11 and HLA-B27, including, inter alia, H chain homodimers of HLA-B27 ("B27$_2$"). In one aspect, the present findings open the possibility to inhibit all HLA ligands of KIR3DL2 by decreasing the number of KIR3DL2 polypeptides present on the cell surface, with or without causing the depleting of the KIR3DL2-expressing cell.

Antibody-induced intracellular internalization was triggered by binding (by anti-D1 antibodies) to a region outside of the ligand-binding region (e.g., outside of the HLA binding pocket) as well as to a region within the ligand binding region (by anti-D0 domain antibodies). In one embodiment, provided is an antibody that binds to KIR2DL2 outside of the HLA binding cleft (or outside the HLA-binding face) and inhibits the activity of the KIR3DL2 polypeptide. Optionally, the antibody causes internalization of the KIR3DL2 polypeptide and thereby inhibits HLA polypeptide-induced KIR3DL2 signaling (e.g. in T cells, CD4 T cells, CD4 Th17 cells (e.g., proinflammatory cells (CD4 T cells or NK cells) that express IL-23R and/or produce IL-17A). In one embodiment, provided is an antibody that binds to KIR3DL2 on the HLA-binding face) and causes internalization of the KIR3DL2 polypeptide.

In another embodiment, the present invention results, inter alia, from the discovery of antibodies that bind the D0 or D1 domain of KIR3DL2 polypeptides with high affinity and specificity for KIR3DL2 over KIR3DL1, and that have improved characteristics for use in flow cytometry. The antibodies bind an epitope that is believed to be particularly exposed on the surface of KIR3DL2-expressing cells, providing increased specificity in flow cytometry applications. Such characteristics are important in detection of KIR3DL2 on lymphocytes, including in particular on malignant lymphocytes (e.g. Sézary Syndrome, Mycosis Fungoides) which generally express KIR3DL2 at relatively low levels and require high specificity and accuracy to enable their use in medical diagnostics. In particular, the antibodies permit an accurate quantification of the number and/or proportion of KIR3DL2-positive cells within a population of cells (e.g. CD4+ T cells). Antibodies, notably 19H12 and antibodies that bind to the same area on KIR3DL2 (e.g., 12B11 and 18B10), are particularly well suited for use in flow cytometry. While the antibodies can internalization upon KIR3DL2 binding, flow cytometry is performed at temperatures (4° C.) that preclude internalization.

In one aspect, the KIR3DL2 protein and may be used as a port of entry for cytotoxic and other payloads to cells of various origin, for example for delivering agents to cells and in selective drug-delivery and therapy of cancers, autoimmune, inflammatory and other disorders.

The inventors have identified (in successive immunization series) several antibodies directed against a single region of the KIR3DL2 polypeptide (all antibodies compete for binding to KIR3DL2 with each other), and each induce intracellular internalization of KIR3DL2 and are internalized into KIR3DL2-expressing cells.

In one embodiment, provided is an KIR3DL2 binding compound, optionally an antibody, optionally a tetrameric antibody comprising two Ig heavy chains and two Ig light chains, that binds to a KIR3DL2 polypeptide (an anti-KIR3DL2 antibody) without substantially binding to a KIR3DL1, KIR3DS1 and/or KIR2DL polypeptide, wherein the antibody has binding affinity ($K_D$), optionally wherein binding affinity is bivalent, for a human KIR3DL2 polypeptide at of less than $10^{-8}$ M, less than $10^{-9}$ M, less than $5*10^{-9}$ M, less than $2*10^{-9}$ M, or less than $10^{-10}$M. Optionally the antibody is a human or humanized antibody comprising light and heavy chains having human FR sequences, optionally wherein a light and/or heavy chain FR sequence further comprises one or more amino acid substitutions (e.g. a back-mutation).

In one embodiment, provided is a KIR3DL2 binding compound, optionally an anti-KIR3DL2 antibody, capable of internalizing into KIR3DL2-expressing cells. The antibodies are optionally capable of inducing and/or increasing intracellular internalization of the KIR3DL2 polypeptide and/or complex comprising the antibody and a KIR3DL2 polypeptide. Optionally, the antibody is capable of selectively binding a KIR3DL2 polypeptide without substantial binding to a KIR3DL1, KIR3DS1 and/or KIR2DL polypeptide, wherein the antibody has binding affinity ($K_D$), optionally wherein binding affinity is bivalent, for a human KIR3DL2 polypeptide at of less than $10^{-8}$ M, optionally less than $10^{-9}$ M, or optionally less than $10^{-10}$M.

In one embodiment, provided is an antibody that binds a KIR3DL2 polypeptide, wherein said antibody does not substantially bind to a KIR3DL1 polypeptide (e.g. wherein the KIR3DL1 polypeptide comprises an amino acid sequence of SEQ ID NO: 169), and wherein said antibody is not internalized into KIR3DL2-expressing cells.

In one embodiment, provided is an antibody that binds at least two KIR3DL2 polypeptides (alleles), and wherein said antibody does not substantially bind to a KIR3DL1 polypeptide (e.g. KIR3DL1 allele *00101 comprising the amino acid sequence shown in SEQ ID NO: 180).

In one embodiment, the antibodies bind to 1, 2, 3, 4 or 5 of the KIR3DL2 polypeptides (alleles *002, *003, *005, *007, and/or *008) of SEQ ID NOS: 1, 170, 172, 174, 176 and/or 177.

In one embodiment, the antibodies bind to each of the KIR3DL2 polypeptides having the amino acid sequence shown in SEQ ID NOS: 1, 171 and 176 (alleles_*002, *001 and *007, respectively). In one embodiment, the antibodies bind to each of the KIR3DL2 polypeptides having the amino acid sequence shown in SEQ ID NOS: 171 and 178 (alleles_*001 and *009, respectively). In one embodiment, the antibodies bind to each of the KIR3DL2 polypeptides having the amino acid sequence shown in SEQ ID NOS: 171, 1, 176 and 178 (alleles_*001, *002, *007 and *009, respectively). In one embodiment, the antibodies bind to each of the KIR3DL2 polypeptides having the amino acid sequence shown in SEQ ID NOS: 171, 1, 172, 174 and 176 (alleles_*001, *002, *003, *005 and *007, respectively). In one embodiment, the antibodies bind to each of the KIR3DL2 polypeptides having the amino acid sequence shown in SEQ ID NOS: 171, 1, 176 and 177 (alleles_*001, *002, *007 and *008, respectively). In one embodiment, the antibodies bind to each of the KIR3DL2 polypeptides having the amino acid sequence shown in SEQ ID NOS: 171, 1, 172, 174, 176 and 177 (alleles_*001, *002, *003, *005, *007 and *008, respectively). In one embodiment of any of the foregoing, the antibodies further bind a KIR3DL2 polypeptide having the amino acid sequence shown in SEQ ID NO: 178 (allele *09). In one embodiment of any of the foregoing, the antibodies further bind a KIR3DL2 polypeptide having the amino acid sequence shown in SEQ ID NO: 173 (allele *004). In one embodiment of any of the foregoing, the antibodies further bind a KIR3DL2 polypeptide allele *010 (having the same extracellular domain of SEQ ID NO: 171 as *001). In one embodiment of any of the foregoing, the antibodies further bind a KIR3DL2 polypeptide allele *011 (having the same extracellular domain (of SEQ ID NO: 179). In one embodiment of any of the foregoing, the antibodies further bind a KIR3DL2 polypeptide allele *006 (having the extracellular domain of SEQ ID NO: 175). Optionally, in each case, the antibody binds to said KIR3DL2 polypeptide expressed on the surface of a cell (e.g. a reporter cell line, wherein KIR3DL2 is in native conformation). Optionally the antibody binds a conformational epitope.

In one embodiment, provided is a KIR3DL2 binding compound, optionally an anti-KIR3DL2 antibody that binds the D0 and/or D1 domain of a KIR3DL2 polypeptide. In one embodiment, an antibody binds a polypeptide comprising or consisting of a KIR3DL2 amino acid sequence of SEQ ID NO: 58 and/or 59. In one embodiment an antibody binds a KIR3DL2 polypeptide of SEQ ID NO: 1 but does not bind a polypeptide comprising a KIR3DL2 amino acid sequence consisting of SEQ ID NO: 57. In one embodiment, an antibody binds a polypeptide comprising or consisting of a KIR3DL2 amino acid sequence of SEQ ID NO: 57. The D0, D1 and D2 domains are located within amino acid residues L1 to G98, N99 to L192 and D193 to V292, respectively, with reference to the KIR3DL2 polypeptide of SEQ ID NO: 1. Optionally, the anti-KIR3DL2 antibody is capable of being internalized into a KIR3DL2-expressing cell. Optionally, the anti-KIR3DL2 antibody is capable of inducing and/or increasing intracellular internalization of the KIR3DL2 polypeptide and/or complex comprising the antibody and a KIR3DL2 polypeptide. Optionally, the anti-KIR3DL2 antibody binds to a KIR3DL2 polypeptide without substantially binding to a KIR3DL1, KIR3DS1 and/or KIR2DL polypeptide, wherein the antibody has binding affinity ($K_D$), optionally wherein binding affinity is bivalent, for a human KIR3DL2 polypeptide at of less than $10^{-8}$ M, p optionally less than $10^{-9}$ M, or optionally less than $10^{-10}$ M.

In one embodiment, provided is a KIR3DL2 binding compound, optionally an anti-KIR3DL2 antibody, further bound to a second moiety, wherein the antibody is capable of delivering the second moiety into a KIR3DL2-expressing cell. Optionally the second moiety is a therapeutic agent, a toxic agent, and/or a detectable agent.

In one embodiment, the antibodies bind to 1, 2, 3, 4 or 5 of the KIR3DL2 polypeptide alleles *002, *003, *005, *007, and/or *008 (e.g. as expressed on the surface of a cell).

In one aspect provided is antibodies that bind the KIR3DL2 polypeptide outside of the ligand (HLA) binding region (e.g. HLA binding pocket). Optionally the antibody binds at least partly on the back face of KIR3DL2 protein from the HLA binding pocket.

In any of the embodiments herein, the antibody binds to an amino acid residue within the D1 domain (residues 99 to 192 of SEQ ID NO: 1). Optionally, the antibodies further bind (or do not bind) at least one amino acid residue within the D0 or D2 domains of a KIR3DL2 polypeptide. Optionally, binding of the antibody to a KIR3DL2 polypeptide having a mutation at a residue within the D1 domain is substantially reduced, in comparison to binding to a wild-type KIR3DL2 polypeptide.

In one aspect provided are antibodies that bind an epitope comprising residues P179 and/or S181 of the KIR3DL2 polypeptide, and/or have reduced binding to a KIR3DL2 polypeptide having a mutation at residues P179 and/or S181 (with reference to SEQ ID NO: 1, e.g. a P179T, S181T mutant). In one aspect the antibodies further bind an epitope comprising residues V178 and/or H180 of the KIR3DL2 polypeptide, and/or have reduced binding to a KIR3DL2 polypeptide having a mutation at residues V178 and/or H180 (with reference to SEQ ID NO: 1, e.g. a V178A, H180S mutant). In one aspect the antibodies further bind an epitope comprising residues E130, H131 and/or R145 of the KIR3DL2 polypeptide, and/or have reduced binding to a KIR3DL2 polypeptide having a mutation at residues E130, H131 and/or R145 (with reference to SEQ ID NO: 1, e.g. a E130S, H131S, R145S mutant). In one aspect the antibodies further bind an epitope comprising residues V147 and/or Q149 of the KIR3DL2 polypeptide, and/or have reduced binding to a KIR3DL2 polypeptide having a mutation at residues V147 and/or Q149 (with reference to SEQ ID NO: 1, e.g. a V147A, Q149S mutant).

In one aspect provided are antibodies that bind an epitope comprising residues V178 and/or H180 of the KIR3DL2 polypeptide, and/or have reduced binding to a KIR3DL2 polypeptide having a mutation at residues V178 and/or H180 (with reference to SEQ ID NO: 1, e.g. a V178A, H180S mutant).

In one aspect provided are antibodies that bind an epitope comprising residues E130, H131 and/or R145 of the KIR3DL2 polypeptide, and/or have reduced binding to a KIR3DL2 polypeptide having a mutation at residues E130, H131 and/or R145 (with reference to SEQ ID NO: 1, e.g. a E130S, H131S, R145S mutant). In one aspect the antibodies further bind an epitope comprising residues I150 and/or M128 of the KIR3DL2 polypeptide, and/or have reduced binding to a KIR3DL2 polypeptide having a mutation at residues I150 and/or M128 (with reference to SEQ ID NO: 1, e.g. a I150A, M128A mutant).

In one aspect provided are antibodies that bind an epitope comprising residues V147 and/or Q149 of the KIR3DL2 polypeptide, and/or have reduced binding to a KIR3DL2 polypeptide having a mutation at residues V147 and/or Q149 (with reference to SEQ ID NO: 1, e.g. a V147A, Q149S mutant).

In one aspect provided are antibodies that bind an epitope comprising residues I150 and/or M128 of the KIR3DL2 polypeptide, and/or have reduced binding to a KIR3DL2 polypeptide having a mutation at residues I150 and/or M128 (with reference to SEQ ID NO: 1, e.g. a I150A, M128A mutant).

In one aspect, the antibodies bind an epitope comprising one, two, three, four, five or more of residues selected from the group consisting of: M128, E130, H131, R145, V147, Q149, I150, V178, P179, H180 and S181 (with reference to SEQ ID NO: 1), and/or the antibodies may or may not have reduced binding to a KIR3DL2 polypeptide having a mutation at a residue selected from the group consisting of: M128, E130, H131, R145, V147, Q149, I150, V178, P179, H180 and/or S181 (with reference to SEQ ID NO: 1).

In one aspect, provided is antibodies that do not interfere with binding of an HLA polypeptide (e.g. HLA-A3, HLA-A11 and/or HLA-B27 (e.g., HLA-B27$_2$)) to a human KIR3DL2 polypeptide, e.g. as assessed in a binding assay between recombinant proteins or generally any assay wherein KIR3DL2 cannot be internalized (e.g. host cells expressing KIR3DL2 which are made to not internalize KIR3DL2. Optionally, the antibodies do not compete with an HLA polypeptide natural ligand of KIR3DL2 for binding to a human KIR3DL2 polypeptide.

The disclosure provides that the use of an anti-KIR3DL2 antibody can be useful for the treatment of cancers, inflammatory disorders and autoimmune disorders, e.g. in human subjects. This antibody can be used with or without coupling to a toxic or other agent, depending on the desired effect or use made of the antibodies. In one embodiment, the anti-KIR3DL2 antibody is a "naked antibody" and is not coupled to a toxic agent. In one embodiment, a naked or coupled antibody comprises a heavy chain comprising a Fc region (e.g. IgG1) that binds Fcγ receptors (e.g. CD16). Optionally wherein such antibody induces complement dependent cytotoxicity (CDC) and/or antibody dependent cellular cytotoxicity (ADCC) toward a cell that expresses KIR3DL2.

Optionally, in any embodiment, the antibody (e.g. IgG4, IgG1, antibody fragment, etc.) further comprises a toxic agent (e.g. a chemotherapeutic agent) that is toxic to a cell upon internalization of the antibody-toxin conjugate. In one embodiment the antibody is conjugated to toxic agent via a linker that is cleaved preferentially intracellularly. For example, an acid-labile linker can be used, e.g. an acid-labile hydrazone linker, disulfide based linkers, non-cleavable thioether linkers, and peptide linkers like citruline-valine.

The present disclosure further provides antibodies, antibody fragments, and derivatives that specifically bind human KIR3DL2. The disclosure provides such antibody compositions, as well their use in any of the methods of the disclosure of treating, preventing and diagnosing disease, e.g. cancer, inflammatory disorders or autoimmune disorders.

In one embodiment, the antibodies have binding affinity ($K_D$) for a human KIR3DL2 polypeptide of less than $10^{-8}$ M, less than $10^{-9}$ M, or less than $10^{-10}$M.

In one aspect of any of the embodiments herein, the antibody may have a heavy and/or light chain having one, two or three CDRs of the respective heavy and/or light chain of an antibody selected from the group consisting of antibody 15C11, 19H12, 22B2, 18B10, 12B11 and 13H1, wherein any CDR(s) may optionally comprise one, two, three, four or more amino acid modifications (e.g. substitutions).

In one aspect of any of the embodiments herein, the antibody competes for binding to a KIR3DL2 polypeptide with any one or any combination of monoclonal antibodies 15C11, 19H12, 22B2, 18B10, 12B11 and 13H1. In one embodiment, an antibody competes for binding to a KIR3DL2 polypeptide, with an antibody selected from the group consisting of:
  (a) an antibody having respectively a VH and VL region of SEQ ID NOS: 2 and 3 (15C11),
  (b) an antibody having respectively a VH and VL region of SEQ ID NOS: 13 and 14 (19H12),
  (c) an antibody having respectively a VH and VL region of SEQ ID NOS: 24 and 25 (22B2),
  (d) an antibody having respectively a VH and VL region of SEQ ID NOS: 32 and 33 (18B10),
  (e) an antibody having respectively a VH and VL region of SEQ ID NOS: 42 and 43 (12B11), and
  (f) an antibody having respectively a VH and VL region of SEQ ID NOS: 46 and 47 (13H1).

In one aspect, provided is an antibody that specifically binds KIR3DL2, wherein the antibody has one or more (including any combination thereof, or all of) of the following properties:
  (a) has a Kd of less than $10^{-8}$ M, less than $10^{-9}$ M, or less than $10^{-10}$M for binding to a KIR3DL2 polypeptide, e.g. a KIR3DL2 polypeptide expressed on the surface of a cell;
  (b) binds to at least one residue in the segment corresponding to residues 1 to 98 or 99-192, of the KIR3DL2 polypeptide of SEQ ID NO: 1;
  (c) competes for binding to a KIR3DL2 polypeptide with antibody 15C11, 19H12, 22B2, 18B10, 12B11 and/or 13H1;
  (d) does not compete with a natural ligand of KIR3DL2 (e.g. HLA polypeptides HLA-A3, HLA-11 and/or HLA-B27) for binding to a KIR3DL2 polypeptide (e.g. in a polypeptide interaction assay);
  (e) inhibits KIR3DL2 signaling induced by a natural ligand of KIR3DL2 (e.g. HLA polypeptides HLA-A3, HLA-11 and/or HLA-B27);
  (f) does not substantially bind to a KIR3DL1, KIR3DS1, KIR3DL3, KIR2DS1, KIR2DS2, KIR2DL3, KIR2DL1 and/or KIR2DS4 polypeptide;
  (g) is capable of being internalized into KIR3DL2-expressing cells;
  (h) binds to an epitope comprising any one or more of amino acid residues M128, E130, H131, R145, V147, Q149, I150, V178, P179, H180 and/or S181 of the KIR3DL2 polypeptide of SEQ ID NO: 1, or to an epitope comprising any one or more of amino acid residues M128, E130, H131, R145, V147, Q149, I150, V178, P179, H180 and/or S181 of the KIR3DL2 polypeptide of SEQ ID NO: 1;
  (i) has reduced binding to a KIR3DL2 polypeptide having a mutation at one or more of residues R13, A25, Q27, Q56, E57, I60 and/or G62 of the KIR3DL2 polypeptide of SEQ ID NO: 1, or has reduced binding to a KIR3DL2 polypeptide having a mutation at one or more of residues R13, A25, Q27, Q56, E57, I60 and/or G62 of the KIR3DL2 polypeptide of SEQ ID NO: 1; and/or
  (j) induces internalization of KIR3DL2 polypeptides on KIR3DL2-expressing cells.

In any of the embodiments herein, an antibody herein may be characterized by any one or more features of (a)-(j), above.

In one embodiment, the antibody is human-suitable. In one embodiment the antibody is chimeric, e.g. contains a non-murine, optionally a human, constant region. In one embodiment, the antibody is human or humanized. In another embodiment, the antibody is a mouse antibody.

In one aspect of any of the embodiments herein, the isotype of the antibody is IgG, optionally IgG1, IgG2, IgG3 or IgG4. In one embodiment the antibody comprises an Fc domain or is of an isotype that is bound by FcγR (e.g. FcγRIIIA), e.g. an antibody of IgG1 or IgG3 isotype.

In one aspect of any of the embodiments herein, the antibody is an antibody fragment selected from Fab, Fab', Fab'-SH, F(ab')2, Fv, diabodies, single-chain antibody fragment, or a multispecific antibody comprising multiple different antibody fragments. In one aspect of any of the embodiments herein, the antibody does not comprise an Fc domain or is of an isotype that is not substantially bound by FcγR. In one embodiment, the antibody is of an IgG4 or IgG2 isotype.

Optionally such antibodies are furthermore tetrameric (two heavy and two light chains) and are thus bivalent (e.g. IgG antibodies).

In certain embodiments, the antibodies further comprise a toxic agent. In one embodiment, the antibodies comprising a toxic agent are able to directly cause the death of cells expressing KIR3DL2. In one embodiment, the antibodies are capable of directly inducing (e.g. in the absence of immune effector cells) at least 20%, 30%, 40% or 50% cell death, e.g. in an in vitro assay, of KIR3DL2-expressing cells.

In one embodiment, provided is a method of testing an anti-KIR3DL2 antibody, said method comprising bringing an antibody that binds a KIR3DL2 polypeptide into contact with a cell expressing a KIR3DL2 polypeptide and assessing whether the antibody is internalized into the KIR3DL2-expressing cells and/or whether the antibody induces and/or increases intracellular internalization of a KIR3DL2 polypeptide.

In another embodiment, provided is a method of producing an antibody that binds a KIR3DL2 polypeptide in a mammalian subject, optionally for the treatment of a cancer, an inflammatory disorder or an autoimmune disorder, said method comprising the steps of: a) providing a plurality of antibodies, optionally immunizing a non-human mammal with an immunogen comprising a human KIR3DL2 polypeptide; and b) selecting (e.g. for production, development, use in therapy, etc.) an antibody from said plurality that:
  (i) binds to the KIR3DL2 polypeptide but not to a KIR3DL1 polypeptide; and/or
  (ii) (a) binds to at least one residue in the segment corresponding to residues 99-192, of the mature KIR3DL2 polypeptide of SEQ ID NO: 1, and/or to any one or more (e.g. 2, 3, 4, 5 or more) of residues M128, E130, H131, R145, V147, Q149. I1150, V178, P179, H180 and/or S181, and/or has reduced binding to a KIR3DL2 polypeptide having an amino acid substitution at said residue(s), or (b) binds to at least one residue in the segment corresponding to residues 1-98, of the mature KIR3DL2 polypeptide of SEQ ID NO: 1, and/or to any one or more (e.g. 2, 3, 4, 5 or more) of residues R13, A25, Q27, Q56, E57, I60 and/or G62; and/or has reduced binding to a KIR3DL2 polypeptide having an amino acid substitution at said residue(s); and/or (iii) is internalized into KIR3DL2-expressing cells and/or induces and/or increases intracellular internalization of a KIR3DL2 polypeptide.

In one aspect, the methods further comprise a step of coupling the selected antibody to a detectable or to a toxic moiety.

In one embodiment, provided is a method of testing an anti-KIR3DL2 antibody, said method comprising bringing an antibody that binds a KIR3DL2 polypeptide, is internalized into KIR3DL2-expressing cells, and is conjugated to a toxic moiety, into contact with a cell expressing a KIR3DL2 polypeptide and assessing whether the antibody causes the death of KIR3DL2-expressing cells.

In another embodiment, provided is a method of producing an antibody that binds a KIR3DL2 polypeptide in a mammalian subject, optionally for the treatment of a cancer, an inflammatory disorder or an autoimmune disorder, said method comprising the steps of: a) providing a plurality of antibodies, optionally immunizing a non-human mammal with an immunogen comprising a human KIR3DL2 polypeptide; b) determining whether each of the plurality of antibodies are capable of binding to 1, 2, 3, 4, 5, or more different KIR3DL2 polypeptides alleles (e.g. alleles *001, *002, *003, *005, *007, *008, *009 and/or *011), optionally in each case wherein the KIR3DL2 polypeptide is expressed on the surface of a cell, and c) selecting (e.g. for production, development, use in therapy, etc.) an antibody from said plurality that are capable of binding to 1, 2, 3, 4, 5, or more different KIR3DL2 polypeptides alleles (e.g. alleles *001, *002, *003, *005, *007, *008, *009 and/or *011), optionally in each case wherein the KIR3DL2 polypeptide is expressed on the surface of a cell. Optionally, the method further comprises determining whether each of the plurality of antibodies are capable of binding to a KIR3DL1 polypeptide, and selecting an antibody from said plurality that are capable of binding to said KIR3DL1 polypeptide.

In one aspect, the disclosure provides methods of inhibiting the biological activity of a KIR3DL2-expressing cell comprising bringing the cell into contact with anti-KIR3DL2 antibodies disclosed herein, in vitro, ex vivo or in vivo. Optionally said brining into contact is in the presence of a ligand (e.g. HLA) of KIR3DL2, optionally a cell expressing a ligand (e.g. HLA) of KIR3DL2. Optionally the KIR3DL2-expressing cell is an immune cell, e.g. a T cell or an NK cell, a malignant T cell or NK cell, a CD4 Th17 cell (e.g., a proinflammatory CD4 T cells that express IL-23R and produces IL-17A) or a proinflammatory NK cell that expresses produces IL-17A. In one embodiment, provided are methods of inhibiting the biological activity of a KIR3DL2-expressing T or NK cell that produces IL-17A comprising bringing the cell into contact with anti-KIR3DL2 antibodies of the disclosure, in vitro, ex vivo or in vivo. Optionally, the biological activity is activation, lytic activity, cytokine (e.g. IL-17A) production and/or cellular proliferation. P Optionally, the biological activity is ligand-induced (e.g. HLA-induced) signaling. In one aspect, provided are methods of inhibiting the biological activity of a KIR3DL2-expressing cell comprising brining the cell into contact with an anti-KIR3DL2 antibodies of the disclosure, in vitro, ex vivo or in vivo.

In one aspect, provided are methods of eliminating or depleting a KIR3DL2-expressing cell comprising bringing the cell into contact with an anti-KIR3DL2 antibodies herein, in vitro, ex vivo or in vivo. The cell may be, e.g. a malignant T cell or NK cell, a T cell or an NK cell, a CD4 Th17 cell (e.g., a proinflammatory CD4 T cells that express IL-23R and produces IL-17A) or a proinflammatory NK cell that expresses produces IL-17A.

In one aspect, provided are methods of treatment using the anti-KIR3DL2 antibodies of the disclosure. The antibodies can be used as prophylactic or therapeutic treatment; in any of the embodiments herein, a therapeutically effective amount of the antibody can be interchanged with a prophylactically effective amount of an antibody. In one aspect, the provided is a method of treating a patient with a cancer, e.g. a T cell lymphoma, a CD4+ or CD8+ CTCL, Sézary syndrome (SS), Mycosis fungoides (MF), a CD30+ T cell lymphoma, the method comprising administering to the patient a pharmaceutically effective amount of an antigen-binding compound according to the disclosure that specifically binds to a KIR3DL2 polypeptide. In another embodiment, the provided is a method of treating a patient with an autoimmune or inflammatory disorder mediated at least in part by KIR3DL2-expressing T cells, the method comprising administering to the patient a pharmaceutically effective amount of an antigen-binding compound according to the disclosure that specifically binds to a KIR3DL2 polypeptide.

The methods of treatment and the anti-KIR3DL2 antibody of the disclosure can be used to a treat an individual in combination with a second therapeutic agent, including immunomodulators (e.g. chemotherapeutic drugs, anti-inflammatory drugs, tumor vaccines, antibodies that bind to tumor-specific antigens on tumor cells, antibodies that induce ADCC toward tumors cells, antibodies that potentiate immune responses, disease-modifying anti-rheumatic drugs (DMARDs), etc.). In one embodiment, the second therapeutic agent is an anti-CD4 antibody or an anti-CD30 antibody.

The present disclosure further concerns a method for diagnosing a disease state mediated by pathogenic KIR3DL2-expressing cells, said method comprising the steps of combining with an ex vivo patient sample a composition comprising a conjugate or complex comprises an antibody that binds specifically to KIR3DL2 expressed on the surface of the pathogenic cells and an imaging agent, and detecting the pathogenic cells that express a receptor for the ligand using flow cytometry.

The present disclosure further concerns a method of determining a prognosis of a cancer by detecting cancer cells in an ex vivo patient sample, said method comprising the steps of: (a) combining with an ex vivo patient sample a composition comprising a conjugate or complex comprises an antibody that binds specifically to KIR3DL2 expressed on the surface of the pathogenic cells and an imaging agent, (b) detecting the pathogenic cells that express a receptor for the ligand using flow cytometry, and (c) determining a prognosis for the cancer.

The present disclosure further concerns a method for quantitating pathogenic cells, said method comprising the steps of combining with an ex vivo patient sample a composition comprising a conjugate or complex comprises an antibody that binds specifically to KIR3DL2 expressed on the surface of the pathogenic cells and an imaging agent, and quantitating said pathogenic cells in the ex vivo patient sample using flow cytometry.

In any of the above flow-cytometry based methods, the antibody binds to a KIR3DL2 polypeptide on the surface of cells but not to a KIR3DL1 polypeptide of SEQ ID NO: 180. Optionally, said pathogenic cells are detected by single photon flow cytometry. Optionally, said pathogenic cells are detected by multiphoton flow cytometry. Optionally, wherein the ex vivo patient sample is a patient body fluid. Optionally, the body fluid is selected from the group consisting of spinal fluid, lymph fluid, urine, mucus, and blood. Optionally, the pathogenic cells are CD4+ T cells. Optionally, the pathogenic cells are lymphoma cancer cells. Optionally, the cancer cells are Mycosis Fungoides and Sézary Syndrome cancer cells. Optionally, the antibody conjugated to an imaging agent is selected from the group consisting of anti-KIR3DL2-fluorescein, anti-KIR3DL2-Oregon Green, anti-KIR3DL2-rhodamine, anti-KIR3DL2-phycoerythrin, anti-KIR3DL2-cys-Texas Red, anti-KIR3DL2-AlexaFluor, and anti-KIR3DL2-DyLight. Optionally, the imaging agent comprises a chromophore. Optionally, the chromophore is a fluorescent chromophore. Optionally, the chromophore comprises a compound selected from the group consisting of fluorescein, Oregon Green, rhodamine, phycoerythrin, Texas Red, DyLight 680, and AlexaFluor 488. Optionally, the methods further comprise the step of quantitating the pathogenic cells in the ex vivo patient sample.

In any of the above flow-cytometry based methods, the antibodies optionally bind to each of the KIR3DL2 polypeptides having the amino acid sequence shown in SEQ ID NOS: 1, 171 and 176 (alleles_*002, *001 and *007, respectively). In one embodiment, the antibodies bind to each of the KIR3DL2 polypeptides having the amino acid sequence shown in SEQ ID NOS: 171 and 178 (alleles_*001 and *009, respectively). In one embodiment, the antibodies bind to each of the KIR3DL2 polypeptides having the amino acid sequence shown in SEQ ID NOS: 171, 1, 176 and 178 (alleles_*001, *002, *007 and *009, respectively). In one embodiment, the antibodies bind to each of the KIR3DL2 polypeptides having the amino acid sequence shown in SEQ ID NOS: 171, 1, 172, 174 and 176 (alleles_*001, *002, *003, *005 and *007, respectively). In one embodiment, the antibodies bind to each of the KIR3DL2 polypeptides having the amino acid sequence shown in SEQ ID NOS: 171, 1, 176 and 177 (alleles_*001, *002, *007 and *008, respectively). In one embodiment, the antibodies bind to each of the KIR3DL2 polypeptides having the amino acid sequence shown in SEQ ID NOS: 171, 1, 172, 174, 176 and 177 (alleles_*001, *002, *003, *005, *007 and *008, respectively).

In any of the above flow-cytometry based methods, the antibody binds an epitope comprising one, two, three, four, five or more of residues selected from the group consisting of: M128, E130, H131, R145, V147, Q149, I150, V178, P179, H180 and S181 (with reference to SEQ ID NO: 1), and/or the antibody may or may not have reduced binding to a KIR3DL2 polypeptide having a mutation at a residue selected from the group consisting of: M128, E130, H131, R145, V147, Q149, I150, V178, P179, H180 and/S181 (with reference to SEQ ID NO: 1 In any of the above flow-cytometry based methods, the antibody binds an epitope comprising residues P179 and/or S181 of the KIR3DL2 polypeptide, and/or has reduced binding to a KIR3DL2 polypeptide having a mutation at residues P179 and/or S181 (with reference to SEQ ID NO: 1, e.g. a P179T, S181T mutant). In one aspect the antibody binds an epitope comprising residues V178 and/or H180 of the KIR3DL2 polypeptide, and/or has reduced binding to a KIR3DL2 polypeptide having a mutation at residues V178 and/or H180 (with reference to SEQ ID NO: 1, e.g. a V178A, H180S mutant). In one aspect the antibody binds an epitope comprising residues E130, H131 and/or R145 of the KIR3DL2 polypeptide, and/or have reduced binding to a KIR3DL2 polypeptide having a mutation at residues E130, H131 and/or R145 (with reference to SEQ ID NO: 1, e.g. a E130S, H131S, R145S mutant). In any of the above flow-cytometry based methods, the antibody is an antibody that competes with, and/or that comprises the heavy and/or light chain CDRs 1, 2 and/or 3 of, antibody 19H12, 12B11 or 19B10.

The present disclosure further concerns a method for selecting subjects having a disease that responds to a treatment using a KIR3DL2 antagonist (e.g. an antibody that binds to a KIR3DL2 polypeptide), the method comprising determining whether disease-related cells in said subject express a KIR3DL2 receptor, the expression of a KIR3DL2 receptor being indicative of a responder subject. Optionally, the method further comprises administering to a responder subject an antibody (e.g. an anti-KIR3DL2 antibody herein) that binds to a KIR3DL2 polypeptide. In one embodiment, the method is used for selecting subjects having a cancer, and the disease-related cells are cancer cells. In one embodiment, the method is used for selecting subjects having an inflammatory or autoimmune disorder, and the disease-related cells are T cells.

In a preferred embodiment, the expression of a KIR3DL2 receptor in said disease-related cell is determined using a KIR3DL2-specific ligand. Optionally, the ligand is an antibody, or a fragment or derivative thereof. In one aspect, provided are compositions comprising, and methods of using monoclonal antibodies, including but not limited to antibody fragments, and derivatives that specifically bind human KIR3DL2.

In another aspect, of the disclosure provides a method (e.g., a method of conducting a diagnostic assay, a responder assay, etc.), comprising assessing whether a patient has disease-related cells expressing a KIR3DL2 polypeptide, e.g. a KIR3DL2 polypeptide (one or more KIR3DL2 alleles) bound by an antibody of the disclosure. Said method may comprise, for example, obtaining a biological sample from a patient comprising disease-related cells, bringing said disease-related cells into contact with such antibody and assessing whether the antibody binds to disease-related cells. A finding that KIR3DL2 is expressed by disease-related cells indicates that the patient has a condition characterized by KIR3DL2-expressing cells and/or is suitable for treatment with an anti-KIR3DL2 antibody of the disclosure. The patient can further be treated with a treatment suitable for the particular disease characterized by KIR3DL2-expressing cells. Optionally the patient is treated with the anti-KIR3DL2 antibody. In one embodiment, the method is used for selecting subjects having a cancer, and the disease-related cells are cancer cells. In one embodiment, the method is used for selecting subjects having an inflammatory or autoimmune disorder, and the disease-related cells are T cells. In one embodiment, the antibody brought into contact with disease-related cells in order to assess whether the antibody binds to disease-related cells is an antibody of the disclosure.

Also provided is a method of treating a patient, the method comprising:
a) determining whether the patient has pathogenic KIR3DL2-expressing cells, and b) if the patient is determined to patient have pathogenic KIR3DL2-expressing cells, administering an antigen-binding compound (e.g., antibody) of the disclosure.

Also provided is a method for the assessment of the development level of a CTCL (staging disease) permitting the evaluation of the proportion (e.g. percentage) of malignant CD4+ CTCL cells present within a certain body compartment of a patient. According to this method, cells from a biological sample collected from said body compartment are brought into contact with an anti-KIR3DL2 antibody of the disclosure and the proportion of CD4+ cells expressing a KIR3DL2 polypeptide at their surface is measured. The proportion of CD4+ CTCL cells that are actually present in said body compartment can be considered as substantially equal to said measured proportion, e.g., within a ±10% range around this measured proportion.

Also provided is a method for CTCL diagnosis, comprising bringing cells from a biological sample from an individual into contact with an anti-KIR3DL2 antibody of the disclosure and the proportion (e.g. percentage) of T cells expressing a KIR3DL2 polypeptide at their surface is measured, and comparing such proportion to the average proportion (e.g. percentage) of T cells expressing a KIR3DL2 polypeptide at their surface observed in non-CTCL humans (optionally in healthy humans), wherein a CTCL-positive diagnosis is made when said measured proportion is significantly higher than said average proportion.

These and additional advantageous aspects and features of the invention may be further described elsewhere herein.

BRIEF DESCRIPTION OF THE DRAWINGS

FIG. 10A shows the dose-effect of 19H12-ADC1 and FIG. 10B shows the effect of mo19H12-ADC1 (15 mg/kg) as compared to mo19H12 (un-conjugated mAb).

DETAILED DESCRIPTION OF THE INVENTION

Introduction

Figure 1A:
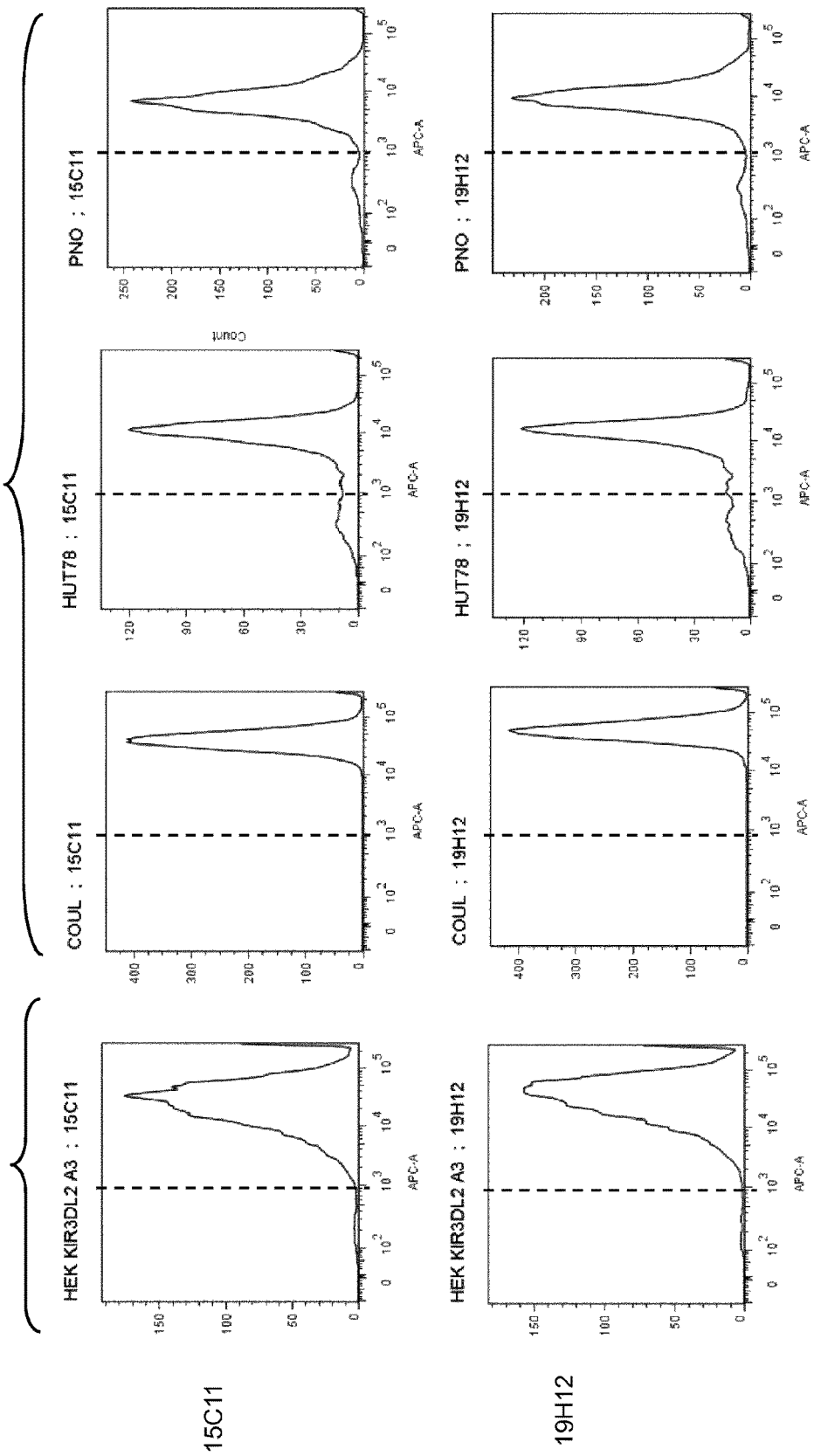
FIGS. 1A and 1B show results of binding to Sézary Syndrome cell lines COUL, HUT78 and PNO for antibodies 15C11, 19H12, and 22B2.

The antibodies of the disclosure are able to directly and specifically target KIR3DL2-expressing cells, notably CD4+, KIR3DL2+ T cells, without targeting other cells such as KIR3DL1+ cells (or KIR3DL2+ KIR3DL1+ cells, KIR3DS1+ cells; or KIR3DS1 KIR3DL2+ cells), and are capable of internalizing into KIR3DL2+ cells (e.g. to deliver a toxic moiety conjugated to the antibody and/or causing the decrease of KIR3DL2 expression on cells to as to inhibit ligand-induced KIR3DL2 signaling. The disclosure provides a number of antibodies having such properties, and which compete with each other for binding to respective regions of KIR3DL2.

KIR3DL2 (CD158k) is a disulphide-linked homodimer of three-Ig domain molecules of about 140 kD, described in Pende et al. (1996) J. Exp. Med. 184: 505-518, the disclosure of which is incorporated herein by reference. KIR3DL1 (CD158e1) is a monomeric molecule of about 70 kD, described in Colonna and Samaridis (1995) Science 268 (5209), 405-408; the HLA binding pocket has been described in Vivian et al. (2011) Nature 479: 401-405. Natural ligands of KIR3DL2 include, inter alia, HLA-A and HLA-B polypeptides, notably HLA-A3 and HLA-A11 (see Hansasuta et al. (2004) Eur. J. Immunol. 34: 1673-1679 and HLA-B27. HLA-B27 (see, e.g., Weiss et al. (1985) Immunobiology 170(5):367-380 for organization, sequence and expression of the HLA-B27 gene, and for HLA-B27 multimers and HLA-B27$_2$ homodimers see Allen et al. (1999) J. Immunol. 162: 5045-5048 and Kollnberger et al (2007) Eur. J. Immunol. 37: 1313-1322. The disclosures of all of the above references are incorporated herein by reference. As used herein, "KIR3D" refers to any KIR3D receptor (e.g. KIR3DL1, KIR3DL2, KIR3DS1) individually or collectively, and the term "KIR3D" may be substituted by the term "KIR3DL1, KIR3DL2 and/or KIR3DS1". Similarly, "KIR3DL" refers to any KIR3DL receptor (e.g. KIR3DL1, KIR3DL2) individually or collectively, and the term "KIR3DL" may be substituted by the term "KIR3DL1 and/or KIR3DL2". The terms "KIR3D", "KIR3DL", "KIR3DL1", "KIR3DL2", "KIR3DS1" each furthermore include any variant, derivative, or isoform of the KIR3D gene or encoded protein(s) to which they refer. Several allelic variants have been reported for KIR3D polypeptides (e.g. KIR3DL2), each of these are encompassed by the respective terms. The amino acid sequence of the mature human KIR3DL2 (allele *002) is shown in SEQ ID NO: 1, corresponding to Genbank accession no. AAB52520 in which the 21 amino acid residue leader sequence has been omitted, and corresponding to IPD KIR database (published by the EMBL-EBI, European Bioinformatics Institute, United Kingdom) accession no. KIR00066. The cDNA of KIR3DL2 (allele *002) is shown in Genbank accession no. U30272. The precursor amino acid sequence (including leader sequence) of a human KIR3DL2 allele *002 is shown in SEQ ID NO: 170, corresponding to Genbank accession no. AAB52520. The amino acid sequence of a human KIR3DL2 allele *001 is shown in SEQ ID NO: 171, corresponding to IPD KIR database accession no. KIR00065. The amino acid sequence of a human KIR3DL2 allele *003 is shown in SEQ ID NO: 172, corresponding to Genbank accession no. AAB36593 and IPD KIR database accession no. KIR00067. The amino acid sequence of a human KIR3DL2 allele *004 is shown in SEQ ID NO: 173, corresponding to IPD KIR database accession no. KIR00068. The amino acid sequence of a human KIR3DL2 allele *005 is shown in SEQ ID NO: 174, corresponding to IPD KIR database accession no. KIR00069. The amino acid sequence of a human KIR3DL2 allele *006 (mature) is shown in SEQ ID NO: 175, corresponding to Genbank accession no. AAK30053 and IPD KIR database accession no. KIR00070. The amino acid sequence of a human KIR3DL2 allele *007 (mature) is shown in SEQ ID NO: 176, corresponding to Genbank accession no. AAK30052 and IPD KIR database accession no. KIR00071. The amino acid sequence of a human KIR3DL2 allele *008 is shown in SEQ ID NO: 177, corresponding to Genbank accession no. AAK30054 and IPD KIR database accession no. KIR00072. The amino acid sequence of a human KIR3DL2 allele *009 is shown in SEQ ID NO: 178, corresponding to IPD KIR database accession no. KIR00457. The amino acid sequence of a human KIR3DL2 allele *011 is shown in SEQ ID NO: 179, corresponding to IPD KIR database accession no. KIR00544. The cDNA encoding a KIR3DL1 (CD158e2) polypeptide (allele *00101) is shown in Genbank accession no. L41269; the encoded amino acid sequence is shown in SEQ ID NO: 180, corresponding to Genbank accession no. AAA69870. Where a leader sequence is present in a particular SEQ ID NO: describing a KIR3DL2 polypeptide sequence (e.g. SEQ ID NOS: 1 and 170 to 180), any reference to amino acid residue positions herein will be to the mature KIR3DL polypeptide.

Provided are methods of using the antigen-binding compounds; for example, provided is a method for inhibiting cell proliferation or activity, for delivering a molecule into a cell (e.g. a toxic molecule, a detectable marker, etc.), for targeting, identifying or purifying a cell, for depleting, killing or eliminating a cell, for reducing cell proliferation, the method comprising exposing a cell, such as a T cell which expresses a KIR3DL polypeptide, to an antigen-binding compound that binds a KIR3DL2 polypeptide. It will be appreciated that for the purposes herein, "cell proliferation" can refer to any aspect of the growth or proliferation of cells, e.g., cell growth, cell division, or any aspect of the cell cycle. The cell may be in cell culture (in vitro) or in a mammal (in vivo), e.g. a mammal suffering from a KIR3DL2-expressing pathology. Also provided is a method for inducing the death of a cell or inhibiting the proliferation or activity of a cell which expresses a KIR3DL2 polypeptide, comprising exposing the cell to an antigen-binding compound that binds a KIR3DL2 polypeptide linked to a toxic agent, in an amount effective to induce death and/or inhibit the proliferation of the cell. Thus, provided is a method for treating a mammal suffering from a proliferative disease, and any condition characterized by a pathogenic expansion or activation of cells expressing of a KIR3DL2 polypeptide, the method comprising administering a pharmaceutically effective amount of an antigen-binding compound disclosed herein to the mammal. Examples of such conditions include Sézary Syndrome, Mycosis Fungoides, CTCL, and autoimmune or inflammatory conditions, e.g. arthritis, cardiovascular disease. Optionally such pathogenically expanded cells express KIR3DL2 but do not prominently express KIR3DL1 (e.g. no more than 20%, 40%, 50% or 60% of pathogenic cells express KIR3DL1, these conditions benefiting particularly from selective antibodies.

Several KIR3DL2-expressing disorders, particularly T and NK cell mediated disorders can be treated or diagnosed using the methods and compositions of the disclosure. The disorders may be for example CD4+ T cell malignancies such as CTCL, MF or SS, or autoimmune or inflammatory disorders where the elimination or inhibiting the activity and/or proliferation of T and/or NK cells would be useful. CD4+ T cells includes for example activated CD4+ T cells, Th17 T cells, CD4+ T cells expressing or not one or more other markers (e.g. CD2+, CD3+, CD5+, CD8−, CD28+, CD28−, CD45RO+ and TCRαβ+). CD4+CD28− T cells, for example, are known to be capable of expressing KIR3DL2 and are present in high frequencies of clonally expanded cells in some autoimmune and inflammatory disorders but are rare in healthy individuals. These T cells can be cytotoxic, secrete large amounts of IFN-gamma, and proliferate upon stimulation with autologous adherent mononuclear cells.

The antibodies of the disclosure have the advantage of binding across different KIR3DL2 alleles permitting a broad use to treat, characterize and diagnose diseases. Cutaneous and circulating MF/SS cells have been reported to not express preferential alleles among nine KIR3DL2 alleles tested. Thirteen alleles have also been described to date. Whereas KIR3DL2 is expressed on a minor subset of NK cells and on rare CD8+ T cells in healthy persons, it appears to be restricted to CTCL tumor CD4+ T cells in MF/SS patients. Other receptors that are usually observed at the surface of NK cells (such as p58.1, p58.2, p70KIRs, CD94/NKG2A) are not found at the surface of malignant CD4+ T cells (Bahler D. W. et al., (2008) Cytometry B Clin. Cytom. 74(3):156-62). SS cells are also typically characterized, in addition to CD4+, by having a mature T lymphocyte phenotype, CD2+, CD3+, CD5+, CD8−, CD28+, CD45RO+ and TCRαβ+.

The methods and compositions of the disclosure can be used in the treatment of autoimmune and inflammatory conditions characterized by KIR3DL2 expression, by eliminating KIR3DL2-expressing cells and/or by inhibiting the biological activity KIR3DL2-expressing cells (i.e. by blocking KIR3DL2 signaling induced by its natural ligands). The antibodies of the disclosure have the advantage of decreasing KIR3DL2 expression on cells such that ligand-induced KIR3DL2 signaling is decreased for all of the various natural ligands (e.g., various HLA ligands). Inhibiting the biological activity KIR3DL2-expressing cells can comprise for example decreasing the proliferation of KIR3DL2-expressing cells, decreasing the reactivity or cytotoxicity of KIR3DL2-expressing cells toward target cells, decreasing activation, activation markers (e.g. CD107 expression) and/or cytokine production (e.g., IFNγ production) by a KIR3DL2-expressing cell, and/or decreasing the frequency in vivo of such activated, reactive, cytotoxic and/or activated KIR3DL2-expressing cells.

For example, it has been shown that several such disorders are mediated at least in part by CD4+ T cells, including particular CD4+CD28null T cells. Activation of CD4+ T cells is generally thought to be governed by interplay between stimulatory and inhibitory receptors, where a predominance of stimulatory signals favors autoimmune reactions. Chan et al. ((2005) Arthrit. Rheumatism 52(11): 3586-3595 report that increased number of peripheral blood and synovial fluid CD4+ T cells and NK cells express KIR3DL2 in spondyloarthritis. In patients with rheumatoid arthritis, expression of the critical costimulatory molecule, CD28, is frequently lost. Instead, a CD4$^+$ T cell population which lacks CD28 (CD4$^+$ CD28$^-$ T cells) express killer immunoglobulin-like receptors (KIRs). CD4+CD28$^{null}$ T cells in particular have been reported to express KIR3D polypeptides. Compared with their CD28$^+$ counterparts, CD4+CD28-cells produce significantly higher levels of IFN-γ giving them the ability to function as proinflammatory cells. CD4$^+$ CD28$^{null}$ T cell clones persist for years in circulation. These T cells are known to differ from CD28$^+$ T cells by being resistant to Fas-mediated apoptosis upon cross-linking of CD3. CD28$^{null}$ T cells progress through the cell cycle, and cells at all stages of the cell cycle are resistant to apoptosis, unlike their CD28$^+$ counterparts. Dysregulation of apoptotic pathways in CD4+CD28$^{null}$ T cells has been shown to favor their clonal outgrowth and maintenance in vivo. Namekawa et al. ((2000) J. Immunol. 165:1138-1145 report that KIR, including KIR3DL2, was present on CD4+CD28null T cells expanded in rheumatoid arthritis. Rheumatoid arthritis involves lymphocyte infiltrates, inflammatory mediators, and synovial hyperplasia resulting from aggressive proliferation of fibroblast-like synoviocytes and macrophages. Prognoses of joint erosions and disease severity correlate with high frequencies of clonally expanded CD4$^+$ CD28$^-$ T cells. Lamprecht et al. (2001) Thorax 56:751-757 report recruitment of CD4$^+$ CD28$^-$ T cells in Wegener's granulomatosis. Markovic-Plese et al. (2001) J Clin Invest. 108: 1185-1194 report the presence of CD4+CD28-costimulation-independent T cells in the CNS, and their associate with multiple sclerosis. The methods and compositions herein can therefore be used in the treatment or prevention of Wegener's granulomatosis, multiple sclerosis or other central nervous system inflammatory or autoimmune disorders, arthritis, or other rheumatic disorders characterized by inflammation.

CD4$^+$ CD28$^-$ T cells have also been associated with cardiovascular disorders. Betjes et al. (2008) Kidney International 74, 760-767 report that the increased risk for atherosclerotic disease in patients with Cytomegalovirus (CMV) seropositivity is associated with age-dependent increase of CD4$^+$ CD28$^-$ T cells, which can comprise over half of the circulating CD4 T cells in individuals. Patients over 50 years of age were reported to have a 50-fold higher percentage of CD4$^+$ CD28$^-$ T cells compared to CMV seronegative patients and a 5-fold higher percentage when compared to seropositive healthy controls. Nakajima et al. ((2003) Circ. Res. 93:106-113) report de novo expression of KIR in acute coronary syndrome, where CD4+ T cells from patients with acute coronary syndrome (ACS) express multiple KIR whereas normal CD4+CD28null T cells from healthy donors do not express KIR. Yen et al. Journal of Experimental Medicine, Volume 193, Number 10, May 21, 2001 1159-1168 studied CD4+CD28$^{null}$ T cell clones established from patients with rheumatoid vasculitis for the expression of inhibitory and stimulatory KIR by RT-PCR. In patients with rheumatoid arthritis and a patient with ACS, the expression patterns favored the inhibitory KIR, including KIR3DL2, whereas expression of stimulatory receptors was highly restricted to KIR2DS2. The methods and compositions of the disclosure can therefore be used in the treatment or prevention of cardiovascular disorders, e.g. ACS, atherosclerotic disease, rheumatoid vasculitis, characterized by inflammation.

Bowness et al (2011) J. Immunol. 186: 2672-2680 report that KIR3DL2+CD4 T cells account for the majority of IL-23R expression by peripheral blood CD4 T cells, and that such KIR3DL2+ cells of the Th17 type produce more IL-17 in the presence of IL-23. Despite KIR3DL2+ cells comprising a mean of just 15% of CD4 T in the peripheral blood of SpA patients, this subset accounted for 70% of the observed increase in Th17 numbers in SpA patients compared with control subjects. TCR-stimulated peripheral blood KIR3DL2+CD4 T cell lines from SpA patients secreted 4-fold more IL-17 than KIR3DL2+ lines from controls or KIR3DL2-CD4 T cells.

Provided are novel methods for producing and using antibodies and other compounds suitable for the treatment of disorders (e.g. cancers, inflammatory and autoimmune disorders) where eliminating KIR3DL2-expressing cells would be useful. Antibodies, antibody derivatives, antibody fragments, and cell producing them are encompassed, as are methods of producing the same and methods of treating patients using the antibodies and compounds.

Since the present antibodies are specific for KIR3DL2, they can be used for a range of purposes, including purifying KIR3DL2 or KIR3DL2-expressing cells, modulating (e.g. activating or inhibiting) KIR3DL2 receptors in vitro, ex vivo, or in vivo, targeting KIR3DL2-expressing cells for destruction in vivo, or specifically labeling/binding KIR3DL2 in vivo, ex vivo, or in vitro, including for methods such as immunoblotting, IHC analysis, i.e. on frozen biopsies, FACS analysis, and immunoprecipitation.

Definitions

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can optionally be replaced by "consisting essentially of" or by "consisting of".

"Treatment of a proliferative disease" or "treatment of a tumor", or "treatment of cancer" or the like, with reference to anti-KIR3DL2 binding agent (e.g. antibody), includes, but is not limited to: (a) method of treatment of a proliferative disease, said method comprising the step of administering (for at least one treatment) an anti-KIR3DL2 binding agent, (e.g., in a pharmaceutically acceptable carrier material) to a warm-blooded animal, especially a human, in need of such treatment, in a dose that allows for the treatment of said disease (a therapeutically effective amount), e.g., in a dose (amount) as specified hereinabove and herein below; (b) the use of an anti-KIR3DL2 binding agent for the treatment of a proliferative disease, or an anti-KIR3DL2 binding agent, for use in said treatment (especially in a human); (c) the use of an anti-KIR3DL2 binding agent, for the manufacture of a pharmaceutical preparation for the treatment of a proliferative disease, a method of using an anti-KIR3DL2 binding agent for the manufacture of a pharmaceutical preparation for the treatment of a proliferative disease, comprising admixing an anti-KIR3DL2 binding agent with a pharmaceutically acceptable carrier, or a pharmaceutical preparation comprising an effective dose of an anti-KIR3DL2 binding agent that is appropriate for the treatment of a proliferative disease; or (d) any combination of a), b), and c), in accordance with the subject matter allowable for patenting in a country where this application is filed. In cases where a particular disease (e.g., inflammatory or autoimmune disease) or a specific tumor (e.g. CTCL) are mentioned instead of "proliferative disease", categories a) to e) are also encompassed, meaning that the respective disease can be filled in under a) to e) above instead of "proliferative disease", in accordance with the patentable subject matter.

The terms "cancer" and "tumor" as used herein are defined as a new growth of cells or tissue comprising uncontrolled and progressive multiplication. In a specific embodiment, upon a natural course the cancer is fatal. In specific embodiments, a cancer is invasive, metastatic, and/or anaplastic (loss of differentiation and of orientation to one another and to their axial framework).

"Autoimmune" disorders include any disorder, condition, or disease in which the immune system mounts a reaction against self cells or tissues, due to a breakdown in the ability to distinguish self from non-self or otherwise. Examples of autoimmune disorders include rheumatoid arthritis, rheumatoid vasculitis, systemic lupus erythematosus, multiple sclerosis, Wegener's granulomatosis, and spondyloarthritis, and others. An "inflammatory disorder" includes any disorder characterized by an unwanted immune response. Autoimmune and inflammatory disorders can involve any component of the immune system, and can target any cell or tissue type in the body.

The term "biopsy" as used herein is defined as removal of a tissue from an organ (e.g., a joint) for the purpose of examination, such as to establish diagnosis. Examples of types of biopsies include by application of suction, such as through a needle attached to a syringe; by instrumental removal of a fragment of tissue; by removal with appropriate instruments through an endoscope; by surgical excision, such as of the whole lesion; and the like.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains, respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed herein, with IgG being particularly preferred, because they are the most common antibodies in the physiological situation and because they are most easily made in a laboratory setting. Optionally, the antibody is a monoclonal antibody. Particularly preferred are humanized, chimeric, human, or otherwise-human-suitable antibodies. "Antibodies" also includes any fragment or derivative of any of the herein described antibodies.

The term "specifically binds to" means that an antibody can bind, optionally in a competitive binding assay, to the binding partner, e.g. KIR3DL2, as assessed using either recombinant forms of the proteins, epitopes therein, or native proteins present on the surface of isolated target cells. Competitive binding assays and other methods for determining specific binding are further described below and are well known in the art.

When an antibody is said to "compete with" a particular monoclonal antibody (e.g. 15C11, 19H12, 22B2, 18B10, 12B11 or 13H1), it means that the antibody competes with the monoclonal antibody in a binding assay using either recombinant KIR3DL2 molecules or surface expressed KIR3DL2 molecules. For example, if a test antibody reduces the binding of 15C11, 19H12, 22B2, 18B10, 12B11 or 13H1 to a KIR3DL2 polypeptide or KIR3DL2-expressing cell in a binding assay, the antibody is said to "compete", respectively, with 15C11, 19H12, 22B2, 18B10, 12B11 or 13H.

The term "affinity", as used herein, means the strength of the binding of an antibody to an epitope. The affinity of an antibody is given by the dissociation constant Kd, defined as $[Ab] \times [Ag]/[Ab\text{-}Ag]$, where [Ab-Ag] is the molar concentration of the antibody-antigen complex, [Ab] is the molar concentration of the unbound antibody and [Ag] is the molar concentration of the unbound antigen. The affinity constant $K_a$ is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of surface plasmon resonance (SPR) screening (such as by analysis with a BIAcore™ SPR analytical device).

As used herein, a "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "intracellular internalization" refers to the molecular, biochemical and cellular events associated with the process of translocating a molecule from the extracellular surface of a cell to the intracellular surface of a cell. The processes responsible for intracellular internalization of molecules are well-known and can involve, inter alia, the internalization of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule). Thus, "inducing and/or increasing intracellular internalization" comprises events wherein intracellular internalization is initiated and/or the rate and/or extent of intracellular internalization is increased.

The term "depleting", with respect to KIR3DL2-expressing cells means a process, method, or compound that can kill, eliminate, lyse or induce such killing, elimination or lysis, so as to negatively affect the number of KIR3DL2-expressing cells present in a sample or in a subject.

The terms "immunoconjugate", "antibody conjugate", "antibody drug conjugate", and "ADC" are used interchangeably and refer to an antibody that is conjugated to another moiety (e.g. any non-antibody moiety, a therapeutic agent or a label).

The term "agent" is used herein to denote a chemical compound, a mixture of chemical compounds, a biological macromolecule, or an extract made from biological materials. The term "therapeutic agent" refers to an agent that has biological activity.

The terms "toxic agent" and "cytotoxic agent" encompass any compound that can slow down, halt, or reverse the proliferation of cells, decrease their activity in any detectable way, or directly or indirectly kill them. Cytotoxic agents may cause cell death primarily by interfering directly with the cell's functioning, and include, but are not limited to, alkylating agents, tumor necrosis factor inhibitors, intercalators, microtubule inhibitors, kinase inhibitors, proteasome inhibitors and topoisomerase inhibitors. A "toxic payload" as used herein refers to a sufficient amount of cytotoxic agent which, when delivered to a cell results in cell death. Delivery of a toxic payload may be accomplished by administration of a sufficient amount of immunoconjugate comprising an antibody or antigen binding fragment and a cytotoxic agent. Delivery of a toxic payload may also be accomplished by administration of a sufficient amount of an immunoconjugate comprising a cytotoxic agent, wherein the immunoconjugate comprises a secondary antibody or antigen binding fragment thereof which recognizes and binds an antibody or antigen binding fragment.

The term "human-suitable", with respect to an antibody, refers to any antibody, derivatized antibody, or antibody fragment that can be safely used in humans for, e.g. the therapeutic methods described herein. Human-suitable antibodies include all types of humanized, chimeric, or fully human antibodies, or any antibodies in which at least a portion of the antibodies is derived from humans or otherwise modified so as to avoid the immune response that is generally provoked when native non-human antibodies are used.

For the purposes herein, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.).

The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils.

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

As used herein, "T cells" refers to a sub-population of lymphocytes that mature in the thymus, and which display, among other molecules T cell receptors on their surface. T cells can be identified by virtue of certain characteristics and biological properties, such as the expression of specific surface antigens including the TCR, CD4 or CD8, optionally CD4 and IL-23R, the ability of certain T cells to kill tumor or infected cells, the ability of certain T cells to activate other cells of the immune system, and the ability to release protein molecules called cytokines that stimulate or inhibit the immune response. Any of these characteristics and activities can be used to identify T cells, using methods well known in the art. As used herein, "active" or "activated" T cells designate biologically active T cells, more particularly T cells having the capacity of cytolysis or of stimulating an immune response by, e.g., secreting cytokines. Active cells can be detected in any of a number of well-known methods, including functional assays and expression-based assays such as the expression of cytokines such as TNF-alpha or IL-17A.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl, propynyl (propargyl), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1] heptane, bicyclo [2.2.2]octane and bicyclo[3.2.2]nonane.

Examples of monocyclic carbocycles include, but are not limited to, cyclopropyl, cyclobutyl, cyclopentyl, 1-cyclopent-1-enyl, 1-cyclopent-2-enyl, 1-cyclopent-3-eny, cyclohexyl, 1-cyclohex-1-enyl, 1-cyclohex-2-enyl, 1-cyclohex-3-enyl, cyciohexadienyl, cycloheptyl, cyclooctyl, cyciononyl, cyclodecyl, eycloundecyl, cyclododecyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene. anthracene, biphenyl, indenyl, indanyl, 1,2-dihydronaphthalene. 1,2,3,4-tet[tau]ahydronaphthyl, and the like. Aryl groups are optionally substituted independently with one or more substituents described herein. The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-. 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl). imidazolyl, imidazopyridinyl, pyrimidinyl (including, for example, 4-hydroxypyrimidinyl), pyrazolyl. triazolyl, pyrazinyl, tetrazolyl, furyl, thienyl, isoxazolyl, thiazolyl, oxazolyl, isothiazolyl, pynrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran. thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridinc, position 2, 3, or 4 of an azetidine, position 2, 3, 4, 5, 6, 7, or 8 of a quinoline or position 1, 3, 4, 5, 6, 7, or 8 of an isoquinoline. By way of example and not limitation, nitrogen bonded heterocycles or heteroaryls are bonded at position 1 of an aziridine. azetidine, pyrrole, pyrrolidine, 2-pyrroline, 3-pyrroline, imidazole, imidazolidine, 2-imidazoline, 3-imidazoline, pyrazole, pyrazoline. 2-pyrazoline, 3-pyrazoitne, piperidine, piperazine, indole, indoline, 1H-indazole, position 2 of a isoindole, or isoindoline, position 4 of a morpholine, and position 9 of a carbazole, or beta-carboline.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene ($-CH_2-$) 1,2-ethyl ($-CH_2CH_2-$), 1,3-propyl ($-CH_2CH_2CH_2-$), 1,4-butyl ($-CH_2CH_2CH_2CH_2-$), and the like.

A "$C_1$-$C_{10}$ alkylene" is a straight chain, saturated hydrocarbon group of the formula $-(CH_2)_{1-10}-$. Examples of a $C_1$-$C_{10}$ alkylene include methylene, ethylene, propylene, butylene, pentylene, hexylene, heptylene, ocytylene, nonylene and decalene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene ($-CH=CH-$).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene ($-C\equiv C-$), propargyl ($-CH_2C\equiv C-$), and 4-pentynyl ($-CH_2CH_2CH_2C\equiv C-$).

An "arylene" is an aryl group which has two covalent bonds and can be in the ortho, meta, or para configurations as shown in the following structures:

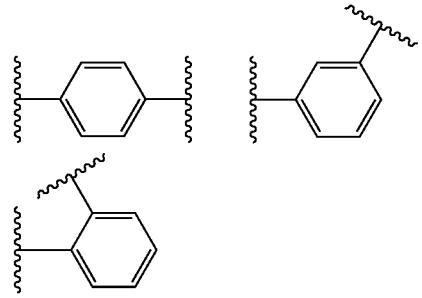

in which the phenyl group can be unsubstituted or substituted with up to four groups including, but not limited to, $-C_1$-$C_8$ alkyl, $-O-(C_1$-$C_8$ alkyl), -aryl, $-C(O)R'$, $-OC(O)R'$, $-C(O)OR'$, $-C(O)NH_2$, $-C(O)NHR'$, $-C(O)N(R')_2$, $-NHC(O)R'$, $-S(O)_2R'$, $-S(O)R'$, $-OH$, -halogen, $-N_3$, $-NH_2$, $-NH(R')$, $-N(R')_2$ and $-CN$; wherein each R' is independently selected from H. $-C_1$-$C_8$ alkyl and aryl.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S). for example: a bicyclo [4,5], [5,5], [5,6], or [6,6] system.

As used herein, the term antibody that "binds" a polypeptide or epitope designates an antibody that binds said determinant with specificity and/or affinity.

Antibodies

The antibodies of the disclosure are antibodies that bind human KIR3DL2. In an embodiment, the antibodies selectively bind KIR3DL2 and do not bind KIR3DL1. In another embodiment, the antibodies bind domains D0 and/or D2 of KIR3DL2. In one embodiment, the antibodies have an affinity (e.g. bivalent binding affinity) for human KIR3DL2 characterized by a $K_D$ of less than $10^{-9}$ M, optionally less than $10^{-10}$ M.

In another embodiment, the antibodies are capable of internalizing into a KIR3DL2-expressing cell rapidly and efficiently, optionally wherein the antibodies induce receptor (KIR3DL2)-mediated internalization of the receptor-antibody complex. Optionally, the antibodies are capable of delivering an agent of interest (e.g. a toxic agent, a detectable agent) into the cytoplasm of a KIR3DL2-expressing cell.

In one embodiment, the antibody competes for binding to the KIR3DL2 polypeptide with any one or more of antibodies 15C11, 19H12, 22B2, 18B10, 12B11 or 13H1. Optionally the antibody recognizes, binds to, or has immunospecificity for substantially or essentially the same, or the same, epitope or "epitopic site" on a KIR3DL2 polypeptide.

Antibody Epitopes

In one aspect, the antibodies bind substantially the same epitope as antibody 15C11, 19H12, 22B2, 18B10, 12B11 or 13H1. In another embodiment, the antibodies at least partially overlaps, or includes at least one residue in the segment corresponding to residues 1-192, residues 1-98, or residues 99-192 of the KIR3DL2 polypeptide of SEQ ID NO: 1 (or a subsequence thereof). In one embodiment, all key residues of the epitope is in a segment corresponding to residues 99-192 or residues 99-292 of the KIR3DL2 polypeptide of SEQ ID NO: 1. In one embodiment, the antibodies bind an epitope comprising 1, 2, 3, 4, 5, 6, 7 or more residues in the segment corresponding to residues 99-192 or 99-292 of the KIR3DL2 polypeptide of SEQ ID NO: 1. Optionally the residues bound by the antibody are present on the surface of the of the KIR3DL2 polypeptide.

In another embodiment, the antibodies bind one or more amino acids present on the surface of the KIR3DL2 polypeptide within the epitopes bound by the anti-KIR3DL2 antibodies of the disclosure, optionally, the antibodies bind 1, 2, 3, 4, 5, 6, 7 or more residues selected from the group consisting of: M128, E130, H131, R145, V147, Q149, I150, V178, P179, H180 and/or S181 of SEQ ID NO: 1, or selected from the group consisting of: F9, S11, R13, A25, Q27, Q56, E57, I60 and/or G62 of SEQ ID NO: 1.

Optionally, the antibodies bind an epitope comprising residues P179 and/or residue S181 of SEQ ID NO: 1. Optionally, the antibodies bind an epitope comprising residues V178 and/or residue H180 of SEQ ID NO: 1. Optionally, the antibodies bind an epitope comprising residues E130, H131 and/or R145 of SEQ ID NO: 1. Optionally, the antibodies bind an epitope comprising residues M128 and/or residue I150 of SEQ ID NO: 1. Optionally, the antibodies bind to an epitope comprising 1, 2, 3, 4, 5, 6 or 7 or more residues selected from the group consisting of: M128, E130, H131, R145, V147, Q149, I150, V178, P179, H180 and/or S181 of SEQ ID NO: 1. Optionally, the antibodies bind to an epitope comprising 1, 2, 3, 4, 5, 6 or 7 or more residues selected from the group consisting of: F9, S11, R13, A25, Q27, Q56, E57, I60 and/or G62 of SEQ ID NO: 1. Optionally, the antibodies do not bind, or do not bind principally, on the face of the human KIR3DL2 polypeptide that contains the HLA-binding pocket.

The Examples section herein describes the construction of a series of mutant human KIR3DL2 polypeptides. Binding of anti-KIR3DL2 antibody to cells transfected with the KIR3DL2 mutants was measured and compared to the ability of anti-KIR3DL2 antibody to bind wild-type KIR3DL2 polypeptide (SEQ ID NO: 1). A reduction in binding between an anti-KIR3DL2 antibody and a mutant KIR3DL2 polypeptide as used herein means that there is a reduction in binding affinity (e.g., as measured by known methods such FACS testing of cells expressing a particular mutant, or by Biacore testing of binding to mutant polypeptides) and/or a reduction in the total binding capacity of the anti-KIR3DL2 antibody (e.g., as evidenced by a decrease in Bmax in a plot of anti-KIR3DL2 antibody concentration versus polypeptide concentration). A significant reduction in binding indicates that the mutated residue is directly involved in binding to the anti-KIR3DL2 antibody or is in close proximity to the binding protein when the anti-KIR3DL2 antibody is bound to KIR3DL2. An antibody epitope will thus optionally include such residue and may include additional residues adjacent to such residue.

In some embodiments, a significant reduction in binding means that the binding affinity and/or capacity between an anti-KIR3DL2 antibody and a mutant KIR3DL2 polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type KIR3DL2 polypeptide (e.g., the polypeptide shown in SEQ ID NO: 1). In certain embodiments, binding is reduced below detectable limits. In some embodiments, a significant reduction in binding is evidenced when binding of an anti-KIR3DL2 antibody to a mutant KIR3DL2 polypeptide is less than 50% (e.g., less than 45%, 40%, 35%, 30%, 25%, 20%, 15% or 10%) of the binding observed between the anti-KIR3DL2 antibody and a wild-type KIR3DL2 polypeptide (e.g., the extracellular domain shown in SEQ ID NO: 1). Such binding measurements can be made using a variety of binding assays known in the art. A specific example of one such assay is described in the Example section.

In some embodiments, anti-KIR3DL2 antibodies are provided that exhibit significantly lower binding for a mutant KIR3DL2 polypeptide in which a residue in a wild-type KIR3DL2 polypeptide (e.g., SEQ ID NO: 1) is substituted. In the shorthand notation used here, the format is: Wild type residue: Position in polypeptide: Mutant residue, with the numbering of the residues as indicated in SEQ ID NO: 1.

In some embodiments, the antibodies have reduced binding to a KIR3DL2 polypeptide having a substitution at residues M128, E130, H131, R145, V147, Q149, I150, V178, P179, H180 and/or S181 of SEQ ID NO: 1. In some embodiments, the antibodies have reduced binding to a KIR3DL2 polypeptide having a substitution at F9, S11, R13, A25, Q27, Q56, E57, I60 and/or G62 of SEQ ID NO: 1.

In some embodiments, an anti-KIR3DL2 antibody binds a wild-type KIR3DL2 polypeptide having a sequence of SEQ ID NO: 1 but has decreased binding to a mutant KIR3DL2 polypeptide having any one or more (e.g., 1, 2, 3 or 4) of the following mutations: P179T, S181T, V178A, H180S, E130S, H131S and/or R145S. Optionally, binding to the mutant KIR3DL2 is significantly reduced compared to binding to the wild-type KIR3DL2. In another embodiment, the antibodies are able of internalizing into a KIR3DL2-expressing cell rapidly and efficiently.

In one embodiment, the antibodies bind an epitope comprising residues R13, A25, and/or Q27. Optionally, the antibodies bind an epitope comprising residues R13, A25, and/or Q27, as well residues 160 and/or G62. Optionally, the antibodies further binds residues Q56 and/or E57. Optionally, the antibodies further binds residues F9 and/or S11.

In the shorthand notation used herein, the format is: Wild type residue: Position in polypeptide: Mutant residue, with the numbering of the residues as indicated in SEQ ID NO: 1.

In some embodiments, anti-KIR3DL2 antibodies are provided that exhibit significantly lower binding for a mutant KIR3DL2 polypeptide in which a residue in a segment corresponding to residues 1-98, residues 99-292, or residues 99-192 (or a subsequence thereof) in a wild-type KIR3DL2 polypeptide (e.g., SEQ ID NO: 1) is substituted with a different amino acid.

Producing Anti-KIR3DL2 Antibodies

The antibodies of the disclosure may be produced by a variety of techniques known in the art. Typically, they are produced by immunization of a non-human animal, optionally a mouse, with an immunogen comprising a KIR3DL2 polypeptide, optionally a human KIR3DL2 polypeptide. The KIR3DL2 polypeptide may comprise the full length sequence of a human KIR3DL2 polypeptide, or a fragment or derivative thereof, typically an immunogenic fragment, i.e., a portion of the polypeptide comprising an epitope exposed on the surface of cells expressing a KIR3DL2 polypeptide, optionally the epitope recognized by the 15C11, 19H12, 22B2, 18B10, 12B11 or 13H1 antibody. Such fragments typically contain at least about 7 or 10 consecutive amino acids of the mature polypeptide sequence. Fragments typically are essentially derived from the extra-cellular domain of the receptor. In one embodiment, the immunogen comprises a wild-type human KIR3DL2 polypeptide in a lipid membrane, typically at the surface of a cell. In a specific embodiment, the immunogen comprises intact cells, particularly intact human cells, optionally treated or lysed. In another preferred embodiment, the polypeptide is a recombinant KIR3DL2 polypeptide. In one embodiment, the immunogen comprises intact SS or MF cells, particularly intact human malignant CD4+ T cells, or CD4+CD28- T cells, optionally treated or lysed. In another preferred embodiment, the polypeptide is a recombinant dimeric KIR3DL2 polypeptide.

The step of immunizing a non-human mammal with an antigen may be carried out in any manner well known in the art for stimulating the production of antibodies in a mouse (see, for example, E. Harlow and D. Lane, Antibodies: A Laboratory Manual, Cold Spring Harbor Laboratory Press, Cold Spring Harbor, N.Y. (1988), the entire disclosure of which is herein incorporated by reference). The immunogen is suspended or dissolved in a buffer, optionally with an adjuvant, such as complete or incomplete Freund's adjuvant. Methods for determining the amount of immunogen, types of buffers and amounts of adjuvant are well known to those of skill in the art and are not limiting in any way. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with an adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be used as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with KIR3DL2 polypeptides.

In an alternate embodiment, lymphocytes from a non-immunized non-human mammal are isolated, grown in vitro, and then exposed to the immunogen in cell culture. The lymphocytes are then harvested and the fusion step described below is carried out.

For preferred monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, U.S.A., X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are optionally from littermates of the non-human mammal used to isolate splenocytes and are typically primed with incomplete Freund's adjuvant or the like several days before plating the hybridomas. Fusion methods are described in Goding, "Monoclonal Antibodies: Principles and Practice," pp. 59-103 (Academic Press, 1986), the disclosure of which is herein incorporated by reference.

The cells are allowed to grow in the selection media for sufficient time for colony formation and antibody production. This is usually between about 7 and about 14 days.

The hybridoma colonies are then assayed for the production of antibodies that specifically bind to KIR3DL2 polypeptide gene products, optionally the epitope specifically recognized by antibody 15C11, 19H12, 22B2, 18B10, 12B11 or 13H1. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody.

Hybridomas that are confirmed to produce a monoclonal antibody can be grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Positive wells with a single apparent colony are typically re-cloned and re-assayed to insure only one monoclonal antibody is being detected and produced.

Antibodies may also be produced by selection of combinatorial libraries of immunoglobulins, as disclosed for instance in (Ward et al. Nature, 341 (1989) p. 544, the entire disclosure of which is herein incorporated by reference).

The identification of one or more antibodies that bind(s) to KIR3DL2, particularly substantially or essentially the same epitope as monoclonal antibody 15C11, 19H12, 22B2, 18B10, 12B11 or 13H1, can be readily determined using any one of a variety of immunological screening assays in which antibody competition can be assessed. Many such assays are routinely practiced and are well known in the art (see, e. g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control (15C11, 19H12, 22B2, 18B10, 12B11 or 13H1, for example) and test antibodies are admixed (or pre-adsorbed) and applied to a sample containing KIR3DL2 polypeptides. Protocols based upon western blotting and the use of BIACORE analysis are suitable for use in such competition studies.

In certain embodiments, one pre-mixes the control antibodies (15C11, 19H12, 22B2, 18B10, 12B11 or 13H1, for example) with varying amounts of the test antibodies (e.g., about 1:10 or about 1:100) for a period of time prior to applying to the KIR3DL2 antigen sample. In other embodiments, the control and varying amounts of test antibodies can simply be admixed during exposure to the KIR3DL2 antigen sample. As long as one can distinguish bound from free antibodies (e. g., by using separation or washing techniques to eliminate unbound antibodies) and 15C11, 19H12, 22B2, 18B10, 12B11 or 13H1 from the test antibodies (e. g., by using species-specific or isotype-specific secondary antibodies or by specifically labeling 15C11, 19H12, 22B2, 18B10, 12B11 or 13H1 with a detectable label) one can determine if the test antibodies reduce the binding of 15C11, 19H12, 22B2, 18B10, 12B11 or 13H1 to the antigens, indicating that the test antibody recognizes substantially the same epitope as 15C11, 19H12, 22B2, 18B10, 12B11 or 13H1. The binding of the (labeled) control antibodies in the absence of a completely irrelevant antibody can serve as the control high value. The control low value can be obtained by incubating the labeled (15C11, 19H12, 22B2, 18B10, 12B11 or 13H1) antibodies with unlabelled antibodies of exactly the same type (15C11, 19H12, 22B2, 18B10, 12B11 or 13H1), where competition would occur and reduce binding of the labeled antibodies. In a test assay, a significant reduction in labeled antibody reactivity in the presence of a test antibody is indicative of a test antibody that recognizes substantially the same epitope, i.e., one that "cross-reacts" or competes with the labeled (15C11, 19H12, 22B2, 18B10, 12B11 or 13H1) antibody. Any test antibody that reduces the binding of 15C11, 19H12, 22B2, 18B10, 12B11 or 13H1 to KIR3DL2 antigens by at least about 50%, such as at least about 60%, or at least about 80% or 90% (e. g., about 65-100%), at any ratio of 15C11, 19H12, 22B2, 18B10, 12B11 or 13H1:test antibody between about 1:10 and about 1:100 is considered to be an antibody that binds to substantially the same epitope or determinant as 15C11, 19H12, 22B2, 18B10, 12B11 or 13H1. Optionally, such test antibody will reduce the binding of 15C11, 19H12, 22B2, 18B10, 12B11 or 13H1 to the KIR3DL2 antigen by at least about 90% (e.g., about 95%).

Competition can also be assessed by, for example, a flow cytometry test. In such a test, cells bearing a given KIR3DL2 polypeptide can be incubated first with 15C11, 19H12, 22B2, 18B10, 12B11 or 13H1, for example, and then with the test antibody labeled with a fluorochrome or biotin. The antibody is said to compete with 15C11, 19H12, 22B2, 18B10, 12B11 or 13H1 if the binding obtained upon preincubation with a saturating amount of 15C11, 19H12, 22B2, 18B10, 12B11 or 13H1 is about 80%, about 50%, about 40% or less (e.g., about 30%, 20% or 10%) of the binding (as measured by mean of fluorescence) obtained by the antibody without preincubation with 15C11, 19H12, 22B2, 18B10, 12B11 or 13H1. Alternatively, an antibody is said to compete with 15C11, 19H12, 22B2, 18B10, 12B11 or 13H1 if the binding obtained with a labeled 15C11, 19H12, 22B2, 18B10, 12B11 or 13H1 antibody (by a fluorochrome or biotin) on cells preincubated with a saturating amount of test antibody is about 80%, about 50%, about 40%, or less (e. g., about 30%, 20% or 10%) of the binding obtained without preincubation with the test antibody.

A simple competition assay in which a test antibody is pre-adsorbed and applied at saturating concentration to a surface onto which a KIR3DL2 antigen is immobilized may also be employed. The surface in the simple competition assay is optionally a BIACORE chip (or other media suitable for surface plasmon resonance analysis). The control antibody (e.g., 15C11, 19H12, 22B2, 18B10, 12B11 or 13H1) is then brought into contact with the surface at a KIR3DL2-saturating concentration and the KIR3DL2 and surface binding of the control antibody is measured. This binding of the control antibody is compared with the binding of the control antibody to the KIR3DL2-containing surface in the absence of test antibody. In a test assay, a significant reduction in binding of the KIR3DL2-containing surface by the control antibody in the presence of a test antibody indicates that the test antibody recognizes substantially the same epitope as the control antibody such that the test antibody "cross-reacts" with the control antibody. Any test antibody that reduces the binding of control (such as 15C11, 19H12, 22B2, 18B10, 12B11 or 13H1) antibody to a KIR3DL2 antigen by at least about 30%, or about 40%, can be considered to be an antibody that binds to substantially the same epitope or determinant as a control (e.g., 15C11, 19H12, 22B2, 18B10, 12B11 or 13H1). Optionally such a test antibody will reduce the binding of the control antibody (e.g., 15C11, 19H12, 22B2, 18B10, 12B11 or 13H1) to the KIR3DL2 antigen by at least about 50% (e. g., at least about 60%, at least about 70%, or more). It will be appreciated that the order of control and test antibodies can be reversed: that is, the control antibody can be first bound to the surface and the test antibody is brought into contact with the surface thereafter in a competition assay. Optionally, the antibody having higher affinity for the KIR3DL2 antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

Optionally, monoclonal antibodies that recognize a KIR3DL2 epitope will react with an epitope that is present on a substantial percentage of or even all relevant cells, e.g., malignant CD4+T cells, cells from a SS or MF patient, but will not significantly react with other cells, i.e., cells that do not express KIR3DL2. In one aspect, the anti-KIR3DL2 antibodies bind KIR3DL2 but do not bind KIR3DL1 and/or KIR3DS1.

Optionally, the antibodies will bind to KIR3DL2-expressing cells from an individual or individuals with a disease characterized by expression of KIR3DL2-positive cells, i.e. an individual that is a candidate for treatment with one of the herein-described methods using an anti-KIR3DL2 antibody of the disclosure. Accordingly, once an antibody that specifically recognizes KIR3DL2 on cells is obtained, it can be tested for its ability to bind to KIR3DL2-positive cells (e.g. malignant CD4+ T cells) taken from a patient with a disorder such as SS or MF. In particular, prior to treating a patient with one of the present antibodies, it will be beneficial to test the ability of the antibody to bind malignant cells taken from the patient, e.g. in a blood sample, to maximize the likelihood that the therapy will be beneficial in the patient.

In one embodiment, the antibodies are validated in an immunoassay to test their ability to bind to KIR3DL2-expressing cells, e.g. malignant CD4+ T cells, pro-inflammatory CD4+ cells. For example, peripheral blood lymphocytes (PBLs) are taken from a plurality of patients, and CD4+ T cells are enriched from the PBLs, e.g., by flow cytometry using relevant antibodies (for malignant CD4+ cells see, e.g., Bagot et al. (2001) Blood 97:1388-1391, the disclosure of which is incorporated herein by reference), or CD4+CD28-cell fractions are isolated by magnetic separation on a MACS column (Miltenyi Biotec). The ability of a given antibody to bind to the cells is then assessed using standard methods well known to those in the art. Antibodies that are found to bind to a substantial proportion (e.g., 20%, 30%, 40%, 50%, 60%, 70%, 80% or more) of cells known to express KIR3DL2, e.g. T cells, from a significant percentage of individuals or patients (e.g., 5%, 10%, 20%, 30%, 40%, 50% or more) are suitable for use, both for diagnostic purposes to determine the presence or level of malignant T cells in a patient or for use in the herein-described therapeutic methods, e.g., for use to increase or decrease malignant T cell number or activity. To assess the binding of the antibodies to the cells, the antibodies can either be directly or indirectly labeled. When indirectly labeled, a secondary, labeled antibody is typically added. The binding of the antibodies to the cells can then be detected using, e.g., cytofluorometric analysis (e.g. FACScan). Such methods are well known to those of skill in the art.

Determination of whether an antibody binds within an epitope region can be carried out in ways known to the person skilled in the art. As one example of such mapping/characterization methods, an epitope region for an anti-KIR3DL2 antibody may be determined by epitope "footprinting" using chemical modification of the exposed amines/carboxyls in the KIR3DL2 protein.

One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e. g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e. g., Ernst Schering Res Found Workshop. 2004; (44): 149-67; Huang et al. Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. See, e.g., Downward, J Mass Spectrom. 2000 April; 35 (4): 493-503 and Kiselar and Downard, Anal Chem. 1999 May 1; 71 (9): 1792-801. Protease digestion techniques also can be useful in the context of epitope mapping and identification. Antigenic determinant-relevant regions/sequences can be determined by protease digestion, e.g. by using trypsin in a ratio of about 1:50 to KIR3DL2 or o/n digestion at and pH 7-8, followed by mass spectrometry (MS) analysis for peptide identification. The peptides protected from trypsin cleavage by the anti-KIR3DL2 binder can subsequently be identified by comparison of samples subjected to trypsin digestion and samples incubated with antibody and then subjected to digestion by e.g. trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the KIR3DL2 polypeptide that is not surface exposed and, accordingly, most likely not relevant in terms of immunogenicity/antigenicity. See, e. g., Manca, Ann Ist Super Sanita. 1991; 27: 15-9 for a discussion of similar techniques.

Site-directed mutagenesis is another technique useful for elucidation of a binding epitope. For example, in "alanine-scanning", each residue within a protein segment is replaced with an alanine residue, and the consequences for binding affinity measured. If the mutation leads to a significant reduction in binding affinity, it is most likely involved in binding. Monoclonal antibodies specific for structural epitopes (i.e., antibodies which do not bind the unfolded protein) can be used to verify that the alanine-replacement does not influence over-all fold of the protein. See, e.g., Clackson and Wells, Science 1995; 267:383-386; and Wells, Proc Natl Acad Sci USA 1996; 93:1-6.

Electron microscopy can also be used for epitope "footprinting". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fagerstam et al., Journal Of Molecular Recognition 1990; 3:208-14; Nice et al., J. Chromatogr. 1993; 646:159-168; Leipert et al., Angew. Chem. Int. Ed. 1998; 37:3308-3311; Kroger et al., Biosensors and Bioelectronics 2002; 17:937-944.

It should also be noted that an antibody binding the same or substantially the same epitope as a specific antibody of interest can be identified in one or more of the exemplary competition assays described herein.

Optionally, cellular uptake or localization is assessed in order to select an antibody that is readily taken up into the cell and/or into the cellular compartment where it KIR3DL2 is present. Cellular uptake or localization will generally be measured in the cells in which the antibody is sought or believed to exert its activity. Cellular uptake or localization can be assessed by standard methods, such as by confocal staining using an antibody marked with a detectable moiety (e.g. a fluorescent moiety).

Upon immunization and production of antibodies in a vertebrate or cell, particular selection steps may be performed to isolate antibodies as claimed. In this regard, in a specific embodiment, provided are methods of producing such antibodies, comprising: (a) immunizing a non-human mammal with an immunogen comprising a KIR3DL2 polypeptide; and (b) preparing antibodies from said immunized animal; and (c) selecting antibodies from step (b) that are capable of binding KIR3DL2. The antibody can then optionally be further tested for and selected on the basis of a desired property (e.g. internalization, inhibition of KIR3DL2 signalling, any activity described in the section "Assessing activity", etc.). In one embodiment, step (c) comprises selecting antibodies from step (b) that are capable of binding to 1, 2, 3, 4, 5, or more different KIR3DL2 polypeptides alleles (e.g. alleles *001, *002, *003, *005, *007, *008, *009 and/or *011), optionally in each case wherein the KIR3DL2 polypeptide is expressed on the surface of a cell.

Typically, an anti-KIR3DL2 antibody has an affinity for a KIR3DL2 polypeptide in the range of about $10^4$ to about $10^{11}$ M$^{-1}$ (e.g., about $10^8$ to about $10^{10}$ M$^{-1}$). For example, in a particular aspect an anti-KIR3DL2 antibody had an average disassociation constant ($K_D$) of less than $1 \times 10^{-9}$ M with respect to KIR3DL2, as determined by, e.g., surface plasmon resonance (SPR) screening (such as by analysis with a BIAcore™ SPR analytical device). In a more particular exemplary aspect, the an anti-KIR3DL2 antibody has a KD of about $1 \times 10^{-8}$ M to about $1 \times 10^{-10}$ M, or about $1 \times 10^{-9}$ M to about $1 \times 10^{-11}$ M, for KIR3DL2.

Antibodies can be characterized for example by a mean $K_D$ of no more than about (i.e. better affinity than) 100, 60, 10, 5, or 1 nanomolar, optionally sub-nanomolar or optionally no more than about 500, 200, 100 or 10 picomolar. $K_D$ can be determined for example for example by immobilizing recombinantly produced human KIR3DL2 proteins on a chip surface, followed by application of the antibody to be tested in solution. In one embodiment, the method further comprises a step (d), selecting antibodies from (b) that are capable of competing for binding to KIR3DL2 with antibody 15C11, 19H12, 22B2, 18B10, 12B11 or 13H1.

In one aspect of any of the embodiments, the antibodies prepared according to the present methods are monoclonal antibodies. In another aspect, the non-human animal used to produce antibodies according to the methods herein is a mammal, such as a rodent, bovine, porcine, fowl, horse, rabbit, goat, or sheep. The antibodies can encompass 15C11, 19H12, 22B2, 18B10, 12B11 or 13H1. Additionally, antibodies can optionally be specified to be antibodies other than any of antibodies Q241 and Q66 (Pende, et al. (1996) J Exp Med 184:505-518), clone 5.133 (Miltenyi Biotech), "AZ158" (Parolini, S., et al. (2002) In Leucocyte typing VII. D. Mason, editor. Oxford University Press, Oxford. 415-417 and WO2010/081890 (e.g. antibodies having the heavy and light chain variable region of SEQ ID NOS: 8 and 10 of WO2010/081890) or derivatives of the foregoing, e.g. that comprise the antigen binding region in whole or in part.

According to an alternate embodiment, the DNA encoding an antibody that binds an epitope present on KIR3DL2 polypeptides is isolated from the hybridoma and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding a monoclonal antibody, e.g., antibody 15C11, 19H12, 22B2, 18B10, 12B11 or 13H1, can be readily isolated and sequenced using conventional procedures (e. g., by using oligonucleotide probes that are capable of binding specifically to genes encoding the heavy and light chains of murine antibodies). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody.

Recombinant expression in bacteria of DNA encoding the antibody is well known in the art (see, for example, Skerra et al., Curr. Opinion in Immunol., 5, pp. 256 (1993); and Pluckthun, Immunol. 130, p. 151 (1992).

Assessing Activity

Once an antigen-binding compound is obtained it will generally be assessed for its ability to internalize into KIR3DL2-expressing target cells or cause KIR3DL2 internalization into KIR3DL2-expressing target cells, to deliver an agent into a KIR3DL2-expressing cell, to kill a KIR3DL2-expressing cell, or to induce ADCC or CDC towards, inhibit the proinflammatory activity and/or proliferation of and/or cause the elimination of KIR3DL2-expressing target cells. Assessing the antigen-binding compound's ability to internalize or to induce ADCC, CDC or otherwise (e.g. by delivery of a toxic agent) lead to the elimination or inhibition of activity of KIR3DL2-expressing target cells, can be carried out at any suitable stage of the method, e.g. as in the examples are provided herein. This assessment can be useful at one or more of the various steps involved in the identification, production and/or development of an antibody (or other compound) destined for therapeutic use. For example, activity may be assessed in the context of a screening method to identify candidate antigen-binding compounds, or in methods where an antigen-binding compound is selected and made human suitable (e.g. made chimeric or humanized in the case of an antibody), where a cell expressing the antigen-binding compound (e.g. a host cell expressing a recombinant antigen-binding compound) has been obtained and is assessed for its ability to produce functional antibodies (or other compounds), and/or where a quantity of antigen-binding compound has been produced and is to be assessed for activity (e.g. to test batches or lots of product). Generally the antigen-binding compound will be known to specifically bind to a KIR3DL2 polypeptide. The step may involve testing a plurality (e.g., a very large number using high throughput screening methods or a smaller number) of antigen-binding compounds.

As used herein, an anti-KIR3DL2 antibody that is "internalized" or that "internalizes" is one that is taken up by (i.e., enters) the cell upon binding to KIR3DL2 on a mammalian cell (i.e. cell surface KIR3DL2). The internalizing antibody will of course include antibody fragments, human or humanized antibody and antibody conjugate. For therapeutic applications, internalization in vivo is contemplated. The number of antibody molecules internalized will be sufficient or adequate to kill a KIR3DL2-expressing cell, especially a KIR3DL2-expressing cancer cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the tumor cell.

Whether an anti-KIR3DL2 antibody internalizes upon binding KIR3DL2 on a mammalian cell, or whether a KIR3DL2 polypeptide undergoes intracellular internalization (e.g. upon being bound by an antibody) can be determined by various assays including those described in the experimental examples herein. For example, to test internalization in vivo, the test antibody is labeled and introduced into an animal known to have KIR3DL2 expressed on the surface of certain cells. The antibody can be radiolabeled or labeled with fluorescent or gold particles, for instance.

Animals suitable for this assay include a mammal such as a nude mouse that contains a human KIR3DL2-expressing tumor transplant or xenograft, or a mouse into which cells transfected with human KIR3DL2 have been introduced, or a transgenic mouse expressing the human KIR3DL2 transgene. Appropriate controls include animals that did not receive the test antibody or that received an unrelated antibody, and animals that received an antibody to another antigen on the cells of interest, which antibody is known to be internalized upon binding to the antigen. The antibody can be administered to the animal, e.g., by intravenous injection. At suitable time intervals, tissue sections of the animal can be prepared using known methods or as described in the experimental examples below, and analyzed by light microscopy or electron microscopy, for internalization as well as the location of the internalized antibody in the cell. For internalization in vitro, the cells can be incubated in tissue culture dishes in the presence or absence of the relevant antibodies added to the culture media and processed for microscopic analysis at desired time points. The presence of an internalized, labeled antibody in the cells can be directly visualized by microscopy or by autoradiography if radiolabeled antibody is used. Optionally, in microscopy, co-localization with a known polypeptide or other cellular component can be assessed; for example co-localization with endosomal/lysosomal marker LAMP-1 (CD107a) can provide information about the subcellular localization of the internalized antibody. Alternatively, in a quantitative biochemical assay, a population of cells comprising KIR3DL2-expressing cells are contacted in vitro or in vivo with a radiolabeled test antibody and the cells (if contacted in vivo, cells are then isolated after a suitable amount of time) are treated with a protease or subjected to an acid wash to remove uninternalized antibody on the cell surface. The cells are ground up and the amount of protease resistant, radioactive counts per minute (cpm) associated with each batch of cells is measured by passing the homogenate through a scintillation counter. Based on the known specific activity of the radiolabeled antibody, the number of antibody molecules internalized per cell can be deduced from the scintillation counts of the ground-up cells. Cells are "contacted" with antibody in vitro optionally in solution form such as by adding the cells to the cell culture media in the culture dish or flask and mixing the antibody well with the media to ensure uniform exposure of the cells to the antibody.

Instead of adding to the culture media, the cells can be contacted with the test antibody in an isotonic solution such as PBS in a test tube for the desired time period. In vivo, the cells are contacted with antibody by any suitable method of administering the test antibody such as the methods of administration described below when administered to a patient.

The faster the rate of internalization of the antibody upon binding to the KIR3DL2-expressing cell in vivo, the faster the desired killing or growth inhibitory effect on the target KIR3DL2-expressing cell can be achieved, e.g., by a cytotoxic immunoconjugate.

Optionally, the kinetics of internalization of the anti-KIR3DL2 antibodies are such that they favor rapid killing of the KIR3DL2-expressing target cell. Therefore, it is desirable that the anti-KIR3DL2 antibody exhibit a rapid rate of internalization optionally y, within 24 hours from administration of the antibody in vivo, or within about 12 hours, or within about 1 hour.

Testing CDC and ADCC can be carried out can be determined by various assays including those described in the experimental examples herein (see Example 8 for CDC assays). Testing ADCC typically involves assessing cell-mediated cytotoxicity in which a KIR3DL2-expressing target cell (e.g. a Cou-L cell, Sézary Syndrome cell or other KIR3DL2-expressing cell) with bound anti-KIR3DL2 antibody is recognized by an effector cell bearing Fc receptors, without the involvement of complement. A cell which does not express a KIR3DL2 antigen can optionally be used as a control. Activation of NK cell cytotoxicity is assessed by measuring an increase in cytokine production (e.g. IFN-γ production) or cytotoxicity markers (e.g. CD107 mobilization). Optionally the antibody will induce an increase in cytokine production, expression of cytotoxicity markers, or target cell lysis of at least 20%, 50%, 80%, 100%, 200% or 500% in the presence of target cells, compared to a control antibody (e.g. an antibody not binding to KIR3DL2, a KIR3DL2 antibody having murine constant regions). In another example, lysis of target cells is detected, e.g. in a chromium release assay, optionally the antibody will induce lysis of at least 10%, 20%, 30%, 40% or 50% of target cells. Where an antigen-binding compound is tested for both its ability to (a) induce both ADCC and (b) internalize into KIR3DL2-expressing cells and/or induce KIR3DL2 internalization, the assays of (a) and (b) can be carried out in any order. However, greater the extent and speed of internalization will generally be expected to be associated with a decrease of the extent of CDC and ADCC activity.

Antibody CDR Sequences

In one aspect of any of the embodiments herein, an antibody may comprise a heavy and/or light chain having CDR1, 2 and/or 3 sequences according to the respective formula selected from Formulas (I) to (XI), or a sequence of at least 4, 5, 6, 7, 8, 9 or 10 contiguous amino acids thereof. In any embodiment herein, a particular HCDR1-3 or LCDR-1-3 may be specified as having a sequence of Formulas (I) to (XI). In one preferred embodiment, the antibody comprises a light chain comprising the three LCDRs and a heavy chain comprising the three HCDRs. Optionally, provided is an antibody where any of the light and/or heavy chain variable regions are fused to an immunoglobulin constant region of the IgG type, optionally a human constant region, optionally an IgG1 or IgG3 isotype.

In one embodiment, LCDR1 comprises a sequence of Formula (I):

$$\text{R-S-S-Q-Xaa}_1\text{-I-V-H-S-N-G-N-T-Y-L-E} \quad \text{(I) (SEQ ID NO: 126)}$$

wherein $Xaa_1$ may be a conservative or non conservative substitution or a deletion or insertion, optionally, wherein $Xaa_1$ may be N, D or T.

In one embodiment, LCDR1 comprises a sequence of Formula (II):

$Xaa_2\text{-}Xaa_3\text{-}S\text{-}Q\text{-}Xaa_4\text{-}I\text{-}Xaa_5\text{-}Xaa_6\text{-}Xaa_7\text{-}N\text{-}Xaa_8\text{-}N\text{-}Xaa_9\text{-}Xaa_{10}\text{-}Xaa_{11}\text{-}Xaa_{12}$ (II) (SEQ ID NO: 127) wherein $Xaa_2$ to $Xaa_{12}$ may be a conservative or non conservative substitution or a deletion or insertion, optionally, wherein $Xaa_2$ may be R or K, $Xaa_3$ may be S or A, $Xaa_4$ may be N, D or T, $Xaa_5$ may be V or a deletion, $Xaa_6$ may be H or a deletion, $Xaa_7$ may be S or a deletion, $Xaa_8$ may be K or G, $Xaa_9$ may be a I or T, $Xaa_{10}$ may A or Y, $Xaa_{11}$ may be L or a deletion, and/or $Xaa_{12}$ may be E or a deletion.

In one embodiment, LCDR2 comprises SEQ ID NO: 22 or a sequence of Formula (III): $Xaa_{13}\text{-}Xaa_{14}\text{-}T\text{-}S\text{-}T\text{-}L\text{-}Q\text{-}Xaa_{15}$ (III) (SEQ ID NO: 128) wherein $Xaa_{13}$ to $Xaa_{15}$ may be a conservative or non-conservative substitution or a deletion or insertion, optionally, wherein $Xaa_{13}$ may be Y, optionally, wherein $Xaa_{14}$ may be a deletion, optionally, and/or wherein $Xaa_{15}$ may be a deletion or P.

In one embodiment, LCDR3 comprises a sequence of Formula (IV): $Xaa_{16}\text{-}Q\text{-}Xaa_{17}\text{-}Xaa_{18}\text{-}Xaa_{19}\text{-}Xaa_{20}\text{-}Xaa_{21}\text{-}Xaa_{22}\text{-}T$ (IV) (SEQ ID NO: 129) wherein $Xaa_{16}$ to $Xaa_{22}$ may be a conservative or non-conservative substitution or a deletion or insertion, optionally, wherein $Xaa_{16}$ may be a F or L, wherein $Xaa_{17}$ may be a G or Y, wherein $Xaa_{18}$ may be a S or D, wherein $Xaa_{19}$ may be a H or N, wherein $Xaa_{20}$ may be a L or V, wherein $Xaa_{21}$ may be a P or a deletion, and/or wherein $Xaa_{22}$ may be a F, L or W.

In one embodiment, LCDR3 comprises a sequence of Formula (V):

$F\text{-}Q\text{-}G\text{-}S\text{-}H\text{-}V\text{-}P\text{-}Xaa_{23}\text{-}T$ (V) (SEQ ID NO: 130) wherein $Xaa_{23}$ may be a conservative or non-conservative substitution or a deletion or insertion, optionally, wherein $Xaa_{23}$ may be F, L or W.

In one embodiment, HCDR1 comprises a sequence of Formula (VI):

$G\text{-}Y\text{-}T\text{-}F\text{-}T\text{-}N\text{-}Xaa_{24}\text{-}G\text{-}M\text{-}N$ (VI) (SEQ ID NO: 131) wherein $Xaa_{24}$ may be a conservative or non-conservative substitution or a deletion or insertion, optionally, wherein $Xaa_{24}$ may be F, A or Y.

In one embodiment, HCDR1 comprises a sequence of Formula (VII):

$G\text{-}Xaa_{25}\text{-}T\text{-}F\text{-}Xaa_{26}\text{-}Xaa_{27}\text{-}Xaa_{28}\text{-}Xaa_{29}\text{-}MXaa_{30}$ (VII) (SEQ ID NO: 132) wherein $Xaa_{25}$ to $Xaa_{30}$ may be a conservative or non-conservative substitution or a deletion or insertion, optionally, wherein $Xaa_{25}$ may be Y or F, wherein $Xaa_{26}$ may be T or S, wherein $Xaa_{27}$ may be N or D, wherein $Xaa_{28}$ may be F, A or Y, wherein $Xaa_{29}$ may be G or W, and/or wherein $Xaa_{30}$ may be N or D.

In one embodiment, HCDR2 comprises a sequence of Formula (VIII):

$N\text{-}Xaa_{31}\text{-}Xaa_{32}\text{-}T\text{-}Y\text{-}Xaa_{33}\text{-}Xaa_{34}\text{-}Xaa_{35}\text{-}Xaa_{36}\text{-}Xaa_{37}\text{-}Y\text{-}A\text{-}Xaa_{38}\text{-}Xaa_{39}\text{-}Xaa_{40}$ (VIII) (SEQ ID NO: 133) wherein $Xaa_{31}$ to $Xaa_{40}$ may be a conservative or non-conservative substitution or a deletion or insertion, optionally, wherein $Xaa_{31}$ may be a deletion or H, wherein $Xaa_{32}$ may be a deletion or A, wherein $Xaa_{33}$ may a deletion or T, wherein $Xaa_{34}$ may be a deletion or G, wherein $Xaa_{35}$ may a deletion or E, wherein $Xaa_{36}$ may be a deletion or P, wherein $Xaa_{37}$ may be a deletion or T, wherein $Xaa_{38}$ may be D or E, wherein $Xaa_{39}$ may be D or S, and/or wherein $Xaa_{40}$ may be F or V.

In one embodiment, HCDR2 comprises a sequence of Formula (IX):

$Xaa_{41}\text{-}Xaa_{42}\text{-}Xaa_{43}\text{-}Xaa_{44}\text{-}Xaa_{45}\text{-}Xaa_{46}\text{-}N\text{-}Xaa_{47}\text{-}Xaa_{48}\text{-}T\text{-}Y\text{-}Xaa_{49}\text{-}Xaa_{50}\text{-}Xaa_{51}\text{-}Xaa_{52}\text{-}Xaa_{53}\text{-}Y\text{-}A\text{-}Xaa_{54}\text{-}Xaa_{55}\text{-}Xaa_{56}$ (IX) (SEQ ID NO: 134) wherein $Xaa_{41}$ to $Xaa_{56}$ may be a conservative or non-conservative substitution or a deletion or insertion, optionally, wherein $Xaa_{41}$ may be a W or I, wherein $Xaa_{42}$ may be a I or R, wherein $Xaa_{43}$ may be a deletion or S, wherein $Xaa_{44}$ may be a deletion or K, wherein $Xaa_{45}$ may be a deletion or A, wherein $Xaa_{46}$ may be a deletion or N, wherein $Xaa_{47}$ may be a deletion or H, wherein $Xaa_{48}$ may be a deletion or A, wherein $Xaa_{49}$ may a deletion or T, wherein $Xaa_{50}$ may be a deletion or G, wherein $Xaa_{51}$ may a deletion or E, wherein $Xaa_{52}$ may be a deletion or P, wherein $Xaa_{53}$ may be a deletion or T, wherein $Xaa_{54}$ may be D or E, wherein $Xaa_{55}$ may be D or S, and/or wherein $Xaa_{56}$ may be F or V.

In one embodiment, HCDR3 comprises a sequence of Formula (X):

$Xaa_{57}\text{-}Xaa_{58}\text{-}Xaa_{59}\text{-}Xaa_{60}\text{-}G\text{-}Xaa_{61}\text{-}Xaa_{62}\text{-}Y\text{-}Xaa_{63}\text{-}D\text{-}Y$ (X) (SEQ ID NO: 135) wherein $Xaa_{57}$ to $Xaa_{62}$ may be a conservative or non-conservative substitution or a deletion or insertion, optionally, wherein $Xaa_{57}$ may be a deletion or N, wherein $Xaa_{58}$ may be a deletion or G, wherein $Xaa_{59}$ may be a deletion, S or N, wherein $Xaa_{60}$ may be a deletion or F, wherein $Xaa_{61}$ may be Y or S, wherein $Xaa_{62}$ may be a deletion or T, and/or wherein $Xaa_{63}$ may be G, P or F.

In one embodiment, HCDR3 comprises a sequence of Formula (XI):

Xaa$_{64}$-F-G-Xaa$_{65}$-Xaa$_{66}$-Y-Xaa$_{67}$-D-Y (XI) (SEQ ID NO: 181) wherein Xaa$_{64}$ to Xaa$_{67}$ may be a conservative or non-conservative substitution or a deletion or insertion, optionally, wherein Xaa$_{64}$ may be a deletion, S or N, wherein Xaa$_{65}$ may be Y or S, wherein Xaa$_{66}$ may be a deletion or T, and/or wherein Xaa$_{67}$ may be G, P or F.

In one embodiment, an antibody may comprise a light chain comprising:

(a) a light chain CDR1 (LCDR1) amino acid sequence selected from SEQ ID NOS: 126 and 127; and/or (b) a light chain CDR2 (LCDR2) amino acid sequence selected from SEQ ID NOS: 22 and 128; and/or (c) a light chain CDR3 (LCDR3) amino acid sequence selected from SEQ ID NOS: 129 and 50.

In one embodiment, an antibody may comprise a heavy chain comprising:

(a) a heavy chain CDR1 (HCDR1) amino acid sequence selected from SEQ ID NOS: 131 and 132; and/or (b) a heavy chain CDR2 (HCDR2) amino acid sequence selected from SEQ ID NOS: 133 and 134; and/or (c) a heavy chain CDR3 (HCDR3) amino acid sequence selected from SEQ ID NOS: 135 and 181.

Antibody 15C11

The amino acid sequence of the heavy chain variable region of antibody 15C11 is listed as SEQ ID NO: 2, the amino acid sequence of the light chain variable region is listed as SEQ ID NO: 3. The amino acid sequences of exemplary heavy chain humanized variable regions of antibody 15C11 are listed as SEQ ID NOS: 114, 116 and 118, the amino acid sequences of exemplary light chain variable regions are listed as SEQ ID NOS: 120, 122 and 124. In a specific embodiment, provided is an antibody that binds essentially the same epitope or determinant as monoclonal antibodies 15C11; optionally the antibody comprises an antigen binding region of antibody 15C11. In any of the embodiments herein, antibody 15C11 can be characterized by its amino acid sequence and/or nucleic acid sequence encoding it. In one preferred embodiment, the monoclonal antibody comprises the Fab or F(ab')$_2$ portion of 15C11. Also provided is a monoclonal antibody that comprises the heavy chain variable region of 15C11. According to one embodiment, the monoclonal antibody comprises the three CDRs of the heavy chain variable region of 15C11 Also provided is a monoclonal antibody that further comprises the variable light chain variable region of 15C11 or one, two or three of the CDRs of the light chain variable region of 15C11. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 15C11 are fused to an immunoglobulin constant region of the human IgG type, optionally a human constant region, optionally a human IgG1 or IgG3 isotype. Optionally, the antibody comprises a heavy chain sequence comprising SEQ ID NOS: 114, 116 or 118 and a light chain sequence comprising SEQ ID NOS: 120, 122 or 124, or a variant of any of the foregoing sequences which is at least 60%, 70%, 80%, 85%, 90% or 95% identical thereto.

In another aspect, provided is a purified polypeptide which encodes an antibody, wherein the antibody comprises: a HCDR1 region comprising an amino acid sequence GFTF-SDAWMD as set forth in SEQ ID NO:6, or a sequence of at least 4, 5, 6, 7, 8, 9 or 10 contiguous amino acids thereof (e.g. DAWMD (SEQ ID NO: 4), GFTFSD (SEQ ID NO: 5)), wherein one or more of these amino acids may be substituted by a different amino acid; a HCDR2 region comprising an amino acid sequence IRSKANNHATYYAESV as set forth in SEQ ID NO:7, or a sequence of at least 4, 5, 6, 7, 8, 9 or 10 contiguous amino acids thereof (e.g. IRSKANNHA (SEQ ID NO: 8)), wherein one or more of these amino acids may be substituted by a different amino acid; a HCDR3 region comprising an amino acid sequence GYYPVY as set forth in SEQ ID NO:9, or a sequence of at least 4, 5, 6, 7, 8, 9 or 10 contiguous amino acids thereof, wherein one or more of these amino acids may be substituted by a different amino acid; a LCDR1 region comprising an amino acid sequence KASQDINKNIA as set forth in SEQ ID NO: 10, or a sequence of at least 4, 5, 6, 7, 8, 9 or 10 contiguous amino acids thereof, wherein one or more of these amino acids may be substituted by a different amino acid; a LCDR2 region comprising an amino acid sequence YTSTLQP as set forth in SEQ ID NO: 11, or a sequence of at least 4, 5, 6, 7, 8, 9 or 10 contiguous amino acids thereof, wherein one or more of these amino acids may be substituted by a different amino acid; a LCDR3 region comprising an amino acid sequence LQYDNLLT as set forth in SEQ ID NO: 12, or a sequence of at least 4, 5, 6, 7, 8, 9 or 10 contiguous amino acids thereof, wherein one or more of these amino acids may be deleted or substituted by a different amino acid.

In another aspect, provided is an antibody that binds human KIR3DL2, comprising:

(a) the heavy chain variable region of SEQ ID NOS: 2, 114, 116 or 118, optionally wherein one, two, three or more amino acid residues may be substituted by a different amino acid; and/or (b) the light chain variable region of SEQ ID NOS: 3, 120, 122 or 124, optionally wherein one, two, three or more amino acid residues may be substituted by a different amino acid; and/or (c) the heavy chain variable region of SEQ ID NOS: 2, 114, 116 or 118, optionally wherein one or more amino acid residues may be substituted by a different amino acid; and the light chain variable region of SEQ ID NOS: 3, 120, 122 or 124, optionally wherein one, two, three or amino acid residues may be substituted by a different amino acid; and/or (d) the heavy chain CDR 1, 2 and 3 (HCDR1, HCDR2, HCDR3) amino acid sequences as shown, respectively, in SEQ ID NOS: 5 (or 6), 8 and 9, optionally wherein one, two, three or more amino acid residues of any CDR may be substituted by a different amino acid; and/or (e) the light chain CDR 1, 2 and 3 (LCDR1, LCDR2, LCDR3) amino acid sequences as shown in SEQ ID NO: 10, 11 and 12, optionally wherein one, two, three or more amino acid residues of any CDR may be substituted by a different amino acid; and/or (f) the heavy chain CDR 1, 2 and 3 (HCDR1, HCDR2, HCDR3) amino acid sequences as shown, respectively, in SEQ ID NO: 5 (or 6), 8 and 9, optionally wherein one or more amino acid residues of any CDR may be substituted by a different amino acid; and the light chain CDRs 1, 2 and 3 (LCDR1, LCDR2, LCDR3) amino acid sequences as shown in SEQ ID NO: 10, 11 and 12, optionally wherein one, two, three or more amino acid residues may be substituted by a different amino acid; and/or (g) the heavy chain variable region which is at least 60%, 70%, 80%, 85%, 90% or 95% identical to the variable region having an amino acid sequence of SEQ ID NOS: 2, 114, 116 or 118, optionally wherein one, two, three or more amino acid residues may be substituted by a different amino acid; and/or (h) the light chain variable region which is at least 60%, 70%, 80%, 85%, 90% or 95% identical to the variable region having an amino acid sequence of SEQ ID NOS: 3, 120, 122 or 124, optionally wherein one, two, three or more amino acid residues may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, provided is an antibody that competes for KIR3DL2 binding with a monoclonal antibody of (a) to (h), above.

Antibody 19H12

The amino acid sequence of the heavy chain variable region of antibody 19H12 is listed in SEQ ID NO:13, the amino acid sequence of the light chain variable region is listed as SEQ ID NO: 14. In one embodiment, provided is an antibody that binds essentially the same epitope or determinant as monoclonal antibodies 19H12; optionally the antibody comprises an antigen binding region of antibody 19H12. In any of the embodiments herein, antibody 19H12 can be characterized by its amino acid sequence and/or nucleic acid sequence encoding it. In one preferred embodiment, the monoclonal antibody comprises the Fab or F(ab')$_2$ portion of 19H12. Also provided is a monoclonal antibody that comprises the heavy chain variable region of 19H12. According to one embodiment, the monoclonal antibody comprises the three CDRs of the heavy chain variable region of 19H12. Also provided is a monoclonal antibody that further comprises the variable light chain variable region of 19H12 or one, two or three of the CDRs of the light chain variable region of 19H12. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 19H12 are fused to an immunoglobulin constant region of the IgG type, optionally a human constant region, optionally an IgG1 or IgG4 isotype. In another aspect, provided is a purified polypeptide which encodes an antibody, wherein the antibody comprises: a HCDR1 region comprising an amino acid sequence GYTFTNFGMN as set forth in SEQ ID NO:17, or a sequence of at least 4, 5, 6, 7, 8, 9 or 10 contiguous amino acids thereof (e.g., NFGMN (SEQ ID NO: 15, GYTFTN (SEQ ID NO: 16)), wherein one or more of these amino acids may be substituted by a different amino acid; a HCDR2 region comprising an amino acid sequence WINTYTGEPTYADDF as set forth in SEQ ID NO: 18, or a sequence of at least 4, 5, 6, 7, 8, 9 or 10 contiguous amino acids thereof (e.g. WINTYTGE (SEQ ID NO: 19)), wherein one or more of these amino acids may be substituted by a different amino acid; a HCDR3 region comprising an amino acid sequence NGNFGYYFDY as set forth in SEQ ID NO: 20, or a sequence of at least 4, 5, 6, 7, 8, 9 or 10 contiguous amino acids thereof, wherein one or more of these amino acids may be substituted by a different amino acid; a LCDR1 region comprising an amino acid sequence RSSQNIVHSNGNTYLE as set forth in SEQ ID NO: 21, or a sequence of at least 4, 5, 6, 7, 8, 9 or 10 contiguous amino acids thereof, wherein one or more of these amino acids may be substituted by a different amino acid; a LCDR2 region comprising an amino acid sequence KVSNRFS as set forth in SEQ ID NO: 22, or a sequence of at least 4, 5, 6, 7, 8, 9 or 10 contiguous amino acids thereof, wherein one or more of these amino acids may be substituted by a different amino acid; and/or a LCDR3 region comprising an amino acid sequence FQGSHVPFT as set forth in SEQ ID NO: 23, or a sequence of at least 4, 5, 6, 7, 8, 9 or 10 contiguous amino acids thereof, wherein one or more of these amino acids may be deleted or substituted by a different amino acid, or where the sequence may comprise an insertion of one or more amino acids.

In another aspect, provided is an antibody that binds human KIR3DL2, comprising:

(a) the heavy chain variable region of SEQ ID NO: 13, optionally wherein one, two, three or more amino acid residues may be substituted by a different amino acid; and/or (b) the light chain variable region of SEQ ID NO: 14, optionally wherein one, two, three or more amino acid residues may be substituted by a different amino acid; and/or (c) the heavy chain variable region of SEQ ID NO: 13, optionally wherein one, two, three or more amino acid residues may be substituted by a different amino acid; and the light chain variable region of SEQ ID NO:14, optionally wherein one or more of these amino acids may be substituted by a different amino acid; and/or (d) the heavy chain CDR 1, 2 and 3 (HCDR1, HCDR2, HCDR3) amino acid sequences as shown in SEQ ID NOS: 15-17, 18-19 and 20, optionally wherein one, two, three or more amino acid residues of any CDR may be substituted by a different amino acid; and/or (e) the light chain CDR 1, 2 and 3 (LCDR1, LCDR2, LCDR3) amino acid sequences as shown in SEQ ID NOS: 21, 22 and 23, respectively, optionally wherein one, two, three or more amino acid residues of any CDR may be substituted by a different amino acid; and/or (f) the heavy chain CDR 1, 2 and 3 (HCDR1, HCDR2, HCDR3) amino acid sequences as shown in SEQ ID NOS: 15-17, 18-19 and 20, optionally wherein one, two, three or more amino acid residues of any CDR may be substituted by a different amino acid; and the light chain CDR 1, 2 and 3 (LCDR1, LCDR2, LCDR3) amino acid sequences as shown in SEQ ID NOS: 21, 22 and 23, optionally wherein one, two, three or more amino acid residues may be substituted by a different amino acid; and/or (g) the heavy chain variable region which is at least 60%, 70%, 80%, 85%, 90% or 95% identical to the variable region having an amino acid sequence of SEQ ID NO:13, optionally wherein one, two, three or more amino acid residues may be substituted by a different amino acid; and/or (h) the light chain variable region which is at least 60%, 70%, 80%, 85%, 90% or 95% identical to the variable region having an amino acid sequence of SEQ ID NO:14, optionally wherein one, two, three or more amino acid residues may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, provided is an antibody that competes for KIR3DL2 binding with a monoclonal antibody of (a) to (h), above.

Antibody 22B2

The amino acid sequence of the heavy chain variable region of 22B2 is listed as SEQ ID NO: 24, the amino acid sequence of the light chain variable region of 22B2 is listed as SEQ ID NO: 25. In a specific embodiment, provided is an antibody that binds essentially the same epitope or determinant as monoclonal antibodies 22B2; optionally the antibody comprises an antigen binding region of antibody 22B2. In any of the embodiments herein, antibody 22B2 can be characterized by its amino acid sequence and/or nucleic acid sequence encoding it. In one preferred embodiment, the monoclonal antibody comprises the Fab or F(ab')$_2$ portion of 22B2. Also provided is a monoclonal antibody that comprises the heavy chain variable region of 22B2. According to one embodiment, the monoclonal antibody comprises the three CDRs of the heavy chain variable region of 22B2. Also provided is a monoclonal antibody that further comprises the variable light chain variable region of 22B2 or one, two or three of the CDRs of the light chain variable region of 22B2. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 22B2 are fused to an immunoglobulin constant region of the IgG type, optionally a human constant region, optionally a human IgG1 or IgG4 isotype.

In another aspect, provided is a purified polypeptide which encodes an antibody, wherein the antibody comprises: a HCDR1 region comprising an amino acid sequence GYTFTNYGMN as set forth in SEQ ID NO:27, or a sequence of at least 4, 5, 6, 7, 8, 9 or 10 contiguous amino acids thereof (e.g., NYGMN (SEQ ID NO: 26), GYTFTN (SEQ ID NO: 16)), wherein one or more of these amino acids may be substituted by a different amino acid; a HCDR2 region comprising an amino acid sequence WINTYTGEPTYADDF as set forth in SEQ ID NO: 18, or a sequence of at least 4, 5, 6, 7, 8, 9 or 10 contiguous amino acids thereof (e.g. WINTYTGE (SEQ ID NO: 19)), wherein one or more of these amino acids may be substituted by a different amino acid; a HCDR3 region comprising an amino acid sequence SFGSTYGDY as set forth in SEQ ID NO:28, or a sequence of at least 4, 5, 6, 7, 8, 9 or 10 contiguous amino acids thereof, wherein one or more of these amino acids may be substituted by a different amino acid; a LCDR1 region comprising an amino acid sequence RSSQTIVHSNGNTYLE as set forth in SEQ ID NO:29, or a sequence of at least 4, 5, 6, 7, 8, 9 or 10 contiguous amino acids thereof, wherein one or more of these amino acids may be substituted by a different amino acid; a LCDR2 region comprising an amino acid sequence KVSNRFS as set forth in SEQ ID NO:30, or a sequence of at least 4, 5, 6, 7, 8, 9 or 10 contiguous amino acids thereof, wherein one or more of these amino acids may be substituted by a different amino acid; a LCDR3 region comprising an amino acid sequence FQGSHVPWT as set forth in SEQ ID NO:31, or a sequence of at least 4, 5, 6, 7, 8, 9 or 10 contiguous amino acids thereof, wherein one or more of these amino acids may be deleted or substituted by a different amino acid, or where the sequence may comprise an insertion of one or more amino acids.

In another aspect, provided is an antibody that binds human KIR3DL2, comprising:

(a) the heavy chain variable region of SEQ ID NO: 24, optionally wherein one, two, three or more amino acid residues may be substituted by a different amino acid; and/or (b) the light chain variable region of SEQ ID NO: 25, optionally wherein one, two, three or more amino acid residues may be substituted by a different amino acid; and/or (c) the heavy chain variable region of SEQ ID NO: 24, optionally wherein one, two, three or more amino acid residues may be substituted by a different amino acid; and the light chain variable region of SEQ ID NO: 25, optionally wherein one, two, three or more amino acid residues may be substituted by a different amino acid; and/or (d) the heavy chain CDR 1, 2 and 3 (HCDR1, HCDR2, HCDR3) amino acid sequences as shown in SEQ ID NOS: 16, 26 or 27, 18-19 and 28, optionally wherein one, two, three or more amino acid residues of any CDR may be substituted by a different amino acid; and/or (e) the light chain CDR 1, 2 and 3 (LCDR1, LCDR2, LCDR3) amino acid sequences as shown in SEQ ID NOS: 29, 30 and 31, optionally wherein one, two, three or more amino acid residues of any CDR may be substituted by a different amino acid; and/or (f) the heavy chain CDR 1, 2 and 3 (HCDR1, HCDR2, HCDR3) amino acid sequences as shown in SEQ ID NOS: 16, 26 or 27, 18-19 and 28, optionally wherein one, two, three or more amino acid residues of any CDR may be substituted by a different amino acid; and the light chain CDR 1, 2 and 3 (LCDR1, LCDR2, LCDR3) amino acid sequences as shown in SEQ ID NOS: 29, 30 and 31, optionally wherein one, two, three or more amino acid residues of any CDR may be substituted by a different amino acid; and/or (g) the heavy chain variable region which is at least 60%, 70%, 80%, 85%, 90% or 95% identical to the variable region having an amino acid sequence of SEQ ID NO: 24, optionally wherein one, two, three or more amino acid residues may be substituted by a different amino acid; and/or (h) the light chain variable region which is at least 60%, 70%, 80%, 85%, 90% or 95% identical to the variable region having an amino acid sequence of SEQ ID NO: 25, optionally wherein one, two, three or more amino acid residues may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, provided is an antibody that competes for KIR3DL2 binding with a monoclonal antibody of (a) to (h), above.

Antibody 18B10

The amino acid sequence of the heavy chain variable region of antibody 18B10 is listed as SEQ ID NO: 32, the amino acid sequence of the light chain variable region is listed as SEQ ID NO: 33. In a specific embodiment, provided is an antibody that binds essentially the same epitope or determinant as monoclonal antibody 18B10; optionally the antibody comprises an antigen binding region of antibody 15C11. In any of the embodiments herein, antibody 18B10 can be characterized by its amino acid sequence and/or nucleic acid sequence encoding it. In one preferred embodiment, the monoclonal antibody comprises the Fab or F(ab')$_2$ portion of 18B10. Also provided is a monoclonal antibody that comprises the heavy chain variable region of 18B10. According to one embodiment, the monoclonal antibody comprises the three CDRs of the heavy chain variable region of 18B10. Also provided is a monoclonal antibody that further comprises the variable light chain variable region of 18B10 or one, two or three of the CDRs of the light chain variable region of 18B10. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 18B10 are fused to an immunoglobulin constant region of the human IgG type, optionally a human constant region, optionally a human IgG1 or IgG3 isotype.

In another aspect, provided is a purified polypeptide which encodes an antibody, wherein the antibody comprises: a HCDR1 region comprising an amino acid sequence GYIFTNYGMN as set forth in SEQ ID NO: 35, or a sequence of at least 4, 5, 6, 7, 8, 9 or 10 contiguous amino acids thereof (e.g. NYGMN (SEQ ID NO: 26), GYIFTN (SEQ ID NO: 34)), wherein one or more of these amino acids may be substituted by a different amino acid; a HCDR2 region comprising an amino acid sequence WINTYTGEPTYADDFKG as set forth in SEQ ID NO: 36, or a sequence of at least 4, 5, 6, 7, 8, 9 or 10 contiguous amino acids thereof (e.g. WINTYTGEPT (SEQ ID NO: 37)), wherein one or more of these amino acids may be substituted by a different amino acid; a HCDR3 region comprising an amino acid sequence GPWLAY as set forth in SEQ ID NO: 38, or a sequence of at least 4, 5, 6, 7, 8, 9 or 10 contiguous amino acids thereof, wherein one or more of these amino acids may be substituted by a different amino acid; a LCDR1 region comprising an amino acid sequence KASQDINSYLS as set forth in SEQ ID NO:39, or a sequence of at least 4, 5, 6, 7, 8, 9 or 10 contiguous amino acids thereof, wherein one or more of these amino acids may be substituted by a different amino acid; a LCDR2 region comprising an amino acid sequence RANRLVD as set forth in SEQ ID NO: 40, or a sequence of at least 4, 5, 6, 7, 8, 9 or 10 contiguous amino acids thereof, wherein one or more of these amino acids may be substituted by a different amino acid; a LCDR3 region comprising an amino acid sequence LQYDELPYT as set forth in SEQ ID NO: 41, or a sequence of at least 4, 5, 6, 7, 8, 9 or 10 contiguous amino acids thereof, wherein one or more of these amino acids may be deleted or substituted by a different amino acid.

In another aspect, provided is an antibody that binds human KIR3DL2, comprising:

(a) the heavy chain variable region of SEQ ID NO: 32, optionally wherein one, two, three or more amino acid residues may be substituted by a different amino acid; and/or (b) the light chain variable region of SEQ ID NO: 33, optionally wherein one, two, three or more amino acid residues may be substituted by a different amino acid; and/or (c) the heavy chain variable region of SEQ ID NO: 32, optionally wherein one or more amino acid residues may be substituted by a different amino acid; and the light chain variable region of SEQ ID NO: 33 optionally wherein one, two, three or more of these amino acids may be substituted by a different amino acid; and/or (d) the heavy chain CDR 1, 2 and 3 (HCDR1, HCDR2, HCDR3) amino acid sequences as shown in SEQ ID NO: 26, 34 or 35, 36-37 and 38, optionally wherein one, two, three or more amino acid residues of any CDR may be substituted by a different amino acid; and/or (e) the light chain CDR 1, 2 and 3 (LCDR1, LCDR2, LCDR3) amino acid sequences as shown in SEQ ID NO: 39, 40 and 41, optionally wherein one, two, three or more amino acid residues of any CDR may be substituted by a different amino acid; and/or (f) the heavy chain CDR 1, 2 and 3 (HCDR1, HCDR2, HCDR3) amino acid sequences as shown in SEQ ID NO: 26, 34 or 35, 36-37 and 38, optionally wherein one or more amino acid residues of any CDR may be substituted by a different amino acid; and the light chain CDRs 1, 2 and 3 (LCDR1, LCDR2, LCDR3) amino acid sequences as shown in SEQ ID NO: 39, 40 and 41, optionally wherein one, two, three or more amino acid residues may be substituted by a different amino acid; and/or (g) the heavy chain variable region which is at least 60%, 70%, 80%, 85%, 90% or 95% identical to the variable region having an amino acid sequence of SEQ ID NO: 32, optionally wherein one, two, three or more amino acid residues may be substituted by a different amino acid; and/or (h) the light chain variable region which is at least 60%, 70%, 80%, 85%, 90% or 95% identical to the variable region having an amino acid sequence of SEQ ID NO: 33, optionally wherein one, two, three or more amino acid residues may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, provided is an antibody that competes for KIR3DL2 binding with a monoclonal antibody of (a) to (h), above.

Antibody 12B11

The amino acid sequence of the heavy chain variable region of antibody 12B11 is listed as SEQ ID NO: 42, the amino acid sequence of the light chain variable region is listed as SEQ ID NO: 43. In a specific embodiment, provided is an antibody that binds essentially the same epitope or determinant as monoclonal antibodies 12B11; optionally the antibody comprises an antigen binding region of antibody 12B11. In any of the embodiments herein, antibody 12B11 can be characterized by its amino acid sequence and/or nucleic acid sequence encoding it. In one preferred embodiment, the monoclonal antibody comprises the Fab or F(ab')$_2$ portion of 12B11. Also provided is a monoclonal antibody that comprises the heavy chain variable region of 12B11. According to one embodiment, the monoclonal antibody comprises the three CDRs of the heavy chain variable region of 12B11. Also provided is a monoclonal antibody that further comprises the variable light chain variable region of 12B11 or one, two or three of the CDRs of the light chain variable region of 12B11. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 12B11 are fused to an immunoglobulin constant region of the human IgG type, optionally a human constant region, optionally a human IgG1 or IgG3 isotype.

In another aspect, provided is a purified polypeptide which encodes an antibody, wherein the antibody comprises: a HCDR1 region comprising an amino acid sequence GYTFTNYGMN as set forth in SEQ ID NO: 27, or a sequence of at least 4, 5, 6, 7, 8, 9 or 10 contiguous amino acids thereof (e.g. NYGMN (SEQ ID NO: 26), GYTFTN (SEQ ID NO: 16)), wherein one or more of these amino acids may be substituted by a different amino acid; a HCDR2 region comprising an amino acid sequence WINTYTGEPTYADDFKG as set forth in SEQ ID NO: 36, or a sequence of at least 4, 5, 6, 7, 8, 9 or 10 contiguous amino acids thereof (e.g. WINTYTGEPT (SEQ ID NO: 37)), wherein one or more of these amino acids may be substituted by a different amino acid; a HCDR3 region comprising an amino acid sequence GPWLAY as set forth in SEQ ID NO: 38, or a sequence of at least 4, 5, 6, 7, 8, 9 or 10 contiguous amino acids thereof, wherein one or more of these amino acids may be substituted by a different amino acid; a LCDR1 region comprising an amino acid sequence KASQDINVYLS as set forth in SEQ ID NO: 44, or a sequence of at least 4, 5, 6, 7, 8, 9 or 10 contiguous amino acids thereof, wherein one or more of these amino acids may be substituted by a different amino acid; a LCDR2 region comprising an amino acid sequence RAIRLVD as set forth in SEQ ID NO: 45, or a sequence of at least 4, 5, 6, 7, 8, 9 or 10 contiguous amino acids thereof, wherein one or more of these amino acids may be substituted by a different amino acid; a LCDR3 region comprising an amino acid sequence LQYDELPYT as set forth in SEQ ID NO: 41, or a sequence of at least 4, 5, 6, 7, 8, 9 or 10 contiguous amino acids thereof, wherein one or more of these amino acids may be deleted or substituted by a different amino acid.

In another aspect, provided is an antibody that binds human KIR3DL2, comprising:

(a) the heavy chain variable region of SEQ ID NO: 42, optionally wherein one, two, three or more amino acid residues may be substituted by a different amino acid; and/or (b) the light chain variable region of SEQ ID NO: 43, optionally wherein one, two, three or more amino acid residues may be substituted by a different amino acid; and/or (c) the heavy chain variable region of SEQ ID NO: 42, optionally wherein one or more amino acid residues may be substituted by a different amino acid; and the light chain variable region of SEQ ID NO: 43, optionally wherein one, two, three or more of these amino acids may be substituted by a different amino acid; and/or (d) the heavy chain CDR 1, 2 and 3 (HCDR1, HCDR2, HCDR3) amino acid sequences as shown in SEQ ID NO: 16, 26 or 27, 36-37 and 38, optionally wherein one, two, three or more o amino acid residues of any CDR may be substituted by a different amino acid; and/or (e) the light chain CDR 1, 2 and 3 (LCDR1, LCDR2, LCDR3) amino acid sequences as shown in SEQ ID NO: 44, 45 and 41, optionally wherein one, two, three or more amino acid residues of any CDR may be substituted by a different amino acid; and/or (f) the heavy chain CDR 1, 2 and 3 (HCDR1, HCDR2, HCDR3) amino acid sequences as shown in SEQ ID NO: 16, 26 or 27, 36-37 and 38, optionally wherein one or more amino acid residues of any CDR may be substituted by a different amino acid; and the light chain CDRs 1, 2 and 3 (LCDR1, LCDR2, LCDR3) amino acid sequences as shown in SEQ ID NO: 44, 45 and 41, optionally wherein one, two, three or more amino acid residues of any CDR may be substituted by a different amino acid; and/or (g) the heavy chain variable region which is at least 60%, 70%, 80%, 85%, 90% or 95% identical to the variable region having an amino acid sequence of SEQ ID NO: 42, optionally wherein one, two, three or more amino acid residues may be substituted by a different amino acid; and/or (h) the light chain variable region which is at least 60%, 70%, 80%, 85%, 90% or 95% identical to the variable region having an amino acid sequence of SEQ ID NO: 43, optionally wherein one, two, three or more amino acid residues may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, provided is an antibody that competes for KIR3DL2 binding with a monoclonal antibody of (a) to (h), above.

Antibody 13H1

The amino acid sequence of the heavy chain variable region of antibody 13H1 is listed as SEQ ID NO: 46, the amino acid sequence of the light chain variable region is listed as SEQ ID NO: 47. In a specific embodiment, provided is an antibody that binds essentially the same epitope or determinant as monoclonal antibodies 13H1; optionally the antibody comprises an antigen binding region of antibody 13H1. In any of the embodiments herein, antibody 13H1 can be characterized by its amino acid sequence and/or nucleic acid sequence encoding it. In one preferred embodiment, the monoclonal antibody comprises the Fab or F(ab')$_2$ portion of 13H1. Also provided is a monoclonal antibody that comprises the heavy chain variable region of 13H1. According to one embodiment, the monoclonal antibody comprises the three CDRs of the heavy chain variable region of 13H1 Also provided is a monoclonal antibody that further comprises the variable light chain variable region of 13H1 or one, two or three of the CDRs of the light chain variable region of 13H1. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 13H1 are fused to an immunoglobulin constant region of the human IgG type, optionally a human constant region, optionally a human IgG1 or IgG3 isotype.

In another aspect, provided is a purified polypeptide which encodes an antibody, wherein the antibody comprises: a HCDR1 region comprising an amino acid sequence HYSFIGYTM as set forth in SEQ ID NO: 50, or a sequence of at least 4, 5, 6, 7, 8, 9 or 10 contiguous amino acids thereof (e.g. GYTMN (SEQ ID NO: 48), HYSFIG (SEQ ID NO: 49)), wherein one or more of these amino acids may be substituted by a different amino acid; a HCDR2 region comprising an amino acid sequence LINPYNGDTTYNQKFKG as set forth in SEQ ID NO: 51, or a sequence of at least 4, 5, 6, 7, 8, 9 or 10 contiguous amino acids thereof (e.g. LINPYNGDTT (SEQ ID NO: 52)), wherein one or more of these amino acids may be substituted by a different amino acid; a HCDR3 region comprising an amino acid sequence ENWGYPYAMDY as set forth in SEQ ID NO: 53, or a sequence of at least 4, 5, 6, 7, 8, 9 or 10 contiguous amino acids thereof, wherein one or more of these amino acids may be substituted by a different amino acid; a LCDR1 region comprising an amino acid sequence RASESVDNFGISFMN as set forth in SEQ ID NO: 54, or a sequence of at least 4, 5, 6, 7, 8, 9 or 10 contiguous amino acids thereof, wherein one or more of these amino acids may be substituted by a different amino acid; a LCDR2 region comprising an amino acid sequence AASNQGS as set forth in SEQ ID NO: 55, or a sequence of at least 4, 5, 6, 7, 8, 9 or 10 contiguous amino acids thereof, wherein one or more of these amino acids may be substituted by a different amino acid; a LCDR3 region comprising an amino acid sequence QQSKEVPYT as set forth in SEQ ID NO: 56, or a sequence of at least 4, 5, 6, 7, 8, 9 or 10 contiguous amino acids thereof, wherein one or more of these amino acids may be deleted or substituted by a different amino acid.

In another aspect, provided is an antibody that binds human KIR3DL2, comprising:

(a) the heavy chain variable region of SEQ ID NO: 46, optionally wherein one, two, three or more amino acid residues may be substituted by a different amino acid; and/or (b) the light chain variable region of SEQ ID NO: 47, optionally wherein one, two, three or more amino acid residues may be substituted by a different amino acid; and/or (c) the heavy chain variable region of SEQ ID NO: 47, optionally wherein one or more amino acid residues may be substituted by a different amino acid; and the light chain variable region of SEQ ID NO: 47, optionally wherein one, two, three or more amino acid residues may be substituted by a different amino acid; and/or (d) the heavy chain CDR 1, 2 and 3 (HCDR1, HCDR2, HCDR3) amino acid sequences as shown in SEQ ID NO: 48-50, 51-52 and 53, respectively, optionally wherein one, two, three or more amino acid residues of any CDR may be substituted by a different amino acid; and/or (e) the light chain CDR 1, 2 and 3 (LCDR1, LCDR2, LCDR3) amino acid sequences as shown in SEQ ID NO: 54, 55 and 56, optionally wherein one, two, three or more amino acid residues of any CDR may be substituted by a different amino acid; and/or (f) the heavy chain CDR 1, 2 and 3 (HCDR1, HCDR2, HCDR3) amino acid sequences as shown in SEQ ID NO: 48-50, 51-52 and 53, respectively, optionally wherein one or more amino acid residues of any CDR may be substituted by a different amino acid; and the light chain CDRs 1, 2 and 3 (LCDR1, LCDR2, LCDR3) amino acid sequences as shown in SEQ ID NO: 54, 55 and 56, optionally wherein one, two, three or more amino acid residues of any CDR may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, provided is an antibody that competes for KIR3DL2 binding with a monoclonal antibody of (a) to (f), above.

In any of the antibodies, e.g., 15C11, 19H12, 22B2, 18B10, 12B11 or 13H1, the specified variable region and CDR sequences may comprise one, two, three, four, five or more conservative sequence modifications. Conservative sequence modifications refers to amino acid modifications that do not significantly affect or alter the binding characteristics of the antibody containing the amino acid sequence. Such conservative modifications include amino acid substitutions, additions and deletions. Modifications can be introduced into an antibody by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for retained function (i.e., the properties set forth herein) using the assays described herein.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

The sequences of the CDRs of exemplary antibodies, according to AbM (Oxford Molecular's AbM antibody modelling software definition), Kabat and Chothia definitions systems, have been summarized in Tables 1 and 2 below. The amino acids sequences described herein are numbered according to Abm, Kabat and Chothia numbering systems. While any suitable numbering system may be used to designated CDR regions, in the absence of any other indication, Abm numbering can be used. Such numbering has been established using the following indications: CDR-L1: Start: approx. residue 24, residue before: always a Cys, residue after: always a Trp (typically Trp-Tyr-Gln, but also, Trp-Leu-Gln, Trp-Phe-Gln, Trp-Tyr-Leu), length: 10 to 17 residues; CDR-L2: Start: always 16 residues after the end of L1, Residues before: generally Ile-Tyr (but also, Val-Tyr, Ile-Lys, Ile-Phe), Length: always 7 residues; CDR-L3, Start: always 33 residues after end of L2, Residue before: always Cys, Residues after: always Phe-Gly-Xaa-Gly, Length: 7 to 11 residues; CDR-H1, Start: approx. residue 26 (always 4 after a Cys) (Chothia/AbM definition, the Kabat definition starts 5 residues later), Residues before: always Cys-Xaa-Xaa-Xaa, Residues after: always a Trp (typically Trp-Val, but also, Trp-Ile, Trp-Ala), Length: 10 to 12 residues (AbM definition, Chothia definition excludes the last 4 residues); CDR-H2, Start: always 15 residues after the end of Kabat/AbM definition of CDR-H1, Residues before: typically Leu-Glu-Trp-Ile-Gly (SEQ ID NO: 182) (but a number of variations, Residues after Lys/Arg-Leu/Ile/Val/Phe/Thr/Ala-Thr/Ser/Ile/Ala), Length: Kabat definition 16 to 19 residues; AbM (and Chothia) definition ends 7 residues earlier; CDR-H3, Start: always 33 residues after end of CDR-H2 (always 2 after a Cys), Residues before: always Cys-Xaa-Xaa (typically Cys-Ala-Arg), Residues after: always Trp-Gly-Xaa-Gly, Length: 3 to 25 residues.

In one embodiment, the antibodies are of the human or mouse IgG1 isotype. In another embodiment, the antibodies are of the human IgG1 isotype. In an embodiment, the antibodies are antibody fragments that retain their binding and/or functional properties.

TABLE 1

| mAb | CDR definition | HCDR1 SEQ ID | Sequence | HCDR2 SEQ ID | Sequence | HCDR3 SEQ ID | Sequence |
|---|---|---|---|---|---|---|---|
| 15C11 | Kabat | 4 | DAWMD | 7 | IRSKANNHATYYAESV | 9 | GYYPVY |
|  | Chotia | 5 | GFTFSD | 8 | IRSKANNHA | 9 | GYYPVY |
|  | AbM | 6 | GFTFSDAWMD | 8 | IRSKANNHA | 9 | GYYPVY |
| 19H12 | Kabat | 15 | NFGMN | 18 | WINTYFGEPTYADDF | 20 | NGNFGYYFDY |
|  | Chotia | 16 | GYTFTN | 19 | WINTYTGE | 20 | NGNFGYYFDY |
|  | AbM | 17 | GYTFTNFGMN | 19 | WINTYTGE | 20 | NGNFGYYFDY |
| 22B2 | Kabat | 26 | NYGMN | 18 | WINTYTGEPTYADDF | 28 | SFGSTYGDY |
|  | Chotia | 16 | GYTFTN | 19 | WINTYTGE | 28 | SFGSTYGDY |
|  | AbM | 27 | GYTFTNYGMN | 19 | WINTYTGE | 28 | SFGSTYGDY |
| 18B10 | Kabat | 26 | NYGMN | 36 | WINTYTGEPTYADDFKG | 38 | GPWLAY |
|  | Chotia | 34 | GYIFTN | 37 | WINTYTGEPT | 38 | GPWLAY |
|  | AbM | 35 | GYIFTNYGMN | 37 | WINTYTGEPT | 38 | GPWLAY |
| 12B11 | Kabat | 26 | NYGMN | 36 | WINTYTGEPTYADDFKG | 38 | GPWLAY |
|  | Chotia | 16 | GYTFTN | 37 | WINTYTGEPT | 38 | GPWLAY |
|  | AbM | 27 | GYTFTNYGMN | 37 | WINTYTGEPT | 38 | GPWLAY |
| 13H1 | Kabat | 48 | GYTMN | 51 | LINPYNGDTTYNQKFKG | 53 | ENWGYPYAMDY |
|  | Chotia | 49 | HYSFIG | 52 | LINPYNGDTT |  | ENWGYPYAMDY |
|  | AbM | 50 | HYSFIGYTMN |  | LINPYNGDTT |  | ENWGYPYAMDY |

TABLE 2

| mAb | CDR definition | LCDR1 SEQ ID | Sequence | LCDR2 SEQ ID | Sequence | LCDR3 SEQ ID | Sequence |
|---|---|---|---|---|---|---|---|
| 15C11 | Kabat, Chotia, AbM | 10 | KASQDINKNIA | 11 | YTSTLQP | 12 | LQYDNLLT |
| 19H12 | Kabat, Chotia, AbM | 21 | RSSQNIVHSNGNTYLE | 22 | KVSNRFS | 23 | FQGSHVPFT |
| 22B2 | Kabat, Chotia, AbM | 29 | RSSQTIVHSNGNTYLE | 30 | KVSNRFS | 31 | FQGSHVPWT |
| 18B10 | Kabat, Chotia, AbM | 39 | KASQDINSYLS | 40 | RANRLVD | 41 | LQYDELPYT |
| 12B11 | Kabat, Chotia, AbM | 44 | KASQDINVYLS | 45 | RAIRLVD | 41 | LQYDELPYT |
| 13H1 | Kabat, Chotia, AbM | 54 | RASESVDNFGISFMN | 55 | AASNQGS | 56 | QQSKEVPYT |

The sequences of the variable chains of the antibodies according are listed in Table 3 below, with the CDRs underlined. In any embodiment herein, a VL or VH sequence can be specified or numbered so as to contain or lack a signal peptide or any part thereof.

TABLE 3

| Antibody portion | SEQ ID NO |  |
|---|---|---|
| 15C11 VH | 2 | EVKLEESGGGLVQPGGSMKLSCAAS<u>GFTFSDAWMD</u>WVRQSPEKGLEWVAE<u>IRSKANNHATYYAESV</u>KGRFTISRDDSKSSVYLRMNSLRAEDTGIYYCTG<u>GYYPVY</u>WGQGTLVTVSA |

TABLE 3-continued

| Antibody portion | SEQ ID NO | |
|---|---|---|
| 15C11 VL | 3 | DIQMTQSPSSLSASLGGKVTITC<u>KASQDINKNIA</u>WYQHKPGKGPRLLIH<u>Y TSTLQP</u>GFPSRFSGSGSGRDYSFSISNLEPEDLATYYC<u>LQYDNLLT</u>FGGG TKLEIK |
| 19H12 VH | 13 | QIQLVQSGPELKKPGETVKISCKAS<u>GYTFTNFGMN</u>WVKQAPGKGLKWMGW<u> INTYTGEPTYADDF</u>KGRFAFSLETSASTAYLQINNLKNEDMATYFCAR<u>NG NFGYYFDY</u>WGQGTTLTVSS |
| 19H12 VL | 14 | DVLMTQTPLSLPVSLGDQASFSC<u>RSSQNIVHSNGNTYLE</u>WYLQKPGQSPS LLIY<u>KVSNRFS</u>GVPDRFSGSGSGTDFTLKITRVEAEDLGVYYC<u>FQGSHVP FT</u>FGSGTKLEIK |
| 22B2 VH | 24 | QIQLVQSGPELKKPGETVKISCKAS<u>GYTFTNYGMN</u>WVKQAPGKGLKWMGW<u> INTYTGEPTYADDF</u>KGRFAFSLETSATTAYLQINNLKNEDMATYFCSR<u>SF GSTYGDY</u>WGQGTTLTVSS |
| 22B2 VL | 25 | DVLMTQTPLSLPVSLGDQASISC<u>RSSQTIVHSNGNTYLE</u>WYLQKPGQSPK LLIY<u>KVSNRFS</u>GVPDRFSGSGSGTDFTLKISRVEAEDLGVYYC<u>FQGSHVP WT</u>FGGGTKLEIK |
| 18B10 VH | 32 | QIQLVQSGPELKNPGETVKISCKASGYIFTNYGMNWVKQAPGKGLKWMGW INTYTGEPTYADDFKGRFAFSLETSASTAYLQINNLKNEDTATYFCAHGP WLAYWGQGTLVTVSTAKTTAPSVYPLAPVCGDTTGSSVTLGCLVKNRIPA AAMAAGA |
| 18B10 VL | 33 | DIKMTQSPSSMYASLGERVTITCKASQDINSYLSWFQLKPGKSPKTLIYR ANRLVDGVPSRFSGSGSGQDFSLTISSLECEDMGIYYCLQYDELPYTFGG GTTLEIK |
| 12B11 VH | 42 | QLVQSGPELKNPGETVKISCKASGYTFTNYGMNWVKQAPGKGLKWMGWIN TYTGEPTYADDFKGRFAFSLETSASTAYLQINNLKNEDTATYFCAHGPWL AYWGQGTLVTVS |
| 12B11 VL | 43 | DIKMTQSPSSMYASLGERVTITCKASQDINVYLSWFQQKPGKSPKTLIYR AIRLVDGVPSRFSGSGSGQDYSLTISSLDYEDMGIYYCLQYDELPYTFGG GTKLEIE |
| 13H1 VH | 46 | EVQLQQSGPELVKPGASMKISCKAS<u>HYSFIGYTMN</u>WVKQRHGKNLEWIGL<u> INPYNGDTTYNQKFKG</u>KASLTVDKSSSTAYMEILSLTSEDSAVYYCAR<u>EN WGYPYAMDY</u>WGQGTSVTVS |
| 13H1 VL | 47 | DIVLTQSPASLAVSLGQRATISC<u>RASESVDNFGISFMN</u>WFQQKPGQPPKL LIY<u>AASNQGS</u>GVPARFSGSRSGTDFSLNIHPMEEDDTAMYFC<u>QQSKEVPY T</u>FGGGTKLEIK |

Fragments and Derivatives

Fragments and derivatives of antibodies (which are encompassed by the term "antibody" or "antibodies" as used in this application, unless otherwise stated or clearly contradicted by context), optionally a 15C11, 19H12, 22B2, 18B10, 12B11 or 13H1-like antibody, can be produced by techniques that are known in the art. "Fragments" comprise a portion of the intact antibody, generally the antigen binding site or variable region. Examples of antibody fragments include Fab, Fab', Fab'-SH, F (ab') 2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Included, inter alia, are a nanobody, domain antibody, single domain antibody or a "dAb".

Fragments of the present antibodies can be obtained using standard methods. For instance, Fab or F (ab') 2 fragments may be produced by protease digestion of the isolated antibodies, according to conventional techniques. It will be appreciated that immunoreactive fragments can be modified using known methods, for example to slow clearance in vivo and obtain a more desirable pharmacokinetic profile the fragment may be modified with polyethylene glycol (PEG). Methods for coupling and site-specifically conjugating PEG to a Fab' fragment are described in, for example, Leong et al, 16 (3): 106-119 (2001) and Delgado et al, Br. J. Cancer 73 (2): 175-182 (1996), the disclosures of which are incorporated herein by reference.

Alternatively, the DNA of a hybridoma producing an antibody, e.g., a 15C11, 19H12, 22B2, 18B10, 12B11 or 13H1-like antibody, may be modified so as to encode a fragment. The modified DNA is then inserted into an expression vector and used to transform or transfect an appropriate cell, which then expresses the desired fragment.

In certain embodiments, the DNA of a hybridoma producing an antibody, e.g., a 15C11, 19H12, 22B2, 18B10, 12B11 or 13H1-like antibody, can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody.

Thus, according to another embodiment, the antibody, e.g., a 15C11, 19H12, 22B2, 18B10, 12B11 or 13H1-like antibody, is humanized. "Humanized" forms of antibodies are specific chimeric immunoglobulins, immunoglobulin chains or fragments thereof (such as Fv, Fab, Fab', F (ab') 2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.) Methods for humanizing the antibodies are well known in the art.

The choice of human variable domains, both light and heavy, to be used in making the humanized antibodies is very important to reduce antigenicity. According to the so-called "best-fit" method, the sequence of the variable domain of an antibody is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, 1987, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al., J. Immunol., 151, p. 2623 (1993)).

It is further important that antibodies be humanized with retention of high affinity for KIR3DL2 receptors and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen (s), is achieved. In general, the CDR residues are directly and most substantially involved in influencing antigen binding.

Another method of making "humanized" monoclonal antibodies is to use a XenoMouse (Abgenix, Fremont, Calif.) as the mouse used for immunization. A XenoMouse is a murine host that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et al., Nature 362 (1993) 255), or by selection of antibody repertoires using phage display methods. Such techniques are known to the skilled person and can be implemented starting from monoclonal antibodies as disclosed in the present application.

The antibodies, e.g., a 15C11, 19H12, 22B2, 18B10, 12B11 or 13H1-like antibody, may also be derivatized to "chimeric" antibodies (immunoglobulins) in which a portion of the heavy/light chain(s) is identical with or homologous to corresponding sequences in the original antibody, while the remainder of the chain (s) is identical with or homologous to corresponding sequences in antibodies derived from another species or belonging to another antibody class or subclass, as well as fragments of such antibodies, so long as they exhibit the desired biological activity and binding specificity (Cabilly et al., supra; Morrison et al., Proc. Natl. Acad. Sci. U.S.A., pp. 6851 (1984)).

Example 12 below describes the design of exemplary humanized anti-KIR3DL2. As shown in the example, anti-KIR3DL2 antibodies may optionally comprise mutations in FR residues in a VH and/or VL, e.g. a h15C11 VL sequence (e.g., SEQ ID NO: 120) may comprise mutations in one or more of the FR residues, for example at residues 38, 49, 69 and/or 71 (Kabat residues or residues in the SEQ ID NO). A h15C11 VH sequence (e.g., SEQ ID NO: 114) may optionally comprise mutations in one or more of the indicated FR residues 49, 50, 58 (residue 61 in SEQ ID NO: 114) or 78 (residue 81 in SEQ ID NO: 114), with amino acid numbering according to Kabat. Table 4 describes exemplary h15C11VL and h15C11VH variants comprising exemplary human-to-murine back-mutations in the h15C11VH and h15C11VL FR sequences, as well as exemplary combinations of FR mutations. In Table 4, the amino acid positions are designated according to Kabat, in which amino acids G49, R50, A58, and L78 in the h15C11VH domain correspond to amino acids G49, R50, A61, and L81 in SEQ ID NO: 114.

TABLE 4

| h15C11VL Variants | H15C11VH Variants |
|---|---|
| None | None |
| Q38H | |
| Y49H | G49A |
| T69R | R50E |
| F71Y | A58Y |
| | L78V |
| Q38H and Y49H | G49A and R50E |
| Q38H and T69R | G49A and A58Y |
| Q38H and F71Y | G49A and L78V |
| Y49H and T69R | R50E and A58Y |
| Y49H and F71Y | R50E and L78V |
| T69R and F71Y | A58Y and L78V |
| Q38H, Y49H and T69R | G49A, R50E and A58Y |
| Q38H, Y49H and F71Y | G49A, R50E and L78V |
| Y49H, T69R and F71Y | R50E, A58Y, and L78V |
| Q38H, Y49H, T69R and F71Y | G49A, R50E, A58Y, and L78V |

Accordingly, provided are humanized versions of an anti-KIR3DL2 humanized antibody herein comprises non-human hypervariable region or CDR residues incorporated into a human VH domain. In one embodiment, the humanized antibody comprises no FR substitution in the VH domain. In another embodiment, the humanized antibody comprises a VH domain FR substitution at one or more positions selected from 49, 50, 58 and 78, utilizing the variable domain numbering system according to Kabat. In another embodiment, the humanized antibody comprises VH domain FR substitutions at two or more of positions 49, 50, 58 and 78; and in other embodiments, at three, four, or all of such positions. In separate and independent embodiments, the humanized antibody comprises one VH domain FR substitution at a position selected from 49, 50, 58 and 78. Fewer rather than more framework substitutions can minimize immunogenicity, but binding efficacy is also an important consideration. Thus, preferred substitutions are back-mutations, i.e., mutations which replace an amino acid at a certain position in the human FR with the amino acid at the corresponding position in a non-human donor FR.

The humanized antibody herein also comprises non-human hypervariable region residues incorporated into a human VL domain. In one embodiment, the humanized antibody comprises no FR substitution in the VL domain. In another embodiment, the humanized antibody comprises a VL domain FR substitution at one of positions 38, 49, 69 and 71, and in other embodiments, at three, four, or all of such positions, utilizing the variable domain numbering system according to Kabat. In another embodiment, the humanized antibody comprises VL domain FR substitutions at two or more of positions 38, 49, 69 and 71. Preferred substitutions are back-mutations, i.e., mutations which replace an amino acid at a certain position in the human FR with the amino acid at the corresponding position in a non-human donor FR.

An exemplary humanized antibody comprises a VH domain comprising a CDR-H1 sequence corresponding to SEQ ID NOS: 4, 5 or 6, a CDR-H2 sequence corresponding to SEQ ID NOS: 8, and a CDR-H3 sequence corresponding to SEQ ID NO: 9. The humanized antibody may further comprise an amino acid at Kabat position 50 which is R or E, and/or an amino acid at Kabat position 58 which is A or Y and/or an amino acid at Kabat position 49 which is G or A and/or an amino acid at Kabat position 78 which is L or V. In one embodiment, the VH domain comprises the sequence of SEQ ID NOS: 114, 116 or 118.

An exemplary humanized antibody may also or alternatively comprise a VL domain comprising a CDR-L1 sequence corresponding to SEQ ID NO: 10, a CDR-L2 sequence corresponding SEQ ID NO: 11, and an CDR-L3 sequence corresponding SEQ ID NO: 12. The humanized antibody may further comprise an amino acid at Kabat position 38 which is Q or H and/or an amino acid at Kabat position 49 which is Y or H, and/or an amino acid at Kabat position 69 which is T or R, and/or an amino acid at Kabat position 71 which is F or Y. In another embodiment, the VH domain comprises the sequence of SEQ ID NOS: 120, 122 or 124.

In one embodiment, the VH comprises the sequence of SEQ NO: 114 and the VL comprises the sequence of SEQ NO: 120, 122 or 124. In one embodiment, the VH comprises the sequence of SEQ NO: 116 and the VL comprises the sequence of SEQ NO: 120, 122 or 124 optionally wherein the VL comprises the sequence of SEQ NO: 122. In one embodiment, the VH comprises the sequence of SEQ NO: 118 and the VL comprises the sequence of SEQ NO: 120, 122 or 124, optionally wherein the VL comprises the sequence of SEQ NO: 124.

Optionally, in a particular aspect, the VH and/or VL domain comprises amino acid modifications of one or more CDR residues, e.g. where the modifications essentially maintain or improve affinity of the antibody. For example, the antibody variant may have one, two, three, or from one to about seven amino acid substitutions in the above VH or VL CDR sequences. Such antibody variants may be prepared by affinity maturation, e.g., as described below.

In a particular aspect, amino acids in the humanized antibody VH CDRs which are different from the amino acids at the corresponding positions in the non-human donor VH CDRs can be substituted to improve the binding properties and/or stability of the humanized antibody. For example, one or more of these amino acids can be substituted for the amino acid at the corresponding position(s) in the non-human donor VH CDR. In one embodiment, the variant antibody comprises CDRH1, CDRH2 and/or CDRH3 substitutions. In another particular aspect, amino acids in the humanized antibody VL CDRs which are different from the amino acids at the corresponding positions in the non-human donor VL CDRs can be substituted to improve the binding properties and/or stability of the humanized antibody. For example, one or more of these amino acids can be substituted for the amino acid at the corresponding position(s) in the non-human donor VL CDR. In one embodiment, the variant antibody comprises CDRL1, CDRL2 and/or CDRL3 substitutions. Optionally, the modifications essentially maintain or improve affinity of the antibody. For example, the antibody variant may have one, two, three, or from one to about seven amino acid substitutions in the above VL or VH CDR sequences. Such antibody variants may be prepared by affinity maturation, e.g., as described below.

In another aspect, provided are humanized antibodies that comprise a VH domain having at least about 80% sequence identity (e.g., at least about 85%, 90%, 95%, 97%, or more identity) to the VH domain of h15C11 (SEQ ID NO: 114, 116 or 118).

In another aspect, provided is an antibody molecule that also or alternatively comprises a VL domain having at least about 80% sequence identity (e.g., at least about 85%, 90%, 95%, 97%, or more identity) to the VL domain of h15C11 (SEQ ID NO: 120, 122 or 124).

A humanized anti-KIR3DL2 antibody may comprise any full-length or partial heavy-chain (HC) comprising a h15C11 VH described herein which may be combined with any h15C11 VL variant described herein in, and the resulting antibody or fragment tested for antigen binding, functional effects on KIR3DL2 expressing cells, and/or immunogenicity.

Various forms of the humanized antibody or affinity-matured antibody are contemplated. For example, the humanized antibody or affinity-matured antibody may be an antibody fragment, such as a Fab. Alternatively, the humanized antibody or affinity-matured antibody may be a full-length or intact antibody, such as a full-length or intact IgG1 or IgG4 antibody. In one embodiment, the humanized antibody is a full-length IgG4 antibody or a fragment thereof. To produce such antibodies, humanized VH and VL regions, or variant versions thereof, can be cloned into expression vectors encoding full-length or truncated constant regions from a human antibody according to standard recombinant methods (see, e.g., Sambrook et al., Molecular Cloning: A Laboratory Manual, $2^{nd}$ Ed., Cold Spring Harbor Laboratory, Cold Spring Harbor, N.Y., 1989). The result is a transfected cell line that expresses and secretes the humanized antibody molecule of interest, comprising the selected VH and VL regions and constant regions. cDNA sequences encoding the constant regions of human antibodies are known.

The constant region may further be modified according to known methods. For example, in an IgG4 constant region, residue S241 may be mutated to a proline (P) residue to allow complete disulphide bridge formation at the hinge (see, e.g., Angal et al., Mol Immunol. 1993; 30:105-8).

Antibody Conjugates

Provided are anti-KIR3DL2 antibodies which are directed to and, in embodiments, are internalized into cells. They are capable of delivering therapeutic (e.g. toxic) agents or detectable agents to or into cells expressing KIR3DL2, but not to or into cells where KIR3DL2 polypeptides are not expressed. Thus, provided also are anti-KIR3DL2 immunoconjugates comprising an anti-KIR3DL2 antibody as described herein, which is conjugated to a therapeutic agent or a detectable agent (or any other moiety that serves as a payload of interest to be delivered to a KIR3DL2-expressing cell. In embodiments, the affinity for KIR3DL2 of an anti-KIR3DL2 immunoconjugate is at least 10, 25, 50, 75, 80, 90, or 95% of that for the unconjugated antibody. This can be determined using cell surface KIR3DL2 or isolated KIR3DL2.

In one aspect, an antibody is capable of being internalized by a target cell is linked to or otherwise associated with a cytotoxic drug or toxin for targeted killing cells expressing KIR3DL2 polypeptides, e.g. CTCL, Sézary or Mycosis Fungoides tumor cells, or cells involved in inflammation or an autoimmune disease. These agents typically include antibody-drug conjugates (ADCs) and immunotoxins, respectively.

In an optional aspect of any such embodiments, a biological sample (e.g. from a patient) is obtained to assess whether the cells (e.g. tumor cells, cells involved in inflammation, etc.) express KIR3DL2, e.g., using the detection methods described herein. If KIR3DL2 is indeed detected on the surface of the tumor cells, then, cytotoxic antibodies can be administered. The cytotoxic antibody is then internalized by the cell and the toxin is released inside of the cell, selectively killing that cell. Such antibodies will therefore be used in methods of treating of cancers and tumors, including but not limited to T cell lymphomas, e.g., CD4+ or CD8+T lymphomas, CD30+T lymphomas, CTCL, Sézary syndrome and Mycosis fungoides, and inflammatory and autoimmune disorders.

The anti-KIR3DL2 antibodies described herein can be functionally linked by any suitable method (e.g., chemical coupling, genetic fusion, noncovalent association or otherwise) to one or more non-antibody molecular entities.

The anti-KIR3DL2 antibody molecule can be modified to act as an immunoconjugate utilizing techniques that are known in the art. See e.g., Vitetta Immunol Today 14:252 (1993). See also U.S. Pat. No. 5,194,594. The preparation of radiolabeled antibodies can also be readily prepared utilizing techniques that are known in the art. See e.g., Junghans et al. in Cancer Chemotherapy and Biotherapy 655-686 (2d edition, Chafner and Longo, eds., Lippincott Raven (1996)). See also U.S. Pat. Nos. 4,681,581, 4,735,210, 5,101,827, 5,102,990 (U.S. Re. Pat. No. 35,500), 5,648,471, and 5,697,902.

In some embodiments, the antibody molecule and non-antibody moiety are connected by means of a linker. In such embodiments, the immunoconjugate is represented by formula (XII):

$$Ab\text{-}(X\text{-}Z)_m \qquad \qquad (XII)$$

wherein,

Ab is an anti-KIR3DL2 antibody molecule described herein;

X is a moiety which connects Ab and Z, e.g., the residue of a linker following covalent linkage to one or both of Ab and Z;

Z is a therapeutic agent (e.g. any cytotoxic agent) or a label, or alternatively any other moiety which is to be delivered to a KIR3DL2-expressing cells; and m ranges from about 1 to about 15.

The variable m represents the number of -X-Z moieties per antibody molecule in an immunoconjugate of formula (XII). In various embodiments, m ranges from 1 to 15, 1 to 10, 1 to 9, 1 to 8, 1 to 7, 1 to 6, 1 to 5, 1 to 4, 1 to 3, or 1 to 2. In some embodiments, m ranges from 2 to 10, 2 to 9, 2 to 8, 2 to 7, 2 to 6, 2 to 5, 2 to 4 or 2 to 3. In other embodiments, m is 1, 2, 3, 4, 5 or 6. In compositions comprising a plurality of immunoconjugates of formula (XII), m is the average number of -X-Z moieties per Ab, also referred to as the average drug loading. Average drug loading may range from 1 to about 15 -X-Z moieties per Ab. In some embodiments, when m represents the average drug loading, m is about 1, about 2, about 3, about 4, about 5, about 6, about 7, or about 8. In exemplary embodiments, m is from about 2 to about 8. In one embodiment, m is about 8. In another embodiment, m is about 4. In another embodiment, m is about 2.

The average number of -X-Z moieties per Ab may be characterized by conventional means such as mass spectroscopy, ELISA assay, and HPLC. The quantitative distribution of immunoconjugates in terms of m may also be determined. In some instances, separation, purification, and characterization of homogeneous immunoconjugates where m is a certain value, as distinguished from immunoconjugates with other drug loadings, may be achieved by means such as reverse phase HPLC or electrophoresis.

The immunoconjugates of formula (XII) may exist as mixtures, wherein each component of the mixture has a different m value. For example, an immunoconjugate of formula (XII) may exist as a mixture comprising or consisting of two, three, four or more separate immunoconjugate components, comprising a first immunoconjugate component wherein m is 1, 2, 3, 4, 5, 6, 7 or 8 and a second immunoconjugate component wherein m is 1, 2, 3, 4, 5, 6, 7 or 8, and optionally a third, and/or fourth, and/or further immunoconjugates. Optionally, the mixture comprises at least a first immunoconjugate component wherein m is 7 and a second immunoconjugate component wherein m is 8. In one embodiment, the immunoconjugate of formula (XII) exists as a mixture comprising or consisting of three separate immunoconjugates wherein m for the three separate immunoconjugates is 1, 2, and 3, respectively; 3, 4 and 5, respectively; 5, 6 and 7, respectively; 7, 8 and 9, respectively; 9, 10 and 11, respectively; 11, 12 and 13, respectively; or 13, 14 and 15, respectively.

A variety of suitable linkers (e.g., heterobifunctional reagents for connecting an antibody molecule to a therapeutic agent or label) and methods for preparing immunoconjugates are known in the art. (See, for example, Chari et al, Cancer Research 52: 127-131 (1992).) The linker can be cleavable, e.g., under physiological conditions, e.g., under intracellular conditions, such that cleavage of the linker releases the drug (therapeutic agent or label) in the intracellular environment. In other embodiments, the linker is not cleavable, and the drug is released, for example, by antibody degradation.

The linker can be bonded to a chemically reactive group on the antibody moiety, e.g., to a free amino, imino, hydroxyl, thiol or carboxyl group (e.g., to the N- or C-terminus, to the epsilon amino group of one or more lysine residues, the free carboxylic acid group of one or more glutamic acid or aspartic acid residues, or to the sulfhydryl group of one or more cysteinyl residues). The site to which the linker is bound can be a natural residue in the amino acid sequence of the antibody moiety or it can be introduced into the antibody moiety, e.g., by DNA recombinant technology (e.g., by introducing a cysteine or protease cleavage site in the amino acid sequence) or by protein biochemistry (e.g., reduction, pH adjustment or proteolysis).

One of the most commonly used non-specific methods of covalent attachment is the carbodiimide reaction to link a carboxy (or amino) group of a compound to amino (or carboxy) groups of the antibody molecule. Additionally, bifunctional agents such as dialdehydes or imidoesters have been used to link the amino group of a compound to amino groups of an antibody molecule. Also available for attachment of drugs to antibody molecules is the Schiff base reaction. This method involves the periodate oxidation of a drug that contains glycol or hydroxy groups, thus forming an aldehyde which is then reacted with the antibody molecule. Attachment occurs via formation of a Schiff base with amino groups of the antibody molecule. Isothiocyanates can also be used as coupling agents for covalently attaching drugs to antibody molecule. Other techniques are known to the skilled artisan.

In certain embodiments, an intermediate, which is the precursor of the linker (X), is reacted with the drug (Z) under appropriate conditions. In certain embodiments, reactive groups are used on the drug and/or the intermediate. The product of the reaction between the drug and the intermediate, or the derivatized drug, is subsequently reacted with the antibody molecule under appropriate conditions.

The immunoconjugate can be purified from reactants by employing methodologies well known to those of skill in the art, e.g., column chromatography (e.g., affinity chromatography, ion exchange chromatography, gel filtration, hydrophobic interaction chromatography), dialysis, diafiltration or precipitation. The immunoconjugate can be evaluated by employing methodologies well known to those skilled in the art, e.g., SDS-PAGE, mass spectroscopy, or capillary electrophoresis.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in KIR3DL2-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). Other examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al, 1989, Biol. Chem. 264: 14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene), SPDB and SMPT (See, e.g., Thorpe et al, 1987, Cancer Res. 47:5924-5931; Wawrzynczak et al, In Immunoconjugates: Antibody Conjugates in Radioimagery and Therapy of Cancer (C. W. Vogel ed., Oxford U. Press, 1987. See also U.S. Pat. No. 4,880,935).

In yet other specific embodiments, the linker is a malonate linker (Johnson et al, 1995, Anticancer Res. 15: 1387-93), a maleimidobenzoyl linker (Lau et al., 1995, BioorgMed Chem. 3(10): 1299-1304), or a 3'-N-amide analog (Lau et al, 1995, Bioorg. Med. Chem. 3(10):1305-12).

In yet other embodiments, the linker unit is not cleavable and the drug is released by antibody degradation. (See for example U.S. Publication No. 20050238649 incorporated by reference herein in its entirety and for all purposes.)

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of immunoconjugate, are cleaved when the immunoconjugate presents in an extracellular environment (e.g., in plasma). Whether a linker is not substantially sensitive to the extracellular environment can be determined, for example, by incubating with plasma the immunoconjugate for a predetermined time period (e.g., 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent or label (Z). In yet other embodiments, the linker promotes cellular internalization when conjugated to both the Z moiety and the anti-KIR3DL2 antibody molecule.

A variety of exemplary linkers that can be used with the present compositions and methods are described in WO2004/010957, U.S. Patent Publication No. 20060074008, U.S. Patent Publication No. 20050238649, and U.S. Patent Publication No. 20060024317 (each of which is incorporated by reference herein in its entirety and for all purposes).

In other embodiments, a linker can function as a spacer to distance an antibody from an agent in order to avoid interference with binding capabilities. In one embodiment, a linker may comprise a stretcher unit, e.g. a molecule that forms a bond with a sulfur atom, a primary or secondary amino group or a carbohydrate group of the antibody, and which stretcher links the antibody to the therapeutic agent or label (Z) or to an amino acid unit which is in turn linked to Z. When the stretcher is linked to an amino acid unit, the amino acid unit can be directly linked to Z or can comprise a spacer element (e.g. a non-self immolative or a self immolative spacer) linking the amino acid unit and Z. The amino acid unit can be a single amino acid or a peptide, e.g. valine-citrulline or phenylanaline-lysine.

Preferred toxic or cytotoxic peptides or small molecules that can be linked to the anti-KIR3DL2 antibodies include any compound that can slow down, halt, or reverse the proliferation of cells, decrease their activity in any detectable way, or directly or indirectly kill them. As used herein, a toxic peptide can include any peptide, polypeptide, or derivative of such, including peptide- or polypeptide-derivatives with unnatural amino acids or modified linkages. A toxic small molecule can include any toxic compound or element, optionally with a size of less than 10 kD, 5 kD, 1 kD, 750 D, 600 D, 500 D, 400 D, 300 D, or smaller.

The one or more moieties Z can be for example taxanes, anthracyclines, camptothecins, epothilones, mytomycins, combretastatins, vinca alkaloids, nitrogen mustards, maytansinoids, calicheamycins, duocarmycins, tubulysmes, dolastatins and auristatins, enediynes, pyrrolobenzodiazepines, ethylenimines, radioisotopes, therapeutic proteins and peptides, and toxins or fragments thereof.

In some embodiments, the therapeutic agent is a cytostatic or cytotoxic agent, e.g. a peptide, polypeptide, nucleic acid or small molecule. Examples include, without limitation, antimetabolites (e.g., azathioprine, 6-mercaptopurine, 6-thioguanine, fludarabine, pentostatin, cladribine, 5-fluorouracil (5FU), floxuridine (FUDR), cytosine arabinoside (cytarabine), methotrexate, trimethoprim, pyrimethamine, pemetrexed); alkylating agents (e.g., cyclophosphamide, mechlorethamine, uramustine, melphalan, chlorambucil, thiotepa/chlorambucil, ifosfamide, carmustine, lomustine, streptozocin, busulfan, dibromomannitol, cisplatin, carboplatin, nedaplatin, oxaliplatin, satraplatin, triplatin tetranitrate, procarbazine, altretamine, dacarbazine, mitozolomide, temozolomide); anthracyclines (e.g., daunorubicin, doxorubicin, epirubicin, idarubicin, valrubicin); antibiotics (e.g., dactinomycin, bleomycin, mithramycin, anthramycin, streptozotocin, gramicidin D, mitomycins (e.g., mitomycin C), calicheamicins; antimitotic agents (including, e.g., maytansinoids, auristatins, dolastatins, cryptophycins, vinca alkaloids (e.g., vincristine, vinblastine, vindesine, vinorelbine), taxanes (e.g., paclitaxel, docetaxel, taxanes of e.g., PCT publication WO 01/38318)), and colchicines; topoisomerase inhibitors (e.g., irinotecan, topotecan, amsacrine, etoposide, teniposide, mitoxantrone); and proteasome inhibitors (e.g., peptidyl boronic acids).

In a preferred embodiment, the one or more moieties Z are each independently selected from the group consisting of: cyclophosphamide, ifosfamide, chlorambucil, 4-(bis(2-chloroethyl)amino)phenol, 4-(bis(2-fluoroethyl)ammo)phenol, N,N-bis(2-chloroethyl)-p-phenylenediamine, N,N-bis(2-fluoro-ethyl)-p-phenylenediamine, carmustine, lomustine, treosulfan, dacarbazine, cisplatin, carboplatin, vincristine, vinblastine, vindesine, vinorelbine, paclitaxel, docetaxel, etoposide, teniposide, topotecan, inirotecan, 9-aminocamptothecin, 9-nitrocamptothecin, 10-hydroxycamptothecin, lurtotecan, camptothecin, crisnatol, mitomycin C, mitomycin A, methotrexate, trimetrexate, mycophenolic acid, tiazofurin, ribavirin, hydroxyurea, deferoxamine, 5-fluorouracil, floxuridine, doxifluridine, raltitrexed, cytarabine, cytosine arabinoside, fludarabine, 6-mercaptopurine, thioguanine, raloxifen, megestrol, goserelin, leuprolide acetate, flutamide, bicalutamide, vertoporfin, phthalocyanine, photosensitizer Pc4, demethoxy-hypocrellin A, interferon-alpha, interferon-gamma, tumor necrosis factor, lovastatin, staurosporine, actinomycin D, bleomycin A2, bleomycin B2, peplomycin, daunorubicin, doxorubicin, N-(5,5-diacetoxypentyl)doxorubicin, morpholino doxorubicin, idarubicin, epirubicin, pirarubicin, zorubicin, mitoxantrone, thapsigargin, $N^8$-acetylspermidine, tallysomycin, esperamycin, butyric acid, retinoic acid, 1,8-dihydroxybicyclo[7.3.1]trideca-4-ene-2,6-diyne-13-one, anguidine, podophyllotoxin, combretastatin A-4, pancratistatin, carminomycin, streptonigrin, elliptmium acetate, maytansine, maytansinol, calicheamycin, mertansine (DM1), N-acetyl-$\gamma_1^I$-calicheamycin, calicheamycin-$\gamma_1^I$, calicheamycin-$\alpha_2^I$, calicheamycin-$\alpha_3^I$, duocarmycin SA, duocarmycin A, CC-1065, CBI-TMI, duocarmycin C2, duocarmycin B2, centanamycin, dolastatin, auristatin E, monomethylauristatin E (MMAE), monomethylauristatin F (MMAF), and derivatives thereof.

Examples include maytansinoid compounds and methods for their conjugation to antibodies are described, for example, in Chari et al, (1992) Cancer Res., 52: 127-131; U.S. Pat. Nos. 5,208,020 and 6,333,410.

In some preferred embodiments, a therapeutic agent (Z) is a dolastatin or a dolastatin peptidic analog or derivative, e.g., an auristatin. Dolastatins such as an auristatin, e.g., auristatin E. Auristatin, compounds and methods for their conjugation to antibodies are described in Doronina et al, (2003) Nature Biotech., 21: 778-784; Hamblett et al, (2004) Clin. Cancer Res., 10: 7063-7070; U.S. Pat. Nos. 7,498,298, 7,091,186, 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278;

4,816,444; and 4,486,414; U.S. Patent Publication Nos. 2009-0010945, 2006-0074008, 2008-0300192, 2005-0009751, 2005-0238649, and 2003-0083236, each of which is incorporated by reference herein in its entirety and for all purposes. The auristatin can be, for example, an ester formed between auristatin E and a keto acid. For example, auristatin E can be reacted with paraacetyl benzoic acid or benzoyl-valeric acid to produce AEB and AEVB, respectively. Other typical auristatins include auristatin phenylalanine phenylenediamine (AFP), monomethyl auristatin E (MMAE), and monomethyl auristatin F (MMAF). Dolastatins and auristatins have been shown to interfere with microtubule dynamics, GTP hydrolysis, and nuclear and cellular division. The dolastatin or auristatin drug moiety may be attached to the antibody through the N (amino) terminus or the C (carboxyl) terminus of the peptidic drug moiety.

Preferred exemplary auristatin embodiments include the N-terminus linked monomethylauristatin drug moieties comprising a structure of any of Formulas XIII and XIV below:

$R^9$ is selected from H and $C_1$-$C_8$ alkyl;
$R^{10}$ is selected from aryl or $C_3$-$C_8$ heterocycle;
Z is O, S, NH, or $NR^{12}$ wherein $R^{12}$ is $C_1$-$C_8$ alkyl;
$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$; m is an integer ranging from 1-1000;
$R^{13}$ is $C_2$-$C_8$ alkyl;
$R^{14}$ is H or $C_1$-$C_8$ alkyl;
each occurrence of $R^{15}$ is independently H, COOH, —$(CH_2)$—$N(R^{16})_2$, —$(CH_2)$—$SO_3$—$C_1$-$C_8$ alkyl;
each occurrence of $R^{16}$ is independently H, $C_1$-$C_8$ alkyl, or —$(CH_2)_n$—COOH;
$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and
n is an integer ranging from 0 to 6.

In one embodiment, $R^3$, $R^4$ and $R^7$ are independently isopropyl or sec-butyl and $R^5$ is —H or methyl. In an exemplary embodiment. $R^3$ and $R^4$ are each isopropyl, $R^5$ is —H, and $R^7$ is sec-butyl.

Formula XIII

Formula XIV wherein the wavy line of XIII and XIV indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_1$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle. aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or R4 and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

In yet another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —$CH(R^{15})_2$, wherein $R^{15}$ is —$(CH_2)$—$N(R^{16})_2$, and $R^{16}$ is —$C_1$-$C_8$ alkyl or —$(CH_2)_n$—COOH.

In another embodiment, when Z is —NH, $R^{11}$ is —CH$(R^{15})_2$, wherein $R^{15}$ is —$(CH_2)$—$SO_3H$.

One exemplary auristatin embodiment of formula XIII is MMAE, wherein the wavy line indicates the covalent attachment to a linker (L) of an antibody-drug conjugate:

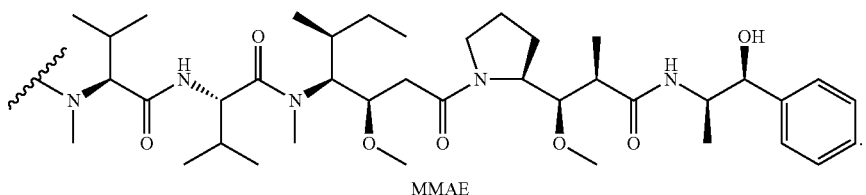 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]
MMAE

An exemplary auristatin embodiment of formula XIV is MMAF, wherein the wavy line indicates the covalent attachment to a linker (L) of an antibody-drug conjugate (see US 2005/0238649 and Doronina et al. (2006) Bioconjugate Cfiem. 17: 1 14-124):

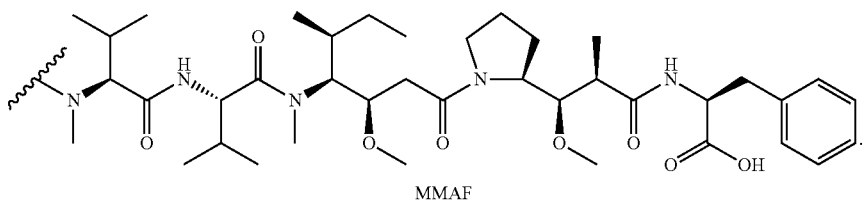
MMAF

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Other drug moieties include the following MMAF derivatives, wherein the wavy line indicates the covalent attachment to a linker (L) of an antibody-drug conjugate:

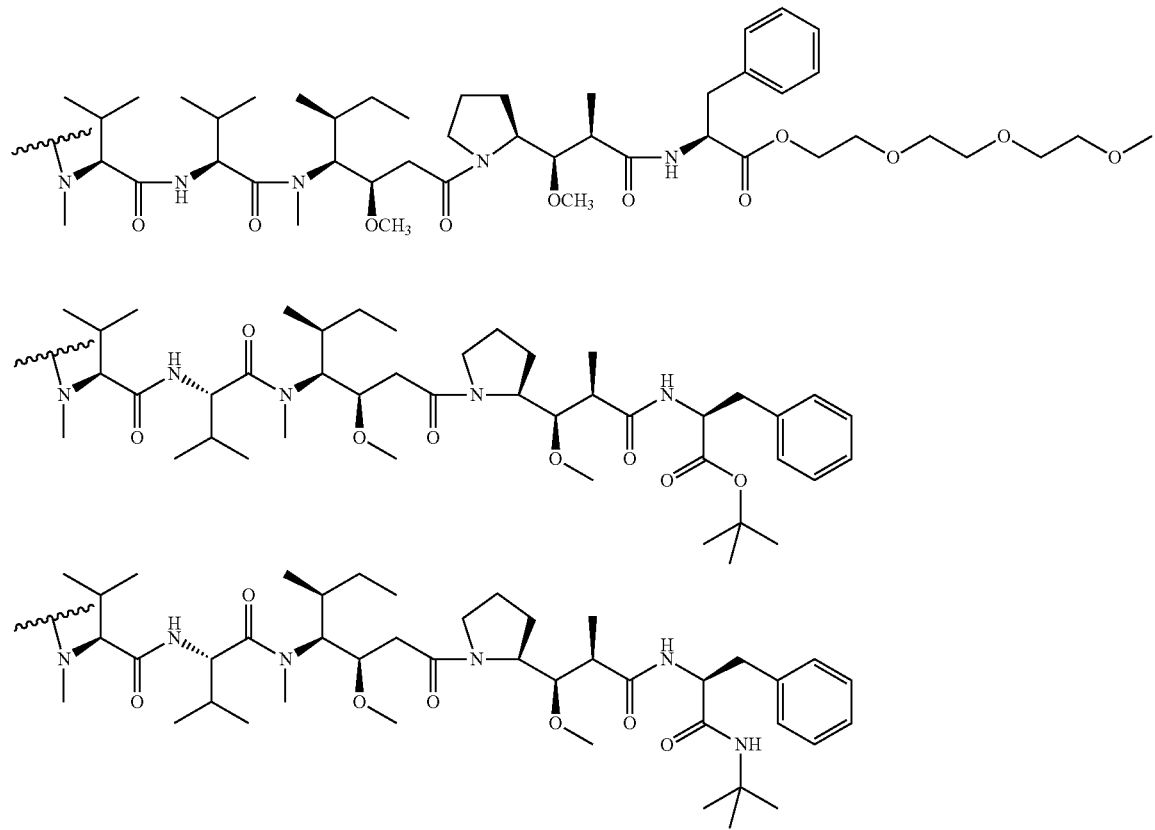

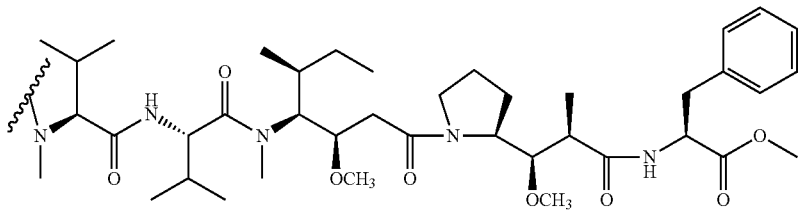
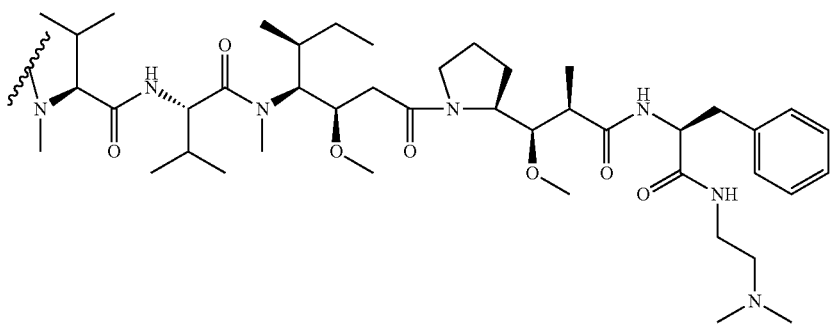
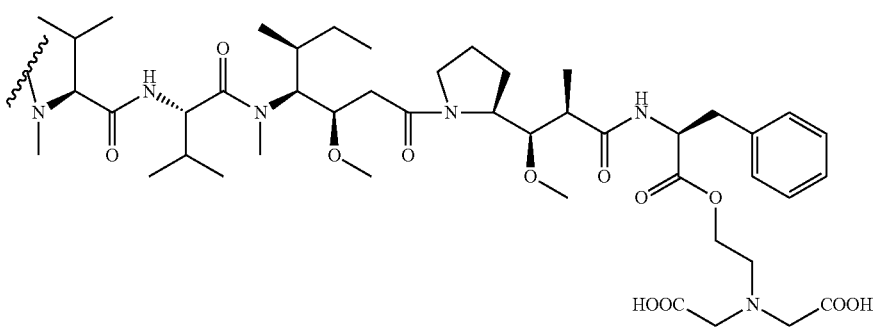
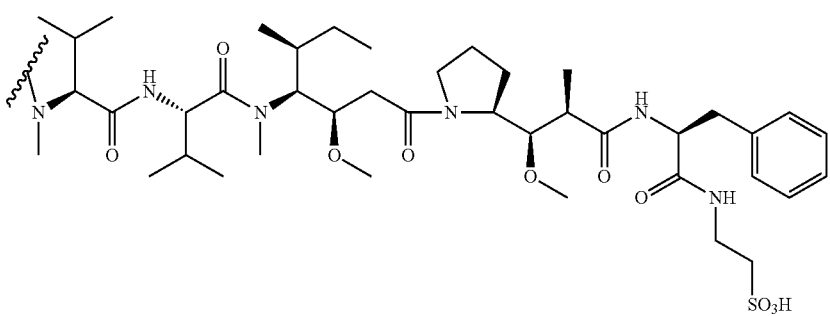
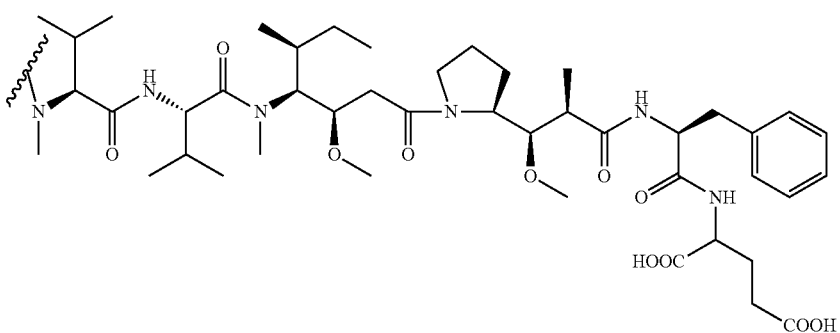

-continued

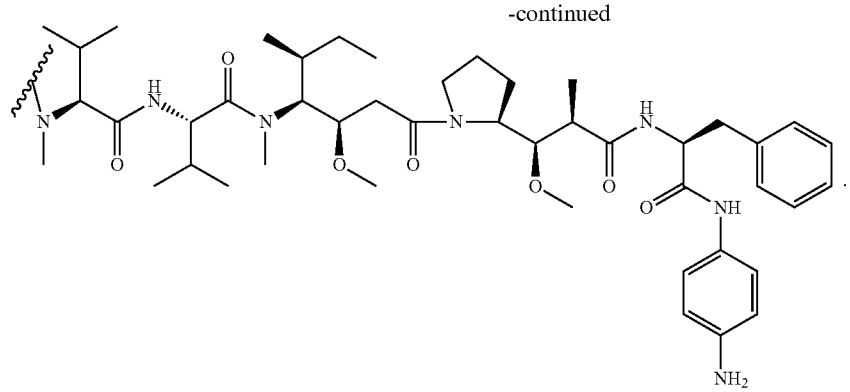

In one aspect, hydrophilic groups including but not limited to, triethylene glycol esters (TEG), as shown above, can be attached to the drug moiety at $R^{11}$. Without being bound by any particular theory, the hydrophilic groups assist in the internalization and non-agglomeration of the drug moiety.

Examples of antibody-drug conjugates include anti-KIR3DL2 antibodies of (Ab) linked to a therapeutic agent (Z) via a moiety (X) which connects Ab and Z, wherein the X-Z moiety has one of the following structures below. Between 1 and 15 such moieties may be linked to each antibody.

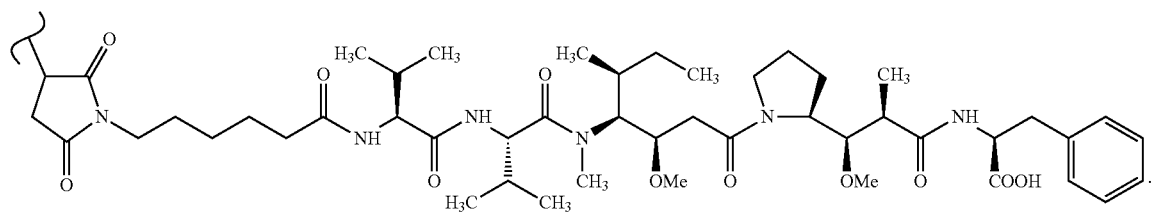

MC-MMAE

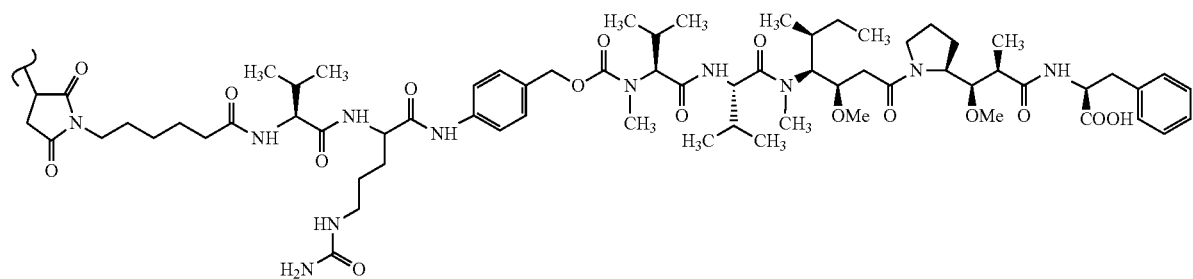

MC-vc-PAB-MMAE

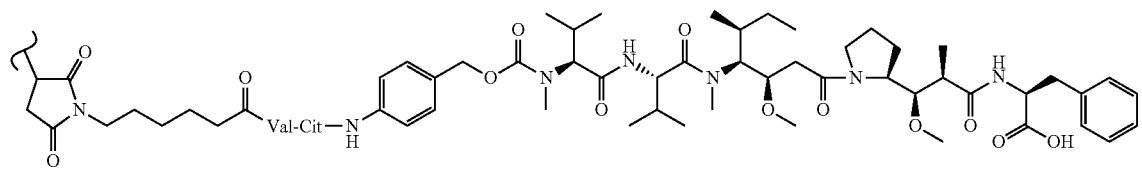

MC-vc-PAB-MMAF

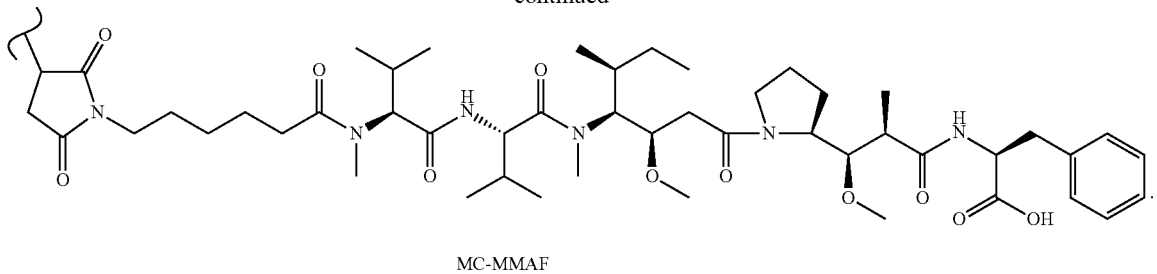

MC-MMAF

Exemplary embodiments of ADCs of Formula XIII and XIV comprising MMAF or MMAE and various linker components further include Ab-MC-PAB-MMAF, Ab-MC-PAB-MMAE, Ab-PAB-MMAF and Ab-PAB-MMAE. In some cases, ADCs comprising MMAF attached to an antibody by a linker that is not proteolytically cleavable have been shown to possess activity comparable to ADCs comprising MMAF attached to an antibody by a proteolytically cleavable linker. In such instances, drug release is believed to be effected by antibody degradation in the cell. ADCs comprising MMAE attached to an antibody by a cleavable linker can be more potent that ADCs comprising MMAE attached to an antibody by a non-cleavable linker.

Typically, peptide-based drug moieties can be prepared by forming a peptide bond between two or more amino acids and/or peptide fragments. Such peptide bonds can be prepared, for example, using liquid phase synthesis methods. Auristatin/dolastatin drug moieties may be prepared according to the methods of: US patent publication no. US 2005-0238649; U.S. Pat. Nos. 5,635,483 and 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat. Biotechnol. 21(7):778-784.

In particular, auristatin/dolastatin drug moieties such as MMAF and derivatives thereof, may be prepared using methods described in US patent publication no. US 2005-0238649 and Doronina et al. (2006) Bioconjugate Chem. 17: 114-124. Auristatin/dolastatin drug moieties of formula DE, such as MMAE and derivatives thereof, may be prepared using methods described in Doronina et al. (2003) Nat. Biotech. 21.778-784. Drug-linker moieties MC-MMAF, MC-MMAE, MC-vc-PAB-MMAF, and MC-vc-PAB-MMAE may be conveniently synthesized by routine methods, e.g., as described in Doronina et al. (2003) Nat. Biotech. 21:778-784, and then conjugated to an antibody of interest.

There are a number of different assays, known in the art, that can be used for determining whether an auristatin or resultant immunoconjugate exerts a cytostatic or cytotoxic effect on a desired cell line. For example, the cytotoxic or cytostatic activity of an immunoconjugate can be measured by: exposing mammalian cells expressing a target protein of the immunoconjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the immunoconjugate.

For determining whether an immunoconjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of $^3$H-thymidine during the final 8 hours of the 72-hour period. The incorporation of $^3$H-thymidine into cells of the culture is measured in the presence and absence of the immunoconjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an immunoconjugate is useful in the treatment of cancers.

Cell viability can be measured by determining in a cell the uptake of a dye such as neutral red, trypan blue, or ALAMAR™ blue. In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytotoxicity. Alternatively, a tetrazolium salt, such as MTT or WST, is used in a quantitative colorimetric assay for mammalian cell survival and proliferation by detecting living, but not dead, cells.

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays. Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., (1995), Cancer Research 55: 3110-16).

The immunoconjugates disclosed herein can be used for modifying a given biological response. The therapeutic agent is not to be construed as limited to classical chemical therapeutic agents. For example, the therapeutic agent may be a nucleic acid, protein, or polypeptide possessing a desired biological activity. For example, the antibody molecule can be conjugated to an antisense molecule, a siRNA molecule, shRNA molecule or miRNA molecule that can interfere with expression of a gene, thereby producing a desired biological effect.

Proteins and polypeptides that can be conjugated to the antibody include, for example, toxins and components thereof, such as abrin, abrin A chain, ricin, ricin A chain, modeccin, modeccin A chain, alpha-sarcin, exotoxin A (from *Pseudomonas aeruginosa*), PE38 (truncated *pseudomonas* exotoxin), gelonin, diphtheria toxin, diphtheria toxin A fragment, certain *Aleurites fordii* proteins, certain *Dianthus caryophyllus* proteins (e.g., dianthin 30 and dianthin 32), certain *Phytolacca Americana* proteins (e.g., PAP, PAPII, and PAP-S), certain *Saponaria officinlis* proteins (e.g., saporin 6), *Momordica charantia* inhibitor, curcin, crotin, mitogillin, restrictocin, phenomycin, and enomycin; proteins to engage the immune system at the tumor or induce an effector function at the tumor, such as tumor necrosis factor, interferon, nerve growth factor, platelet derived growth factor, and tissue plasminogen activator; and biological response modifiers such as, for example, cytokines and lymphokines (e.g., interleukin-1, interleukin-2, interleukin-6, granulocyte macrophase colony stimulating factor ("GM-CSF"), and granulocyte colony stimulating factor ("G-CSF")), and other growth factors. In one embodiment, an antibody can be conjugated to a second antibody to form an antibody heteroconjugate as described by Segal in U.S. Pat. No. 4,676,980. The formation of cross-linked antibodies can target the immune system to specific types of cells, for example, cancer or diseased cells expressing KIR3DL2.

The antibodies can also be conjugated or fused to viral surface proteins present on viral particles. For example, a single-chain anti-KIR3DL2 antibody can be fused (e.g., to form a fusion protein) to a viral surface protein. Alternatively, a whole anti-KIR3DL2 antibody, or a fragment thereof, could be chemically conjugated (e.g., via a chemical linker) to a viral surface protein. Optionally, the virus is one that fuses with endocytic membranes, e.g., an influenza virus, such that the virus is internalized along with the anti-KIR3DL2 antibody and thereby infects KIR3DL2-expressing cells. The virus can be genetically engineered as a cellular toxin. For example, the virus could express or induce the expression of genes that are toxic to cells, e.g., cell death promoting genes. Optionally, such viruses would be incapable of viral replication.

An anti-KIR3DL2 antibody can also be conjugated to a prodrug or prodrug activator. In a method to kill or suppress tumor cells, a first anti-KIR3DL2 antibody is conjugated with a prodrug that is activated only when in close proximity with a prodrug activator.

Therapeutically active radioisotopes can also be coupled to anti-KIR3DL2 antibodies, or antigen binding fragments, or derivatives thereof. Radioactive isotopes can be used in diagnostic or therapeutic applications. Radioactive isotopes that can be coupled to the anti-KIR3DL2 antibodies include, but are not limited to α-, β-, or γ-emitters, or β- and γ-emitters. Such radioactive isotopes include, but are not limited to copper ($^{64}$Cu), iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga).

Useful detectable agents with which an antibody or an antibody portion may be derivatized (or labeled) include fluorescent compounds, various enzymes, prosthetic groups, luminescent materials, bioluminescent materials, fluorescent emitting metal atoms, e.g., europium (Eu), and other anthanides, and radioactive materials (described above). Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin. Alternatively, the anti-KIR3DL2 antibody may be associated with a second antibody that binds to the anti-KIR3DL2 antibody, wherein the second antibody is derivatized with a detectable label; binding said second antibody into contact with the anti-KIR3DL2 antibody, in vitro or in vivo, will allow the anti-KIR3DL2 to serve as a labeled antibody.

Conjugation to a detectable moiety is useful, inter alia, when an antibody is used for diagnostic purposes. Such purposes include, but are not limited to, assaying biological samples, e.g., a blood sample or tissue biopsy, for the presence of KIR3DL2-expressing cells, and detecting the presence, level, or activity of KIR3DL2-expressing cells in an individual. Such assay and detection methods can be used in the diagnostic/therapeutic methods, e.g., involving detecting KIR3DL2 expression in cells of a patient and if the patient's cells are determined to express KIR3DL2, subsequently administering a KIR3DL2 modulating antibody.

In certain embodiments, the present antibodies are used to purify KIR3DL2-expressing cells from a biological sample. Biological samples can be obtained from a patient, e.g. for diagnostic or ex vivo therapeutic purposes, or from individuals or non-human primates to obtain a source of such cells for research purposes.

In one such embodiment, labeled antibodies can be used in FACS sorting to purify or isolate KIR3DL2-expressing cells from a biological sample. Alternatively, in some embodiments conjugation of an antibody to a solid support can be useful as a tool for affinity purification of cells bearing a KIR3DL2 receptor on their cell surface from a biological sample, such as a blood sample or cells from a tissue biopsy from an individual. This method of purification is another alternate embodiment, as is the resulting purified population of cells.

Regardless of the method used to isolate or purify the KIR3DL2-expressing cells, the ability to do so is useful for numerous purposes, e.g. to diagnose a KIR3DL2-associated disorder by assessing the number or activity of KIR3DL2- expressing cells, e.g., prior to administration of anti-KIR3DL2 antibodies as described herein. Further, purified KIR3DL2-expressing cells are useful in a research context, e.g., to better characterize the cells and their various properties and behaviors, as well as to identify compounds or methods that can be used to modulate their behavior, activity, survival, or proliferation.

Uses in Diagnostics and Therapy

In certain embodiments, the present antibodies are used to purify or identify KIR3DL2 positive cells from a biological sample. Biological samples can be obtained from a patient, e.g. for diagnostic or ex vivo therapeutic purposes, or from individuals or non-human primates to obtain a source of such cells for research purposes.

KIR3DL2 positive cells can be purified or identified using the present antibodies with any of a number of standard methods. For example, peripheral blood cells can be sorted using a FACS scanner using labeled antibodies specific for KIR3DL2, and optionally to other cell surface molecules typically present on cells, e.g., CD4, CD8 or CD30 for T cell (e.g. lymphomas); CD4 CD2+, CD3+, CD5+, CD8−, CD28+, CD45RO+ and/or TCRαβ+ for malignant cells in Sézary Syndrome; CD4+(optionally CD4+ and CD28−) in inflammatory, autoimmune or cardiovascular diseases.

In addition, the antibodies can be conjugated or covalently linked to a solid support and used to purify or identify KIR3DL2 positive cells or any cells expressing KIR3DL2 from a biological sample, e.g., from a blood sample or mucosal tissue biopsy from a patient or other individual. Specifically, the biological sample is placed into contact with the antibodies under conditions that allow cells within the sample to bind to the antibody, and then the cells are eluted from the solid-support-bound antibody.

Regardless of the method used to isolate, purify or identify the KIR3DL2 positive cells, the ability to do so is useful for numerous purposes, e.g. to diagnose a disorder characterized by a pathogenic expansion of KIR3DL2-expressing cells, by assessing the number or activity or other characteristics of KIR3DL2 positive cells obtained from a patient, or to evaluate the ability of the antibodies, or fragments or derivatives thereof, to modulate the activity or behavior of the cells of a patient prior, e.g., to one of the herein-described treatments using the antibodies. Further, purified KIR3DL2 positive cells are useful in a research context, e.g., to better characterize the cells and their various properties and behaviors, as well as to identify compounds or methods that can be used to modulate their behavior, activity, or proliferation. The antibodies can also be useful in diagnostic methods, for example in methods of detecting KIR polypeptides on cells, e.g. disease cells from a patient.

Also provided are pharmaceutical compositions that comprise an antibody according to the disclosure which specifically binds to KIR3DL2 polypeptides on the surface of cells. The antibody optionally inhibits the growth or activity of the cells and/or leads to the elimination of the KIR3DL2 positive cells, optionally or by delivery of a toxic agent, but optionally additionally via induction of CDC and/or ADCC. The composition further comprises a pharmaceutically acceptable carrier.

Further provided is a method of inhibiting the growth or activity of, and/or depleting, KIR3DL2-positive cells, in a patient in need thereof, comprising the step of administering to said patient a composition according to the disclosure. Such treatment methods can be used for a number of disorders, including, but not limited to CTCL, SS and MF, inflammatory, autoimmune and cardiovascular disorders.

KIR3DL2 is a membranar differentiation antigen characteristic of malignant T cells, and notably of malignant CD4+ T cells, and that regardless of the form of CD4+ CTCL, there are malignant CD4+ T cells which express KIR3DL2 at their surface. KIR3DL2 thus covers the range of CD4+ CTCL, and notably the Sézary Syndrome ("SS"), transformed Mycosis Fungoides ("transformed MF"), Lymphomatoide Papulosis ("LP"), and CD30+ lymphomas.

A diagnosis (e.g. a CTCL diagnosis) may be based on the analysis of the presence of KIR3DL2 at the surface of CD4+ cells collected from the suspected body area (e.g. sample of skin erythroderma when transformed MF is suspected, or sample of peripheral blood when a more aggressive CTCL form, such as SS, is suspected). It can typically be concluded that a CD4+ T cell is tumoral as soon as there are KIR3DL2 polypeptides detected at the surface of these CD4+ T cells. The percentage of CD4+ KIR3DL2+ T cells can measured in a sample of peripheral blood collected from a patient for whom a SS is suspected, and such percentage will substantially correspond to the percentage of malignant SS cells that are actually present in the peripheral blood of this patient (generally within a ±10% range or even a ±5% range for KIR3DL2+, CD4+ cells. KIR3DL2 and the anti-KIR3DL2 antibodies therefore can be used in the staging of disease, particularly SS.

Insofar as KIR3DL2 is a universal marker for CTCL, the antibodies of the disclosure can be used in combination with other treatments or diagnostic markers for CTCL. For example, CD30 of which presence at the surface of malignant CD4+ T cells indicates that the patient has a particular form of CD4+ CTCL which is referred to in the art as CD30+ lymphoma. CD30 is therefore a CTCL marker for a particular form of CTCL (CD30+ lymphomas), however CD30 does not cover every form of CD4+ CTCL since for CD4+ CTCL such as SS, transformed MF, or LP, there does not necessarily exist a malignant CD4+ T cell which would express CD30 at its surface. CD30 can therefore be used in addition to KIR3DL2 as a marker in CTCL diagnosis and therapy. Furthermore, a finding that a patient has CD4+ CTCL which expresses CD30 can indicate that the patient is suitable for treatment with an anti-KIR3DL2 antibody of the disclosure and an anti-CD30 antibody; optionally the patient can then be treated anti-KIR3DL2 antibody of the disclosure and an anti-CD30 antibody.

In some embodiments, prior to the administration of the anti-KIR3DL2 antibody or composition, the presence of CD2, CD3, CD4, CD5, CD8, CD28, CD30, CD45RO and/or TCRαβ will be assessed on cells (e.g. pathogenic cells) from a patient. A patient whose cells express (or do not express, in accordance with the particular disorder and cells sought to be targeted) a marker can then be treated with an anti-KIR3DL2 antibody or composition. In some embodiments, prior to the administration of the anti-KIR3DL2 antibody or composition, the presence of KIR3DL2 on cells of the patient will be assessed, e.g., to determine the relative level and activity of KIR3DL2-positive cells in the patient as well as to confirm the binding efficacy of the antibodies to the cells of the patient. A patient whose cells express KIR3DL2 can then be treated with an anti-KIR3DL2 antibody or composition. This can be accomplished by obtaining a sample of PBLs or cells from the site of the disorder, and testing e.g., using immunoassays, to determine the relative prominence of markers such as CD4, CD8, CD30 or KIR3DL2 on the cells.

In one embodiment, where it is sought to inhibit the activity or growth of, or deplete, a patient's KIR3DL2-positive cells, the ability of the anti-KIR3DL2 antibody to inhibit proliferation of or deplete a patient's KIR3DL2-positive cells is assessed. If the KIR3DL2-positive cells are depleted by the anti-KIR3DL2 antibody or composition, the patient is determined to be responsive to therapy with an anti-KIR3DL2 antibody or composition, and optionally the patient is treated with an anti-KIR3DL2 antibody or composition.

In some embodiments, the method may comprise the additional step of administering to said patient an appropriate additional (second) therapeutic agent selected from an immunomodulatory agent, an immunosuppressive agent, a hormonal agent, a chemotherapeutic agent, a second antibody (e.g. a depleting antibody) that binds to a polypeptide present on a KIR3DL2-expressing cell. Such additional agents can be administered to said patient as a single dosage form together with said antibody, or as a separate dosage form. The dosage of the antibody (or antibody and the dosage of the additional therapeutic agent collectively) are sufficient to detectably induce, promote, and/or enhance a therapeutic response in the patient. Where administered separately, the antibody, fragment, or derivative and the additional therapeutic agent are desirably administered under conditions (e.g., with respect to timing, number of doses, etc.) that result in a detectable combined therapeutic benefit to the patient.

Mycosis fungoides and the more aggressive Sézary syndrome represent the most common forms of CTCL. The clinical course of MF/SS is usually indolent, with pruritic erythematous areas slowly developing over long periods. Eventually, however, the erythematous patches become progressively infiltrated, developing into plaques and finally to ulcerating tumors. The prognosis of MF/SS is based on the extent of disease at presentation. Patients with stage I disease have a median survival of 20 years or more, in comparison with a median survival of approximately 3 to 4 years for patients with stage III/IV disease.

The compositions of the disclosure can be used for treatment in combination with any agent known to be useful in the treatment of the particular T cell malignancy. Various treatments for CTCL are in use, including corticosteroids, nitrogen mustard, carmustine, topical tacrolimus (Protopic®), imiquimod (Aldara®; 3M Inc.), topical retinoids, and rexinoids (bexarotene; Targretin®; Ligand Pharmaceuticals, San Diego, Calif.)), as well as ultraviolet light therapy (Psoralen+UVA (PUVA), narrowband UVB, and UVB), Photodynamic therapy (PDT) and body irradiation. Treatments also include histone deacetylase inhibitors such as vorinostat (suberoylanilide hydroxamic acid, Zolinza®) and Romidepsin (depsipeptide, FK-228, Istodax®), a cyclic peptide that selectively inhibits histone deacetylase isotypes 1, 2, 4 and 6. Chemotherapy or combination chemotherapy are also used. Examples include gemcitabine, antifolate analogues such as Pralatrexate (Folotyn®). Further therapies include IMiDs (immunomodulatory drugs), analogs derived from thalidomide that have a wide range of effects, including both immune and non-immune related effects. Representatives of the IMiD class include CC-5013 (lenalidomide; Revlimid®), CC-4047 (Actimid), and ENMD-0995. Further treatments include proteosome inhibitors such as bortezomib (Velcade®), a reversible 26S proteasome inhibitor. Stem cell transplantation is also used.

Although there is no current standard of care for MF/SS, there is a general tendency to rely on topical interventions for early disease delaying systemic and more toxic therapy until the development of extensive symptoms. Psoralen and ultraviolet A radiation (PUVA), combined or not with low doses of interferon-α, is effective in early-stage MF/SS, inducing complete remission (CR) in most patients. Local radiotherapy or total-skin electron-beam irradiation (TSEB) has been used with success to control advanced skin disease. Extra corporeal photopheresis may also be used successfully but is not generally available. Once the disease becomes refractory to topical therapy, interferon-α, the rexinoid bexarotene (Targretin®, Ligand Pharmaceuticals, San Diego, Calif.), a synthetic retinoid analog targeting the retinoid X receptor, single-agent chemotherapy or combination chemotherapy may be given. Treatments, particularly skin-directed therapies, include, e.g., corticosteroids, nitrogen mustard, carmustine, topical tacrolimus (Protopic®) and imiquimod (Aldara®; 3M Inc.). The duration of response is however often less than 1 year, and ultimately all patients have relapses and the disease becomes refractory. The recombinant IL2-diphteria toxin denileukin diftitox (DAB389IL-2, ONTAK®, Ligand Pharmaceuticals, San Diego, Calif.) is active in patients with stage Ib to stage IV CTCL refractory to previous treatments (overall objective response in 30% of 71 patients with a median duration response of 7 months) and appears to have a beneficial effect in symptoms relief and quality of life. More recently, denileukin diftitox have been tested in a Phase I trial in combination with bexarotene, since it induces CD25 up regulation in vitro. The combination was well tolerated and induced objective response in 67% of 14 patients. The most significant adverse events were those already reported with bexarotene alone (hypertriglyceridemia and suppression of thyroid function due to decreased TSH production) and grade 3 or 4 lymphopenia but resolving within one month of cessation of therapy. The time to treatment failure was not reported in this study. In other studies, anti-CD4 antibodies that deplete CD4 expressing cells have been developed. Examples include the fully human IgG1 anti-CD4 antibody zanolimumab (HuMax-CD4; Genmab A/S and TenX BioPharma Inc.), and the chimeric monoclonal anti-CD4 (cM-T412, Centocor, Malvern, Pa.) was administered to 8 patients with MF and induced objective response in 7 of them but with a median response duration of only 5 months. Uvadex® (methoxsalen, Therakos Inc. Exton, Pa.) in extra corporal photopheresis, has also shown signs of efficacy. The humanized monoclonal antibody alemtuzumab (hu-IgG$_1$ anti-CD52 mAb, Campath®, Millennium Pharmaceuticals, Inc. and ILEX Oncology, Inc., marketed and distributed in the US by Berlex Laboratories, Inc., Montville, N.J.) is indicated for the treatment of B-cell chronic lymphocytic leukemia (B-CLL) in patients who have been treated with alkylating agents and who have failed fludarabine therapy. It has been tested in patients with advanced MF/SS (stage III or IV disease) and led to objective responses in at least half of cases (55% of 22 patients). Its side effect profile consists mainly of immunosuppression and infusion reactions. An independent retrospective study described also significant cardiac toxicity in 4 out of 8 patients. With long lasting remissions observed (median time to treatment failure 12 months, range 5 to 32+ months), alemtuzumab therapy appears to be the treatment with the more favorable median response duration compared to all treatments reported to date. Other agents that may be useful include anti-CCR4 (C-C chemokine receptor 4; CD194) antibodies. One example is mogamulizumab (KW-0761; AMG-761; trade name Poteligeo, Kyowa Hakko Kirin Ltd., Japan and Amgen, USA), and humanized anti-CCR4 antibody. Other agents that may be useful include anti-CD30 antibodies. One example is SGN-35 is an antibody-drug conjugate (ADC) containing the potent antimitotic drug, monomethylauristatin E (MMAE), linked to the anti-CD30 monoclonal antibody, cAC 10 (Okeley et al. (2010) Clin. Cancer Res. 16(3): 888-897); another examples is the human anti-CD30 immunoglobulin (Ig) GiK monoclonal antibody MDX-060 (Medarex Inc. and Bristol Myers Squibb; Ansell et al. (2007) J. Clin. Oncol. 25: 2767-2769). Each of these treatments can be used in combination with the antibodies of the disclosure.

The antibodies produced using the present methods are particularly effective at treating autoimmune and inflammatory disorders, as well as cardiovascular disorders most particularly acute coronary syndrome, arthritis, rheumatoid arthritis, rheumatoid vasculitis, systemic lupus erythematosus, multiple sclerosis, Wegener's granulomatosis, and spondyloarthritis. In general, the present methods can be used to treat any disorder caused at least in part by the presence or activity of KIR3DL-expressing cells, e.g., NK cells or T cells, proinflammatory T or NK cells producing IL-17A, T cells such as Th17 cells or $CD4^+$ $CD28^-$ cells expressing KIR3DL2, and which can therefore be effectively treated by selectively killing or inhibiting the proliferation or activation of KIR3DL2-expressing cells.

In some embodiments, prior to the administration of the anti-KIR3DL2 antibody, the expression of KIR3DL2 on cells underlying the particular disorder will be assessed. This can be accomplished by obtaining a sample of PBLs or cells from the site of the disorder (e.g., from the synovium in RA patients), and testing e.g., using immunoassays, to determine the relative prominence of markers such as CD4, CD28, etc., as well as KIR3DL2 on the cells. Other methods can also be used to detect expression of KIR3D2 and other genes, such as RNA-based methods, e.g., RT-PCR or Northern blotting.

The treatment may involve multiple rounds of antibody or compound administration. For example, following an initial round of administration, the level and/or activity of KIR3DL-expressing T or NK cells (e.g., $CD4^+$ $CD28^-$ T cells, malignant CD4+ T cells), in the patient will generally be re-measured, and, if still elevated, an additional round of administration can be performed. In this way, multiple rounds of receptor detection and antibody or compound administration can be performed, e.g., until the disorder is brought under control.

When used for the treatment of autoimmune or inflammatory disorders, the anti-KIR3DL2 antibodies of the disclosure can be used for treatment in combination with any agent known to be useful in the treatment of the particular inflammatory disorder, autoimmune disorder, or cardiovascular disorder. Anti-KIR3DL2 antibodies can be combined for example with steroidal anti-inflammatory agents, non-steroidal anti-inflammatory agents, anti-metabolites and other agents used in treating cardiovascular, inflammatory or autoimmune diseases. In some embodiments, anti-inflammatory agents comprise steroidal anti-inflammatory agents, which include glucocorticosteroids and mineralocorticosteroids. These may be administered by any methods suitable for treating the inflammatory disorders, including, among others, oral, intravenous, intramuscular, dermal, or nasal routes. In some embodiments, the anti-inflammatory agents comprise non-steroidal anti-inflammatory agents. These agents generally act by inhibiting the action of cyclooxygenase and lipoxygenase enzymes, or receptors for mediators generated by these enzymes. The non-steroidal anti-inflammatory compounds include non-selective COX inhibitors, selective COX inhibitors, as well as FLAP antagonists and 5-lipoxygenase antagonists. In some embodiments, the anti-inflammatory agents can comprise anti-metabolites that affect proliferation of cells involved in the immune response. Suitable anti-metabolites include folate analogs, such as methotrexate; inosine monophosphate dehydrogenase (IMPDH) inhibitors, such as mycophenolate mofetil; and azathiopurine. Compounds of this group generally affect production of the substrates necessary for DNA replication, thereby inhibiting the proliferation of cells involved or activated in response to an inflammatory reaction. In some embodiments, the anti-inflammatory agent is an agent that blocks the action of TNF-alpha, the major cytokine implicated in inflammatory disorders. In some embodiments, the anti-TNF is an antibody that blocks the action of TNFalpha. An exemplary anti-TNF antibody is infliximab (Remicade®). In other embodiments, the anti-TNFalpha agent is a receptor construct that binds TNFalpha and prevents its interaction with TNF receptors on present on cells, e.g. entanercept (Enbrel®). In other embodiments, the anti-inflammatory agent is any other agent (e.g. an antibody agent) having immunosuppressive properties and useful in the treatment of the disorder being treated with the KIR3DL2 antibody of the disclosure.

Pharmaceutical Formulations

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The antibodies of the disclosure may be employed in a method of modulating, e.g. inhibiting, the activity of KIR3DL2-expressing cells in a patient. This method comprises the step of contacting said composition with said patient. Such method will be useful for both prophylaxis and therapeutic purposes.

For use in administration to a patient, the composition will be formulated for administration to the patient. The compositions of the disclosure may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. The antibody can be present in a single dose in an amount, for example, of between about 25 mg and 500 mg.

Sterile injectable forms of the compositions of the disclosure may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added.

Alternatively, the compositions may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The compositions may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The present antibodies can be included in kits. The kits may optionally further contain any number of antibodies and/or other compounds, e.g., 1, 2, 3, 4, or any other number of therapeutic antibodies and/or compounds. It will be appreciated that this description of the contents of the kits is not limiting in any way. For example, the kit may contain other types of therapeutic compounds. Optionally, the kits also include instructions for using the antibodies, e.g., detailing the herein-described methods.

Dosage Forms

Therapeutic formulations of the antibodies can be prepared for storage by mixing the antibodies having the desired degree of purity with optional pharmaceutically acceptable carriers, excipients, or stabilizers in the form of lyophilized formulations or aqueous solutions. For general information concerning formulations, see, e.g., Gilman et al. (eds.), The Pharmacological Bases of Therapeutics, 8$^{th}$ Ed. (Pergamon Press, 1990); Gennaro (ed.), Remington's Pharmaceutical Sciences, 18$^{th}$ Edition (Mack Publishing Co., Easton, Pa., 1990); Avis et al. (eds.), Pharmaceutical Dosage Forms: Parenteral Medications (Dekker, New York, 1993); Lieberman et al. (eds.), Pharmaceutical Dosage Forms: Tablets (Dekker, New York, 1990); Lieberman et al. (eds.) Pharmaceutical Dosage Forms: Disperse Systems (Dekker, New York, 1990); and Walters (ed.), Dermatological and Transdermal Formulations (Drugs and the Pharmaceutical Sciences), Vol 119 (Dekker, New York, 2002).

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular-weight (less than about 10 residues) polypeptides; proteins such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as ethylenediaminetetraacetic acid (EDTA); sugars such as sucrose, mannitol, trehalose, or sorbitol; salt-forming counter-ions such as sodium; metal complexes (e.g., Zn-protein complexes); and/or non-ionic surfactants such as TWEEN™, PLURONICS™, or PEG.

Exemplary antibody formulations are described for instance in WO 1998/56418, which describes a liquid multidose formulation for an anti-CD20 antibody, comprising 40 mg/mL rituximab, 25 mM acetate, 150 mM trehalose, 0.9% benzyl alcohol, and 0.02% Polysorbate20™ at pH 5.0 that has a minimum shelf life of two years storage at 2-8° C. Another anti-CD20 formulation of interest comprises 10 mg/mL rituximab in 9.0 mg/mL sodium chloride, 7.35 mg/mL sodium citrate dihydrate, 0.7 mg/mL Polysorbate80™, and Sterile Water for Injection, pH 6.5.

Lyophilized formulations adapted for subcutaneous administration are described, for example, in U.S. Pat. No. 6,267,958 (Andya et al.). Such lyophilized formulations may be reconstituted with a suitable diluent to a high protein concentration and the reconstituted formulation may be administered subcutaneously to the mammal to be treated herein.

The formulation herein may also contain more than one active compound (a second medicament as noted above), optionally those with complementary activities that do not adversely affect each other. The type and effective amounts of such medicaments depend, for example, on the amount and type of B-cell antagonist present in the formulation, and clinical parameters of the subjects. The preferred such second medicaments are noted above.

The active ingredients may also be entrapped in microcapsules prepared, e.g., by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's Pharmaceutical Sciences, supra, for example.

Sustained-release formulations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Further aspects and advantages of this invention will be disclosed in the following experimental section, which should be regarded as illustrative and not limiting the scope of this application.

EXAMPLES

Example 1—Generation of Anti-KIR3DL2 Antibodies

Materials and Methods for Primary and Secondary Flow Cytometry Screenings

Anti-KIR3DL2 mAbs were primarily screened in flow cytometry for binding to KIR3DL2-expressing Sézary cell lines (HUT78 and COU-L) and to KIR3DL2-transfected tumor cell lines (HEK-293T). Flow cytometry devices include: FACSarray (BD Biosciences, primary screen), FACSCanto II no 1 et no 2 (BD Biosciences) (secondary screens) and FC500 (Beckman Coulter) (secondary screens). The KIR3DL2+ and other tumor cell lines used included:

HUT-78 (KIR3DL2 positive Sézary cell line) grown in complete IMDM;
HEK-293T (human kidney cancer)/KIR3DL2 and HEK-293T/KIR3DL2 Domain 0-eGFP cell lines (grown in complete DMEM); see Example 3 for preparation of Domain 0 transfectants;
COU-L (KIR3DL2 positive Sézary cell line) (grown in complete RPMI complemented with 10% human serum AB);
HEK-293T/KIR3DL1 and HEK-293T/KIR3DL1-eGFP cell lines (grown in complete DMEM);
B221 (B-lymphoblastoid, CD20 positive human cell line)/ KIR3DL2 cell line (grown in complete RPMI containing FCS serum); and
RAJI (Burkitt's lymphoma CD20 positive human cell line)/KIR3DL2 cell line (grown in complete RPMI containing FCS serum).

Whereas none of the Sézary cell lines used grow after IV or SC transfer to immune compromised mice, KIR3DL2-transfected B221 or RAJI cells grow as disseminated (IV) or solid (SC) tumors after injection to mice.

Based on the information available in Gardiner et al, *Journal of Immunology* 2001 (vol 166, p 2992-3001), the KIR3DL2 gene alleles present in the tumor cell lines used were determined. We established that the Sézary cell line COU-L is heterozygous for alleles 3DL2*003 and 3DL2*008 and HUT-78 is heterozygous for alleles 3DL2*002 and 3DL2*007. All 4 alleles 3DL2*003, 3DL2*008, 3DL2*002 and 3DL2*007 encode KIR3DL2 protein variants bearing differences in their extracellular domains. Of note, the commercially available recombinant KIR3DL2-Fc fusion protein that was used to immunize mice is encoded by different KIR3DL2 gene alleles 3DL2*006 and 3DL2*007 (clone 1.1, both alleles encoding the same extracellular domain protein sequence).

Immunization #1

Primary screen. To obtain anti-human KIR3DL2 antibodies, Balb/c mice were immunized with a recombinant human KIR3DL2 extracellular domain recombinant protein (R&D Systems).

Mice received one primo-immunization with an emulsion of 50 μg KIR3DL2 protein and Complete Freund Adjuvant, intraperitoneally, a $2^{nd}$ immunization with an emulsion of 50 μg KIR3DL2 protein and Incomplete Freund Adjuvant, intraperitoneally, and three boosts with 10 μg KIR3DL2 protein, intravenously. Immune spleen cells were fused with X63.Ag8.653 immortalized B cells, and cultured in the presence of irradiated spleen cells. Supernatant (SN) of growing clones were tested in a primary screen by flow cytometry using the HEK-293T cell line transfected with a KIR3DL2 construct and the Hut-78 cell line. Positive supernatants were selected and tested for lack of binding by flow cytometry to a KIR3DL1 transfected cell line (HEK-293T). Briefly, for FACS screening, the presence of reacting antibodies in supernatants was revealed by Goat anti-mouse polyclonal antibody (pAb) labeled with PE. Potentially interesting hybridomas selected from the initial screening were cloned by limiting dilution techniques in 96-wells plates.

Secondary screen; selection of hybridomas of interest. Supernatants of the subclones were tested by flow cytometry on the same cell lines as already described. Positive subclones were injected into mice to produce ascitis and antibodies of interest were purified followed by testing in a Biacore assay using rec KIR3DL2 chips, followed by various assays formats based on binding to human KIR3DL2-expressing cells.

Among the clones selected were 15C11 (IgG2a/K isotype).

Immunization #2

A second series of immunizations was carried out in which supernatants (SN) of the growing hybridomas were tested by flow cytometry on HEK-293T cells transfected either with KIR3DL2 or KIR3DL1 (KIR3DL2 on the first day and KIR3DL1+ KIR3DL2 on the second day). Potentially interesting hybridomas selected from the initial screening were cloned by limiting dilution techniques in 96-wells plates.

Secondary screen; selection of hybridomas of interest. Supernatants of the subclones were tested by flow cytometry on the HEK-293T/KIR3DL2 cell line and on the Hut-78 cell line. Positive subclones were injected into mice to produce ascitis and antibodies of interest were purified before being tested in a Biacore assay using rec KIR3DL2 chips, followed by various assays formats based on binding to human KIR3DL2-expressing cells.

Among the clones selected were supernatants from wells 19H12 (murine IgG2b/K) and 22B2 (murine IgG1/K).

Immunization #3

A third series of immunizations was carried out in which supernatant (SN) of the growing hybridomas were tested by flow cytometry on HUT78, COU-L and HEK-293T/ KIR3DL2 Domain 0-eGFP. Potentially interesting hybridomas selected from the initial screening were cloned by limiting dilution techniques in 96-wells plates. The secondary screen involved selection of hybridomas of interest by testing supernatants of the subclones by flow cytometry on HUT78, COU-L, HEK-293T/KIR3DL1 Domain 0-eGFP and HEK-293T/KIR3DL2 Domain 0-eGFP. Positive subclones were injected into mice to produce ascitis and antibodies of interest were purified before being tested in a Biacore assay using rec KIR3DL2 chips, followed by various assays formats based on binding to human KIR3DL2-expressing cells. Among the clones selected were supernatants for antibodies 18B10, 12B11, 13H1 and 4B5.

Figure 1B:
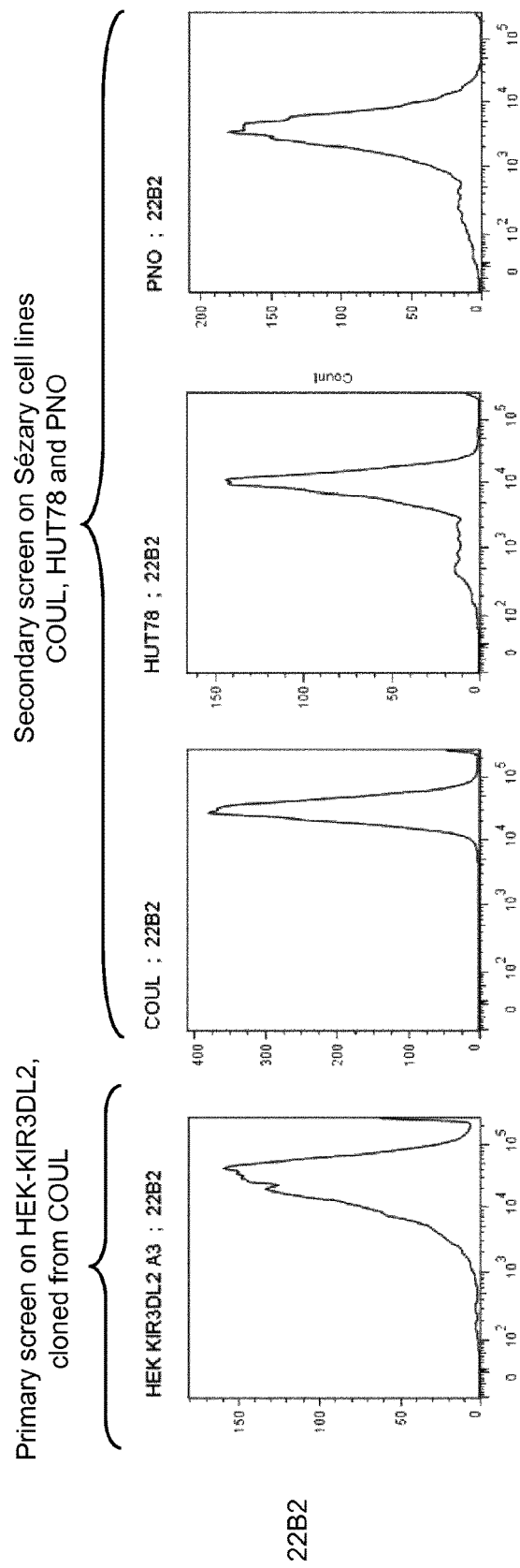

Representative results of binding to Sézary Syndrome cell lines COUL, HUT78 and PNO (Sézary Syndrome cell line) for antibodies 15C11, 19H12, 22B2 are shown in FIGS. 1A and 1B.

Sequences of the variable domains of heavy (VH) and light (VL) chain of each antibody were amplified by PCR from the cDNA of each antibody. Sequences amplified were run on agarose gel then purified using the Qiagen Gel Extraction kit. VH and VL sequences were then sub-cloned into the Lonza expression vectors (Double-Gene Vectors) using the InFusion system (Clontech) according to the manufacturer's instructions. After sequencing, vectors containing the VH and VL sequences were prepared as Maxiprep using the Promega PureYield™ Plasmid Maxiprep System. Vectors were then used for HEK-293T cell transfection using Invitrogen's Lipofectamine 2000 according to the manufacturer instructions.

Example 2—Binding to Immobilized KIR3DL2 Proteins

The binding of 15C11, 19H12, 22B2, 18B10, 12B11, 13H1 and 4B5 as well as chimeric AZ158 ("chAZ158", see WO 2010/081890) to KIR3DL2 recombinant proteins (R&D systems) was analyzed by Surface Plasmon Resonance (SPR) using a Biacore T100 apparatus. Antibodies (range of concentrations) were injected at a constant rate of 10 µl/min over the KIR3DL2 flow-cells (CM5). Background signals were subtracted online by co-injecting onto the reference flow cell (dextran alone).

Binding to KIR3DL2 was determined in standard HBS conditions, and K(D) values (bivalent affinity) were calculated. The results are shown in Table 5.

TABLE 5

| Antibody | Mean $K_D$ (M) at pH 7.2 |
| --- | --- |
| 15C11 | $7.8 \times 10^{-10}$ |
| 19H12 | $4.9 \times 10^{-10}$ |
| 22B2 | $2.2 \times 10^{-9}$ |

Example 3—Binding to KIR3DL2 Domains

Cells and Reagents.

HEK293T/17 cells were cultured in DMEM (Gibco) supplemented with sodium pyruvate (1 mM), penicillin (100 U/ml), streptomycin (100 µg/ml) and 10% heat inactivated FCS (PAN biotech). Lipofectamine 2000 reagent, Trizol, SuperScript II reverse Transcriptase, pcDNA3.1 vector and anti-V5-FITC antibodies were purchased from Invitrogen. Goat anti-mouse (H+L)-PE was purchased from Beckman Coulter.

RNA Extraction and cDNA Preparation.

PBMC ($5 \times 10^6$ cells) from *Homo Sapiens* were re-suspended into 1 ml of Trizol reagent. RNA extraction was performed by adding 200 µl chloroform. After centrifugation (15 min, 13,000 rpm), RNA was precipitated from aqueous phase with 500 µl isopropanol. After incubation (10 min, RT) and centrifugation (10 min, 13,000), RNA was washed with 70% ethanol and re-centrifugated (5 min, 13,000 rpm). RNA was re-suspended in $H_2O$ Rnase free water. cDNA was obtained using SuperScript II reverse Transcriptase using 2 µg of specific RNA and following manufacturer instructions.

Cloning of KIR3DL2 Domains 0, 1 and 2.

Human KIR3DL2 (accession number U30272) domain 0, domain 1 and domain 2 sequences are shown in Table 6.

TABLE 6

| Ig-like domain of KIR3DL2 | SEQ ID NO: | Amino acid sequence |
| --- | --- | --- |
| Domain 0 | 57 | PLMGGQDKPF LSARPSTVVP RGGHVALQCH YRRGFNNFML YKEDRSHVPI FHGRIFQESF IMGPVTPAHA GTYRCRGSRP HSLTGWSAPS NPLVIMVTGN HRKPSLLAHP GPLLKSG |
| Domain 1 | 58 | TVILQCWSDV MFEHFFLHRE GISEDPSRLV GQIHDGVSKA NFSIGPLMPV LAGTYRCYGS VPHSPYQLSA PSDPLDIVIT GLYEKPSLSA QPGPTVQAGE |
| Domain 2 | 59 | NVTLSCSSWS SYDIYHLSRE GEAHERRLRA VPKVNRTFQA DFPLGPATHG GTYRCFGSFR ALPCVWSNSS DPLLVSVTGN PSSSWPSPTE PSSKSGICRH LH |

*Homo Sapiens* KIR3DL2 (accession number U30272) domain 0, domain 1 and domain 2 sequences were amplified by PCR reaction from cDNA using 5' AA GCT AGC GGT AAG CCT ATC CCT AAC CCT CTC CTC GGT CTC GAT TCT ACG CTC ATG GGT GGT CAG GAC AAA C (SEQ ID NO: 60) (forward) and 3' AA GGA TCC CTC TCC TGA TTT CAG CAG GGT (SEQ ID NO: 61) (reverse); 5' AA GCT AGC GGT AAG CCT ATC CCT AAC CCT CTC CTC GGT CTC GAT TCT ACG ACA GTC ATC CTG CAA TGT TGG (SEQ ID NO: 62) (forward) and 3' AA GGA TCC CTC TCC TGC CTG AAC CGT GGG (SEQ ID NO: 63) (reverse); 5' AA GCT AGC GGT AAG CCT ATC CCT AAC CCT CTC CTC GGT CTC GAT TCT ACG AAC GTG ACC TTG TCC TGT AGC (SEQ ID NO: 64) (forward) and 3' AA GGA TCC ATG CAG GTG TCT GCA GAT ACC (SEQ ID NO: 65) (reverse) oligonucleotides, respectively. After TA-cloning and sequencing, sequences were cloned into pcDNA3.1 vector between NheI and BamHI restriction sites. These constructs were inserted between the CD33 peptide leader and the CD24 GPI anchor (CD24 GPI anchor DNA and amino acid sequences are shown in SEQ ID NOS: 66 and 67, respectively) synthesized by MWG Biotech (inserted between BamHI and HindIII restriction sites).

Transfection.

HEK-293T/17 cells were seeded 24 hours prior to transfection into 6 wells plates ($5 \cdot 10^5$ cells/well) in DMEM without antibiotics. Transfections were performed using 5 µg of the different pcDNA3.1/KIR3DL2 domain 0, pcDNA3.1/KIR3DL2 domain 1 or pcDNA3.1/KIR3DL2 domain 2 constructs using Lipofectamine 2000 according to manufacturer instructions. To ensure DNA purity for transfection, Maxi-prep endotoxin free kit from Qiagen was used. The Lipofectamine/DNA ratio used was fixed at 2/1. Cells were harvested 48 hours after transfection for flow cytometry experiments.

Flow Cytometry.

Cells were harvested and stained in PBS 1×/BSA 0.2%/EDTA 2 mM buffer during 1 H at 4° C. using 5 µg/ml of antibody. After two washes in staining buffer, cells were stained for 30 min at 4° C. with goat anti-mouse (H+L)-PE antibodies (1/200). After two washes, stainings were acquired on a BD FACS Canto II and analyzed using the FlowJo software.

Results

Figure 2:
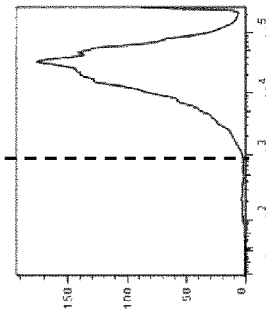
FIG. 2 shows binding of antibodies 15C11, 19H12, and 22B2 bind to HEK cells transfected with different KIR receptors or domains thereof. 15C11, 19H12, and 22B2 bind KIR3DL2 but not KIR3DL1 while antibody AZ158 bound to both KIR3DL2 and KIR3DL1. 15C11, 19H12, and 22B2 bind to domain 1-2 KIR3DL2 polypeptide but not to the domain 0 KIR3DL2 polypeptide. AZ158, on the other hand, binds to domain 0 KIR3DL2 polypeptide but not to the domain 1-2 KIR3DL2 polypeptide.
Figure 2:
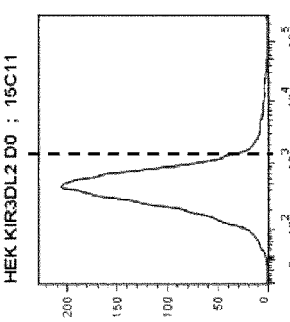
Figure 2:
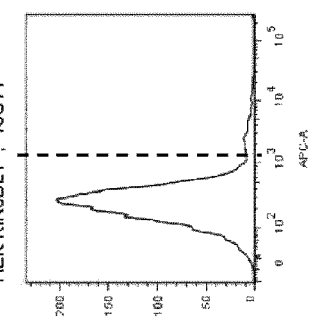

Representative results are shown in FIG. 2. 15C11, 19H12 and 22B2 were found to bind to KIR3DL2 but not KIR3DL1. Antibody AZ158, however, bound to both KIR3DL2 and KIR3DL1. 15C11, 19H12 and 22B2 bind to domain 1-2 KIR3DL2 polypeptide but not to the domain 0 KIR3DL2 polypeptide. AZ158, on the other hand, binds to domain 0 KIR3DL2 polypeptide but not to the domain 1-2 KIR3DL2 polypeptide. Therefore, it can be concluded from this flow cytometry experiment that the 15C11, 19H12 and 22B2 antibodies bind to KIR3DL2 within the part of KIR3DL2 that comprises extracellular domains 1 and 2 but that the antibodies do not bind to domain 0.

Example 4—Binding to KIR2D Receptors

The binding of antibody 15C11 was tested by FACS on BWZ cells transfected and each made to express a different receptor selected from KIR2DS1, KIR2DS2, KIR2DL3, KIR2DL1 and KIR2DS4. Cells were harvested and stained in PBS 1×/BSA 0.2%/EDTA 2 mM buffer during 1 H at 4° C. using 10 µg/ml of 15C11 antibody. After two washes in staining buffer, cells were stained for 30 min at 4° C. with goat anti-mouse (H+L)-PE polyclonal antibodies (1/200). After two washes, stainings were acquired on a BD FACS Canto II and analyzed using the FlowJo software. Binding was analyzed by flow cytometry. Antibody 15C11 did not show binding to any of the BWZ-KIR2DS1, KIR2DS2, KIR2DL3, KIR2DL1 or KIR2DS4 cells.

Example 5—Epitope Mapping

Competition assays were conducted by flow cytometry according to the methods described. Hut-78 cells were harvested and stained in PBS 1×/BSA 0.2%/EDTA 2 mM buffer during 1 H at 4° C. using 5 µg/ml of 15C11-PE antibody and increasing concentrations of the 15C11, 19H12, 22B2, 18B10 and 12B11 and AZ158 naked antibodies (0.006-200 µg/ml). After two washes, staining data were acquired on a BD FACS Canto II and analyzed using the FlowJo software.

Figure 3:
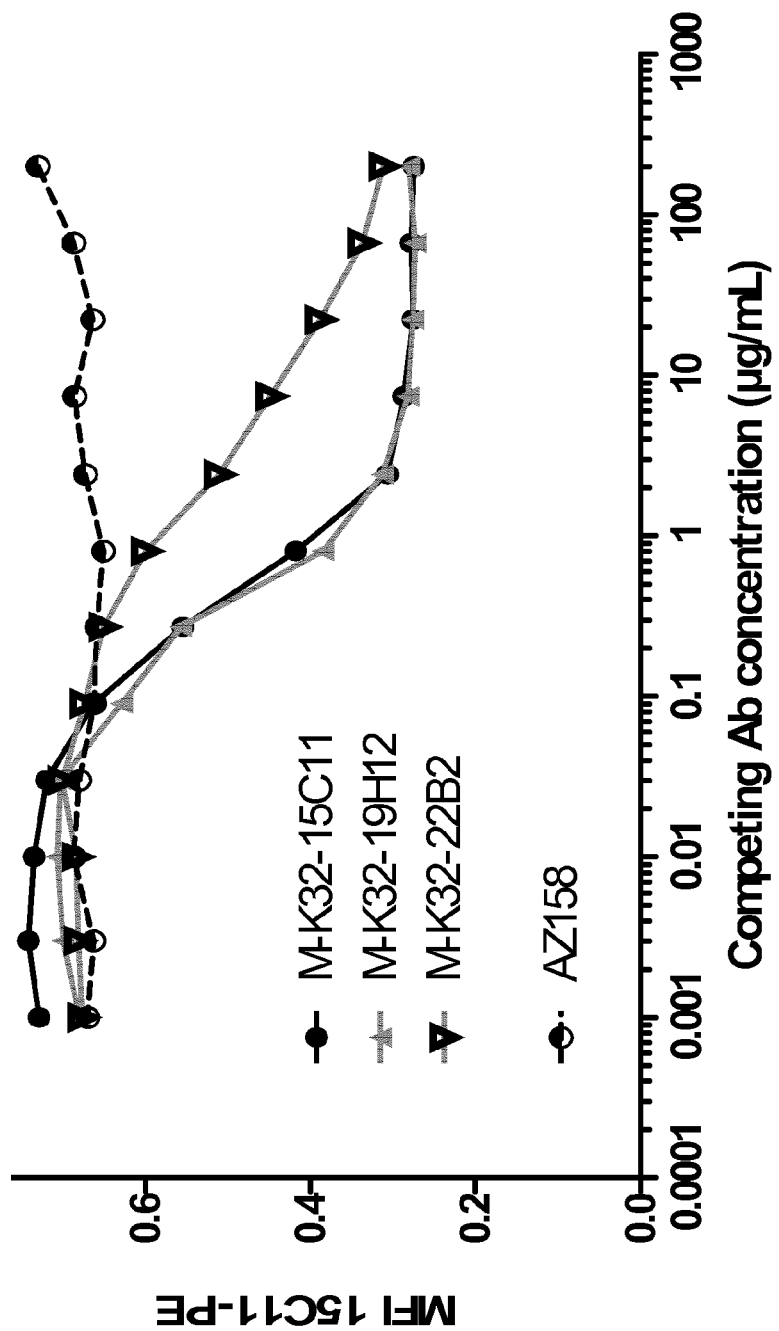
FIG. 3 shows competition for binding to epitopes on KIR3DL2. Increasing concentrations of (naked) 15C11, 19H12, 22B2 and AZ158 were used to shift 15C11-PE bound on KIR3DL2 at the surface of HUT78 SS cell lines. Each of the antibodies 15C11, 19H12, 22B2 (but not AZ158) compete with the 15C11-PE antibody for binding to KIR3DL2 at the surface of HUT78 SS cell lines.

Increasing concentrations of (naked) 15C11, 19H12, 22B2, 18B10 and 12B11, and AZ158 were used to shift 15C11-PE bound on KIR3DL2 at the surface of HUT78 SS cell lines. FIG. 3 is a representative figure showing that each of the antibodies 15C11, 19H12, 22B2 compete with the 15C11-PE antibody for binding to KIR3DL2 at the surface of HUT78 SS cell lines. 18B10 and 12B11 also each competed with one another for binding to KIR3DL2 at the surface of HUT78 SS cell lines. By comparison, antibody AZ158 (anti-D0 domain antibody) does not compete with the 15C11-PE antibody or the other KIR3DL2 antibodies for binding to KIR3DL2.

KIR3DL2 mutants were developed to identify the binding regions on KIR3DL2 of the antibodies. Antibodies 15C11, 19H12, 18B10, 12B11, 13H1 and 4B5 and 12B11 were further tested for binding to various KIR3DL2 mutants. KIR3DL2 mutants were generated by PCR (see Table 7A below). All the Mx-R primers were used with the following 5' primer ACCCAAGCTGGCTAGCATGTCGCTCACG-GTCGTCAGCATG (SEQ ID NO: 68). All the Mx-F primers were used with the following 3' primer AGCACAGTG-GCGGCCGCCTAGAAAA CCCCCTCAAGACC (SEQ ID NO: 69). The sequences amplified were run on agarose gel then purified using the Qiagen Gel Extraction kit.

To create mutants 12 and 21, it was necessary to do a third PCR. Primers used for these PCR were: M12a-F primer (5'-GCCACAGGTGCATATGAGAAACCTTCTCTCTCA-GCC-3') (SEQ ID NO: 70) with the M12b-R primer (5'-TGGGTCACTTGCGGCTGACCACACGCAGGGCA-GGG-3') (SEQ ID NO: 71) and M21a-F primer (5'-CGTGCCCTGCCCTACGTGTGGTCAAACTCAAGTGA-C-3') (SEQ ID NO: 72) with the M21b-R primer (5'-ATG CAGGTGTCTGGGGATACCAGATTTGGAGCTTG-GTTC-3') (SEQ ID NO: 73).

The two or three PCR products generated for each mutant were then ligated into a pcDNA3.1 vector, digested with the restriction enzyme NheI and NotI, with the InFusion system (Clontech) according to the manufacturer's instructions.

After sequencing, the vectors containing the mutated sequences were prepared as Maxiprep using the Promega PureYield™ Plasmid Maxiprep System. Vectors were then used for HEK-293T cell transfection using Invitrogen's Lipofectamine 2000 according to the manufacturer instructions.

TABLE 7A

| Mutants | Reverse primers | Forward primers |
| --- | --- | --- |
| Number 1<br>R13W +<br>A25T +<br>Q27R | M1-R<br>5'-ccgaagagtcacgtgtcctcctcgaggcaccac agtgctgggccaggcaga-3'<br>(SEQ ID NO 74) | M1-F<br>5'-cacgtgactcttcggtgtcactatcgtcgtggg-3'<br>(SEQ ID NO 75) |
| Number 2<br>I60N +<br>G62S | M2-R<br>5'-cacagggctcatgttgaagctctcctggaatat tc-3'<br>(SEQ ID NO 76) | M2-F<br>5'-aacatgagccctgtgacccagcacatg-3'<br>(SEQ ID NO 77) |

TABLE 7A-continued

| Mutants | Reverse primers | Forward primers |
|---|---|---|
| Number 3<br>R32H +<br>G33R | M3-R<br>5'-attgttaaacctatgacgatagtgacactgaag<br>ag-3'<br>(SEQ ID NO 78) | M3-F<br>5'-cataggtttaacaatttcatgctgtac-3'<br>(SEQ ID NO 79) |
| Number 4<br>S45I +<br>V45I | M4-R<br>5'-gatgggaatgtggattctgtcttctttgtacag<br>catg-3'<br>(SEQ ID NO 80) | M4-F<br>5'-atccacattcccatcttccacggcagaatattc-3'<br>(SEQ ID NO 81) |
| Number 5<br>P66T | M5-R<br>5'-atgtgctgtggtcacagggcccatgatgaa<br>g-3'<br>(SEQ ID NO 82) | M5-F<br>5'-gtgaccacagcacatgcagggacctacag-3'<br>(SEQ ID NO 83) |
| Number 6<br>R78H +<br>L82P | M6-R<br>5'-gggggagtgtgggtgtgaaccccgacatctgta<br>g-3'<br>(SEQ ID NO 84) | M6-F<br>5'-cacccacactcccccactgggtggtcggcac-3'<br>(SEQ ID NO 85) |
| Number 7<br>L113V +<br>T118R | M7-R<br>5'-ttgcaggatgactctctctcctgatttcaccag<br>ggg-3'<br>(SEQ ID NO 86) | M7-F<br>5'-agagtcatcctgcaatgttggtcagatgtc-3'<br>(SEQ ID NO 87) |
| Number 8<br>V127I | M8-R<br>5'-ctcaaacatgatatctgaccaacattgcaggat<br>gac-3'<br>(SEQ ID NO 88) | M8-F<br>5'-gatatcatgtttgagcacttctttctgcac-3'<br>(SEQ ID NO 89) |
| Number 9<br>L164M +<br>P166L +<br>V167A | M9-R<br>5'-aagggcaagcatcatgggaccgatggagaagtt<br>ggccttg-3'<br>(SEQ ID NO 90) | M9-F<br>5'-atgatgcttgcccttgcaggaacctacagatgtta<br>t gg-3'<br>(SEQ ID NO 91) |
| Number 10<br>R136K +<br>E141K | M10-R<br>5'-tagagatcccatctttgtgcagaaagaagtgct<br>caaacat-3'<br>(SEQ ID NO 92) | M10-F<br>5'-aagatgggatctctaaggacccctcacgcctcgtt<br>gg-3'<br>(SEQ ID NO 93) |
| Number 11<br>P179T +<br>S181T | M11-R<br>5'-gggggtgtgagtaacagaaccataacatctgta<br>gg-3'<br>(SEQ ID NO 94) | M11-F<br>5'-gttactcacacccctatcagttgtcagctc-3'<br>(SEQ ID NO 95) |
| Number 12<br>I196A +<br>L199A +<br>N285A +<br>S286A | M12a-R<br>5'-atatgcacctgtggccacgatgtccagggggtc<br>actgg-3'<br>(SEQ ID NO 96) | M12b-F<br>5'-gccgcaagtgacccactgcttgtttctgtc-3'<br>(SEQ ID NO 97) |
| Number 13<br>T212A +<br>N218A | M13-R<br>5'-ggcctctcctgcctgaaccgcggggcccggctg<br>ggctgag-3'<br>(SEQ ID NO 98) | M13-F<br>5'-caggcaggagaggccgtgaccttgtcctgtagctc<br>c-3'<br>(SEQ ID NO 99) |
| Number 14<br>W226A | M14-R<br>5'-ataggagctcgcggagctacaggacaaggtca<br>c-3'<br>(SEQ ID NO 100) | M14-F<br>5'-tccgcgagctcctatgacatctaccatctgtcc-3'<br>(SEQ ID NO 101) |
| Number 15<br>I231M +<br>R246P | M15-R<br>5'-atgggcctcccccttccctggacagatggtacat<br>gtcatagga-3'<br>(SEQ ID NO 102) | M15-F<br>5'-gaaggggaggcccatgaacgtaggctccctgcagt<br>g-3'<br>(SEQ ID NO 103) |
| Number 16<br>E239G | M16-R<br>5'-atgtgctccaccttccctggacagatggtagat<br>gtc-3'<br>(SEQ ID NO 104) | M16-F<br>5'-gaaggtggagcacatgaacgtaggctccgtgcagt<br>g-3'<br>(SEQ ID NO 105) |
| Number 17<br>P249A | M17-R<br>5'-tctgttgaccttggccactgcacggagcctacg<br>ttc-3'<br>(SEQ ID NO 106) | M17-F<br>5'-gccaaggtcaacagaacattccaggcagac-3'<br>(SEQ ID NO 107) |

TABLE 7A-continued

| Mutants | Reverse primers | Forward primers |
| --- | --- | --- |
| Number 18<br>A278H +<br>L279A +<br>C281A +<br>V282A | M18-R<br>5'-cgcggcgggcgcgtgacggaaagagccgaagca tctg-3'<br>(SEQ ID NO 108) | M18-F<br>5'-cacgcgcccgccgcgtggtcaaactcaagtgacc c-3'<br>(SEQ ID NO 109) |
| Number 19<br>A278H +<br>L279S +<br>V282E | M19-R<br>5'-ctcgcagggcgagtgacggaaagagccgaagca tctgtag-3'<br>(SEQ ID NO 110) | M19-F<br>5'-cactcgccctgcgagtggtcaaactcaagtgacc c-3'<br>(SEQ ID NO 111) |
| Number 21<br>C281Y +<br>C315P | M21a-R<br>5'-gtagggcagggcacggaaagagccgaagca-3'<br>(SEQ ID NO 112) | M21b-F<br>5'-cccagacacctgcatgttctgattg-3'<br>(SEQ ID NO 113) |
| Number 22<br>(5 + 11)<br>P66T +<br>P179T +<br>S181T | M22a-R<br>5'-tgt ggt cac agg gcc cat gat gaa gct ctc ctg gaa tat tc-3'<br>(SEQ ID NO: 136) | M22a-F<br>5'-ggc cct gtg aac Aca gca cat gca ggg acc tac aga-3'<br>(SEQ ID NO: 137) |
| Number 22<br>(5 + 11) | M22b-R<br>5'-gtc act ggg agc tga caa ctg ata ggg ggT gtg agT aac-3'<br>(SEQ ID NO: 138) | M22b-F<br>5'-tca gct ccc agt gac ccc ctg gac atc gtg atc aca gg-3'<br>(SEQ ID NO: 139) |
| Number 23<br>(8 + 11)<br>V127I +<br>P179T +<br>S181T | M23a-R<br>5'-gaT atc tga cca aca ttg cag gat gac tgt ctc tcc-3'<br>(SEQ ID NO: 140) | M23a-F<br>5'-tgt tgg tca gat Atc atg ttt gag cac ttc ttt ctg-3'<br>(SEQ ID NO: 141) |
| Number 23<br>(8 + 11)<br>V127I +<br>P179T +<br>S181T | Same primers as M22b-R | Same primers as M22b-F |
| Number 24<br>(11A1)<br>V178A +<br>H180S | M24-R<br>5'-gga gGA agg aGc aga acc ata aca tct gta ggt tcc-3'<br>(SEQ ID NO: 142) | M24-F<br>5'-tct gCt cct TCc Tcc ccc tat cag ttg tca gct ccc-3'<br>(SEQ ID NO: 143) |
| Number 26<br>(11A3)<br>Q184A +<br>H100S +<br>N99S | M26a-R<br>5'-gat cac cag ggg gtt gct ggg agc cag cca ccc-3'<br>(SEQ ID NO: 144) | M26a-F<br>5'-aac ccc ctg tga atc atg gtc aca gga aGc TCc AGA AAA CCT TCC-3'<br>(SEQ ID NO: 145) |
| Number 26<br>(11A3)<br>Q184A +<br>H100S +<br>N99S | M26b-R<br>5'-gtc cag ggg gtc act ccc agc tga caa cGC ata ggg gga gtg agg-3'<br>(SEQ ID NO: 146) | M26b-F<br>5'-agt gac ccc ctg gac atc gtg atc aca ggt c-3'<br>(SEQ ID NO: 147) |
| Number 27<br>(11A4)<br>E130S +<br>H131S +<br>R145S | M27-R<br>5'-aga gat ccc atc tct gtg cag aaa gaa gGA cGA aaa c-3'<br>(SEQ ID NO: 148) | M27-F<br>5'-aga gat ggg atc tct Gag gac ccc tca Agc ctc-3'<br>(SEQ ID NO: 149) |
| Number 28<br>(11A5)<br>V147A +<br>Q149S | M28-R<br>5'-atg gat cGA tcc aGc gag gcg tga ggg gtc ctc-3'<br>(SEQ ID NO: 150) | M28-F<br>5'-gCt gga TCg atc cat gat ggg gtc tcc aag gcc-3'<br>(SEQ ID NO: 151) |
| Number 29<br>(11A6)<br>I150A +<br>M128A | M29-R<br>5'-ctc aga gat ccc atc tct gtg cag aaa gaa gtg ctc aaa cGC gac-3'<br>(SEQ ID NO: 152) | M29-F<br>5'-gat ggg atc tct Gag gac ccc tca cgc ctc gtt gga cag GCc cat g-3'<br>(SEQ ID NO: 153) |
| Number 30<br>(1 + 2)<br>R13W +<br>A25T +<br>Q27R +<br>I60N + G62S | M30a-R<br>5'-tcc tcc tcg agg cac cac agt gct ggg ccA ggc ag-3'<br>(SEQ ID NO: 154) | M30a-F<br>5'-gtg cct cga Gga gga cac gtg Act ctt cGg tgt cac tat cg-3'<br>(SEQ ID NO: 155) |

TABLE 7A-continued

| Mutants | Reverse primers | Forward primers |
|---|---|---|
| Number 30 (1 + 2) R13W + A25T + Q27R + I60N + G62S | M30b-R 5'-tgg ggt cac agg gcT cat gTt gaa gct ctc ctg g-3' (SEQ ID NO: 156) | M30b-F 5'-Agc cct gtg acc cca gca cat gca ggg acc tac aga tgt cg-3' (SEQ ID NO: 157) |
| Number 31 (D0-HLA1) F9S + S11A | M31-R 5'-ggc agC cag gGa ggg ttt gtc ctg acc acc cat g-3' (SEQ ID NO: 158) | M31-F 5'-ccc tCc ctg Gct gcc cgg ccc agc act gtg gtg cc-3' (SEQ ID NO: 159) |
| Number 32 (D0-HLA2) H29S + F34A | M32-R 5'-ccc acg acg ata gGA aca ctg aag agc cac gtg tcc-3' (SEQ ID NO: 160) | M32-F 5'-TCc tat cgt cgt ggg GCt aac aat ttc atg ctg tac-3' (SEQ ID NO: 161) |
| Number 33 (1 + 2 A1) F50A + R53S | M33-R 5'-tat Gct gcc gtg gGC gat ggg aac gtg gct tct g-3' (SEQ ID NO: 162) | M33-F 5'-GCc cac ggc agC ata ttc cag gag agc ttc atc-3' (SEQ ID NO: 163) |
| Number 34 (1 + 2 A2) Q56S + E57A | M34-R 5'-gaa gct cGc cGA gaa tat tct gcc gtg gaa gat gg-3' (SEQ ID NO: 164) | M34-F 5'-ttc TCg gCg agc ttc atc Atg ggc cct gtg acc-3' (SEQ ID NO: 165) |
| Number 35 (1 + 2 A3) P14S + S15A + S H23 | M35-R 5'-tcc tcg agg cac cac agt gGC ggA ccg ggc aga cag-3' (SEQ ID NO: 166) | M35-F 5'-gtg gtg cct cga Gga gga TCc gtg gct ctt cag tgt c-3' (SEQ ID NO: 167) |
| Number 37 (1 + 2 A5) S140Q | M37-R 5'-gtc ctc TTG gat ccc atc tct gtg cag aaa g-3' (SEQ ID NO: 168) | M37-F 5'-ggg atc CAA Gag gac ccc tca cgc ctc gtt gg-3' (SEQ ID NO: 169) |

Each antibody was tested for binding to wild-type KIR3DL2 and to each of the D0, D1 and D2 domain mutants. Results for exemplary anti-D0 antibodies are shown in Table 7B ("+" indicates no significant loss of binding, "+/−" indicates a decrease in binding (or partial loss of binding) and "−" indicates substantially complete loss of binding). Antibodies 19H12, 18B10 and 12B11 did not show any loss of binding to unmutated wild type KIR3DL2 (WTaKIR3DL2), but lost binding to mutant 11 having P179T and S181T substitutions as well as to mutant 11A1 having V178A and H180S substitutions. The principal epitope of these antibodies 19H12, 18B10 and 12B11 therefore includes residues P179, S181, V178 and/or H180. These residues at positions 179 and 181 in mutant 11 correspond to the residues present at in KIR3DL1 (KIR3DL1 has T179 and T181). Residues P179 and S181 in particular are within the D1 domain of KIR3DL2 and on the opposite face on the KIR3DL2 protein of the HLA-binding regions (i.e. the HLA binding pocket). Each of antibodies 15C11, 19H12, 18B10 and 12B11 had reduced binding (full loss of binding for 15C11 and 19H12) to mutant M11A4 having substitutions E130S, H131S and R145S. Antibody 15C11 furthermore had loss of binding to mutant M11A6 having substitutions 1150A and M128A. Antibody 18B10 furthermore had loss of binding to mutant M11A5 having substitutions V147A and Q149S. The epitope of these antibodies 15C11, 19H12, 18B10 and 12B11 can therefore include residues E130, H131 and/or R145. The epitope of antibody 15C11 can include residues I150 and/or M128. The epitope of antibody 18B10 can include residues V147 and/or Q149.

Antibody 13H1 showed decreased binding to mutant 1, 2, 2A2 and MD0/HLA1. Antibody 13H1 had loss of binding to both mutant 1 having R13W, A25T and Q27R and to mutant 2 having 160N and G62S substitutions. 13H1 also had decreased binding to mutant 2A2 (Q56S, E57A) and mutant MD0/HLA1 (F9S, S11A). The epitope of 13H1 therefore includes residues F9, S11, Q56 and/or E57, in addition to R13, A25, Q27, 160 and/or G62. These residues are within the D0 domain.

Surface-exposed residues adjacent to these mutated residues can also contribute to the epitopes of the antibodies located at the surface of KIR3DL2 in the region of the P179/S181 epitope but outside of the region of the KIR3DL2 mutations which did not result in loss of binding of the antibodies (e.g., mutant 5 (residue P66) and mutant 8 (residues V127)).

FIG. 12 shows a view of the KIR3DL2 polypeptide, including portions within the D1 domain, showing amino acid residues mutated indicated as "Mutant 11" which resulted in loss of binding by antibodies 19H12, 18B10 and 12B11, as well as adjacent "Mutant 5" and "Mutant 8" that did not result in loss of biding of antibodies. Also shown shaded are residues adjacent to residues (N99, H100, E130, H131, F132, V178, H180, P182, Y183, and Q184).

Antibody 13H1 had loss of binding to both mutant 1 having R13W, A25T and Q27R and to mutant 2 having 160N and G62S substitutions. 13H1 also had decreased binding to mutant 2A2 (Q56S, E57A) and mutant MD0/

HLA1 (F9S, S11A). The epitope of 13H1 therefore includes residues F9S, S11A, Q56 and/or E57. These residues are within the D0 domain.

Example 6-15C11, 19H12, 22B2, 18B10, 12B11, 13H1 and 4B5 Antibodies Induce KIR3DL2 Internalization Briefly, either no antibody or 20 µg/mL of an anti-KIR3DL2 domain 0 antibody, or antibody 15C11, 19H12, 22B2, 18B10, 12B11, 13H1 or 4B5 were incubated with fresh Sézary Syndrome cells from 5 different human donors, for 24 h at 37° C. Cells were then washed, fixed and permeabilized using IntraPrep permeabilization reagent from Beckman Coulter. Presence of KIR3DL2-bound 15C11, 19H12, 22B2, 18B10, 12B11, 13H1 or 4B5 Ab was revealed with a goat anti-mouse Ab, labelled with GAM-PE. Tables 8A, 8B, 8C and 8D represent the fluorescence induced by the binding to KIR3DL2 protein of 15C11, 22B2, 19H12 and anti-KIR3DL2 domain 0 antibody, after 24 h incubation, respectively. The table shows a strong decrease in fluorescence for each of antibodies 15C11, 19H12 and 22B2 in each of the different donors, confirming that the binding of these antibodies down-modulates the expression of KIR3DL2 on SS cells. Conversely, the anti-KIR3DL2 domain 0 antibody did not result in a decrease in fluorescence indicating that this antibody did not down-modulate the expression of KIR3DL2 on SS cells.

TABLE 8A

| Patient | KIR3DL2 mfi after 24 h-incubation in medium, stained with 15C11/GAM-PE | KIR3DL2 mfi after 24 h-incubation with 20 m/ml 15C11, stained with 15C11/GAM-PE |
| --- | --- | --- |
| MOT | 3698 | 1640 |
| GAI | 6847 | 1226 |
| SUE | 2025 | 580 |
| RUB | 2793 | 594 |
| CHAP | 9377 | 1569 |

TABLE 8B

| Patient | KIR3DL2 mfi after 24 h-incubation in medium, stained with 22B2/GAM-PE | KIR3DL2 mfi after 24 h-incubation with 20 µg/ml 22B2, stained with 22B2/GAM-PE |
| --- | --- | --- |
| MOT | 3461 | 2590 |
| GAI | 4594 | 808 |
| SUE | 1186 | 870 |
| RUB | 1384 | 726 |
| CHAP | 9981 | 1951 |

TABLE 8C

| Patient | KIR3DL2 mfi after 24 h-incubation in medium, stained with 19H12/GAM-PE | KIR3DL2 mfi after 24 h-incubation with 20 µg/ml 15C11, stained with 19H12/GAM-PE |
| --- | --- | --- |
| MOT | 8289 | 3650 |
| GAI | 10747 | 4263 |
| SUE | 3187 | 2101 |
| RUB | 3635 | 1872 |
| CHAP | 17666 | 4272 |

TABLE 8D

| Patient | KIR3DL2 mfi after 24 h-incubation in medium, stained with D0 mAb/GAM-PE | KIR3DL2 mfi after 24 h-incubation with 20 µg/ml D0 mAb, stained with D0 mAb/GAM-PE |
| --- | --- | --- |
| MOT | 3211 | 3592 |
| GAI | 1118 | 2210 |
| SUE | 525 | 676 |
| RUB | 697 | 741 |
| CHAP | 2645 | 3738 |

Further experiments were carried out with antibody 18B10, as well as human-mouse chimeric antibodies having the variable regions of murine antibodies 15C11 (chim15C11), 19H12 (chim19H12) or 18B10 (chim18B10). Experimental settings were as in preceding experiments, except that 10 µg/mL anti-KIR3DL2 mAb is used.

For murine antibody 18B10, one human donor was tested. Antibody 18B10 displayed an MFI or 329 after incubation for 24 h with antibody, compared to an MFI of 534 after incubation in the absence of antibody.

Tables 9A, 9B, 9C and 9D represent the fluorescence induced by the binding to KIR3DL2 protein of chimeric antibodies 15C11, 19H12, 18B10 or 13H1 after 24 h incubation, respectively. The tables show a strong decrease in fluorescence for each of chimeric antibodies 15C11, 19H12, 18B10 or 13H1 in each of the different donors, confirming that the binding of these antibodies down-modulate the expression of KIR3DL2 on SS cells. Similar results were obtained for antibody 4B5.

TABLE 9A

| | Chim15C11 | |
| --- | --- | --- |
| Patient | KIR3DL2 mfi after 24 h incubation without mAb | KIR3DL2 mfi after 24 h incubation with 10 µg/ml mAb |
| KLU | 2383 | 1697 |
| HAE | 3716 | 1851 |
| STA | 1484 | 997 |
| CER | 726 | 353 |

TABLE 9B

| | Chim19H12 | |
| --- | --- | --- |
| Patient | KIR3DL2 mfi after 24 h incubation without mAb | KIR3DL2 mfi after 24 h incubation with 10 µg/ml mAb |
| KLU | 2812 | 1845 |
| HAE | 3873 | 3022 |
| STA | 2149 | 2006 |
| CER | 665 | 513 |

TABLE 9C

| | Chim18B10 | |
| --- | --- | --- |
| Patient | KIR3DL2 mfi after 24 h incubation without mAb | KIR3DL2 mfi after 24 h incubation with 10 µg/ml mAb |
| KLU | 3158 | 2035 |
| HAE | 4792 | 2717 |
| STA | 2287 | 1743 |
| CER | 722 | 415 |

TABLE 9D

| | 13H1 | |
|---|---|---|
| Patient | KIR3DL2 mfi after 24 h incubation without mAb | KIR3DL2 mfi after 24 h incubation with 10 µg/ml mAb |
| KLU | 1426 | 592 |
| HAE | 2676 | 871 |
| STA | 1095 | 544 |
| CER | 475 | 197 |

Example 7-15C11, 19H12, 22B2, 18B10, 12B11, 13H1 and 4B5 Antibodies are Internalized into Sézary Syndrome Cell Line Internalization of antibodies 15C11, 19H12, 22B2, 18B10, 12B11, 13H1 and 4B5 as well as antibody AZ158 (an anti-Domain 0 mAb) was assessed by fluoro-microscopy using the HUT78 SS cell line.
Materials and Methods:
Hut-78 cells were incubated during 1H at 4° C. with 10 µg/ml of the different antibodies. After this incubation cells were either fixed (t=0H) or incubated for 2H at 37° C. Cells incubated for 2H were then fixed and stained. 15C11, 19H12, 22B2, 18B10, 12B11, 13H1 and 4B5 and AZ158 antibodies were stained using goat anti-mouse antibodies coupled to Alexa594 (Invitrogen, A11032). LAMP-1 compartments were stained using rabbit anti-LAMP-1 antibodies (Abcam, ab24170) revealed by goat anti-rabbit polyclonal antibodies coupled to FITC (Abcam ab6717). Pictures were acquired using an Apotome device (Zeiss) and analyzed using the Axiovision software.
Results:
Anti-KIR3DL2 mAbs were visible in red while LAMP-1 compartments were visible in green. At the time of addition of antibodies, KIR3DL2 staining in red was visible at the cell surface while green LAMP-1 were visible intracellularly in green. However, at 2 hours following the addition of antibodies, each of antibodies 15C11, 19H12, 22B2, 18B10, 12B11, 13H1 and 4B5 caused red staining to be colocalized with green staining, along with a decrease in red staining at the cell surface, indicating that each of antibodies 15C11, 19H12, 22B2, 18B10, 13H1, 4B5 and 12B11 was rapidly internalized. Antibody AZ158 was not internalized, and at 2 hours following the addition of AZ158, red staining remained entirely on the cell surface.

Example 8—Antibodies are Able to Kill KIR3DL2 Expressing Targets Via Complement-Dependent Mechanism (CDC)

19H12 is a murine IgG2b, an isotype known to recruit complement, was tested for its ability to mediate CDC, as compared with rituximab (anti-CD20 antibody) and chimeric AZ158.
Briefly, 50 µl of 20 µg/ml antibodies (2× concentrated) diluted were provided in standard medium a White clear bottom P96 wells (Ref 655098—Greiner), to which were added 50p of a cell suspension at 2 million per ml (100,000 cells per well) in standard medium, and incubated for 30 min at 4° C. 5 µl per well of freshly reconstituted complement (Ref CL3441—Cedarlan) was added, followed by incubation 1H at 37° C. 100 µl per well of Cell Titer Glo (Ref G7572—Promega) was added followed by incubation 10 min at room temperature protect from light. Results were read using a luminometer (VICTOR).

Figure 4:
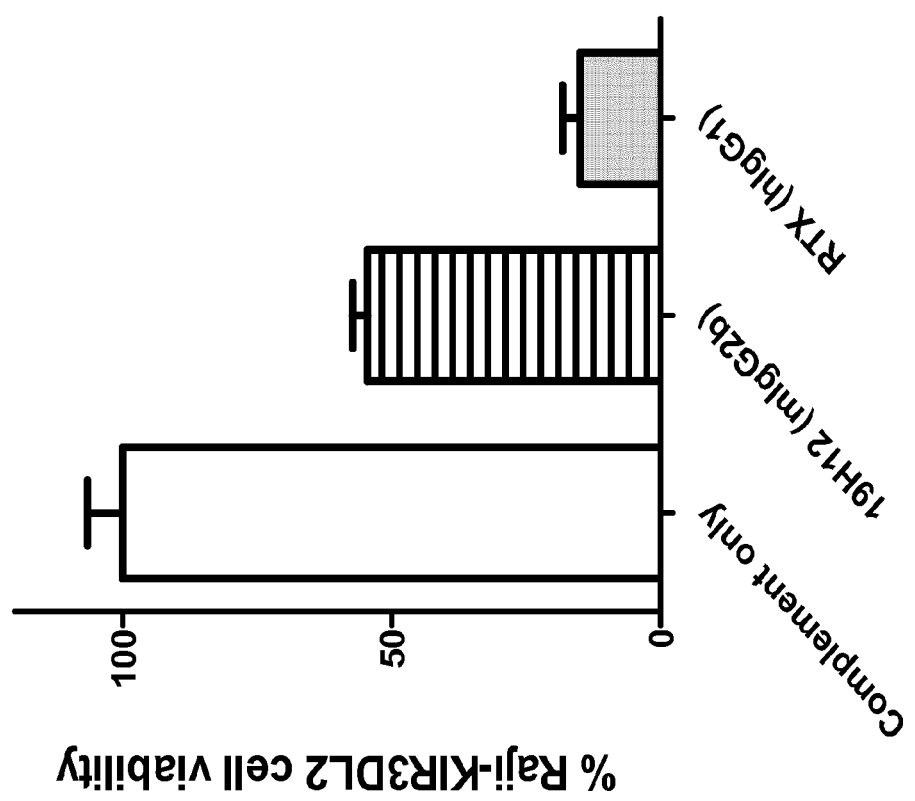
FIG. 4 shows viability of KIR3DL2-expressing RAJI cells, in the presence of complement; antibody 19H12 causes a decrease in cell viability. Rituximab (RTX) is used as positive control.

Results are shown in FIG. 4. The results show viability of KIR3DL2-expressing RAJI cells, in the presence of complement. The results show that 19H12 causes a decrease in cell viability. However, chimerized AZ158 antibody (see WO2010/081890) having a human IgG1 and theoretically able to recruit complement did not mediate CDC. Rituximab (RTX) is used as positive control. Antibody 19H12 therefore is able to induce CDC; nevertheless is it believed that CDC activity is significantly limited by the rapid and extensive internalization of the antibody in KIR3DL2-expressing cells.

Example 9-15C11, 19H12, 22B2, 18B10, 12B11, 13H1 and 4B5 Antibodies Show Efficacy in NOD-SCID Mice Receiving RAJI-KIR3DL2 Xenografts NOD-SCID mice are pooled in groups and treated either with vehicle (PBS) or anti-KIR3DL2 antibody (300 µg/mouse, IP). Raji-KIR3DL2 were human Burkitt's lymphoma cells transfected with KIR3DL2 and sub-cloned to obtain an homogeneous expression. It is a suspension cell line. Raji-KIR3DL2 were cultured in complete RPMI 1640 culture medium containing supplemented with 10% of Fetal Bovine Serum Heat Inactivated, 1% L-glutamine and without antibodies. All cells were counted in Malassez with trypan blue. Each mouse received 5 million cells/100 µl/PBS 1×/IV with a needle 30 G. Cells were injected very slowly. KIR3DL2 expression on Raji cells was confirmed before their injection. Mice were conditioned one day before (D-1) receiving Raji-KIR3DL2 xenografts using cyclophosphamide, 200 mg/kg/100 µl PBS, as one injection by IP. Mice received Raji-KIR3DL2 cells (Day 0, D0) and treatment with antibodies (300 µg) began one day after Raji-KIR3DL2 administration at a frequency of twice per week.
In summary, groups of 8 mice were performed the day of the tumoral cells injection, as follows:
n=8 (cyclo 200 mg/kg D-1) RAJI KIR3DL2 (5M IV)+ PBS
n=5 (cyclo 200 mg/kg D-1) RAJI KIR3DL2 (5M IV)+ 15C11 300 µg 2×/week from D1
n=8 (cyclo 200 mg/kg D-1) RAJI KIR3DL2 (5M IV)+ 19H12 300 µg 2×/week from D1
n=8 (cyclo 200 mg/kg D-1) RAJI KIR3DL2 (5M IV)+22B2 300 µg 2×/week from D1
Increase in life span (ILS) was assessed as follows:

$$\% \text{ ILS} = 100 \times (T-C)/C$$

Figure 5:
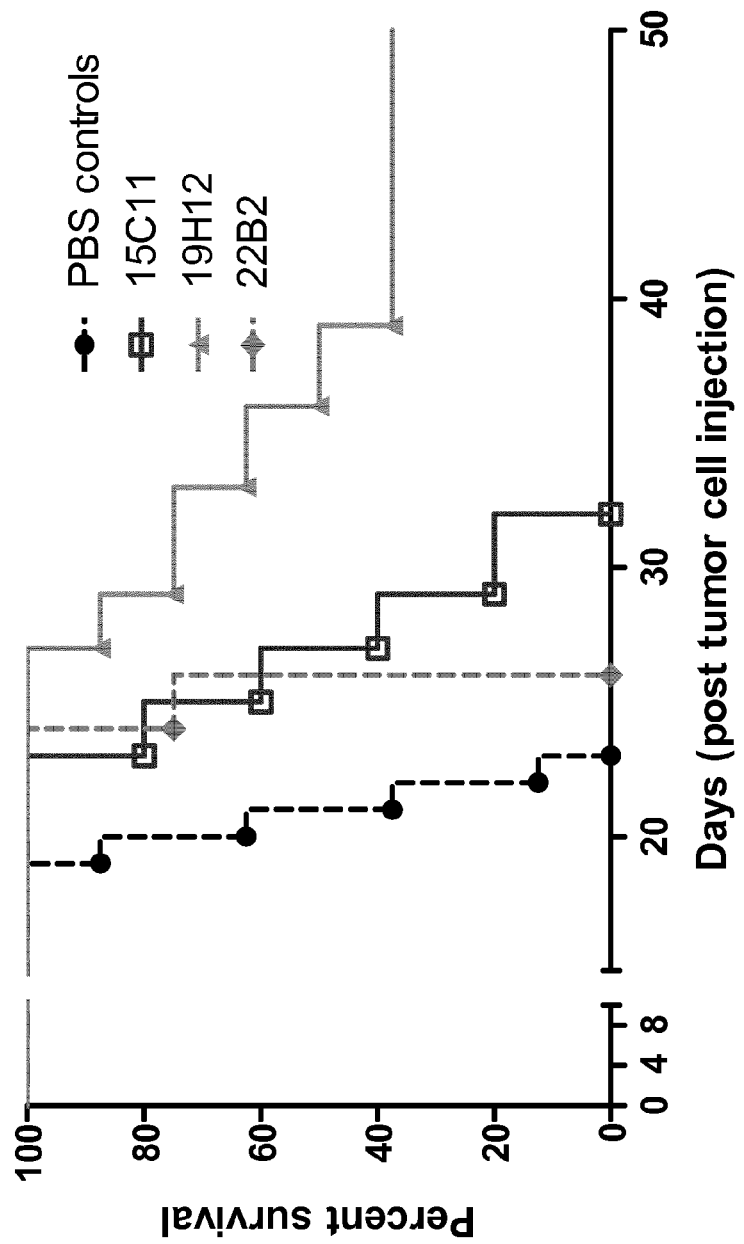
FIG. 5 shows percent survival of mice as a function of the days post tumor cell injection. Anti-KIR3DL2 antibodies increased survival of mice; 15C11 increased life span of mice by 28.5% compared to PBS.

T: median day of death of treated group
C: median day of death of control group
Curve comparisons were analyzed with Log-rank (Mantel—Cox) Test on GraphPad Prism software. Results showed that anti-KIR3DL2 antibodies increased survival of the mice, as shown in FIG. 5. 15C11 yielded an ILS of 28.5%, similar to that obtained in two previous studies of 34% and 25%, respectively.

Example 10—In Vitro and In Vivo Testing of Antibody Drug Conjugates

Material and Methods
Anti-KIR3DL2 Antibody-Drug Conjugates
Two different anti-KIR3DL2 mAbs were prepared as ADCs: murine 19H12 (mo19H12) and chimeric 15C11 of human IgG1 Fc isotype (chim15C11).
Mo19H12 was coupled to the drug MMAF using either a non-cleavable linker (resulting in mo19H12-ADC1 molecule) or a cleavable linker (resulting in the mo19H12-

ADC2 reagent). Chim15C11 was coupled to MMAF with a cleavable linker (chim15C11-ADC2).

The total structure of linker+drug in ADC1 was:

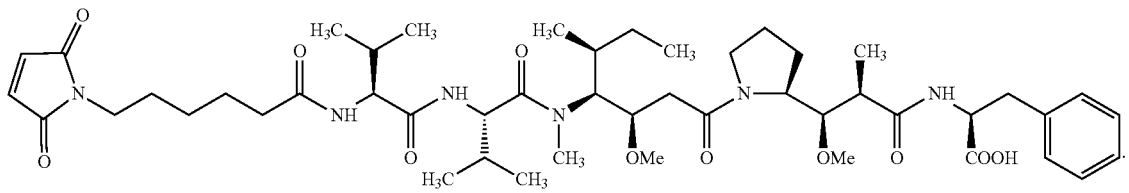 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NC(=O)CCCCCN1C(=O)C=CC1=O)C(C)C)C(C)C]

The total structure of linker+drug in ADC2 was:

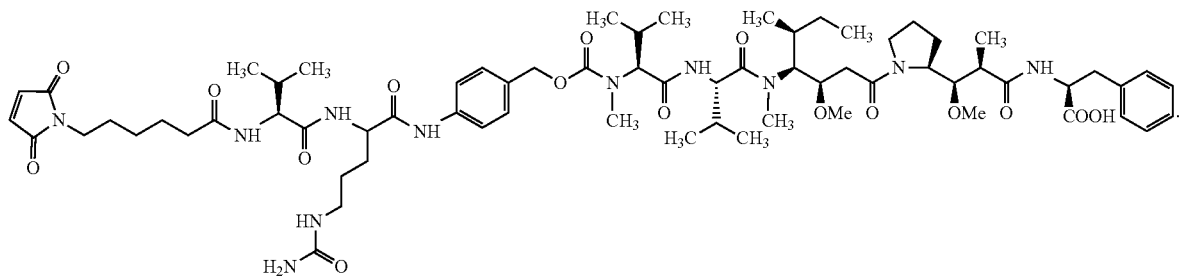 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)OCc1ccc(NC(=O)C(CCCNC(N)=O)NC(=O)[C@@H](NC(=O)CCCCCN2C(=O)C=CC2=O)C(C)C)cc1)C(C)C]

KIR3DL2+ Tumor Cell Lines

HUT78 is a KIR3DL2 positive Sézary cell line; HUT78 cells grow in culture in RPMI medium supplemented with 10% FSC but do not grow after SC or IV engraftment to immune compromised mice;

B221 and RAJI are, respectively, B-lymphoblastoid and Burkitt's lymphoma CD20 positive human cell lines that were transfected with a construct aiming at the stable expression of the human kir3dl2 gene. B221-KIR3DL2 and RAJI-KIR3DL2 cells grow in RPMI medium supplemented with 10% FSC. They grow as disseminated (IV) or solid (SC) tumors after injection to immune compromised mice;

B221-KIR3DL2 and RAJI-KIR3DL2 cell lines were also sub cloned in order to select transfectants bearing lower levels of expression of KIR3DL2, i.e. closer to the physiological levels observed on Sézary patient cells. It resulted in the generation of 3 different tools for each cell line (1 "parental" with the highest expression and 2 subclones, noted B221-KIR3DL2$^{med}$/RAJI-KIR3DL2$^{med}$ and B221-KIR3DL2$^{low}$/RAJI-KIR3DL2$^{low}$);

HEK-KIR3DL2 is a human kidney cancer cell line transfected with a construct aiming at the stable expression of the human kir3dl2 gene that grows in RPMI+10% SVF.

In Vitro Proliferation Assays

Target cells (HUT78, B221-KIR3DL2 or RAJI-KIR3DL2) were seeded at 5,000 cells/well in 96-well plates, in RPMI medium+10% SVF, in triplicate for each condition. ADCs were added to the medium once at the beginning of the culture, at final concentrations ranging from 0.1 to 10 µg/mL depending on the drug/the cell line. Cultures were incubated at 37° C. and analyzed at different time-points over several days for cell viability, using the Cell Titer Glo® kit (the luminescent signal being proportional to cellular metabolic activity, and hence a surrogate marker of cell proliferation). Controls included, depending on the experiments, incubation in medium only, incubation with the same final concentration of un-conjugated mAb and/or incubation with an irrelevant ADC (i.e. directed against an Ag not expressed on the target cells such as HER2neu).

Human Tumor Xenograft Mouse Models

Immune compromised mice used for B221-KIR3DL2 and RAJI-KIR3DL2 models were NOD-SCID purchased from Charles River Laboratories. In the following models, 5 million human tumor cells (in 100 µl PBS as vehicle) were engrafted IV on Day 0 (D0), i.e. 1 day before treatment initiation (D1). From D1, mice were treated IV with different doses of mAbs (doses are adapted to mouse body weight) diluted in PBS. In ADC experiments, test items were given weekly, for a total of 3 injections.

Control groups included, depending on the experiment:

PBS/placebo-treated mice as a control of normal/unaffected tumor growth;

mice injected with the same dose of identical naked (i.e. non-drug conjugate) mAbs, as a control of difference in activity between naked versus ADC;

mice injected with an irrelevant ADC (anti-HER2neu-MMAF, knowing that neither B221 nor RAJI express the HER2neu Ag);

mice engrafted with untransfected B221 or RAJI, as a control of unspecific activity of ADCs against tumors not bearing the target Ag KIR3DL2.

Mice were weighed and observed for clinical signs every 2 to 5 days depending on the model. Percent of body weight changes were calculated as compared to body weight at D0 before tumor engraftment or to the highest body weight reached during the experiment. Mouse deaths or important weight losses were recorded and used to draw survival Kaplan-Meier curves and calculate improvement in survival as compared to control groups of mice.

Results

Inhibition of Tumor Cell Growth In Vitro

Figure 6A:
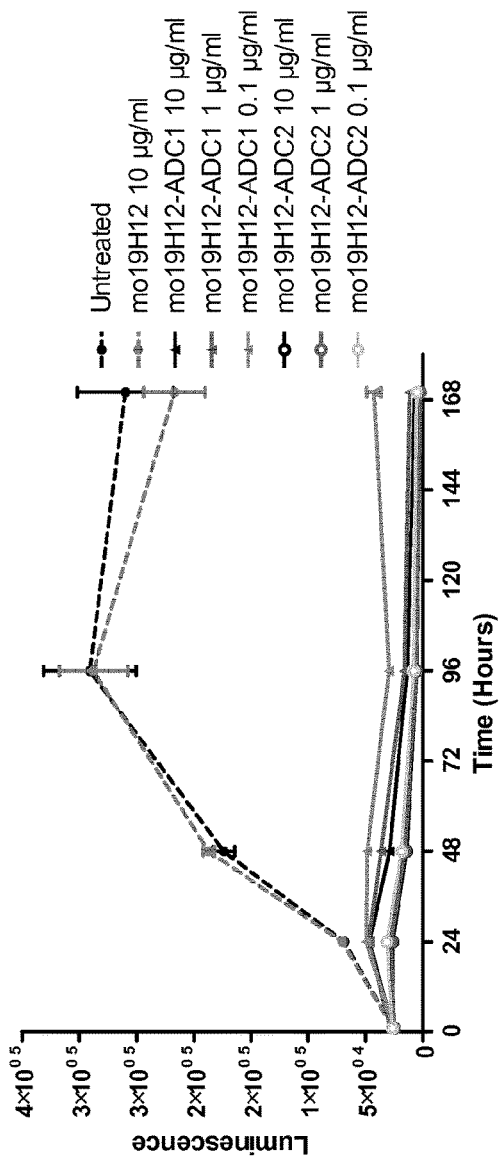
FIGS. 6A and 6B show, respectively, inhibition of in vitro growth of B221-KIR3DL2 cells by mo19H12-ADC1 and mo19H12-ADC2 (6A) and inhibition of in vitro growth of RAJI-KIR3DL2 cells by mo19H12-ADC1 and mo19H12-ADC2 (6B).
Figure 6B:
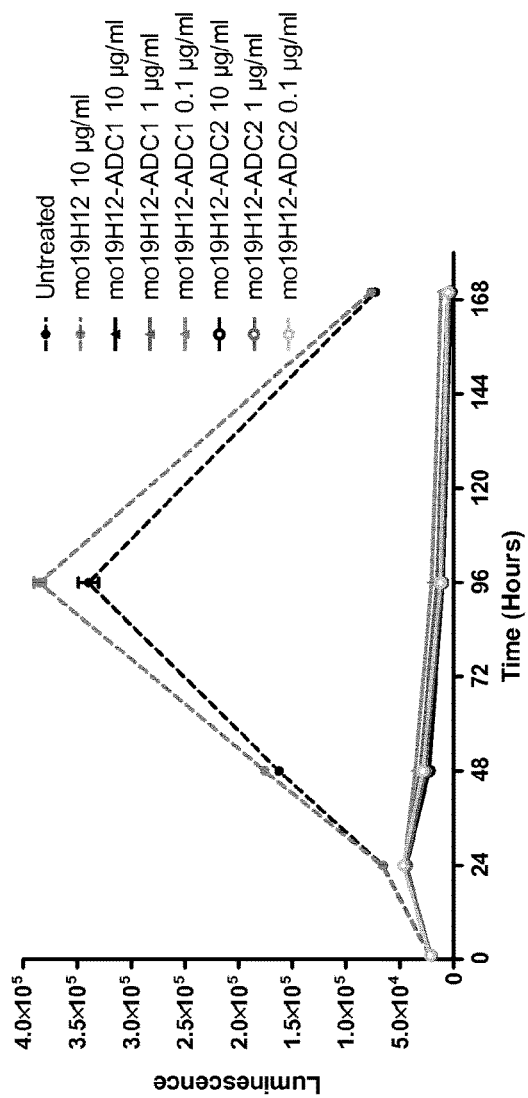

A 1$^{st}$ series of experiments evaluated murine 19H12-ADC1 (mo19H12-ADC1) and murine 19H12-ADC2 (mo19H12-ADC2) against HUT78, RAJI-KIR3DL2 and B221-KIR3DL2, 3 final concentrations of each ADC were tested: 0.1, 1 and 10 μg/ml. All 3 concentrations of both drugs inhibited totally the proliferation of B221-KIR3DL2 and RAJI-KIR3DL2 in vitro cultures, over a 180 hour-period (see FIGS. 6A and 6B). As a negative control, mo19H12 (un-conjugated) had no effect on cell viability at the highest concentration tested. Inhibition of in vitro growth of B221-KIR3DL2 cells by mo19H12-ADC1 and mo19H12-ADC2 is shown in FIG. 6A. Inhibition of in vitro growth of RAJI-KIR3DL2 cells by mo19H12-ADC1 and mo19H12-ADC2 is shown in FIG. 6B.

Figure 7:
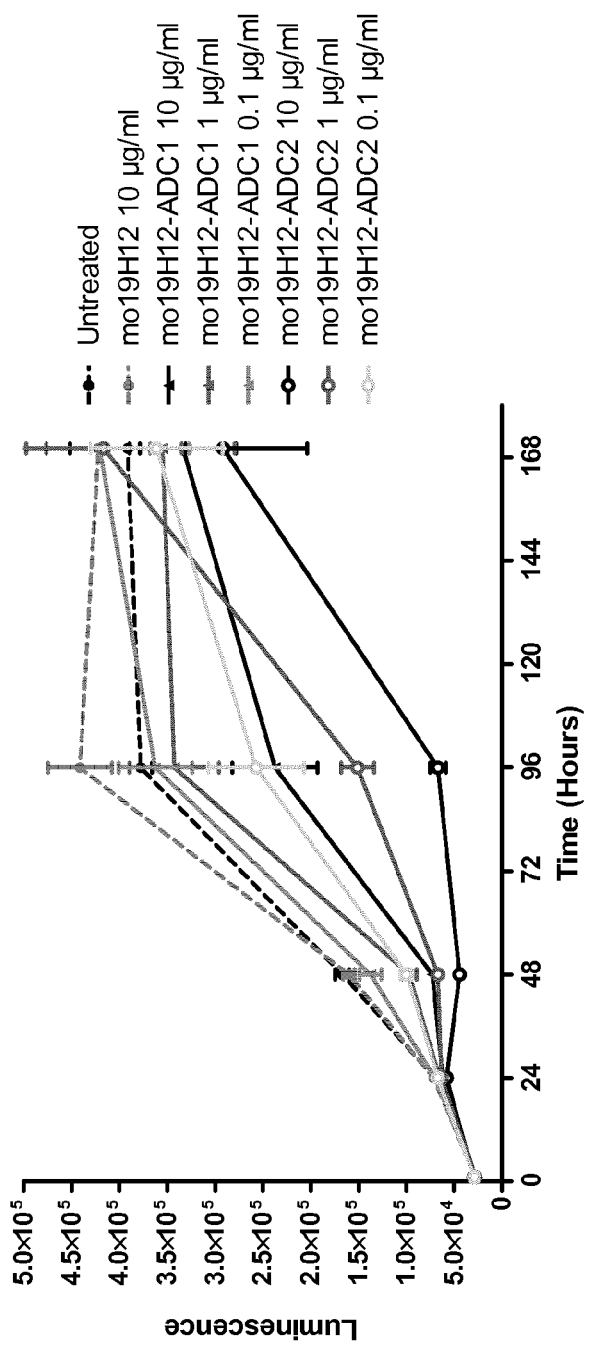
FIG. 7 shows inhibition of in vitro growth of HUT78 cells by mo19H12-ADC1 and mo19H12-ADC2.

On HUT78 Sézary cell lines, the inhibition of proliferation was less strong, in particular for mo19H12-ADC1 (same drug as mo19H12-ADC2 but with a non cleavable linker). However, 10 μg/mL mo19H12-ADC2 significantly and rapidly altered HUT78 cell viability. Inhibition of in vitro growth of HUT78 cells by mo19H12-ADC1 and mo19H12-ADC2 is shown in FIG. 7.

Figure 8A:
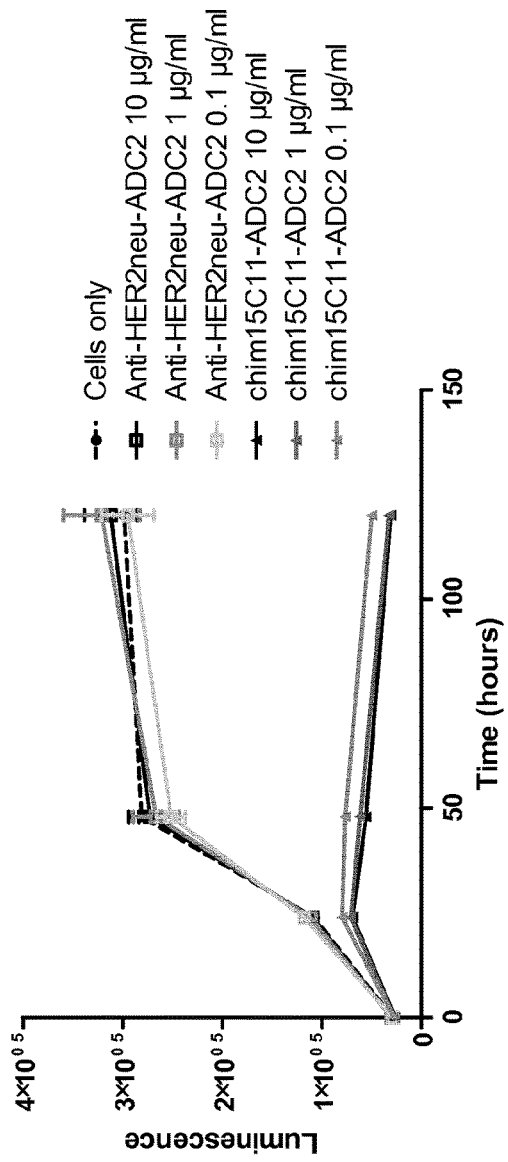
FIGS. 8A and 8B show inhibition of in vitro growth of B221-KIR3DL2 cells by chim15C11-ADC2 (8A) and inhibition of in vitro growth of RAJI-KIR3DL2 cells by chim15C11-ADC2 (8B).
Figure 8B:
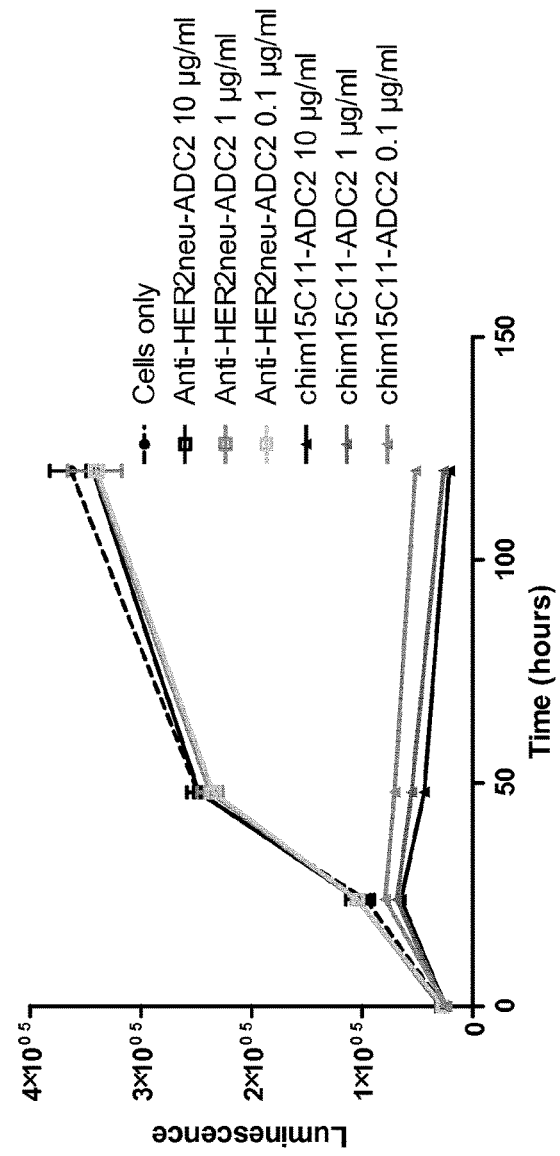

In a second series of experiment, chim15C11-ADC2 was evaluated for its inhibition of proliferation of three target cell lines, in parallel to the irrelevant anti-HER2neu-ADC2 control (B221-KIR3DL2 and RAJI-KIR3DL2 are negative for HER2neu expression while HEK-KIR3DL2 is HER2neu positive). While the irrelevant ADC has no efficacy against the HER2neu negative cell lines, chim15C11-ADC2 strongly affects viability of B221-KIR3DL2 and RAJI-KIR3DL2, as low as 0.1 μg/mL. Inhibition of in vitro growth of B221-KIR3DL2 cells by chim15C11-ADC2 is shown in FIG. 8A. Inhibition of in vitro growth of RAJI-KIR3DL2 cells by chim15C11-ADC2 is shown in FIG. 8B.

Figure 9A:
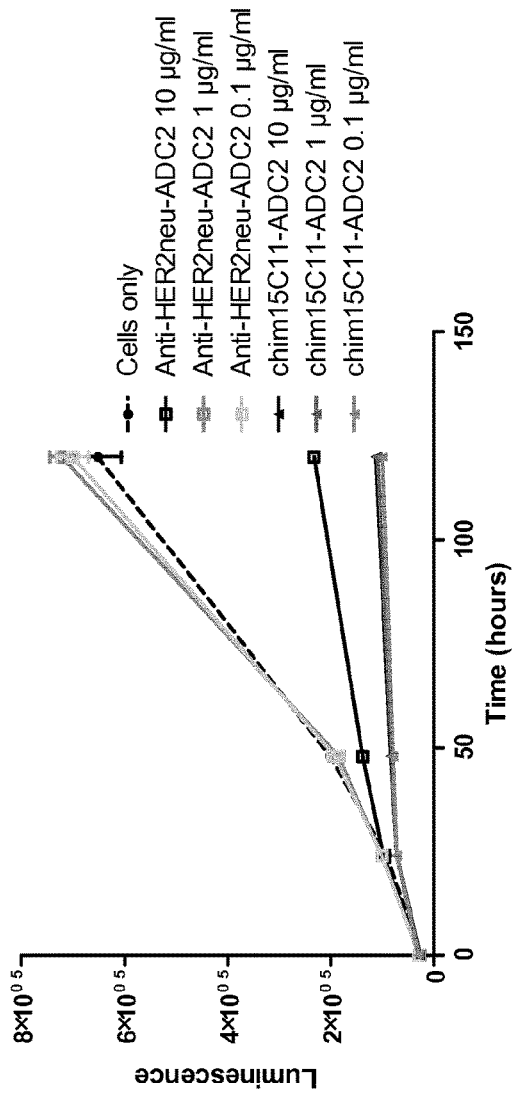
FIG. 9A shows the inhibition of HK-KIR3DL2 growth in vitro resulting from treatment with chim15C11-ADC2 against HEK-KIR3DL2, a target cell line naturally expressing HER2neu, in comparison to anti-HER2neu-ADC2 mAb.

In a further experiment, the efficacy of chim15C11-ADC2 was evaluated in vitro against HEK-KIR3DL2, a target cell line naturally expressing HER2neu, in parallel to anti-HER2neu-ADC2 mAb. Chim15C11-ADC2 was found much more potent than anti-HER2neu-ADC2 to inhibit HK-KIR3DL2 growth in vitro (see FIG. 9A).

Figure 9B:
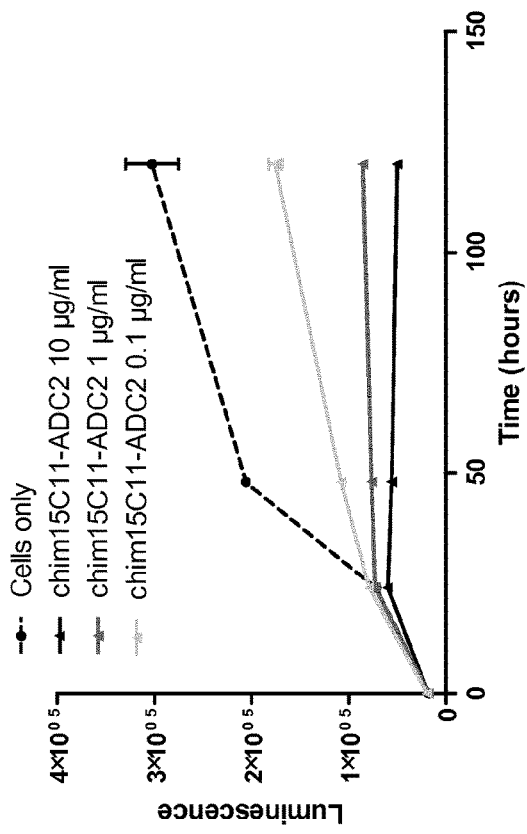
FIG. 9B shows inhibition of in vitro growth of a sub clone of RAJI-KIR3DL2 expression a lower level of KIR3DL2 (i.e. RAJI-KIR3DL2$^{med}$) by chim15C11-ADC2, even at the lowest concentration of 0.1 μg/mL.

Finally, we investigated chim15C11-ADC2 efficacy against the sub clone of RAJI-KIR3DL2 expression a lower level of KIR3DL2 (i.e. RAJI-KIR3DL2$^{med}$). Chim15C11-ADC2 still retains a good level of activity against RAJI-KIR3DL2$^{med}$ cells in vitro, even at the lowest concentration of 0.1 μg/mL. Inhibition of in vitro growth of RAJI-KIR3DL2$^{med}$ cells by chim15C11-ADC2 is shown in FIG. 9B.

Inhibition of Tumor Cell Growth In Vivo in Mouse Xenografts

Figure 10A:
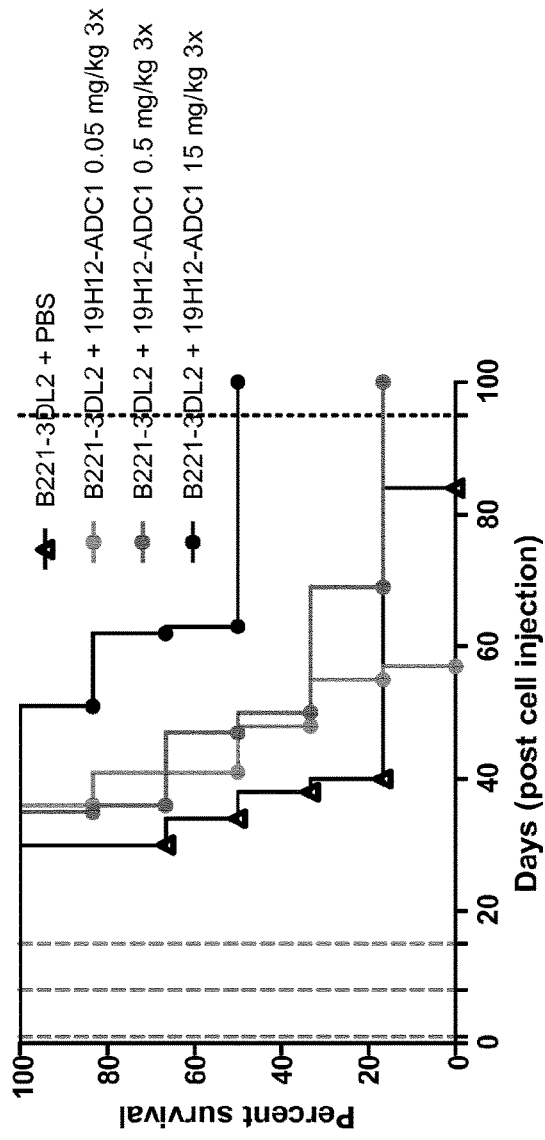
FIGS. 10A and 10B show inhibition of tumor growth by mo19H12-ADC1 mAb in the B221-KIR3DL2 xenograft model.
Figure 10B:
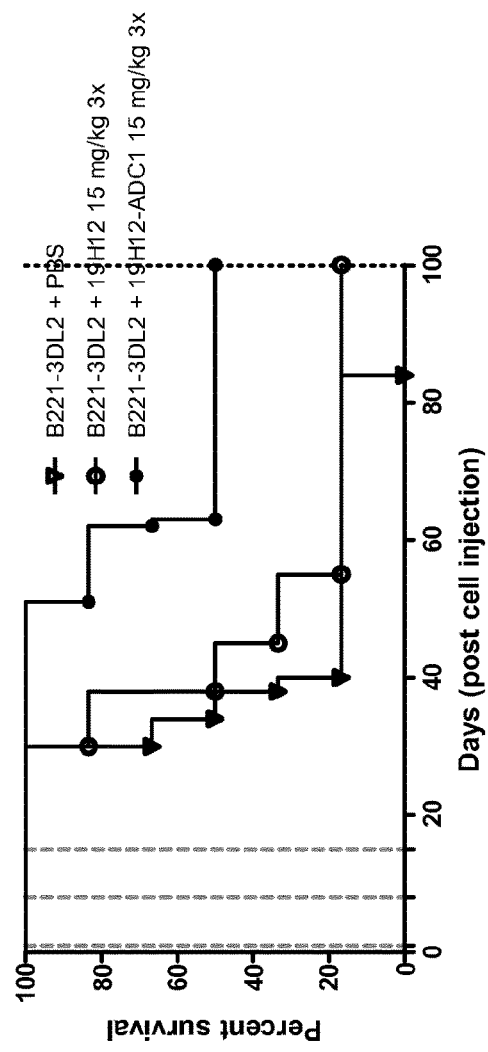

Inhibition of tumor growth by mo19H12-ADC1 mAb was evaluated in the B221-KIR3DL2 xenograft model. Mo19H12-ADC1 was tested at 0.05, 0.5 and 15 mg/kg IV, given 3 times weekly. N=6 mice per group were used. A relationship between mo19H12-ADC1 dose and improvement of survival is observed in those mice, where mo19H12-ADC1 mAb improves survival. FIG. 10A shows the dose-effect of 19H12-ADC1. In the same experiment, the non-drug conjugated version of mAb mo19H12 did not provide significant survival benefit, at the same dose as mo19H12-ADC1 (here shown for 15 mg/kg 3 times weekly); FIG. 10B shows the effect of mo19H12-ADC1 (15 mg/kg) as compared to mo19H12 (un-conjugated mAb).

Figure 11A:
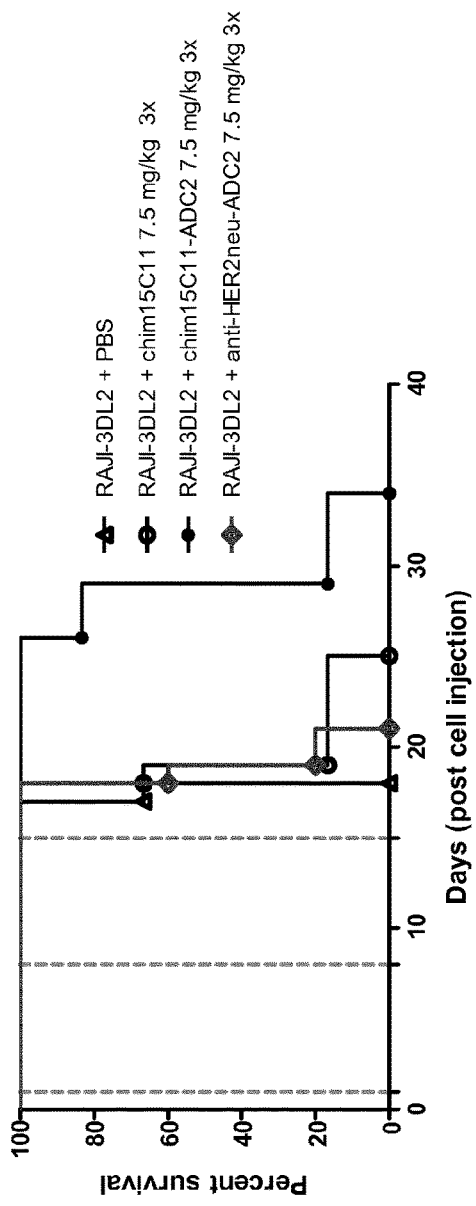
FIG. 11A shows the results for the inhibition by chim15C11-ADC2 of growth of RAJI-KIR3DL2$^{med}$ xenografts in NOD-SCID mice at 7.5 mg/kg dose level.
Figure 11B:
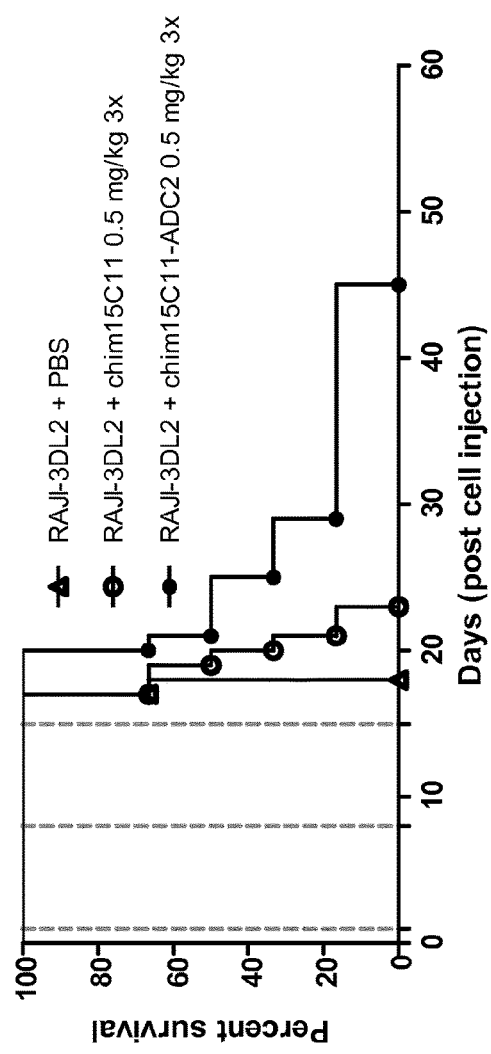
FIG. 11B shows the results for the inhibition by chim15C11-ADC2 of growth of RAJI-KIR3DL2$^{med}$ xenografts in NOD-SCID mice at 0.5 mg/kg dose level.
Figure 12:
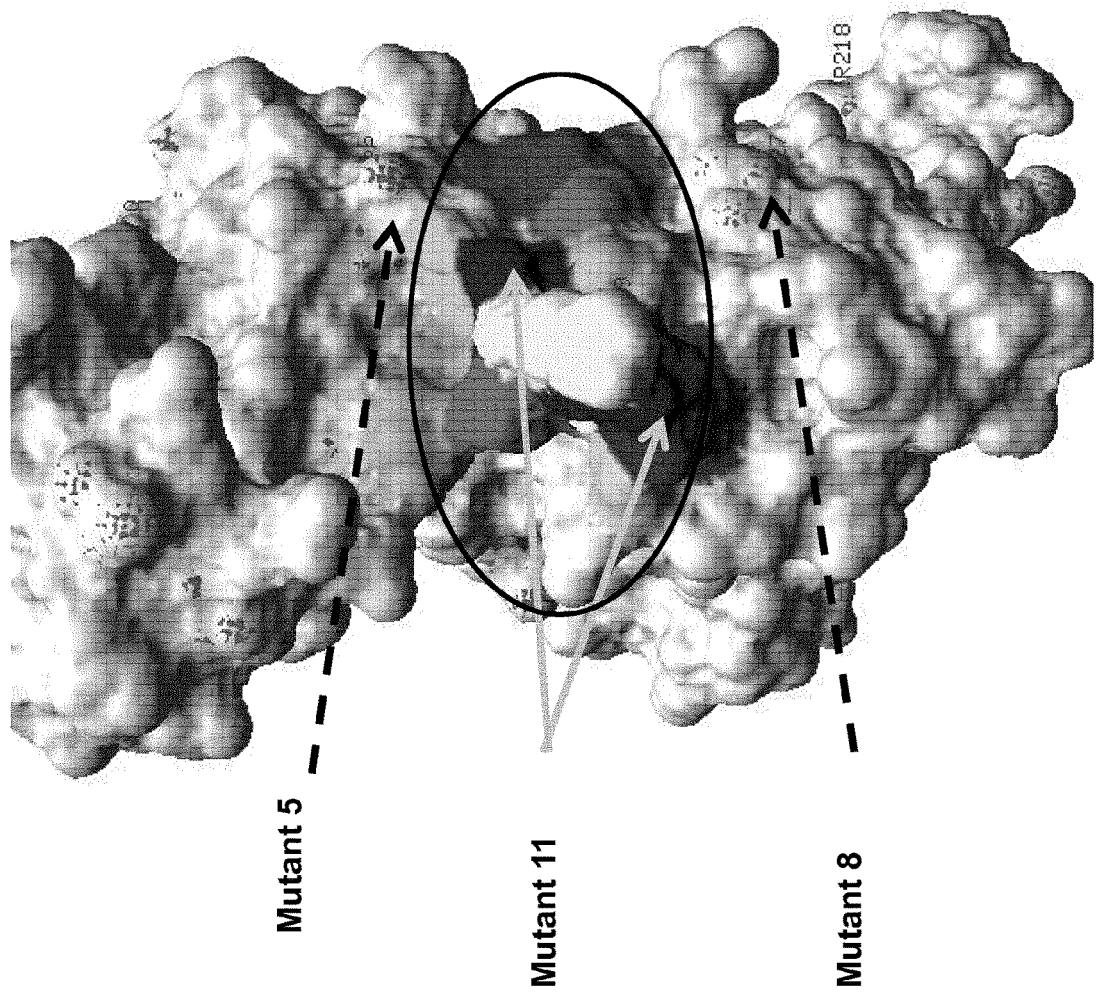
FIG. 12 shows a view of the KIR3DL2 polypeptide, including portions within the D1 domain, showing amino acid residues mutated indicated as "Mutant 11" (P179T and S181T) which resulted in loss of binding by antibodies, as well as adjacent "Mutant 5" and "Mutant 8" that did not result in loss of biding of antibodies. Also shown in darker shading are residues adjacent to mutated residues P179 and S181 that may also be bound by the antibodies (N99, H100, E130, H131, F132, V178, H180, P182, Y183, and Q184).

In a further experiment, another anti-KIR3DL2 ADC, chim15C11-ADC2 was evaluated for the inhibition of growth of RAJI-KIR3DL2$^{med}$ xenografts in NOD-SCID mice. Chim15C11-ADC2 was given at 0.5 or 7.5 mg/kg 3 times weekly to groups of N=6 mice. The irrelevant anti-HER2neu-ADC2 mAb was used as negative control, as RAJI-KIR3DL2$^{med}$ cells are negative for HER2neu expression. Chim15C11-ADC2 improves significantly and specifically survival of mice engrafted with KIR3DL2 positive targets, with doses as low as 0.5 mg/kg or 7.5 mg/kg 3 times weekly. FIG. 11A shows the results for the 7.5 mg/kg dose of chim15C11-ADC2 and FIG. 11B shows results for the 0.5 mg/kg dose of chim15C11-ADC2.

Chim15C11-ADC2 was further evaluated for the inhibition of 2 tumors xenografts in mice, B221-KIR3DL2$^{high}$ and B221-KIR3DL2$^{low}$, the latter being a sub-clone of the former with lower surface expression of KIR3DL2. On both models, chim15C11-ADC2 was tested at 0.5 and 7.5 mg/kg weekly for a total of 3 weeks.

Superimposed flow cytometry staining of surface KIR3DL2 on HUT78 Sézary cell line, as well as B221-KIR3DL2$^{high}$ and B221-KIR3DL2$^{low}$ cells illustrated the difference in levels of expression of the Ag on those targets: B221-KIR3DL2$^{low}$ was closer to the "physiological" level of expression observed on HUT78 than B221-KIR3DL2$^{high}$.

Example 11—Diagnostics by Flow Cytometry to Detect Cell Surface KIR3DL2

Anti-KIR3DL2 mAbs AZ158, 15C11, 19H12, 22B2, as well as a range of KIR3DL2-specific antibodies were tested in flow cytometry for binding to cells in samples obtained from patients having Sézary Syndrome. Briefly, 100 μl whole blood from Sézary Syndrome patient was taken on citrate and stained with (1) 50 μL anti-KIR3DL2 antibody hybridoma supernatant+GAM-PE, and (2) anti-CD4-FITC.

Figure 13:
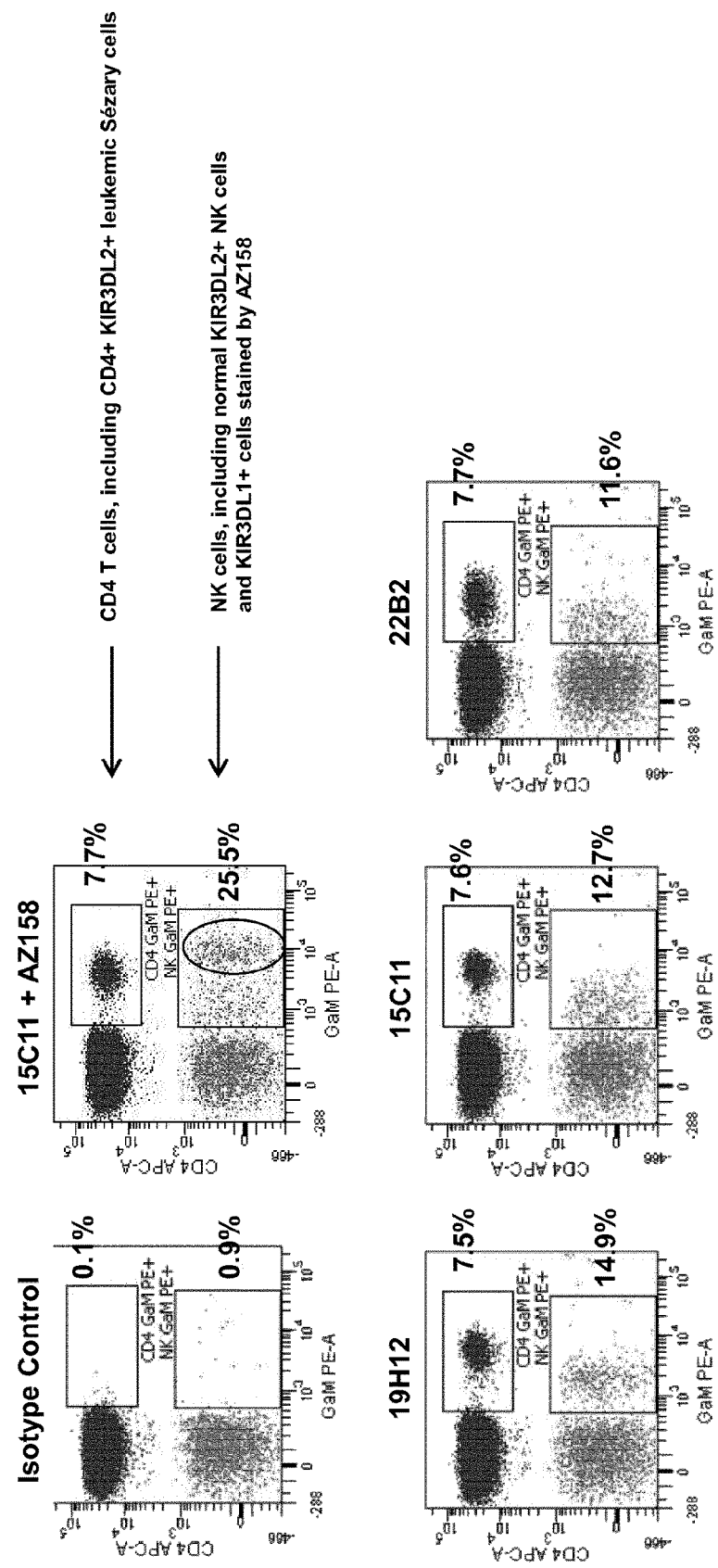
FIG. 13 shows results of flow cytometry staining for CD4 and KIR3DL2 on samples from a Sézary Syndrome patient. Shown are isotype control, and antibodies_15C11, 19H12, 22B2 and 15C11+AZ158.

NK cells, including normal KIR3DL2+NK cells and KIR3DL1+ cells stained by AZ158. Antibodies 15C11 and 22B2 provided good detection of KIR3DL2, antibody 19H12 provided greater specificity, with positive and negative cell population being more clearly distinguished with antibody 19H12. Antibodies 12B11 and 18B10 provided similar profile as 19H12. Representative results are shown in FIG. 13, where CD4 and KIR3DL2 staining is shown for isotype control, antibody 15C11, 19H12, 22B2 and 15C11+ AZ158.

Example 12—Humanization of Anti-KIR3DL2 Antibodies

Humanized sequences were designed according to CDR-grafting methods (see below). For purposes of evaluation, three light and heavy chains were combined to generate nine humanized 15C11 variants (Table 12). CDR-grafting methods are well documented and described in the literature (Foote J, and Winter G. J Mol Biol 1992; 224(2):487-99); Makabe et al., 528. J Biol Chem. 2008; 283(2):1156-66; Robert et al., Protein Sci. 2010; 19(2):299-308; Rogusta et al., PNAS. 1994 Feb. 1; 91(3):969-73). The main standard and validated methods were carefully examined and a consensus "Design Cycle" was established. Firstly, parental murine antibodies were sequenced and the VH, DH, JH and VL, JL genes identified and annotated to define the CDRs (Lefranc et al., Immunology. 2003; 27(1):55-77). Secondly, in order to pick up the human germline genes showing the closest homology with the murine antibody donor sequences, the parental murine VH and VL gene amino-acid sequences were aligned with the corresponding human genes using the "blast for Ig sequence" web service. Then the identified human genes were confronted to the humanized antibody database (IMGT/mAbDB) or to the published humanized antibodies to check if these specific human VH and VL genes had already been used for humanization and if their 3D-structure is already known. A model of the acceptor frameworks can be built and used to graft the murine CDRs by homology with the known humanized structures.

In order to refine the preliminary grafting design, six major elements were considered:

Conservation of FW amino-acids which flank the CDRs;

Conservation of FW amino-acids of the Vernier zone (Makabe);

Conservation of FW amino-acids at the VH/VL domain interface (Singer et al., J. Immunol. 1993 (150):2844-2857);

Back-mutations already described in the literature (if applicable);

3D structure models (if applicable);

Somatic hypermutations of parental VH and VL genes.

Three different humanized variants of each V domain were designed and combined to construct nine different 15C11 humanized versions. The three V domain variants differed from one another by the gradual introduction of back-mutations according to the six major elements described above. The 15C11-h2 chain had back mutations at residues 50 and 61 of SEQ ID NO: 114 (Kabat residues 50 and 58, respectively). The 15C11-h3 chain had back mutations at residues 49, 50, 61 and 81 of SEQ ID NO: 114 (Kabat residues 49, 50, 58 and 78, respectively). The 15C11-12 chain had back mutations at residues 38 and 49 of SEQ ID NO: 120 (Kabat residues 39 and 49, respectively). The 15C11-13 chain had back mutations at residues 38, 49, 69 and 71 of SEQ ID NO: 120 (Kabat residues 38, 49, 69 and 71, respectively). Therefore, including the murine parental chimeric antibody, ten different antibodies were produced (Table 13).

Amino acid and nucleic acid sequences for the respective 15C11-humanized heavy and light chains H1, H2 and H3 are show in Table 10 and 11, respectively.

TABLE 10

Heavy chain variable regions of humanized 15C11 mAbs

| Antibody | Amino acid sequence | DNA sequence |
| --- | --- | --- |
| 15C11-h1 | EVQLVESGGGLVQPGGSLR<br>LSCAASGFTFSDAWMDWVR<br>QAPGKGLEWVGRIRSKANN<br>HATAYAASVKGRFTISRDD<br>SKNSLYLQMNSLKTEDTAV<br>YYCTGGYYPVYWGQGTLVT<br>VSS<br>(SEQ ID NO 114) | GAGGTGCAGCTGGTGGAGTCTGGGGGAGGCTTGGTCCAGCC<br>TGGAGGGTCCCTGAGACTCTCCTGTGCAGCCTCTGGATTCA<br>CCTTCAGTGACGCCTGGATGGACTGGGTCCGCCAGGCTCCA<br>GGGAAGGGGCTGGAGTGGGTTGGCCGTATTAGAAGCAAAGC<br>TAACAATCACGCCACAGCATACGCCGCGTCTGTGAAAGGCA<br>GATTCACCATCTCAAGAGATGATTCAAAGAACTCACTGTAT<br>CTGCAAATGAACAGCCTGAAAACCGAGGACACGGCCGTGTA<br>TTACTGTACCGGTGGTTACTACCCTGTTTACTGGGGCCAAG<br>GGACTCTGGTCACTGTCTCTTCA<br>(SEQ ID NO 115) |
| 15C11-h2 | EVQLVESGGGLVQPGGSLR<br>LSCAASGFTFSDAWMDWVR<br>QAPGKGLEWVGEIRSKANN<br>HATYYAASVKGRFTISRDD<br>SKNSLYLQMNSLKTEDTAV<br>YYCTGGYYPVYWGQGTLVT<br>VSS<br>(SEQ ID NO 116) | GAGGTGCAGCTGGTGGAGTCTGGGGGAGGCTTGGTCCAGCC<br>TGGAGGGTCCCTGAGACTCTCCTGTGCAGCCTCTGGATTCA<br>CCTTCAGTGACGCCTGGATGGACTGGGTCCGCCAGGCTCCA<br>GGGAAGGGGCTGGAGTGGGTTGGCGAGATTAGAAGCAAAGC<br>TAACAATCACGCCACATACTACGCCGCGTCTGTGAAAGGCA<br>GATTCACCATCTCAAGAGATGATTCAAAGAACTCACTGTAT<br>CTGCAAATGAACAGCCTGAAAACCGAGGACACGGCCGTGTA<br>TTACTGTACCGGTGGTTACTACCCTGTTTACTGGGGCCAAG<br>GGACTCTGGTCACTGTCTCTTCA<br>(SEQ ID NO 117) |
| 15C11-h3 | EVQLVESGGGLVQPGGSLR<br>LSCAASGFTFSDAWMDWVR<br>QAPGKGLEWVAEIRSKANN<br>HATYYAASVKGRFTISRDD<br>SKNSVYLQMNSLKTEDTAV<br>YYCTGGYYPVYWGQGTLVT<br>VSS<br>(SEQ ID NO 118) | GAGGTGCAGCTGGTGGAGTCTGGGGGAGGCTTGGTCCAGCC<br>TGGAGGGTCCCTGAGACTCTCCTGTGCAGCCTCTGGATTCA<br>CCTTCAGTGACGCCTGGATGGACTGGGTCCGCCAGGCTCCA<br>GGGAAGGGGCTGGAGTGGGTTGCCGAGATTAGAAGCAAAGC<br>TAACAATCACGCCACATACTACGCCGCGTCTGTGAAAGGCA<br>GATTCACCATCTCAAGAGATGATTCAAAGAACTCAGTGTAT<br>CTGCAAATGAACAGCCTGAAAACCGAGGACACGGCCGTGTA<br>TTACTGTACCGGTGGTTACTACCCTGTTTACTGGGGCCAAG<br>GGACTCTGGTCACTGTCTCTTCA<br>(SEQ ID NO 119) |

TABLE 11 light chain variable regions of humanized 15C11 mAbs

| Antibody | Amino acid sequence | DNA sequence |
|---|---|---|
| 15C1 1-11 | DIQMTQSPSSLSASVGDRV TITCKASQDINKNIAWYQQ KPGKAPKLLIYYTSTLQPG VPSRFSGSGSGTDFTFTIS SLQPEDIATYYCLQYDNLL TFGGGTKVEIK (SEQ ID NO 120) | GACATCCAGATGACCCAGTCTCCATCCTCCCTGTCTGCAT CTGTAGGAGACAGAGTCACCATCACTTGCAAGGCGAGTCA GGACATTAACAAGAATATAGCTTGGTATCAGCAGAAACCA GGGAAAGCCCCTAAGCTCCTGATCTACTATACATCCACTT TGCAACCAGGGGTCCCATCAAGGTTCAGTGGAAGTGGATC TGGGACAGATTTTACTTTCACCATCAGCAGCCTGCAGCCT GAAGATATTGCAACATATTACTGTCTACAGTATGATAATC TCCTTACGTTCGGAGGGGGGACCAAGGTGGAAATAAAA (SEQ ID NO 121) |
| 15C1 1-12 | DIQMTQSPSSLSASVGDRV TITCKASQDINKNIAWYQH KPGKAPKLLIHYTSTLQPG VPSRFSGSGSGTDFTFTIS SLQPEDIATYYCLQYDNLL TFGGGTKVEIK (SEQ ID NO 122) | GACATCCAGATGACCCAGTCTCCATCCTCCCTGTCTGCAT CTGTAGGAGACAGAGTCACCATCACTTGCAAGGCGAGTCA GGACATTAACAAGAATATAGCTTGGTATCAGCATAAACCA GGGAAAGCCCCTAAGCTCCTGATCCACTATACATCCACTT TGCAACCAGGGGTCCCATCAAGGTTCAGTGGAAGTGGATC TGGGACAGATTTTACTTTCACCATCAGCAGCCTGCAGCCT GAAGATATTGCAACATATTACTGTCTACAGTATGATAATC TCCTTCGTTCGGAGGGGGGACCAAGGTGGAAATAAAA (SEQ ID NO 123) |
| 15C1 1-13 | DIQMTQSPSSLSASVGDRV TITCKASQDINKNIAWYQH KPGKAPKLLIHYTSTLQPG VPSRFSGSGSGRDYTFTIS SLQPEDIATYYCLQYDNLL TFGGGTKVEIK (SEQ ID NO 124) | GACATCCAGATGACCCAGTCTCCATCCTCCCTGTCTGCA TCTGTAGGAGACAGAGTCACCATCACTTGCAAGGCGAGT CAGGACATTAACAAGAATATAGCTTGGTATCAGCATAAA CCAGGGAAAGCCCCTAAGCTCCTGATCCACTATACATCC ACTTTGCAACCAGGGGTCCCATCAAGGTTCAGTGGAAGT GGATCTGGGAGAGATTATACTTTCACCATCAGCAGCCTG CAGCCTGAAGATATTGCAACATATTACTGTCTACAGTAT GATAATCTCCTTACGTTCGGAGGGGGGACCAAGGTGGAA ATAAAA (SEQ ID NO 125) |

TABLE 12

Combination of humanized heavy and light chains

| Mouse VH | Mouse VL mVH/mVL | Humanized L1 | Humanized L2 | Humanized L3 |
|---|---|---|---|---|
| Humanized H1 | | H1/L1 | H1/L2 (Hum12) | H1/L3 (Hum13) |
| Humanized H2 | | H2/L1 | H2/L2 (Hum22) | H2/L3 (Hum23) |
| Humanized H3 | | H3/L1 | H3/L2 (Hum32) | H3/L3 (Hum33) |

The VH and VL humanized cDNA variants were generated by gene synthesis and sub-cloned into expression vectors. Vectors coding for light and heavy chains were co-transfected into HEK cells for transient expression of the corresponding antibody variants.

Affinities were determined by both SCK and regular kinetic following methods and protocols recommended by the apparatus manufacturer. For each kinetic method, experiments were performed once for purpose of preliminary guidance.

Only the six variants that retained binding to the antigen were used for affinity measurements. The variants were compared to the parental M-K32-15C11 and the chimeric version Chim-K32-15C11. The six antibody variants tested retained globally a good affinity for the antigen compared to the mouse parental antibody. For instance, less than one log decrease was observed for the worst variant H1-L2 ($K_D$=1.63 nanoM vs 0.37 nanoM for M-K32-15C11 by SCK). The H3-L3 variant, which had the most back mutations was completely equivalent to both M-K32-15C11 and Chim-K32-15C11 antibodies. The humanized variant H3-L3 also showed a remarkably slower dissociation rate than the other mAbs tested, resulting in a more stable association to antigen (see Table 13).

TABLE 13

Affinity analysis by SCK and regular kinetic methods

| | SCK | | Regular | |
|---|---|---|---|---|
| Antibody | KD (nanoM) | koff (s$^{-1}$) | KD (nanoM) | koff (s$^{-1}$) |
| M-K32-15C11 | 0.37 | 1.10E-4 | ND | ND |
| Chim-K32-15C11 | 0.22 | 1.08E-4 | 0.68 | 2.90E-4 |
| Hum33-K32-15C11 | 0.33 | 0.78E-4 | 0.78 | 1.80E-4 |
| Hum32-K32-15C11 | 0.51 | 1.04E-4 | 1.29 | 2.50E-4 |
| Hum23-K32-15C11 | 0.50 | 1.40E-4 | 1.24 | 3.29E-4 |
| Hum22-K32-15C11 | 0.65 | 1.56E-4 | 1.74 | 3.85E-4 |
| Hum13-K32-15C11 | 1.13 | 2.86E-4 | 4.59 | 10.52E-4 |
| Hum12-K32-15C11 | 1.63 | 1.09E-4 | 5.61 | 13.20E-4 |

TABLE 7B

| | | KIR3DL2 D1 Antibodies | | | |
|---|---|---|---|---|---|
| Mutants | Mutations | 19H12 | 15C11 | 12B11 | 18B10 |
| M7 | L113V;T118R | + | + | + | + |
| M8 | V127I | + | + | + | + |
| M9 | L164M;P166L;V167A | + | + | + | + |
| M10 | R136K;E141K | + | + | + | + |
| M11 | P179T;S181T | − | + | − | − |
| M11A1 | V178A;H180S | +/− | + | − | − |
| M11A3 | N99S;H100S;Q184A | + | + | + | + |
| M11A4 | E130S;H131S;R145S | − | − | +/− | +/− |
| M11A5 | V147A;Q149S | + | + | + | +/− |
| M11A6 | I150A;M128A | + | − | + | + |
| M5 + 11 | P66T;P179T;S181T | +/− | +/− | − | − |
| M8 + 11 | V127I;P179T;S181T | − | + | − | − |

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e. g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The invention claimed is:

1. An isolated monoclonal antibody selected from the group consisting of:
   (a) a monoclonal antibody having (i) a heavy chain comprising CDR 1, 2 and 3 (HCDR1, HCDR2, HCDR3) comprising a sequence of SEQ ID NO: 4 (HCDR1), SEQ ID NO: 7 (HCDR2) and SEQ ID NO: 9 (HCDR3), respectively, and (ii) a light chain comprising CDR 1, 2 and 3 (LCDR1, LCDR2, LCDR3) comprising a sequence of SEQ ID NO: 10, 11 and 12, respectively;
   (b) a monoclonal antibody having (i) a heavy chain comprising CDR 1, 2 and 3 (HCDR1, HCDR2, HCDR3) comprising a sequence of SEQ ID NO: 15 (HCDR1), SEQ ID NO: 18 (HCDR2) and SEQ ID NO: 20 (HCDR3) respectively, and (ii) a light chain comprising CDR 1, 2 and 3 (LCDR1, LCDR2, LCDR3) comprising a sequence of SEQ ID NO: 21, 22 and 23, respectively;
   (c) a monoclonal antibody having (i) a heavy chain comprising CDR 1, 2 and 3 (HCDR1, HCDR2, HCDR3) comprising a sequence of SEQ ID NO: 16 (HCDR1), SEQ ID NO: 18 (HCDR2) and SEQ ID NO: 28 (HCDR3), respectively, and (ii) a light chain comprising CDR 1, 2 and 3 (LCDR1, LCDR2, LCDR3) comprising a sequence of SEQ ID NO: 29, 30 and 31, respectively;
   (d) a monoclonal antibody having (i) a heavy chain comprising CDR 1, 2 and 3 (HCDR1, HCDR2, HCDR3) comprising a sequence of SEQ ID NO: 26 (HCDR1), SEQ ID NO: 36 (HCDR2) and SEQ ID NO: 38 (HCDR3), respectively, and (ii) a light chain comprising CDR 1, 2 and 3 (LCDR1, LCDR2, LCDR3) comprising a sequence of SEQ ID NO: 39, 40 and 41, respectively;
   (e) a monoclonal antibody having (i) a heavy chain comprising CDR 1, 2 and 3 (HCDR1, HCDR2, HCDR3) comprising a sequence of SEQ ID NO: 16 (HCDR1), SEQ ID NO: 36 (HCDR2) and SEQ ID NO: 38 (HCDR3), respectively, and (ii) a light chain comprising CDR 1, 2 and 3 (LCDR1, LCDR2, LCDR3) comprising a sequence of SEQ ID NO: 44, 45 and 41, respectively; and
   (f) a monoclonal antibody having (i) a heavy chain comprising CDR 1, 2 and 3 (HCDR1, HCDR2, HCDR3) comprising a sequence of SEQ ID NO: 48 (HCDR1), SEQ ID NO: 51 (HCDR2) and SEQ ID NO: 53 (HCDR3), respectively, and (ii) a light chain comprising CDR 1, 2 and 3 (LCDR1, LCDR2, LCDR3) comprising a sequence of SEQ ID NO: 54, 55 and 56, respectively.

2. The antibody of claim 1, wherein said antibody has reduced binding to a mutant KIR3DL2 polypeptide comprising a mutation at residues V178 and P179, a mutant KIR3DL2 polypeptide comprising a mutation at residues H180 and S181, and/or a mutant KIR3DL2 polypeptide comprising a mutation at residues E130, H131 and R145, relative to binding between the antibody and a wild-type KIR3DL2 polypeptide of SEQ ID NO: 1.

3. The antibody of claim 1, wherein said antibody comprises a human IgG heavy chain constant region.

4. The antibody of claim 1, wherein said antibody is a chimeric, human or humanized antibody.

5. The antibody of claim 1, wherein said antibody is conjugated or covalently bound to a toxic agent.

6. A pharmaceutical composition comprising an antibody of claim 1, and a pharmaceutically acceptable carrier.

7. A method for the treatment of a KIR3DL2-expressing CD4+ T cell cancer in a patient in need thereof, the method comprising administering to said patient an effective amount of a pharmaceutical composition comprising a pharmaceutically acceptable carrier and a monoclonal antibody selected from the group consisting of:
   (a) a monoclonal antibody having (i) a heavy chain comprising CDR 1, 2 and 3 (HCDR1, HCDR2, HCDR3) comprising a sequence of SEQ ID NO: 4 (HCDR1), SEQ ID NO: 7 (HCDR2) and SEQ ID NO: 9 (HCDR3), respectively, and (ii) a light chain comprising CDR 1, 2 and 3 (LCDR1, LCDR2, LCDR3) comprising a sequence of SEQ ID NO: 10, 11 and 12, respectively;
   (b) a monoclonal antibody having (i) a heavy chain comprising CDR 1, 2 and 3 (HCDR1, HCDR2, HCDR3) comprising a sequence of SEQ ID NO: 15 (HCDR1), SEQ ID NO: 18 (HCDR2) and SEQ ID NO: 20 (HCDR3), respectively, and (ii) a light chain comprising CDR 1, 2 and 3 (LCDR1, LCDR2, LCDR3) comprising a sequence of SEQ ID NO: 21, 22 and 23, respectively;
   (c) a monoclonal antibody having (i) a heavy chain comprising CDR 1, 2 and 3 (HCDR1, HCDR2, HCDR3) comprising a sequence of SEQ ID NO: 16 (HCDR1), SEQ ID NO: 18 (HCDR2) and SEQ ID NO: 28 (HCDR3), respectively, and (ii) a light chain comprising CDR 1, 2 and 3 (LCDR1, LCDR2, LCDR3) comprising a sequence of SEQ ID NO: 29, 30 and 31, respectively;
   (d) a monoclonal antibody having (i) a heavy chain comprising CDR 1, 2 and 3 (HCDR1, HCDR2, HCDR3) comprising a sequence of SEQ ID NO: 26 (HCDR1), SEQ ID NO: 36 (HCDR2) and SEQ ID NO: 38 (HCDR3), respectively, and (ii) a light chain comprising CDR 1, 2 and 3 (LCDR1, LCDR2, LCDR3) comprising a sequence of SEQ ID NO: 39, 40 and 41, respectively;
   (e) a monoclonal antibody having (i) a heavy chain comprising CDR 1, 2 and 3 (HCDR1, HCDR2, HCDR3) comprising a sequence of SEQ ID NO: 16 (HCDR1), SEQ ID NO: 36 (HCDR2) and SEQ ID NO: 38 (HCDR3), respectively, and (ii) a light chain comprising CDR 1, 2 and 3 (LCDR1, LCDR2, LCDR3) comprising a sequence of SEQ ID NO: 44, 45 and 41, respectively; and
   (f) a monoclonal antibody having (i) a heavy chain comprising CDR 1, 2 and 3 (HCDR1, HCDR2, HCDR3) comprising a sequence of SEQ ID NO: 48 (HCDR1), SEQ ID NO: 51 (HCDR2) and SEQ ID NO: 53 (HCDR3), respectively, and (ii) a light chain comprising CDR 1, 2 and 3 (LCDR1, LCDR2, LCDR3) comprising a sequence of SEQ ID NO: 54, 55 and 56, respectively.

8. The method of claim 7, wherein said cancer is selected from Mycosis fungoides and Sézary Syndrome.

9. The method of claim 7, said monoclonal antibody having (i) a heavy chain comprising CDR 1, 2 and 3 (HCDR1, HCDR2, HCDR3) comprising a sequence of SEQ ID NO: 4 (HCDR1), SEQ ID NO: 7 (HCDR2) and SEQ ID NO: 9 (HCDR3), respectively, and (ii) a light chain comprising CDR 1, 2 and 3 (LCDR1, LCDR2, LCDR3) comprising a sequence of SEQ ID NO: 10, 11 and 12, respectively.

10. The method of claim 7, said monoclonal antibody having (i) a heavy chain comprising CDR 1, 2 and 3 (HCDR1, HCDR2, HCDR3) comprising a sequence of SEQ ID NO: 15 (HCDR1), SEQ ID NO: 18 (HCDR2) and SEQ ID NO: 20 (HCDR3), respectively, and (ii) a light chain comprising CDR 1, 2 and 3 (LCDR1, LCDR2, LCDR3) comprising a sequence of SEQ ID NO: 21, 22 and 23, respectively.

11. The method of claim 7, said monoclonal antibody having (i) a heavy chain comprising CDR 1, 2 and 3 (HCDR1, HCDR2, HCDR3) comprising a sequence of SEQ ID NO: 16 (HCDR1), SEQ ID NO: 18 (HCDR2) and SEQ ID NO: 28 (HCDR3), respectively, and (ii) a light chain comprising CDR 1, 2 and 3 (LCDR1, LCDR2, LCDR3) comprising a sequence of SEQ ID NO: 29, 30 and 31, respectively.

12. The method of claim 7, said monoclonal antibody having (i) a heavy chain comprising CDR 1, 2 and 3 (HCDR1, HCDR2, HCDR3) comprising a sequence of SEQ ID NO: 26 (HCDR1), SEQ ID NO: 36 (HCDR2) and SEQ ID NO: 38 (HCDR3), respectively, and (ii) a 7 light chain comprising CDR 1, 2 and 3 (LCDR1, LCDR2, LCDR3) comprising a sequence of SEQ ID NO: 39, 40 and 41, respectively.

13. The method of claim 7, said monoclonal antibody having (i) a heavy chain comprising CDR 1, 2 and 3 (HCDR1, HCDR2, HCDR3) comprising a sequence of SEQ ID NO: 16 (HCDR1), SEQ ID NO: 36 (HCDR2) and SEQ ID NO: 38 (HCDR3), respectively, and (ii) a light chain comprising CDR 1, 2 and 3 (LCDR1, LCDR2, LCDR3) comprising a sequence of SEQ ID NO: 44, 45 and 41, respectively.

14. The method of claim 7, said monoclonal antibody having (i) a heavy chain comprising CDR 1, 2 and 3 (HCDR1, HCDR2, HCDR3) comprising a sequence of SEQ ID NO: 48 (HCDR1), SEQ ID NO: 51 (HCDR2) and SEQ ID NO: 53 (HCDR3), respectively, and (ii) a light chain comprising CDR 1, 2 and 3 (LCDR1, LCDR2, LCDR3) comprising a sequence of SEQ ID NO: 54, 55 and 56, respectively.

15. The isolated monoclonal antibody of claim 1, said monoclonal antibody having (i) a heavy chain comprising CDR 1, 2 and 3 (HCDR1, HCDR2, HCDR3) comprising a sequence of SEQ ID NO: 4 (HCDR1), SEQ ID NO: 7 (HCDR2) and SEQ ID NO: 9 (HCDR3), respectively, and (ii) a light chain comprising CDR 1, 2 and 3 (LCDR1, LCDR2, LCDR3) comprising a sequence of SEQ ID NO: 10, 11 and 12, respectively.

16. The isolated monoclonal antibody of claim 1, said monoclonal an antibody having (i) a heavy chain comprising CDR 1, 2 and 3 (HCDR1, HCDR2, HCDR3) comprising a sequence of SEQ ID NO: 15 (HCDR1), SEQ ID NO: 18 (HCDR2) and SEQ ID NO: 20 (HCDR3), respectively, and (ii) a light chain comprising CDR 1, 2 and 3 (LCDR1, LCDR2, LCDR3) comprising a sequence of SEQ ID NO: 21, 22 and 23, respectively.

17. The isolated monoclonal antibody of claim 1, said monoclonal antibody having (i) a heavy chain comprising CDR 1, 2 and 3 (HCDR1, HCDR2, HCDR3) comprising a sequence of SEQ ID NO: 16 (HCDR1), SEQ ID NO: 18 (HCDR2) and SEQ ID NO: 28 (HCDR3), respectively, and (ii) a light chain comprising CDR 1, 2 and 3 (LCDR1, LCDR2, LCDR3) comprising a sequence of SEQ ID NO: 29, 30 and 31, respectively.

18. The isolated monoclonal antibody of claim 1, said monoclonal an antibody having (i) a heavy chain comprising CDR 1, 2 and 3 (HCDR1, HCDR2, HCDR3) comprising a sequence of SEQ ID NO: 26 (HCDR1), SEQ ID NO: 36 (HCDR2) and SEQ ID NO: 38 (HCDR3), respectively, and (ii) a light chain comprising CDR 1, 2 and 3 (LCDR1, LCDR2, LCDR3) comprising a sequence of SEQ ID NO: 39, 40 and 41, respectively.

19. The isolated monoclonal antibody of claim 1, said monoclonal antibody having (i) a heavy chain comprising CDR 1, 2 and 3 (HCDR1, HCDR2, HCDR3) comprising a sequence of SEQ ID NO: 16 (HCDR1), SEQ ID NO: 36 (HCDR2) and SEQ ID NO: 38 (HCDR3), respectively, and (ii) a light chain comprising CDR 1, 2 and 3 (LCDR1, LCDR2, LCDR3) comprising a sequence of SEQ ID NO: 44, 45 and 41, respectively.

20. The isolated monoclonal antibody of claim 1, said monoclonal antibody having (i) a heavy chain comprising CDR 1, 2 and 3 (HCDR1, HCDR2, HCDR3) comprising a sequence of SEQ ID NO: 48 (HCDR1), SEQ ID NO: 51 (HCDR2) and SEQ ID NO: 53 (HCDR3), respectively, and (ii) a light chain comprising CDR 1, 2 and 3 (LCDR1, LCDR2, LCDR3) comprising a sequence of SEQ ID NO: 54, 55 and 56, respectively.

* * * * *

UNITED STATES PATENT AND TRADEMARK OFFICE
CERTIFICATE OF CORRECTION

PATENT NO. : 10,246,510 B2
APPLICATION NO. : 14/429416
DATED : April 2, 2019
INVENTOR(S) : Laurent Gauthier et al.

It is certified that error appears in the above-identified patent and that said Letters Patent is hereby corrected as shown below:

In the Specification

Column 6,
Line 13, "residues 1150" should read --residues I150--.
Line 16, "residues 1150" should read --residues I150--.
Line 25, "residues 1150" should read --residues I150--.
Line 27, "residues 1150" should read --residues I150--.
Line 33, "Q149, 1150" should read --Q149, I150--.

Column 7,
Line 67, "1150, V178" should read --I150, V178--.

Column 8,
Line 7, "E57, 160" should read --E57, I60--.
Line 10, "E57, 160" should read --E57, I60--.

Column 9,
Line 2, "I1150, V178" should read --I150, V178--.
Line 10, "E57, 160" should read --E57, I60--.

Column 11,
Line 55, "1150, V178" should read --I150, V178--.

Column 27,
Line 48, "Q149, 1150" should read --Q149, I150--.
Line 51, "E57, 160" should read --E57, I60--.
Line 59, "residue 1150" should read --residue I150--.
Line 62, "I1150, V178" should read --I150, V178--.
Line 66, "E57, 160" should read --E57, I60--.

Signed and Sealed this
Twenty-fourth Day of September, 2019

Andrei Iancu
*Director of the United States Patent and Trademark Office*

Page 1 of 3

CERTIFICATE OF CORRECTION (continued)
U.S. Pat. No. 10,246,510 B2

Column 28,
Line 53, "Q149, 1150" should read --Q149, I150--.
Line 57, "E57, 160" should read --E57, I60--.

Column 29,
Line 4, "residues 160" should read --residues I60--.

Column 54,
Line 18, "18 WINTYFGEPTYADDF" should read --18 WINTYTGEPTYADDF--.

Column 59,
Line 9, "G49A and R5OE" should read --G49A and R50E--.

Column 68,
Line 60, "$R^{15}$ is -(CH$_2$)-N($R^{16}$)$_2$" should read --$R^{15}$ is -(CH$_2$)$_n$-N($R^{16}$)$_2$--.
Line 64, "$R^{15}$ is -(CH$_2$)-SO$_3$H" should read --$R^{15}$ is -(CH$_2$)$_n$-SO$_3$H--.

Column 73,
Lines 28-54,

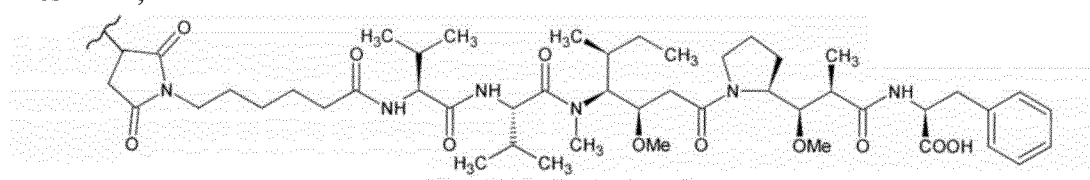

MC-MMAE

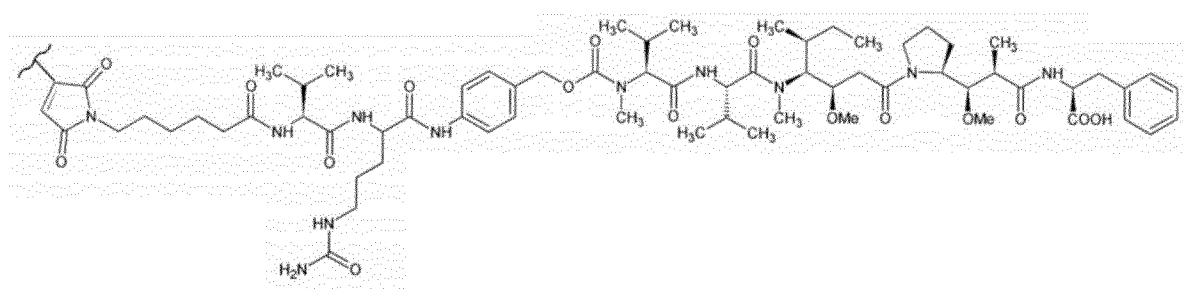

" MC-vc-PAB-MMAE "

should read

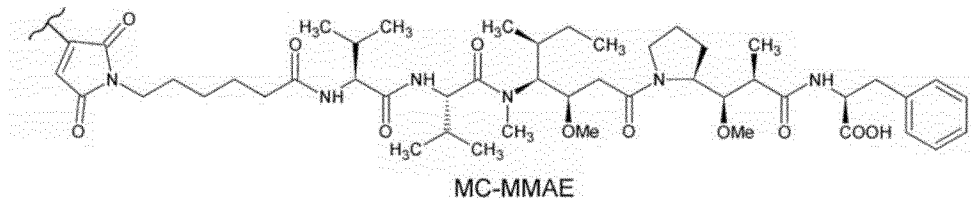

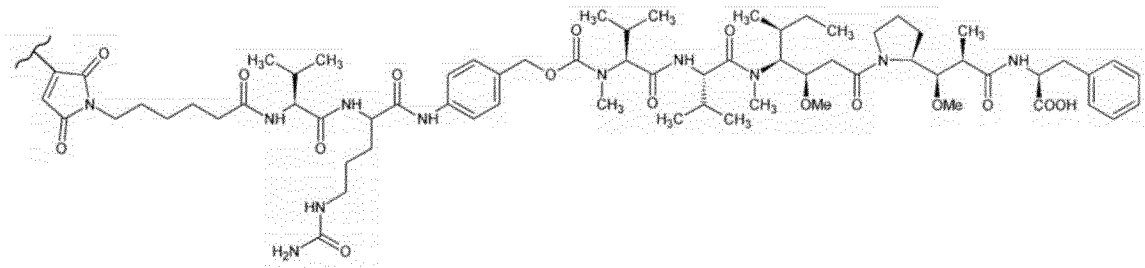

-- --.

Column 83,
Line 3, "GiK monoclonal" should read --G1κ monoclonal--.

Column 88,
Lines 44-45, "(IgG2a/K isotype)" should read --(IgG2a/κ isotype)--.
Line 64, "(murine IgG2b/K) and 22B2 (murine IgG1/K)" should read --(murine IgG2b/κ) and 22B2 (murine IgG1/κ)--.

Column 97,
Line 60, "1150A" should read --I150A--.

Column 98,
Line 41, "160N" should read --I60N--.
Line 66, "160N" should read --I60N--.

Column 99,
Line 34, "with 20 m/ml" should read --with 20 μg/ml--.

In the Claims

Column 203,
Line 35, "a 7 light chain" should read --a light chain--.